US012606565B2

(12) United States Patent
Pal et al.

(10) Patent No.: US 12,606,565 B2
(45) Date of Patent: Apr. 21, 2026

(54) METHODS FOR PREPARING TYROSINE RECEPTOR KINASE INHIBITORS

(71) Applicant: PYRAMID BIOSCIENCES, INC., Waltham, MA (US)

(72) Inventors: Kollol Pal, Needham, MA (US); Prasant Deb, Noida (IN); Hari Prakash, Greater Noida (IN); Avinash Borude, Ahmednager (IN)

(73) Assignee: PYRAMID BIOSCIENCES, INC., Waltham, MA (US)

( * ) Notice: Subject to any disclaimer, the term of this patent is extended or adjusted under 35 U.S.C. 154(b) by 710 days.

(21) Appl. No.: 17/918,880

(22) PCT Filed: Apr. 15, 2021

(86) PCT No.: PCT/US2021/027538

§ 371 (c)(1),
(2) Date: Oct. 13, 2022

(87) PCT Pub. No.: WO2021/211882

PCT Pub. Date: Oct. 21, 2021

(65) Prior Publication Data

US 2023/0242536 A1 Aug. 3, 2023

Related U.S. Application Data

(60) Provisional application No. 63/010,108, filed on Apr. 15, 2020.

(51) Int. Cl.

| | |
|---|---|
| ***C07D 487/04*** | (2006.01) |
| ***C07D 231/12*** | (2006.01) |
| ***C07D 403/04*** | (2006.01) |

(52) U.S. Cl.

CPC ......... *C07D 487/04* (2013.01); *C07D 231/12* (2013.01); *C07D 403/04* (2013.01)

(58) Field of Classification Search

CPC .. C07D 231/12; C07D 231/38; C07D 403/04; C07D 487/04

See application file for complete search history.

(56) References Cited

U.S. PATENT DOCUMENTS

| | | | |
|---|---|---|---|
| 4,861,760 | A | 8/1989 | Mazuel et al. |
| 4,911,920 | A | 3/1990 | Jani et al. |
| 5,212,162 | A | 5/1993 | Tissel et al. |
| 5,403,841 | A | 4/1995 | Lang et al. |
| 2011/0166133 | A1 | 7/2011 | Albaugh et al. |
| 2016/0185785 | A1 | 6/2016 | Ioannidis et al. |
| 2021/0094956 | A1 | 4/2021 | Pal et al. |
| 2022/0023055 | A1 | 1/2022 | Deransart et al. |

FOREIGN PATENT DOCUMENTS

| | | | |
|---|---|---|---|
| JP | 2011520887 | | 7/2011 |
| WO | 2008037477 | A1 | 4/2008 |
| WO | WO2009/140128 | | 11/2009 |
| WO | WO2010/048314 | | 4/2010 |
| WO | WO2010/051549 | | 5/2010 |
| WO | WO2016/097869 | | 6/2016 |
| WO | WO2016/185785 | | 11/2016 |
| WO | WO2019/118584 | | 6/2019 |
| WO | PCT/US2021/027538 | | 10/2021 |
| WO | WO2021/211882 | | 10/2021 |

OTHER PUBLICATIONS

Rao et al., Recent developments of collagen-based materials for medical applications and drug delivery systems, J. Biomater Sci. Polym. Ed. 7:623-645, 1995.
Gao et al., Controlled release of a contraceptive steroid from biodegradable and injectable gel formulations: in vitro evaluation, Pharm. Res. 12:857-863, 1995.
Eyles et al., Oral delivery and fate of poly(lactic acid) microsphere-encapsulated interferon in rats, J. Pharm. Pharmacol. 49:669-674, 1997.
Al-Muhammed et al., In-vivo studies on dexamethasone sodium phosphate liposomes, J. Microencapsul. 13:293-306, 1996.
Chonn et al., Recent advances in liposomal drug-delivery systems, Curr. Opin. Biotechnol. 6:698-708, 1995.

(Continued)

*Primary Examiner* — Valerie Rodriguez-Garcia
(74) *Attorney, Agent, or Firm* — Ballard Spahr LLP

(57) ABSTRACT

The present disclosure relates to methods of making pyrazolo[1,5-a]pyrimidine compounds having a structure:

(XV)

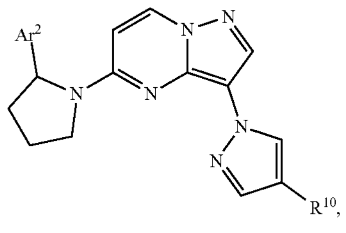

via a coupling reaction between an activated pyrazolo[1,5-a]pyrimidine and an amine. The disclosed pyrazolo[1,5-a]pyrimidine compounds can be useful as TRK inhibitors, as further detailed herein. Also disclosed are compounds useful in preparing pyrazolo[1,5-a]pyrimidine compounds and methods of making and using same.

11 Claims, 18 Drawing Sheets

(56) References Cited

OTHER PUBLICATIONS

Ostro et al., Use of liposomes as injectable-drug delivery systems, Am. J. Hosp. Pharm. 46:1576-1587, 1989.
Thiele, C. J., et al., "on Trk-The TrkB Signal Transduction Pathway is an Increasingly Important Target in Cancer Biology," Clin Cancer Res, 15(19): 5962-5967, 2009.
Vaishnavi, A., et al., "TRKing DOwn an Old Oncogene in a New Era of Targeted Therapy," Cancer Discov, 5(1):25-34, 2014.
Amatu, et al. "NTRK gene fusions as novel targets of cancer therapy across multiple tumour types," ESMO Open 2016; 1:e000023.
Liu, et al. "Entrectinib: an orally available, selective tyrpsine kinase inhibitor for the Treatment of NTRK, ROSI, and ALK fusion-positive solid tumors" (2018) ther Clin Risk Manag 14:1247-1252.
U.S. Appl. No. 63/010,108, filed Apr. 15, 2020, Pal et al.
U.S. Appl. No. 62/599,490, filed Dec. 15, 2017, Kollol Pal.
U.S. Appl. No. 16/772,253 (now U.S. Pat. No. 11,230,546), filed Dec. 12, 2018, Kollol Pal.

| | | |
|---|---|---|
| NAME | J1163-15861-PF | |
| EXPNO | 2 | |
| PROCNO | 1 | |
| Date_ | 20190826 | |
| Time | 18.18 | h |
| INSTRUM | spect | |
| PROBHD | Z108618_1050 ( | |
| PULPROG | zg30 | |
| TD | 41664 | |
| SOLVENT | DMSO | |
| NS | 64 | |
| DS | 0 | |
| SWH | 10416.667 | Hz |
| FIDRES | 0.500032 | Hz |
| AQ | 1.9999220 | sec |
| RG | 193.93 | |
| DW | 48.000 | usec |
| DE | 6.50 | usec |
| TE | 297.3 | K |
| D1 | 1.00000000 | sec |
| TD0 | 1 | |
| SFO1 | 400.1324708 | MHz |
| NUC1 | 1H | |
| P1 | 14.00 | usec |
| SI | 65536 | |
| SF | 400.1300030 | MHz |
| WDW | EM | |
| SSB | 0 | |
| LB | 0.30 | Hz |
| GB | 0 | |
| PC | 1.00 | |

FIG. 2A (Cont.)

| | | |
|---|---|---|
| NAME | J1163-15861-PF | |
| EXPNO | 2 | |
| PROCNO | 1 | |
| Date_ | 20190826 | |
| Time | 18.18 | h |
| INSTRUM | spect | |
| PROBHD | Z108618_1050 ( | |
| PULPROG | zg30 | |
| TD | 41664 | |
| SOLVENT | DMSO | |
| NS | 64 | |
| DS | 0 | |
| SWH | 10416.667 | Hz |
| FIDRES | 0.500032 | Hz |
| AQ | 1.9999220 | sec |
| RG | 193.93 | |
| DW | 48.000 | usec |
| DE | 6.50 | usec |
| TE | 297.3 | K |
| D1 | 1.00000000 | sec |
| TD0 | 1 | |
| SFO1 | 400.1324708 | MHz |
| NUC1 | 1H | |
| P1 | 14.00 | usec |
| SI | 65536 | |
| SF | 400.1300030 | MHz |
| WDW | EM | |
| SSB | 0 | |
| LB | 0.30 | Hz |
| GB | 0 | |
| PC | 1.00 | |

FIG. 2B (Cont.)

| | | |
|---|---|---|
| NAME | J1163-15861-PF | |
| EXPNO | 1 | |
| PROCNO | 1 | |
| Date_ | 20190828 | |
| Time | 9.31 | h |
| INSTRUM | spect | |
| PROBHD | Z108618_1050 ( | |
| PULPROG | zg30 | |
| TD | 41664 | |
| SOLVENT | DMSO | |
| NS | 64 | |
| DS | 0 | |
| SWH | 10416.667 | Hz |
| FIDRES | 0.500032 | Hz |
| AQ | 1.9999220 | sec |
| RG | 193.93 | |
| DW | 48.000 | usec |
| DE | 6.50 | usec |
| TE | 353.0 | K |
| D1 | 1.00000000 | sec |
| TD0 | 1 | |
| SFO1 | 400.1324708 | MHz |
| NUC1 | 1H | |
| P1 | 14.00 | usec |
| SI | 65536 | |
| SF | 400.1300027 | MHz |
| WDW | EM | |
| SSB | 0 | |
| LB | 0.30 | Hz |
| GB | 0 | |
| PC | 1.00 | |

FIG. 2C (Cont.)

| | | |
|---|---|---|
| NAME | J1163-15861-PF | |
| EXPNO | 1 | |
| PROCNO | 1 | |
| Date_ | 20190828 | |
| Time | 9.31 | h |
| INSTRUM | spect | |
| PROBHD | Z108618_1050 ( | |
| PULPROG | zg30 | |
| TD | 41664 | |
| SOLVENT | DMSO | |
| NS | 64 | |
| DS | 0 | |
| SWH | 10416.667 | Hz |
| FIDRES | 0.500032 | Hz |
| AQ | 1.9999220 | sec |
| RG | 193.93 | |
| DW | 48.000 | usec |
| DE | 6.50 | usec |
| TE | 353.0 | K |
| D1 | 1.00000000 | sec |
| TD0 | 1 | |
| SFO1 | 400.1324708 | MHz |
| NUC1 | 1H | |
| P1 | 14.00 | usec |
| SI | 65536 | |
| SF | 400.1300027 | MHz |
| WDW | EM | |
| SSB | 0 | |
| LB | 0.30 | Hz |
| GB | 0 | |
| PC | 1.00 | |

FIG. 2D (Cont.)

Peak Results

| | Name | RT | Area | %Area | RT Ratio |
|---|---|---|---|---|---|
| 1 | Peak1 | 11.44 | 594 | 0.01 | 0.60 |
| 2 | Peak2 | 12.96 | 2070 | 0.03 | 0.68 |
| 3 | Peak3 | 13.48 | 4775 | 0.07 | 0.71 |
| 4 | Peak4 | 13.67 | 1444 | 0.02 | 0.72 |
| 5 | Peak5 | 14.67 | 403 | 0.01 | 0.77 |
| 6 | Peak6 | 16.60 | 1880 | 0.03 | 0.87 |
| 7 | Peak7 | 18.74 | 6399 | 0.09 | 0.98 |
| 8 | Peak8 | 19.11 | 7128345 | 99.75 | 1.00 |

Peak Results

| | RT | Area | Height | %Area |
|---|---|---|---|---|
| 1 | 3.127 | 48909 | 10977 | 1.11 |
| 2 | 3.514 | 4354173 | 795530 | 98.89 |

METHODS FOR PREPARING TYROSINE RECEPTOR KINASE INHIBITORS

CROSS-REFERENCE TO RELATED APPLICATIONS

This Application is a national phase application filed under 35 U.S.C. § 371 claiming priority to International Application No. PCT/US2021/027538, filed on Apr. 15, 2021, which claims priority to U.S. Application No. 63/010, 108, filed on Apr. 15, 2020.

BACKGROUND

Growth factors are important signaling molecules that promote the growth, development and homeostasis of many cellular systems. Neurotrophins are growth factors that are responsible for central and peripheral neuronal growth, maturation, and death. Neurotrophins activate cell surface receptors called tropomyosin-like receptors, which in turn regulate intracellular kinases called tropomyosin receptor kinases (TRKs). The TRK family of receptors includes TRKA, TRKB, and TRKC, and serve as high affinity cell surface receptors for the growth factors NGF, BDNF, and NT3, respectively. Inhibition of these receptors may lead to the modulation or inhibition of intracellular signaling cascades that regulate cell growth and proliferation, cellular communication between cells that regulate signaling, feedback mechanism, and homeostasis. These growth factors have been implicated in the growth and proliferation of both neuronal and non-neuronal cells.

TRK inhibitors have the potential to be used in the treatment or prevention of various diseases including inflammatory diseases, infections, autoimmune disorders, stroke, ischemia, cardiac disorder, neurological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, neuropathic pain, and other disorders. Despite the widespread therapeutic utility of TRK inhibitors, methods of making these compounds that are amenable to scale-up for large-scale manufacturing processes have remained elusive. Accordingly, there remains a need for compounds useful as intermediates in preparing TRK inhibitors, methods of making these intermediary compounds, and methods of making TRK inhibitors. These needs and others are met by the invention.

SUMMARY

In accordance with the purpose(s) of the invention, as embodied and broadly described herein, the invention, in some embodiments, relates to pyrazolo[1,5-a]pyrimidine compounds useful as TRK inhibitors and compounds useful in preparing pyrazolo[1,5-a]pyrimidine compounds, and methods of making and using same.

Thus, in some embodiments, the present disclosure provides methods for making a compound having the structure represented by formula (XXV):

(XXV)

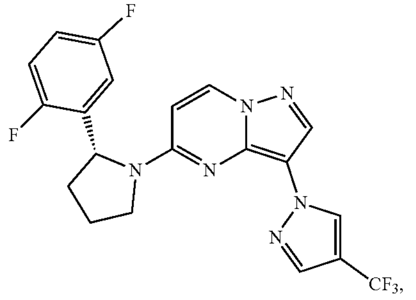

or a pharmaceutically acceptable salt thereof, the method comprising coupling a compound having the structure represented by formula (XXVI):

(XXVI)

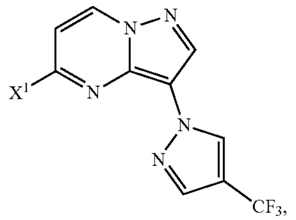

and a compound having the structure represented by formula:

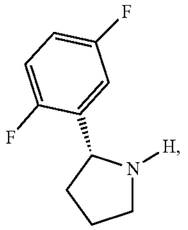

whereby

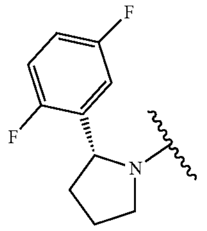 [SMILES: *N1CCC[C@@H]1c1cc(F)ccc1F]

replaces $X^1$, and wherein $X^1$ is a leaving group.

In some embodiments, the present disclosure provides methods for making a compound having the structure:

(XXV)

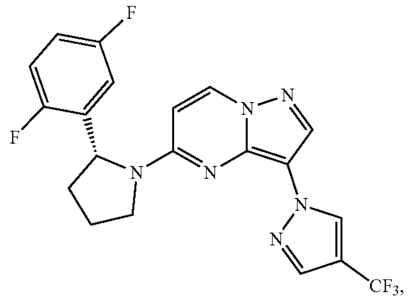

or a pharmaceutically acceptable salt thereof, the method comprising: (a) preparing a nitrile having the structure:

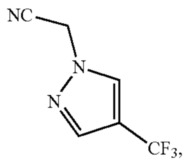

via reacting a heteroaryl having the structure:

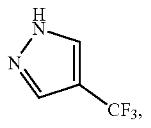

and a haloacetonitrile having the structure represented by formula (XXIV):

(XXIV)

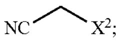

(b) preparing an acrylonitrile having the structure:

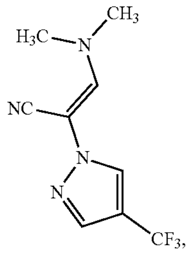 [SMILES: CN(C)/C=C(\C#N)n1cc(C(F)(F)F)cn1]

via reacting the nitrile and a formamidine acetal; (c) preparing an amine having the structure:

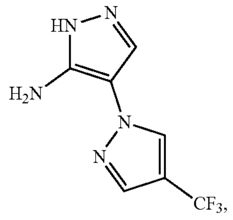 [SMILES: Nc1[nH]ncc1-n1cc(C(F)(F)F)cn1]

via reacting the acrylonitrile with a hydrazine; (d) preparing an amide having the structure:

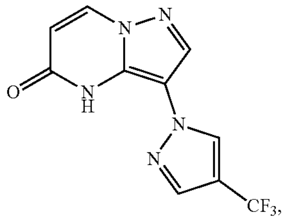 [SMILES: O=c1ccn2ncc(-n3cc(C(F)(F)F)cn3)c2[nH]1]

via reacting the amine and a uracil having the structure:

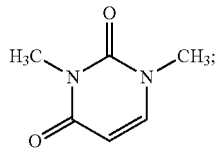

(e) preparing a compound having the structure represented by formula (XXVI):

(XXVI)

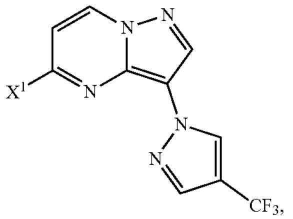

via reacting the amide and a halogenating agent; and (f) preparing the compound of formula (XXV) via coupling the compound of formula (XXVI) and a compound having the structure:

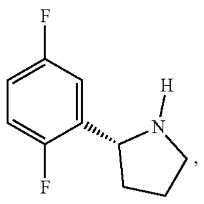

wherein $X^1$ is a leaving group; and wherein $X^2$ is a halogen.

In some embodiments, the present disclosure provides methods for making a compound having the structure represented by formula (XV):

(XV)

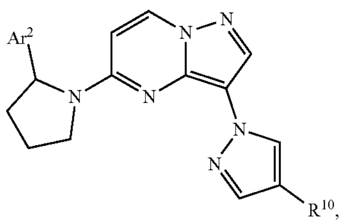

or a pharmaceutically acceptable salt thereof, the method comprising coupling a compound of formula (XVI):

(XVI)

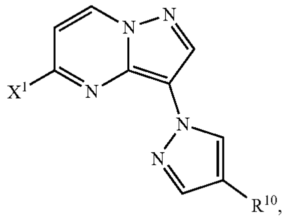

and a compound of formula (XVII):

(XVII)

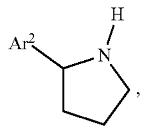

whereby

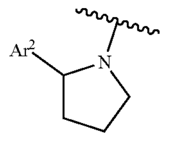

replaces $X^1$; wherein $X^1$ is a leaving group; wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy.

In some embodiments, the present disclosure provides methods for making a compound having the structure represented by formula (XV):

(XV)

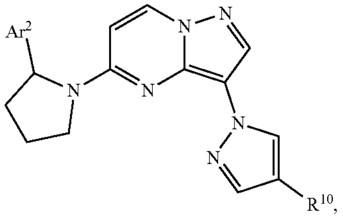

or a pharmaceutically acceptable salt thereof, the method comprising: (a) preparing a nitrile having the structure represented by formula (XXII):

(XXII)

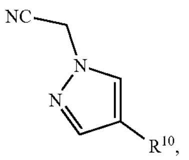

via reacting a heteroaryl having the structure represented by formula (XXIII):

(XXIII)

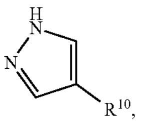

and a haloacetonitrile having the structure represented by formula (XXIV):

(XXIV)

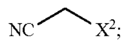

(b) preparing an acrylonitrile having the structure represented by formula (XXI):

(XXI)

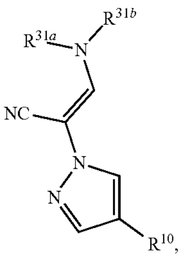

via reacting the nitrile of formula (XXII) and a formamidine acetal; (c) preparing an amine having the structure represented by formula (XIX):

(XIX)

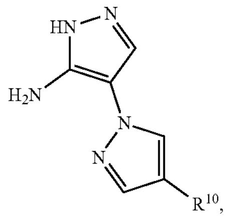

via cyclizing the acrylonitrile of formula (XXI) with a hydrazine; (d) preparing an amide having the structure represented by formula (XVIII):

(XVIII)

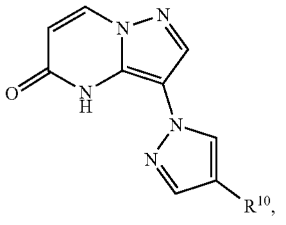

via reacting the amine of formula (XIX) and a uracil having the structure represented by formula (XX):

(XX)

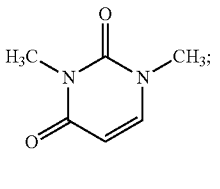

(e) preparing a compound having the structure represented by formula (XVI):

(XVI)

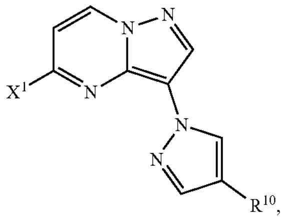

via reacting the amide of formula (XVIII) and a halogenating agent; and (f) preparing the compound of formula (XV) via coupling the compound of formula (XVI) and a compound having the structure represented by formula (XVII):

(XVII)

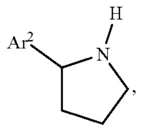

wherein $X^1$ is a leaving group; wherein $X^2$ is a halogen; wherein $X^1$ is a leaving group; wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl) $NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy; and wherein each of $R^{31a}$ and $R^{31b}$ is independently C1-C4 alkyl.

In some embodiments, the present disclosure provides a compound prepared by a disclosed method.

In some embodiments, the present disclosure provides compounds having the structure represented by formula (XVI):

(XVI)

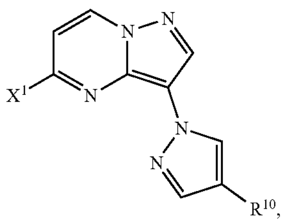

wherein $X^1$ is a leaving group; wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl) $NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In some embodiments, the present disclosure provides methods for making a compound having the structure represented by formula (XVI):

(XVI)

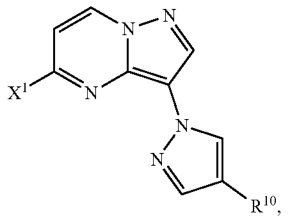

or a pharmaceutically acceptable salt thereof, the method comprising reacting an amide having the structure represented by formula (XVIII):

(XVIII)

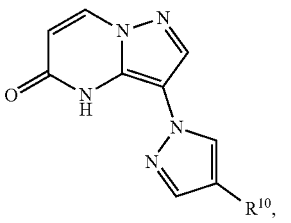

and an activating agent, wherein $X^1$ is a leaving group; wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In some embodiments, the present disclosure provides compounds having the structure represented by formula (XVIII):

(XVIII)

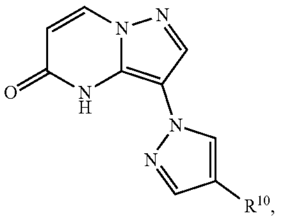

wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In some embodiments, the present disclosure provides methods for making a compound having the structure represented by formula (XVIII):

(XVIII)

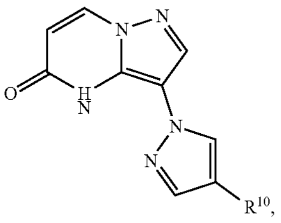

or a pharmaceutically acceptable salt thereof, the method comprising reacting an amine having the structure represented by formula (XIX):

(XIX)

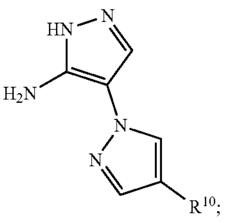

and a uracil having the structure represented by formula (XX):

(XX)

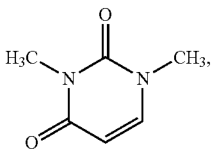

wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In some embodiments, the present disclosure provides compounds having the structure:

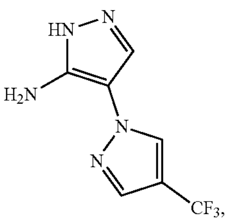 [SMILES: Nc1[nH]ncc1-n1cc(C(F)(F)F)cn1]

or a pharmaceutically acceptable salt thereof.

In some embodiments, the present disclosure provides compounds having the structure:

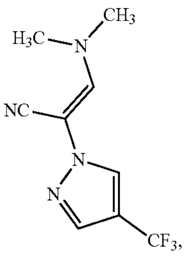 [SMILES: CN(C)/C=C(\C#N)n1cc(C(F)(F)F)cn1]

or a pharmaceutically acceptable salt thereof.

In some embodiments, the present disclosure provides a method of preparing a compound of Formula (X):

(X)

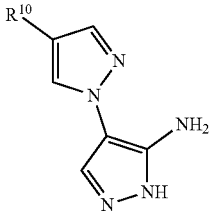

or a salt thereof, comprising one or more of steps (i-1) to (i-3): (i-1) contacting a compound of Formula (VII):

(VII)

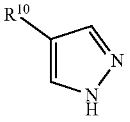

with an acetonitrile addition agent, thereby forming a compound of Formula (VIII):

(VIII)

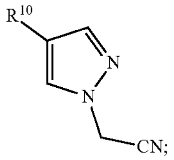

(i-2) contacting the compound of Formula (VIII) with N,N-dimethylformamide diethyl acetal or a synthetic equivalent thereof, thereby forming a compound of Formula (IX):

(IX)

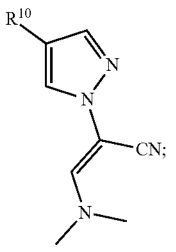

(i-3) contacting the compound of Formula (IX) with hydrazine, thereby forming a compound of Formula (X):

(X)

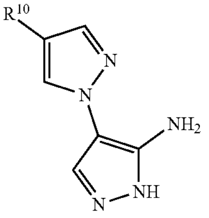

or a salt thereof, wherein $R^{10}$ is as described above.

In some embodiments, the present disclosure provides a use of compound of Formula (VII) in the manufacture of a compound of Formula (X) or a salt thereof, comprising one or more of steps (i-1) to (i-3).

In some embodiments, the present disclosure provides a method of preparing a compound of Formula (XIV):

(XIV)

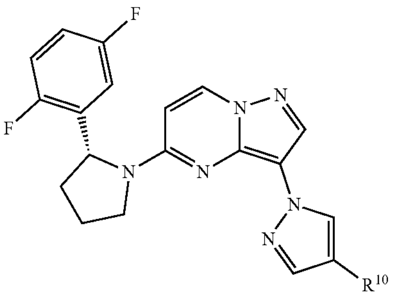

or a salt thereof, comprising one or more of the following steps (f-1) to (f-3): (f-1) contacting a compound of Formula (X):

(X)

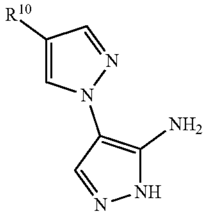

or a salt thereof, with Compound No. 11:

(Compound No. 11)

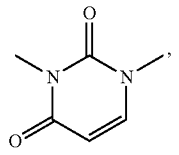

or a synthetic equivalent thereof, thereby forming a compound of Formula (XII):

(XII)

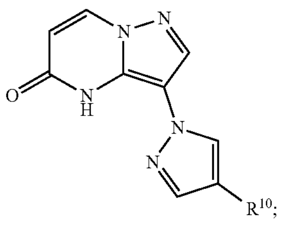

(f-2) contacting the compound of Formula (XII) with a chlorination agent, thereby forming a compound of Formula (XIII):

(XIII)

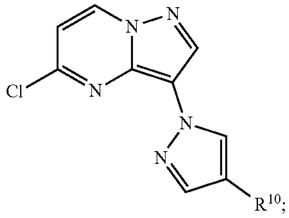

or (f-3) contacting the compound of Formula (XIII) with Compound No. 6:

(Compound No. 6)

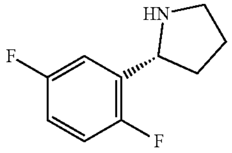

or a salt thereof, thereby forming a compound of Formula (XIV):

(XIV)

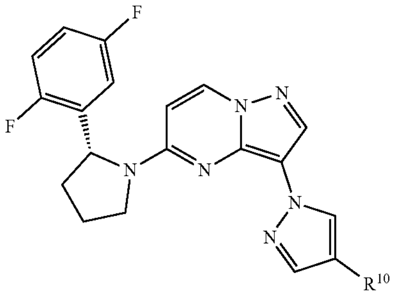

or a salt thereof, wherein $R^{10}$ is as described above.

In some embodiments, the present disclosure provides a use of a compound of Formula (X) or a salt thereof, in the manufacture of a compound of Formula (XIV) or a salt thereof, comprising one or more of steps (f-1) to (f-3).

In some embodiments, the present disclosure provides a combination comprising a compound of Formula (VII) and an acetonitrile addition agent. In these types of reactions, a suitable acetonitrile addition agent is a haloacetonitrile such as bromoacetonitrile.

In some embodiments, the present disclosure provides a combination comprising a compound of Formula (VII) and an acetonitrile addition agent for preparing a compound of Formula (X) or a salt thereof.

In some embodiments, the present disclosure provides a combination comprising a compound of Formula (VIII) and N,N-dimethylformamide diethyl acetal or a synthetic equivalent thereof. The term "formamidine acetal" is used in this context to refer to N,N-dimethylformamide diethyl acetal or a synthetic equivalent thereof.

In some embodiments, the present disclosure provides a combination comprising a compound of Formula (VIII) and N,N-dimethylformamide diethyl acetal or a synthetic equivalent thereof, for preparing a compound of Formula (X) or a salt thereof.

In some embodiments, the present disclosure provides a combination comprising a compound of Formula (IX) and hydrazine.

In some embodiments, the present disclosure provides a combination comprising a compound of Formula (IX) and hydrazine, useful for preparing a compound of Formula (X) or a salt thereof.

In some embodiments, the present disclosure provides a combination comprising a compound of Formula (X) or a salt thereof, and Compound No. 11, or a synthetic equivalent thereof.

In some embodiments, the present disclosure provides a combination comprising a compound of Formula (X) or a salt thereof, and Compound No. 11, or a synthetic equivalent thereof, useful for preparing a compound of Formula (XIV) or a salt thereof.

In some embodiments, the present disclosure provides a combination comprising a compound of Formula (XII) and a chlorination agent.

In some embodiments, the present disclosure provides a combination comprising a compound of Formula (XII) and a chlorination agent, useful for preparing a compound of Formula (XIV) or a salt thereof.

In some embodiments, the present disclosure provides a combination comprising a compound of Formula (XIII) and Compound No. 6 or a salt thereof.

In some embodiments, the present disclosure provides a combination comprising a compound of Formula (XIII) and Compound No. 6 or a salt thereof, useful for preparing a compound of Formula (XIV) or a salt thereof.

In some embodiments, the present disclosure provides a compound of any of Formulae (VII)-(X) and (XII)-(XIV), wherein: $R^{10}$ is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more $R^{1S}$; and each $R^{1S}$ independently is halogen, —O—($C_1$-$C_6$ alkyl), or —N($R^{1Sa}$)$_2$.

In some embodiments, the present disclosure provides a compound of any of Formulae (X) and (XIV) or a salt thereof, wherein: $R^{10}$ is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more $R^{1S}$; and each $R^{1S}$ independently is halogen, —O—($C_1$-$C_6$ alkyl), or —N($R^{1Sa}$).

In some embodiments, the present disclosure provides a compound being prepared by a method described herein.

In some embodiments, the present disclosure provides a pharmaceutical composition comprising a compound described herein, and one or more pharmaceutically acceptable carriers or excipients.

In some embodiments, the present disclosure provides a pharmaceutical composition comprising a compound prepared by a method described herein, and one or more pharmaceutically acceptable carriers or excipients.

In some embodiments, the present disclosure provides a method of inhibiting a tyrosine receptor kinase (TRK) in a subject, comprising administering to the subject a pharmaceutically effective amount of a compound described herein.

In some embodiments, the present disclosure provides a use of a compound described herein in the manufacture of a medicament for inhibiting a tyrosine receptor kinase (TRK) in a subject.

In some embodiments, the present disclosure provides a method of preventing or treating a disease or disorder in a subject, comprising administering to the subject a pharmaceutically effective amount of a compound described herein.

In some embodiments, the present disclosure provides a use of a compound described herein in the manufacture of a medicament for preventing or treating a disease or disorder in a subject.

The structures of Formulae (VII)-(X) and (XII)-(XIV) and the structures of Compound Nos. 1-14 are as described in Table 1 below, wherein all variables are as described elsewhere herein.

TABLE 1

| Formula No. | Structure | Compound No. | Structure |
|---|---|---|---|
| | | 1 | 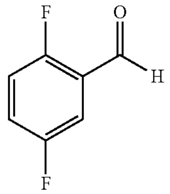 |
| | | 2 | 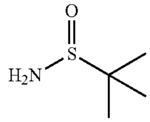 |
| | | 2R | 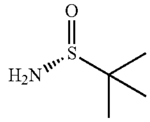 |

TABLE 1-continued
| Formula No. | Structure | Compound No. | Structure |
|---|---|---|---|
| | | 2S | 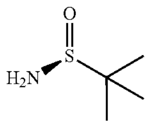 |
| | | 3 | 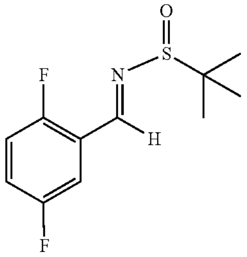 [SMILES: CC(C)(C)S(=O)/N=C/c1cc(F)ccc1F] |
| | | 3R | 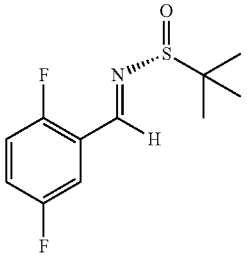 [SMILES: CC(C)(C)[S@@](=O)/N=C/c1cc(F)ccc1F] |
| | | 3S | 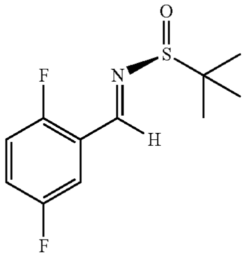 [SMILES: CC(C)(C)[S@](=O)/N=C/c1cc(F)ccc1F] |
| | | 4 | 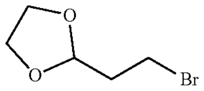 |
| | | 4a | 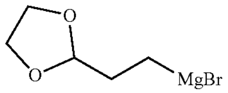 |
| | | 5 | 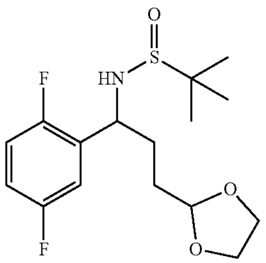 [SMILES: CC(C)(C)S(=O)NC(CCC1OCCO1)c1cc(F)ccc1F] |

TABLE 1-continued
| Formula No. | Structure | Compound No. | Structure |
|---|---|---|---|
| | | 5R | 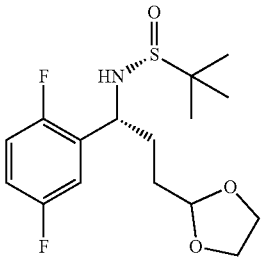 [SMILES: CC(C)(C)[S@@](=O)N[C@H](CCC1OCCO1)c1cc(F)ccc1F] |
| | | 5S | 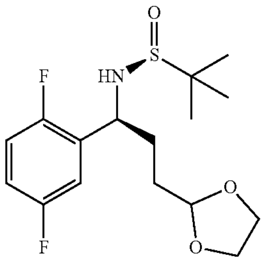 [SMILES: CC(C)(C)[S@](=O)N[C@@H](CCC1OCCO1)c1cc(F)ccc1F] |
| | | 6 | 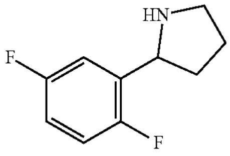 |
| | | 6R | 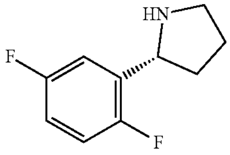 [SMILES: Fc1ccc(F)c([C@H]2CCCN2)c1] |
| | | 6S | 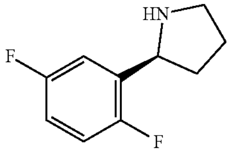 [SMILES: Fc1ccc(F)c([C@@H]2CCCN2)c1] |
| VII | 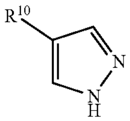 | 7 | 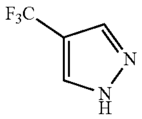 |
| VIII | 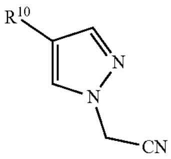 | 8 | 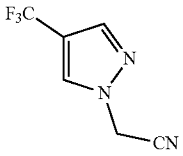 [SMILES: N#CCn1cc(C(F)(F)F)cn1] |
| IX | 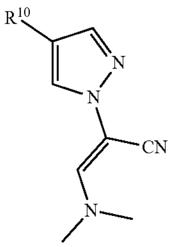 | 9 | 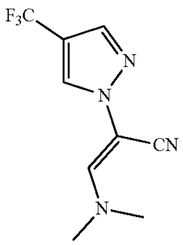 [SMILES: CN(C)/C=C(\C#N)n1cc(C(F)(F)F)cn1] |

TABLE 1-continued
| Formula No. | Structure | Compound No. | Structure |
|---|---|---|---|
| X | 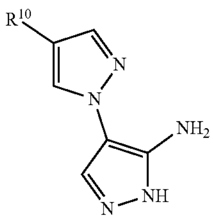 | 10 | 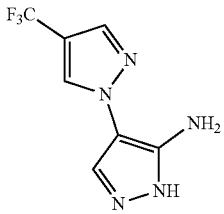 [SMILES: Nc1[nH]ncc1-n1cc(C(F)(F)F)cn1] |
| | | 11 | 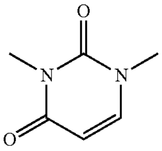 |
| XII | 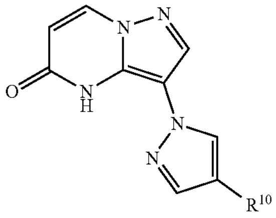 | 12 | 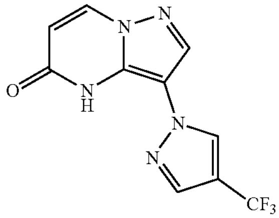 [SMILES: O=c1ccn2ncc(-n3cc(C(F)(F)F)cn3)c2[nH]1] |
| XIII | 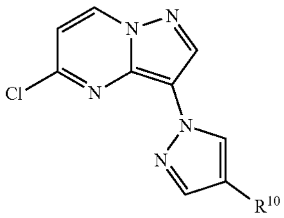 | 13 | 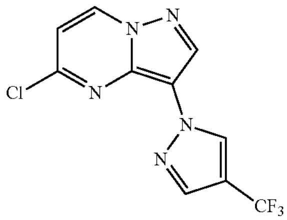 [SMILES: FC(F)(F)c1cnn(-c2cnn3ccc(Cl)nc23)c1] |
| XIV | 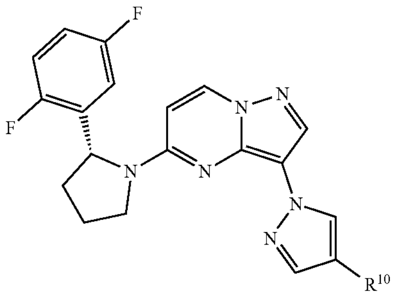 | 14 | 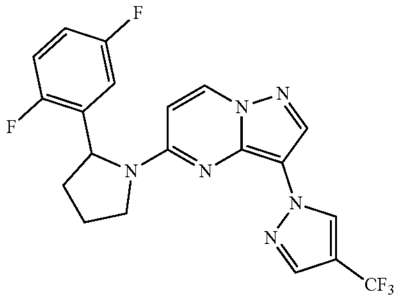 [SMILES: Fc1ccc(F)c([C@H]2CCCN2c2ccn3ncc(-n4cc(C(F)(F)F)cn4)c3n2)c1] |
| | | 14R | 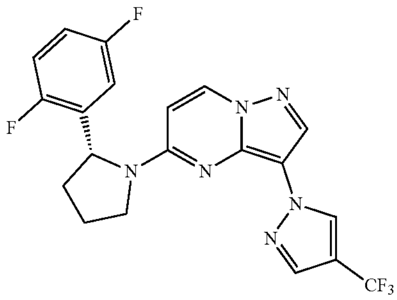 |

TABLE 1-continued
| Formula No. | Structure | Compound No. | Structure |
|---|---|---|---|
| | | 14S | 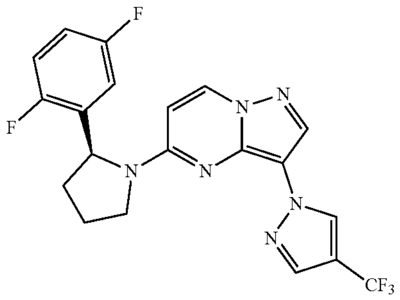 [SMILES: Fc1ccc(F)c([C@@H]2CCCN2c2ccn3ncc(-n4cc(C(F)(F)F)cn4)c3n2)c1] |
| XV | 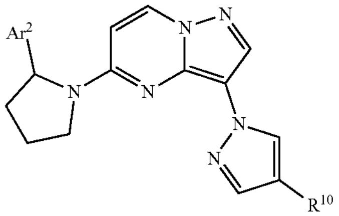 | 14R | 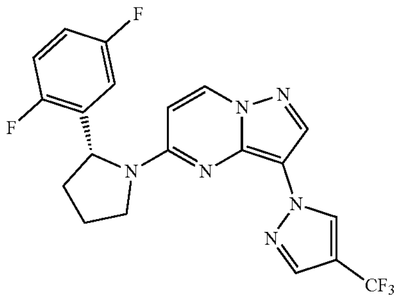 [SMILES: Fc1ccc(F)c([C@H]2CCCN2c2ccn3ncc(-n4cc(C(F)(F)F)cn4)c3n2)c1] |
| XVI | 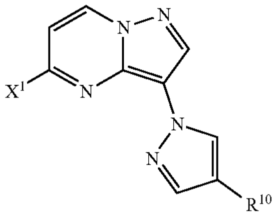 | 13 | 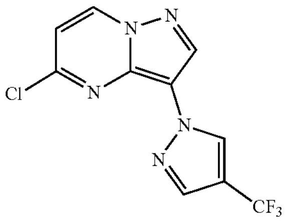 [SMILES: FC(F)(F)c1cnn(-c2cnn3ccc(Cl)nc23)c1] |
| XVII | 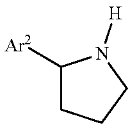 | 6R | 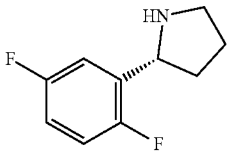 [SMILES: Fc1ccc(F)c([C@H]2CCCN2)c1] |
| XVIII | 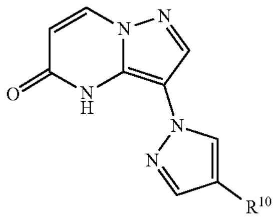 | 12 | 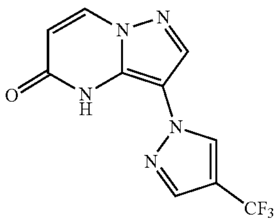 [SMILES: O=c1ccn2ncc(-n3cc(C(F)(F)F)cn3)c2[nH]1] |
| XIX | 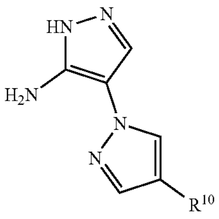 | 10 | 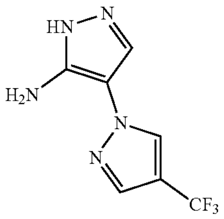 [SMILES: Nc1[nH]ncc1-n1cc(C(F)(F)F)cn1] |

TABLE 1-continued
| Formula No. | Structure | Compound No. | Structure |
|---|---|---|---|
| XX | 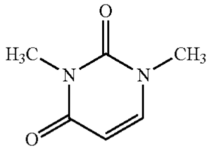 | 11 | 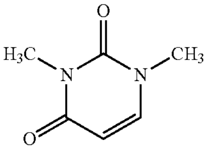 |
| XXI | 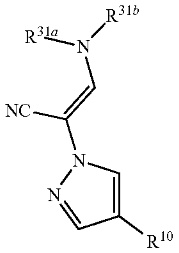 | 9 | 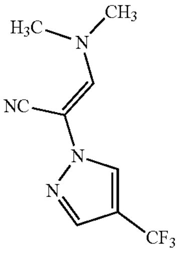 [SMILES: CN(C)/C=C(\C#N)n1cc(C(F)(F)F)cn1] |
| XXII | 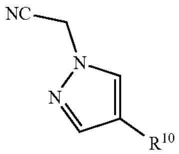 | 8 | 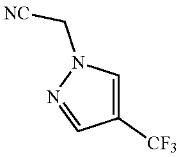 [SMILES: N#CCn1cc(C(F)(F)F)cn1] |
| XXIII | 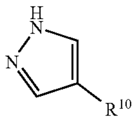 | 7 | 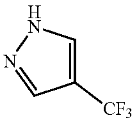 |
| XXIV | 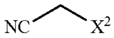 | | 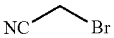 |
| XXV | 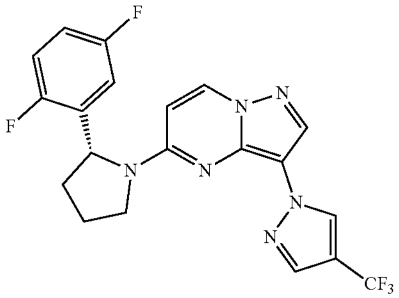 [SMILES: Fc1ccc(F)c([C@H]2CCCN2c2ccn3ncc(-n4cc(C(F)(F)F)cn4)c3n2)c1] | 14R | 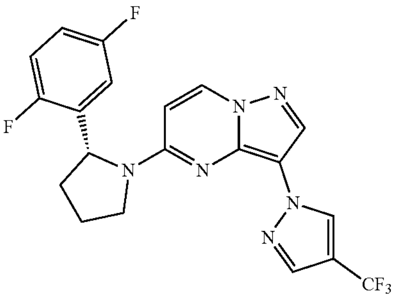 |
| XXVI | 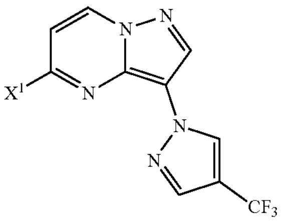 | 13 | 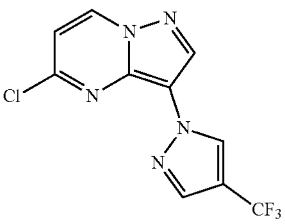 [SMILES: FC(F)(F)c1cnn(-c2cnn3ccc(Cl)nc23)c1] |

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTION OF THE FIGURES

The accompanying figures, which are incorporated in and constitute a part of this specification, illustrate several aspects and together with the description serve to explain the principles of the invention.

Figure 1A:
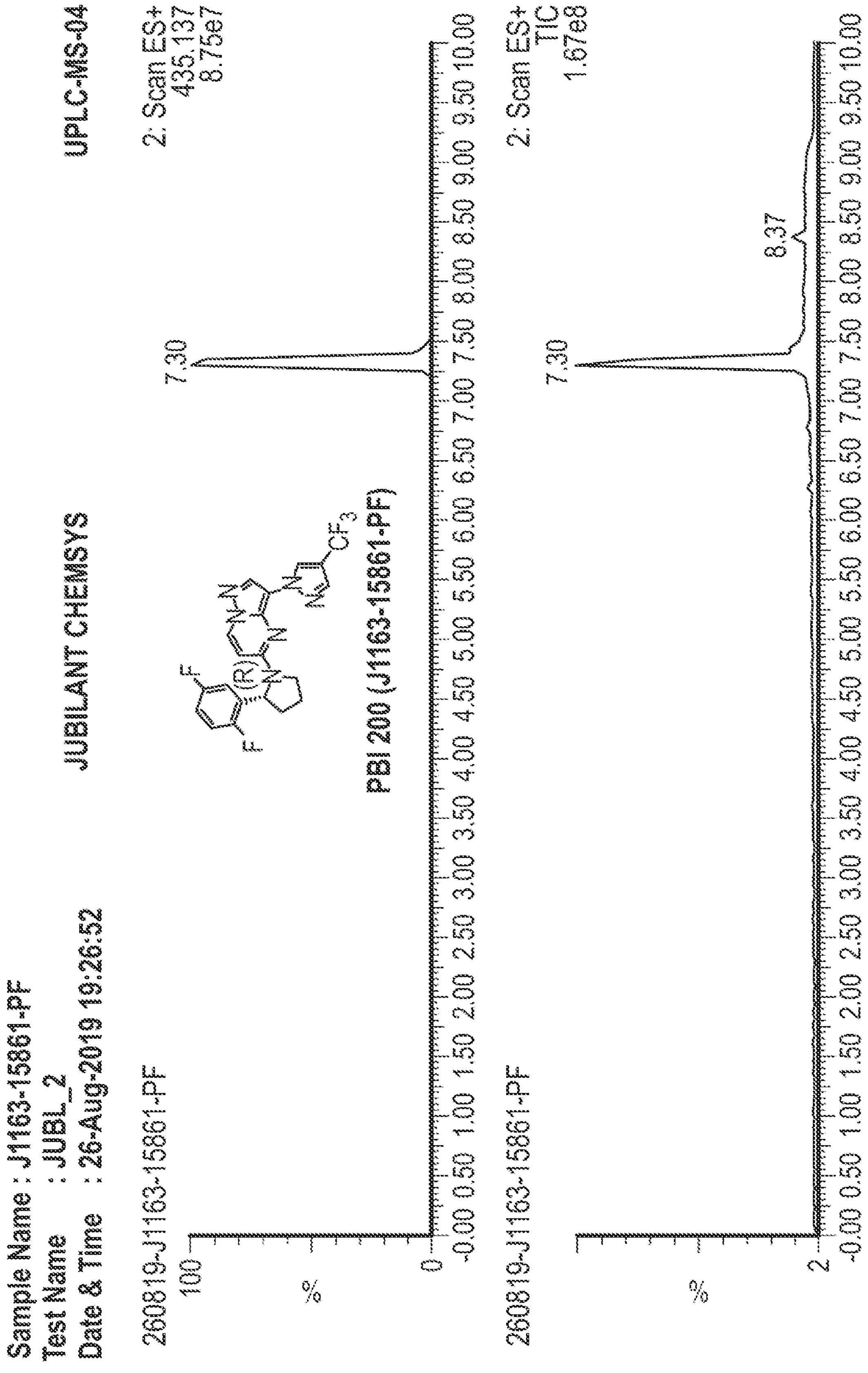
FIG. 1A-D show representative ultra performance liquid chromatography-tandem mass spectrometer (UPLC-MS) spectral data of compound no. 14R.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting. Although any methods and materials similar or equivalent to those described herein can be used in the practice or testing of the present invention, example methods and materials are now described.

While embodiments of the present invention can be described and claimed in a particular statutory class, such as the system statutory class, this is for convenience only and one of skill in the art will understand that each embodiment of the present invention can be described and claimed in any statutory class. Unless otherwise expressly stated, it is in no way intended that any method or embodiment set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

A. DEFINITIONS

Listed below are definitions of various terms used to describe this invention. These definitions apply to the terms as they are used throughout this specification, unless otherwise limited in specific instances, either individually or as part of a larger group.

As used herein, the terms "a" or "an" means that "at least one" or "one or more" unless the context clearly indicates otherwise. The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in various embodiments, to A without B (optionally including elements other than B); in another embodiment, to B without A (optionally including elements other than A); in yet another embodiment, to both A and B (optionally including other elements); etc.

The term "or" as used herein shall only be interpreted as indicating exclusive alternatives (i.e., "one or the other but not both") when preceded by terms of exclusivity, "either," "one of," "only one of," or "exactly one of."

As used herein, the terms "comprising" (and any form of comprising, such as "comprise," "comprises," and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "about" refers to a range covering any normal fluctuations appreciated by one of ordinary skill in the relevant art. In some embodiments, the term "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The abbreviations used herein have their conventional meaning within the chemical and biological arts. The chemical structures and formulae set forth herein are constructed according to the standard rules of chemical valency known in the chemical arts.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" mean that the subsequently described event or circumstance can or cannot occur, and that the description includes instances where said event or circumstance occurs and instances where it does not.

As used herein, the term "elevated temperature" means a temperature above 25° C. Thus, for example, an elevated temperature can refer to a temperature of at least about 30° C., at least about 40° C., at least about 50° C., at least about 60° C., at least about 70° C., at least about 80° C., at least about 90° C., at least about 100° C., or at least about 110° C. In some embodiments, the elevated temperature is in the range of about 70° C. to about 110° C., about 70° C. to about 100° C., about 70° C. to about 90° C., about 70° C. to about 80° C., about 80° C. to about 110° C., about 90° C. to about 110° C., about 110° C. to about 110° C., about 80° C. to about 100° C., or about 85° C. to about 95° C. In further embodiments, the elevated temperature is in the range of about 80° C. to about 120° C., about 80° C. to about 110° C., about 80° C. to about 100° C., about 80° C. to about 90° C., about 90° C. to about 120° C., about 100° C. to about 120° C., about 110° C. to about 120° C., about 90° C. to about 110° C., or about 95° C. to about 105° C.

As used herein, the term "diagnosed" means having been subjected to an examination by a person of skill, for example, a physician, and found to have a disease, disorder, or condition that can treated by the compounds, compositions, or methods disclosed herein. In some embodiments of the disclosed methods, the subject has been diagnosed with a disorder associated with abnormal TRK activity such as, for example, inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, and neuropathic pain, prior to the administering step. As used herein, the phrase "identified to be in need of treatment for a disorder," or the like, refers to selection of a subject based upon need for treatment of the disorder. It is contemplated that the identification can, in some embodiments, be performed by a person different from the person making the diagnosis. It is also contemplated, in further embodiments, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various embodiments, a preparation can be administered therapeutically; that is, administered to treat an existing disease or condition. In further various embodiments, a preparation can be administered prophylactically; that is, administered for prevention of a disease or condition.

The compound of the disclosure can be administered alone or can be co-administered to the patient. Co-administration is meant to include simultaneous or sequential administration of the compound individually or in combination (more than one compound or agent). Thus, the preparations can also be combined, when desired, with other active substances (e.g., to reduce metabolic degradation). The compositions of the present disclosure can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present disclosure can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In embodiments, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989). The compositions of the present disclosure can also be delivered as nanoparticles.

Pharmaceutical compositions provided by the present disclosure include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g., TRK), and/or reducing, eliminating, or slowing the progression of disease symptoms (e.g., symptoms of inflammatory diseases, infections, autoimmune disorders, stroke, ischemia, cardiac disorder, neurological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, and/or neuropathic pain). Determination of a therapeutically effective amount of a compound of the disclosure is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., symptoms of inflammatory diseases, infections, autoimmune disorders, stroke, ischemia, cardiac disorder, neurological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, and/or neuropathic pain, and severity of such symptoms), kind of concurrent treatment, complications from the disease being treated or other health-related problems. Other therapeutic regimens or agents can be used in conjunction with the methods and compounds of Applicants' disclosure. Adjustment and manipulation of established dosages (e.g., frequency and duration) are well within the ability of those skilled in the art. In various embodiments, a disclosed compound can be administered at a dosage of from about 10 mg/day to about 1000 mg/day, about 10 mg/day to about 900 mg/day, about 10 mg/day to about 800 mg/day, about 10 mg/day to about 700 mg/day, about 10 mg/day to about 600 mg/day, about 10 mg/day to about 500 mg/day, about 10 mg/day to about 400 mg/day, about 10 mg/day to about 300 mg/day, about 10 mg/day to about 200 mg/day, about 10 mg/day to about 100 mg/day, about 10 mg/day to about 50 mg/day, about 50 mg/day to about 1000 mg/day, about 100 mg/day to about 1000 mg/day, about 200 mg/day to about 1000 mg/day, about 300 mg/day to about 1000 mg/day, about 400 mg/day to about 1000 mg/day, about 500 mg/day to about 1000 mg/day, about 600 mg/day to about 1000 mg/day, about 700 mg/day to about 1000 mg/day, about 800 mg/day to about 1000 mg/day, about 900 mg/day to about 1000 mg/day, about 50 mg/day to about 900 mg/day, about 100 mg/day to about 800 mg/day, about 200 mg/day to about 700 mg/day, about 300 mg/day to about 600 mg/day, or about 400 mg/day to about 500 mg/day. In various further embodiments, a disclosed compound can be administered more than once per day such as, for example, two times per day. Thus, in various embodiments, a disclosed compound can be administered at a dosage of from about 10 mg to about 500 mg, wherein each dosage is administered two times per day.

For any compound described herein, the therapeutically effective dose can be determined from cell culture assays, animal studies, and/or human clinical trials. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to affect a beneficial therapeutic response in the patient over time. The amount of the dose also will be determined by the existence, nature, and extent of any adverse side-effects. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

As used herein, the term "synthetic equivalent" refers to an agent (e.g., a compound) which is suitable for replacing the referenced agent (e.g., the referenced compound) in the method or use disclosed herein. It is known in the art that suitable synthetic equivalents of a referenced agent (e.g., a referenced compound) can be readily recognized, or be assessed with routine experimentation, by a skilled artisan (e.g., a synthetic chemist).

The term "leaving group" refers to an atom (or a group of atoms) that breaks away from the rest of the molecule, taking with it the bonding electrons. Examples of suitable leaving groups include sulfonate esters, including triflate, mesylate, tosylate, brosylate, and halides.

As used herein, the term "substituted" is contemplated to include only permissible substituents of organic compounds that are chemically stable. In a broad embodiment, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain embodiments, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

As used herein, "alkyl", "$C_1$, $C_2$, $C_3$, $C_4$, $C_5$, or $C_6$ alkyl" or "$C_1$-$C_6$ alkyl" is intended to include $C_1$, $C_2$, $C_3$, $C_4$, $C_5$, or $C_6$ straight chain (linear) saturated aliphatic hydrocarbon groups and $C_3$, $C_4$, $C_5$, or $C_6$ branched saturated aliphatic hydrocarbon groups. For example, $C_1$-$C_6$ alkyl is intended to include $C_1$, $C_2$, $C_3$, $C_4$, $C_5$, or $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl. In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "heteroalkyl," as used herein refers to an alkyl group containing at least one heteroatom. Suitable heteroatoms include, but are not limited to, O, N, Si, P, and S, wherein the nitrogen, phosphorous and sulfur atoms are optionally oxidized, and the nitrogen heteroatom is optionally quaternized. Heteroalkyls can be substituted as defined above for alkyl groups.

The term "haloalkyl" includes mono, poly, and perhaloalkyl groups where the halogens are independently selected from fluorine, chlorine, bromine, and iodine.

"Alkoxy" is an alkyl group which is attached to another moiety via an oxygen linker (—O(alkyl)). Non-limiting examples include methoxy, ethoxy, propoxy, and butoxy.

"Haloalkoxy" is a haloalkyl group which is attached to another moiety via an oxygen atom such as, e.g., but are not limited to —$OCHF_2$ or —$OCF_3$.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." The heterocycle can be monocyclic, bicyclic (e.g., spiro or bridged), polycyclic, or a fused system that is saturated or partially saturated. Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group, which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like. In the case of multicyclic non-aromatic rings, only one of the rings needs to be non-aromatic (e.g., 1,2,3,4-tetrahydronaphthalenyl or 2,3-dihydroindole).

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity,"

pages 477-497, incorporated herein by reference in its entirety. The term "aromatic group" is inclusive of both aryl and heteroaryl groups.

As used herein, the term "aryl" includes groups with aromaticity, including "conjugated," or multicyclic systems with one or more aromatic rings and do not contain any heteroatom in the ring structure. Examples of aryl groups include, but are not limited to, phenyl, biphenyl, naphthyl and the like. In some embodiments, an aryl is phenyl. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, $-NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

It is understood that the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $-NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is $-NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $-N(\text{-alkyl})_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula $-OC(O)A^1$ or $-C(O)OA^1$, where $A^1$ can be alkyl, cycloalkyl, alkenyl, cycloalkenyl, alkynyl, cycloalkynyl, aryl, or heteroaryl group as described herein.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain embodiments, unless expressly indicated to the contrary, individual substituents can be further optionally substituted (i.e., further substituted or unsubstituted).

In some embodiments, the structure of a compound can be represented by formula:

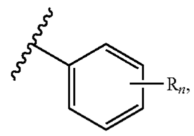

which is understood to be equivalent to formula:

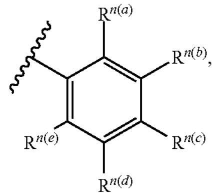

wherein n is typically an integer. That is, $R^n$ is understood to represent five independent substituents, $R^{n(a)}$, $R^{n(b)}$, $R^{n(c)}$, $R^{n(d)}$, $R^{n(e)}$. In each such case, each of the five $R^n$ can be hydrogen or a recited substituent. By "independent substituents," it is meant that each R substituent can be independently defined. For example, if in one instance $R^{n(a)}$ is halogen, then $R^{n(b)}$ is not necessarily halogen in that instance.

In some yet further embodiments, the structure of a compound can be represented by formula:

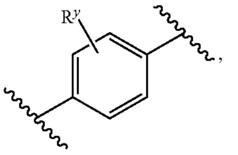

wherein $R^y$ represents, for example, 0-2 independent substituents selected from $A^1$, $A^2$, and $A^3$, which is understood to be equivalent to the groups of formulae:

wherein $R^y$ represents 0 independent substituents

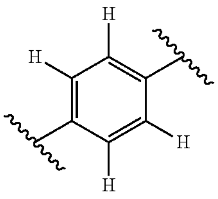

wherein $R^y$ represents 1 independent substituent

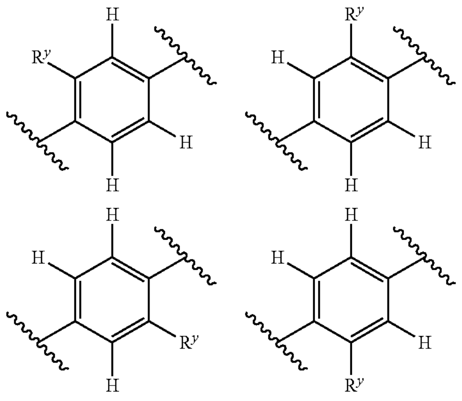

wherein $R^y$ represents 2 independent substituents

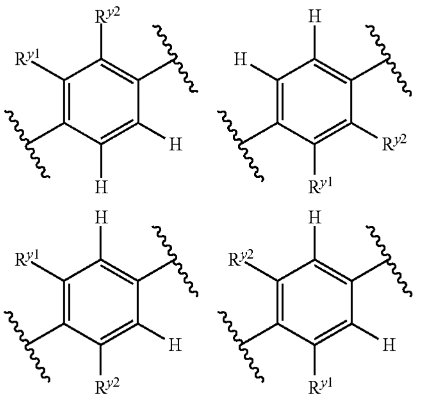

-continued

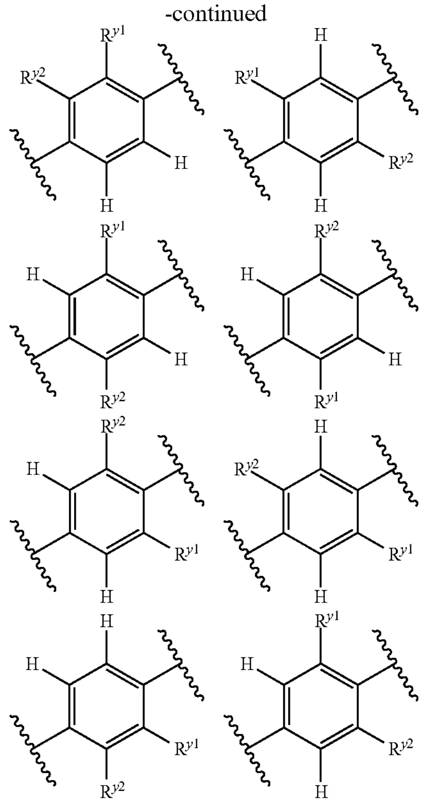

Again, by "independent substituents," it is meant that each R substituent can be independently defined. For example, if in one instance $R^{y1}$ is $A^1$, then $R^{y2}$ is not necessarily $A^1$ in that instance.

In some further embodiments, the structure of a compound can be represented by formula,

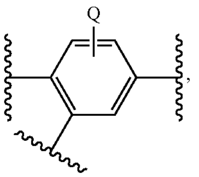

wherein, for example, Q comprises three substituents independently selected from hydrogen and A, which is understood to be equivalent to formula:

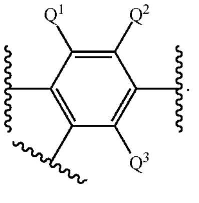

Again, by "independent substituents," it is meant that each Q substituent is independently defined as hydrogen or A, which is understood to be equivalent to the groups of formulae:

wherein Q comprises three substituents independently selected from H and A

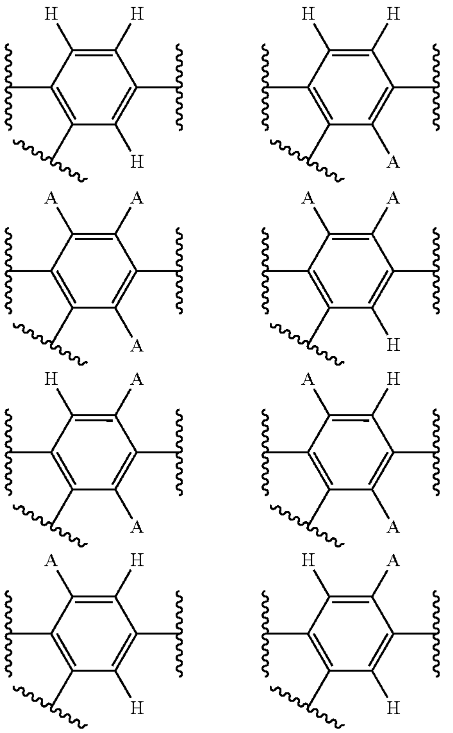

In some embodiments, the disclosed compounds exist as geometric isomers. “Geometric isomer” refers to isomers that differ in the orientation of substituent atoms in relationship to a cycloalkyl ring, i.e., cis or trans isomers. When a disclosed compound is named or depicted by structure without indicating a particular cis or trans geometric isomer form, it is to be understood that the name or structure encompasses one geometric isomer free of other geometric isomers, mixtures of geometric isomers, or mixtures enriched in one geometric isomer relative to its corresponding geometric isomer. When a particular geometric isomer is depicted, i.e., cis or trans, the depicted isomer is at least about 60%, 70%, 80%, 90%, 99%, or 99.9% by weight pure relative to the other geometric isomer.

Unless stated to the contrary, formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Compounds of this invention may exist in optically active forms having the ability to rotate the plane of plane-polarized light. In describing an optically active compound, the prefixes D and L or R and S are used to denote the absolute configuration of the molecule about its chiral center(s). The prefixes d and 1 or (+) and (−) are employed to designate the sign of rotation of plane-polarized light by the compound, with (−) or meaning that the compound is levorotatory. A compound prefixed with (+) or d is dextrorotatory. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds may exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R, R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

As used herein, the term “purified” means that when isolated, the isolate contains at least about 90%, at least about 95%, at least about 98%, or at least about 99% of a compound described herein by weight of the isolate.

As used herein, the term “solution/suspension” means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

It is further appreciated that certain features described herein, which are, for clarity, described in the context of separate embodiments, can also be provided in combination in a single embodiment. Conversely, various features that are, for brevity, described in the context of a single embodiment, can also be provided separately or in any suitable subcombination.

It should be noted that any embodiment of the invention can optionally exclude one or more embodiment for purposes of claiming the subject matter.

In some embodiments, the compounds, or salts thereof, are substantially isolated. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

As used herein, the terms "subject" and "patient" may be used interchangeable, and are also interchangeable with the term "subject in need thereof," all of which refer to a subject having a disease or having an increased risk of developing the disease. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In some embodiments, the mammal is a human.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

As used herein, the term "preventing" or "prevent" describes reducing or eliminating the onset of the symptoms or complications of such disease, condition or disorder.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing formulation that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, the term "salt" or "pharmaceutically acceptable salt" refers to a derivative of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc. Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3. It is to be understood that all references to pharmaceutically acceptable salts include solvent addition forms (solvates) or crystal forms (polymorphs) as defined herein, of the same salt.

The term "effective amount" or "therapeutically effective amount" refers to an amount that is sufficient to achieve the desired result (e.g., that will elicit a biological or medical response of a subject e.g., a dosage of between 0.5-1000 mg/kg body weight/day) or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various embodiments, a preparation can be administered in a “prophylactically effective amount”; that is, an amount effective for prevention of a disease or condition.

As used herein, the term “salt” refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term “associated” or “associated with” in the context of a substance or substance activity or function associated with a disease (e.g., a protein associated disease, a symptom associated with an inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, or neuropathic pain,) means that the disease (e.g., inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, or neuropathic pain) is caused by (in whole or in part), or a symptom of the disease is caused by (in whole or in part) the substance or substance activity or function. For example, a symptom of a disease or condition associated with an increase in the level of TRK activity may be a symptom that results (entirely or partially) from an increase in the level of TRK activity (e.g., gain of function mutation, gene deletion, gene fusion, or modulation of TRK signal transduction pathway). As used herein, what is described as being associated with a disease, if a causative agent, could be a target for treatment of the disease. For example, a disease associated with TRK may be treated with an agent (e.g., compound as described herein) effective for decreasing the level of activity of TRK.

“Control” or “control experiment” is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As defined herein, the term “inhibition,” “inhibit,” “inhibiting,” and the like in reference to a protein-inhibitor (e.g., antagonist) interaction means negatively affecting (e.g., decreasing) the activity or function of the protein (e.g., TRK) relative to the activity or function of the protein in the absence of the inhibitor (e.g., compound described herein). In embodiments inhibition refers to reduction of a disease or symptoms of disease. In embodiments, inhibition refers to a reduction in the activity of a signal transduction pathway or signaling pathway (e.g., TRK pathway). Thus, inhibition includes, at least in part, partially or totally blocking stimulation, decreasing, preventing, or delaying activation, or inactivating, desensitizing, or down-regulating signal transduction or enzymatic activity or the amount of a protein.

The symbol “〰” denotes the point of attachment of a chemical moiety to the remainder of a molecule or chemical formula.

As defined herein, the term “activation,” “activate,” “activating” and the like in reference to a protein-activator (e.g., agonist) interaction means positively affecting (e.g., increasing) the activity or function of the protein relative to the activity or function of the protein in the absence of the activator. In embodiments, activation refers to an increase in the activity of a signal transduction pathway or signaling pathway. Thus, activation may include, at least in part, partially or totally increasing stimulation, increasing or enabling activation, or activating, sensitizing, or up-regulating signal transduction or enzymatic activity or the amount of a protein The term “modulator” refers to a composition that increases or decreases the level of a target molecule or the function of a target molecule. In embodiments, the modulator is a modulator of TRK. In embodiments, the modulator is a modulator of TRK, and is a compound that reduces the severity of one or more symptoms of a disease associated with TRK (e.g., reduction of the level of TRK activity or protein associated with inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, or neuropathic pain). In embodiments, a modulator is a compound that reduces the severity of one or more symptoms of a disease or disorder selected from inflammatory diseases, infections, autoimmune disorders, stroke, ischemia, cardiac disorder, neurological disorders, fibrogenic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, and neuropathic pain, wherein the disease or disorder is not caused or characterized by TRK (e.g., gain of TRK function) but may benefit from modulation of TRK activity (e.g., decrease in level of TRK or TRK activity).

“Disease,” “condition,” or “disorder” refer to a state of being or health status of a patient or subject capable of being treated with a compound, pharmaceutical composition, or method provided herein. In embodiments, the disease is a disease related to (e.g., characterized by) an increase in the level of TRK. In embodiments, the disease is inflammatory diseases, infections, autoimmune disorders, stroke, ischemia, cardiac disorder, neurological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atherosclerosis, rheumatoid arthritis, osteoarthritis, chronic pain, or neuropathic pain.

The term "signaling pathway" as used herein refers to a series of interactions between cellular and optionally extracellular components (e.g., proteins, nucleic acids, small molecules, ions, lipids) that conveys a change in one component to one or more other components, which in turn may convey a change to additional components, which is optionally propagated to other signaling pathway components.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

B. COMPOUNDS

In various embodiments, disclosed are pyrazolo[1,5-a] pyrimidine compounds that can be prepared by the disclosed methods (e.g., compounds prepared by coupling a compound of formula (XVI) and a compound of formula XVII). It is understood that a disclosed compound can be provided by the disclosed methods.

In various embodiments, the disclosed pyrazolo[1,5-a] pyrimidine compounds are useful as TRK inhibitors.

In various embodiments, the disclosed pyrazolo[1,5-a] pyrimidine compounds are useful in treating a disorder associated with TRK activity in a mammal. In a further embodiment, the disclosed pyrazolo[1,5-a]pyrimidine compounds are useful in treating TRK activity in a human.

In some embodiments, the present disclosure provides a compound of any of Formulae (VII)-(X) and (XII)-(XIV), wherein: $R^{10}$ is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more $R^{1S}$; and each $R^{1S}$ independently is halogen, —O—($C_1$-$C_6$ alkyl), or —N($C_1$-$C_6$ alkyl)$_2$.

In some embodiments, the present disclosure provides a compound of any of Formulae (X) and (XIV) or a salt thereof, wherein: $R^{10}$ is $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl, wherein the $C_1$-$C_6$ alkyl, $C_3$-$C_8$ cycloalkyl, $C_6$-$C_{10}$ aryl, 3- to 8-membered heterocycloalkyl, or 5- to 10-membered heteroaryl is optionally substituted with one or more $R^{1S}$; and each $R^{1S}$ independently is halogen, —O—($C_1$-$C_6$ alkyl), or —N($C_1$-$C_6$ alkyl)$_2$.

In some embodiments, $R^{10}$ is $C_1$-$C_6$ alkyl optionally substituted with one or more $R^{1S}$.

In some embodiments, $R^{10}$ is $C_1$-$C_6$ alkyl optionally substituted with one or more halogen (e.g., F, Cl, Br, or I).

In some embodiments, $R^{10}$ is $C_1$-$C_6$ alkyl optionally substituted with one or more F.

In some embodiments, $R^{10}$ is methyl optionally substituted with one or more $R^{1S}$.

In some embodiments, $R^{10}$ is methyl optionally substituted with one or more halogen (e.g., F, Cl, Br, or I).

In some embodiments, $R^{10}$ is $CF_3$.

In some embodiments, $R^{10}$ is $C_3$-$C_8$ cycloalkyl, $C_6$-$C_{10}$ aryl, 3- to 8-membered heterocycloalkyl, or 5- to 10-membered heteroaryl, wherein the $C_3$-$C_8$ cycloalkyl, $C_6$-$C_{10}$ aryl, 3- to 8-membered heterocycloalkyl, or 5- to 10-membered heteroaryl is optionally substituted with one or more $R^{1S}$.

In some embodiments, $R^{10}$ is $C_3$-$C_8$ cycloalkyl optionally substituted with one or more $R^{1S}$.

In some embodiments, $R^{10}$ is $C_6$-$C_{10}$ aryl optionally substituted with one or more $R^{1S}$.

In some embodiments, $R^{10}$ is 3- to 8-membered heterocycloalkyl optionally substituted with one or more $R^{1S}$.

In some embodiments, $R^{10}$ is 5- to 10-membered heteroaryl optionally substituted with one or more $R^{1S}$.

In some embodiments, at least one $R^{1S}$ is halogen (e.g., F, Cl, Br, or I).

In some embodiments, at least one $R^{1S}$ is F.

In some embodiments, at least one $R^{1S}$ is —O—($C_1$-$C_6$ alkyl).

In some embodiments, at least one $R^{1S}$ is —N($C_1$-$C_6$ alkyl)$_2$.

In some embodiments, the compound of Formula (VII) is Compound No. 7.

In some embodiments, the compound of Formula (VIII) is Compound No. 8.

In some embodiments, the compound of Formula (IX) is Compound No. 9.

In some embodiments, the compound of Formula (X) is Compound No. 10.

In some embodiments, the compound of Formula (XII) is Compound No. 12.

In some embodiments, the compound of Formula (XIII) is Compound No. 13.

In some embodiments, the compound of Formula (XIV) is Compound No. 14 (e.g., Compound No. 14R or 14S (e.g., Compound No. 14R)).

In some embodiments, the compound is selected from Compound Nos. 1-14.

In some embodiments, the compound is selected from Compound Nos. 6, 10, 14, and salts thereof.

In some embodiments, the compound is selected from Compound Nos. 6, 10, and 14.

In some embodiments, the compound is selected from Compound Nos. 7-14.

In some embodiments, the compound is selected from Compound Nos. 9-10 and 12-13.

In embodiments, the present disclosure provides a compound being prepared by the method described herein.

In some embodiments, the present disclosure provides a compound being prepared by a method disclosed herein, wherein the compound is selected from Compound Nos. 1-14.

In some embodiments, the present disclosure provides a compound being prepared by a method disclosed herein, wherein the compound is selected from Compound Nos. 6, 10, 14, and salts thereof.

In some embodiments, the present disclosure provides a compound being prepared by a method disclosed herein, wherein the compound is selected from Compound Nos. 6, 10, and 14.

In some embodiments, the present disclosure provides a compound being prepared by a method disclosed herein, wherein the compound is selected from Compound Nos. 7-10.

In some embodiments, the present disclosure provides a compound being prepared by a method disclosed herein, wherein the compound is selected from Compound Nos. 12-14.

In some embodiments, the present disclosure provides Compound No. 14 (e.g., Compound No. 14R or 14S (e.g., Compound No. 14R)) or a salt thereof, being prepared by a method disclosed herein.

In some embodiments, the present disclosure provides Compound No. 14 (e.g., Compound No. 14R or 14S (e.g., Compound No. 14R)) being prepared by a method disclosed herein.

1. Structure

In some embodiments, the present disclosure provides a compound of formula (XXV):

(XXV)

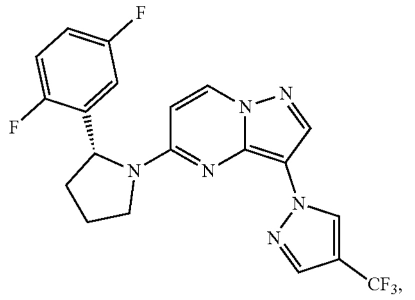

or a pharmaceutically acceptable salt thereof.

In some embodiments, the present disclosure provides a compound of formula (XV): F (XV)

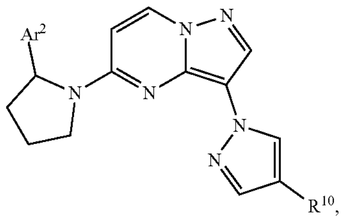

or a pharmaceutically acceptable salt thereof, wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy.

In some embodiments, a compound of formula (XV) has the structure represented by formula selected from:

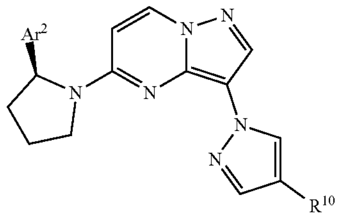

and

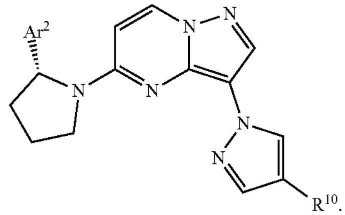

In some embodiments, the compound of formula (XV) has the structure represented by formula:

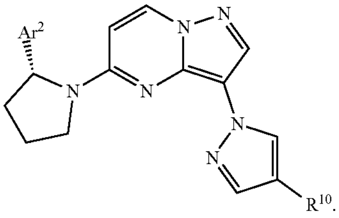

In some embodiments, the compound of formula (XV) has the structure represented by formula:

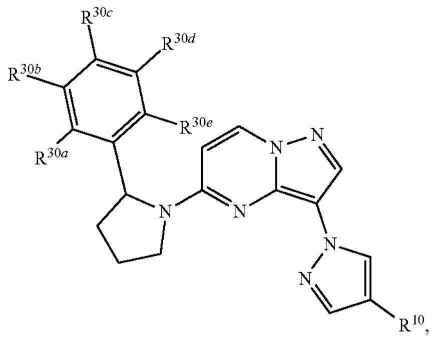

wherein each of $R^{30a}$, $R^{30b}$, $R^{30c}$, $R^{30d}$, and $R^{30e}$ is independently selected from hydrogen, halogen, $C_1$-$C_6$ alkyl, $C_1$-$C_6$ haloalkyl, $C_1$-$C_6$ alkoxy, and $C_1$-$C_6$ haloalkoxy, provided that at least two of $R^{30a}$, $R^{30b}$, $R^{30c}$, $R^{30d}$, and $R^{30e}$ are hydrogen.

In some embodiments, compound of formula (XV) has the structure represented by formula selected from:
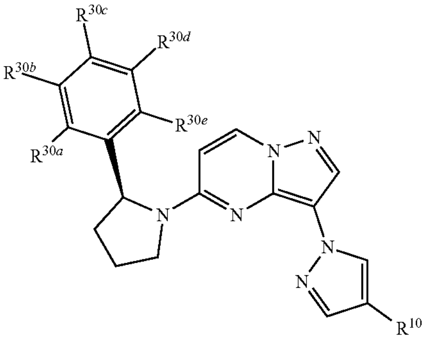
and
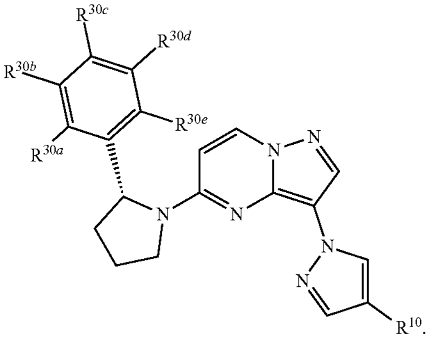
In some embodiments, the compound of formula (XV) has the structure represented by formula:
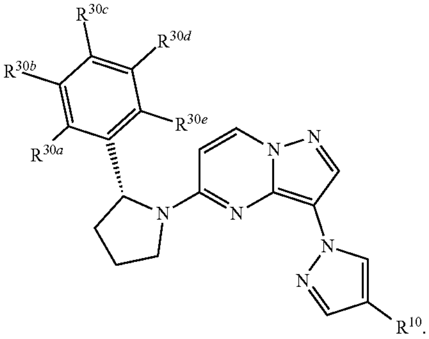
In some embodiments, the compound of formula (XV) is selected from:
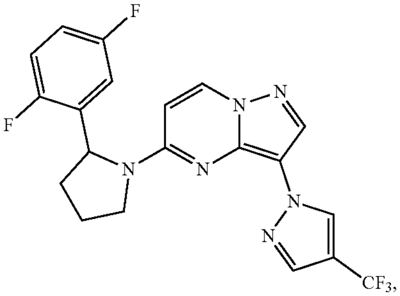
-continued
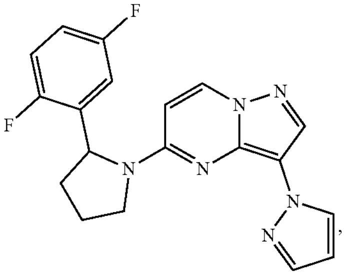
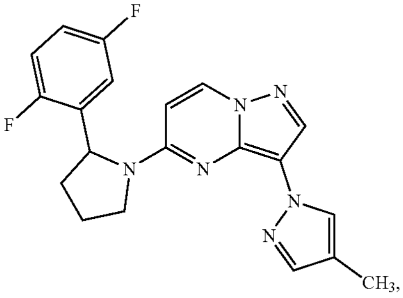
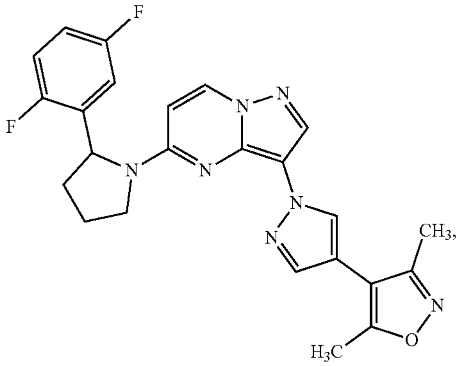
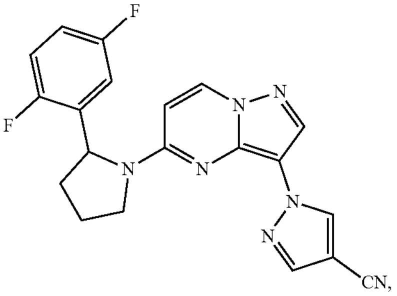
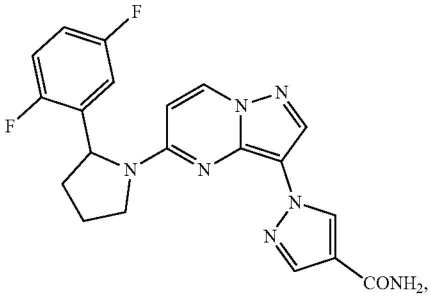

-continued
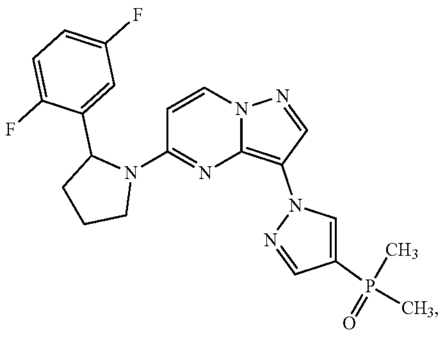
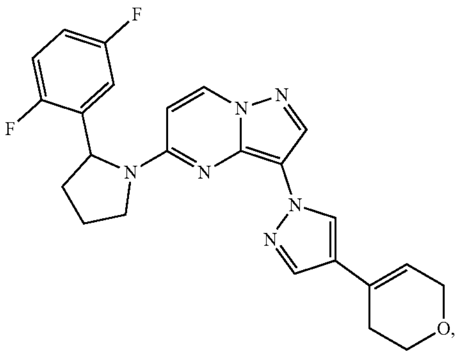
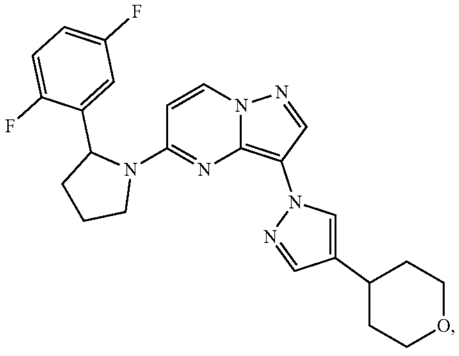
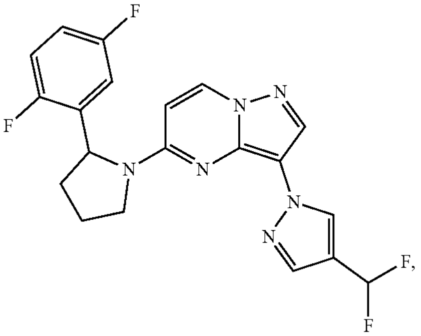
-continued
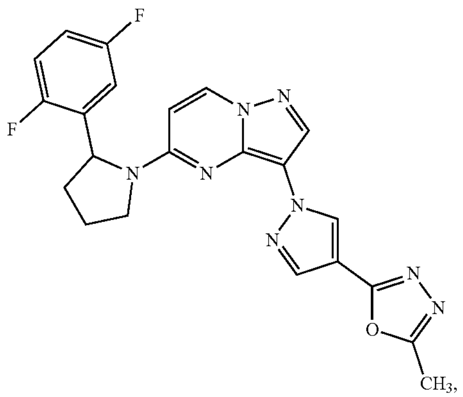
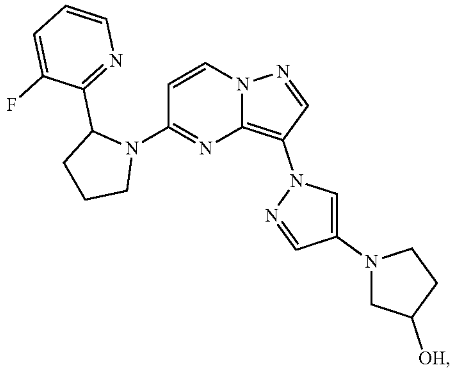
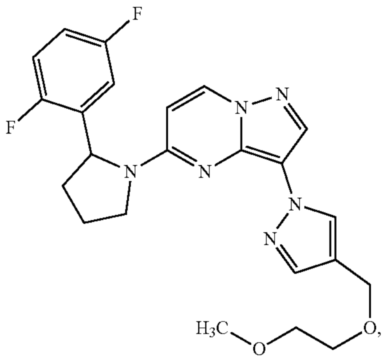
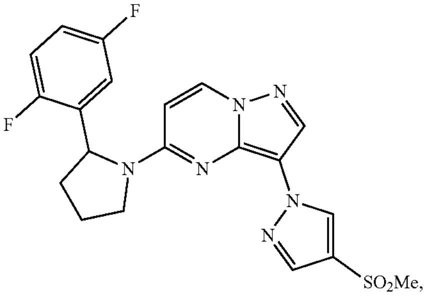
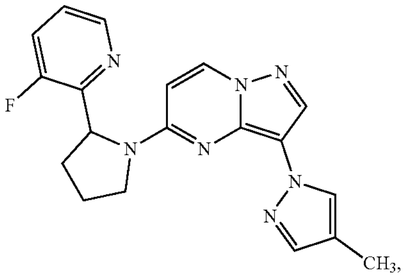

-continued
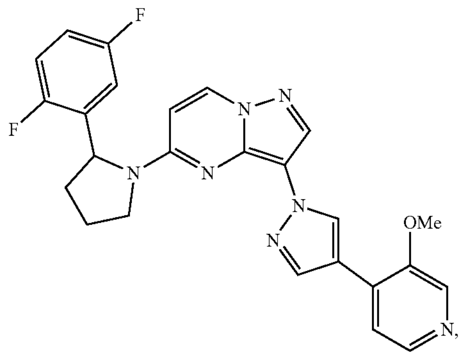
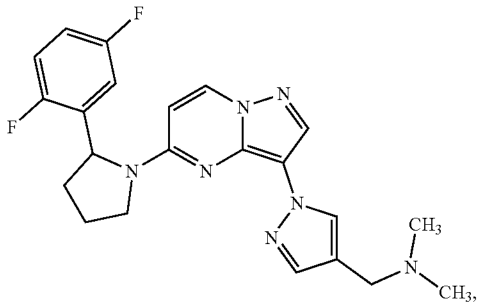
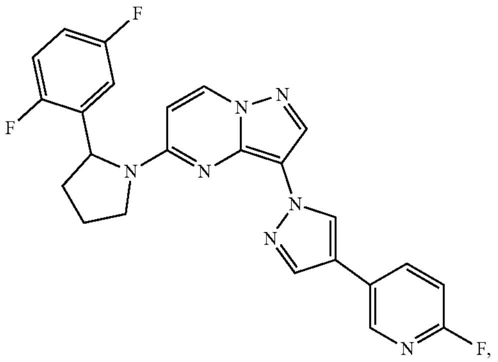
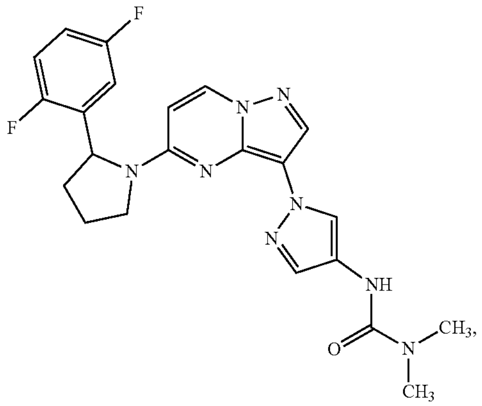
-continued
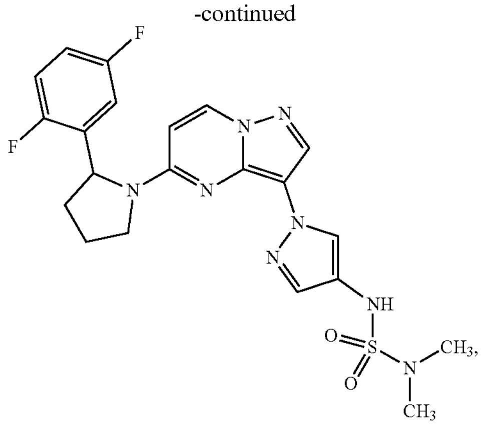
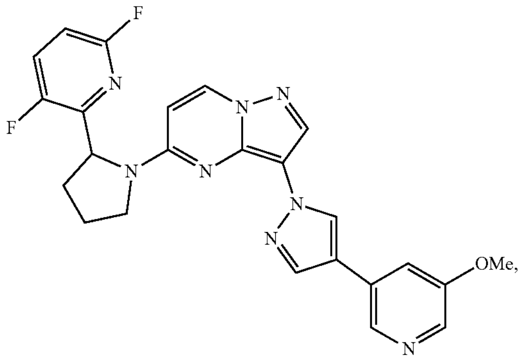
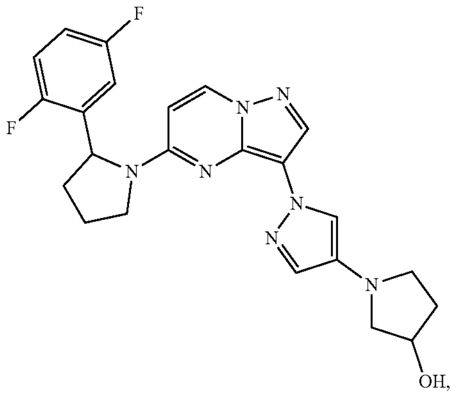
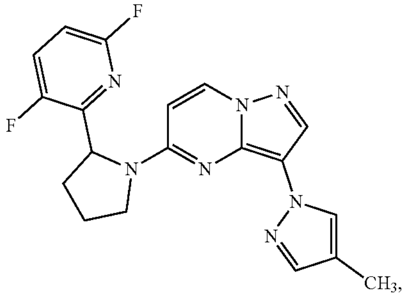

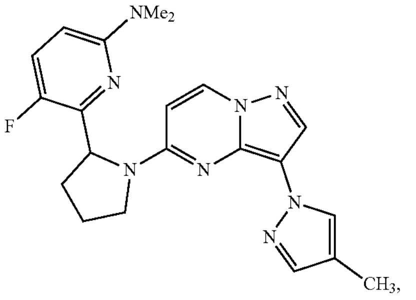
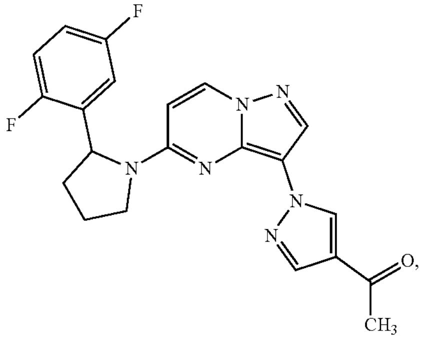
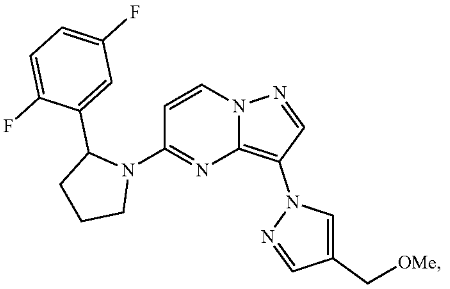
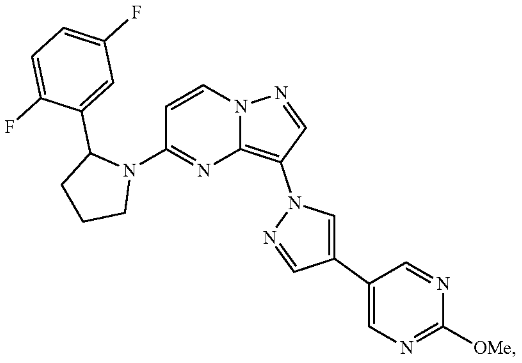
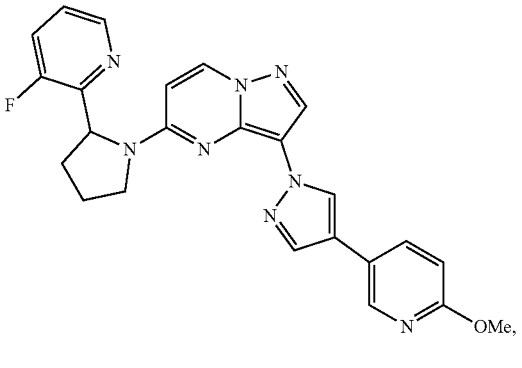
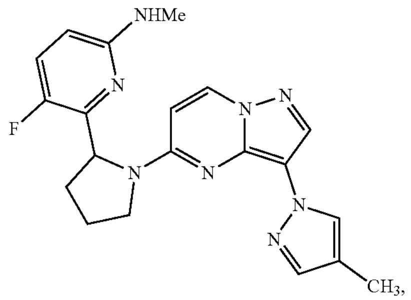
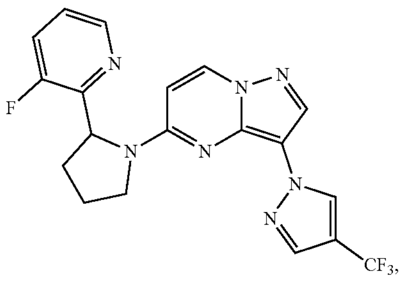
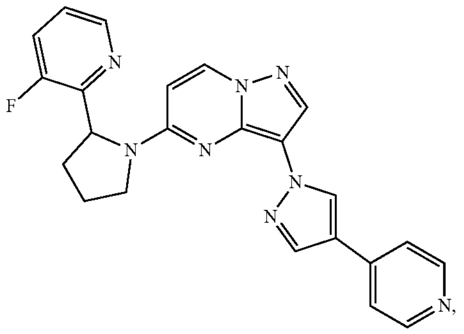
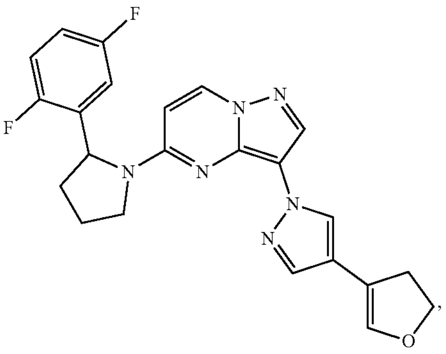
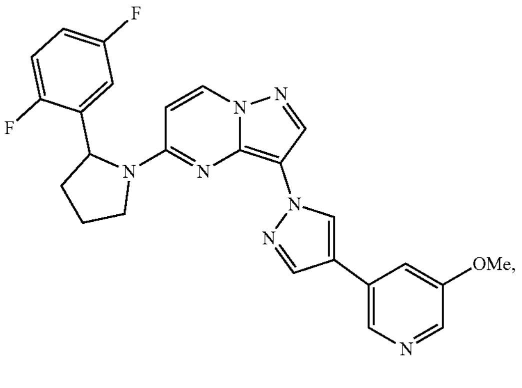

-continued
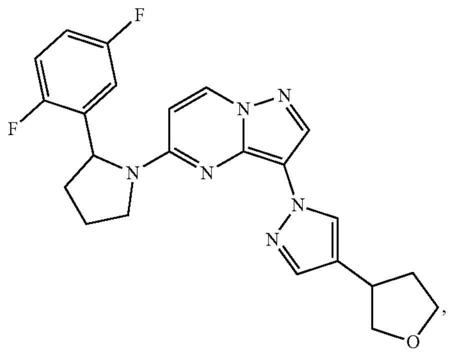
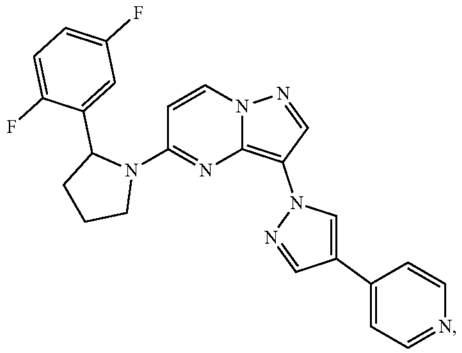
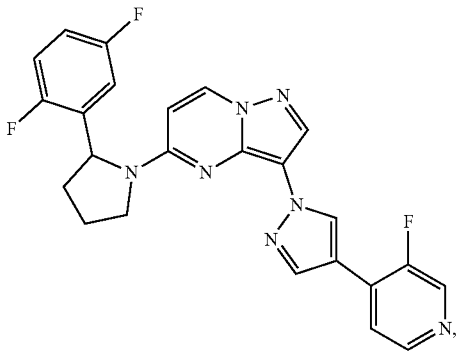
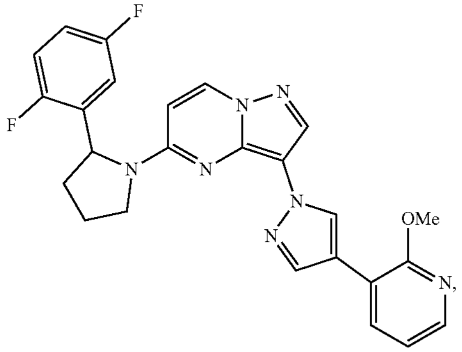
-continued
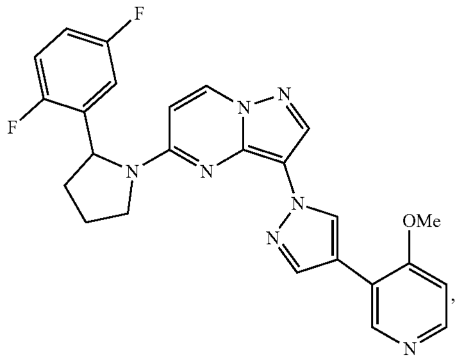
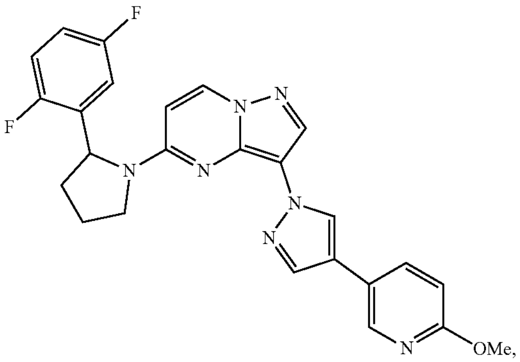
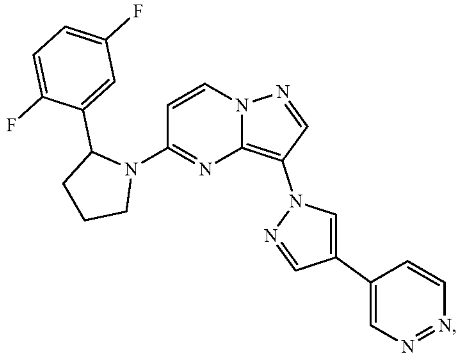
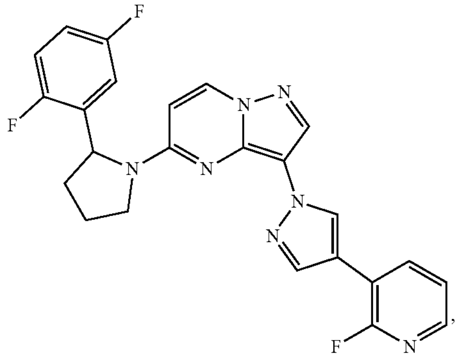

-continued
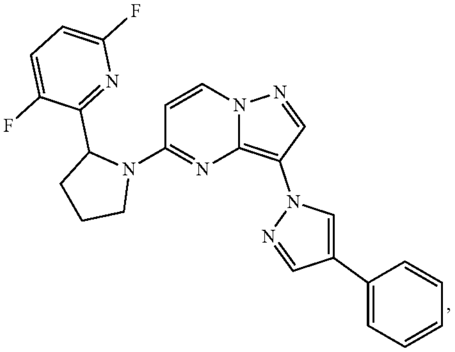
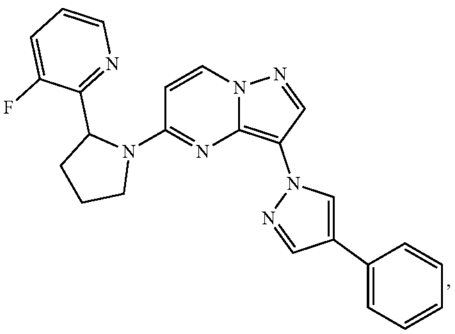
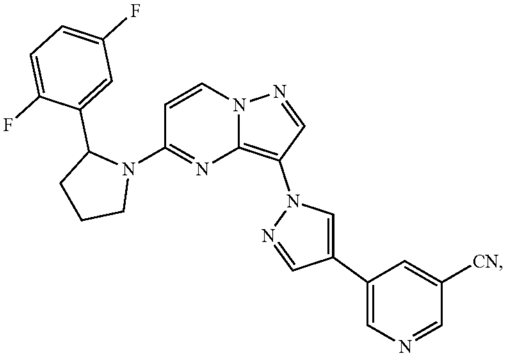
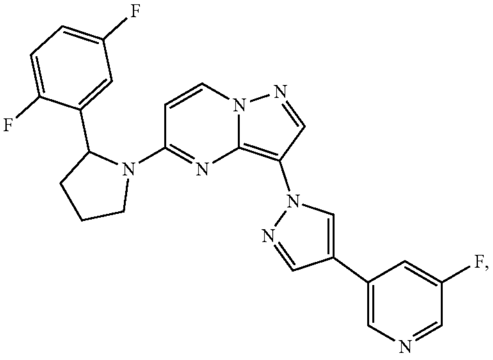
-continued
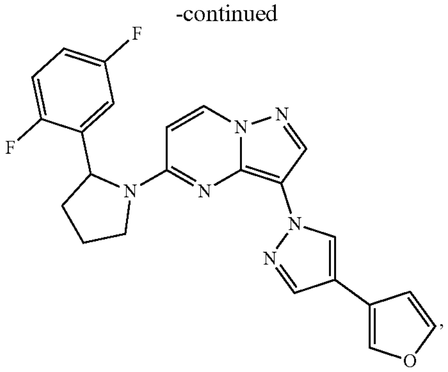
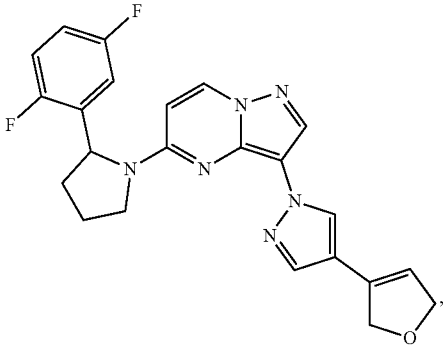
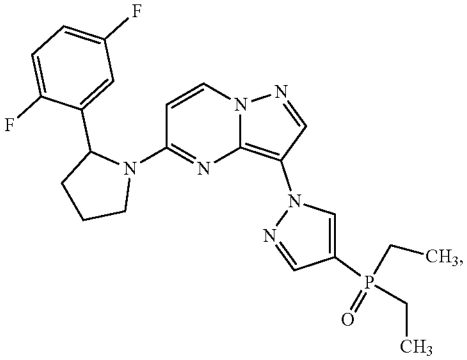
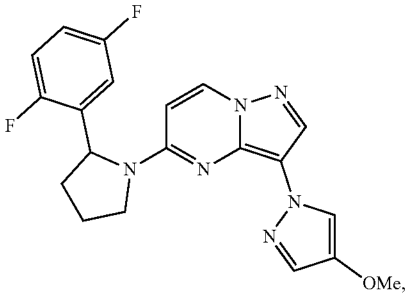
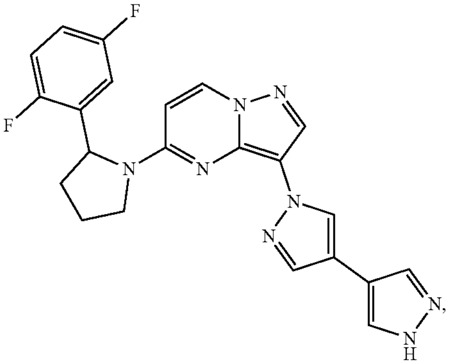

-continued
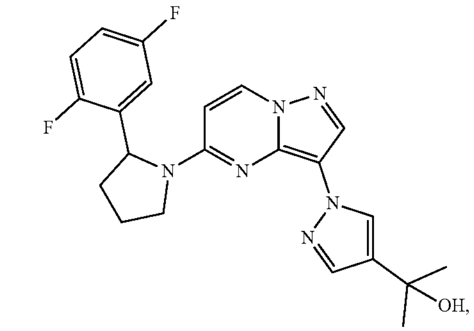
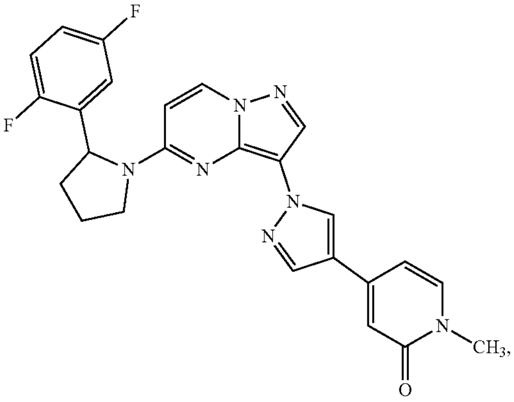
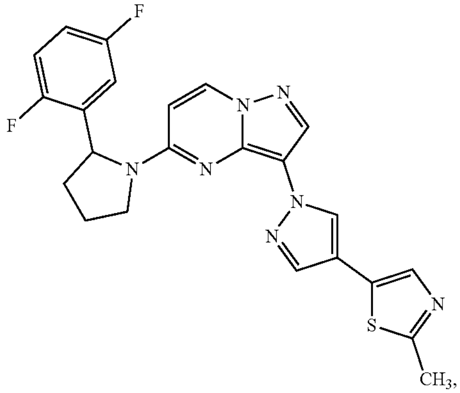
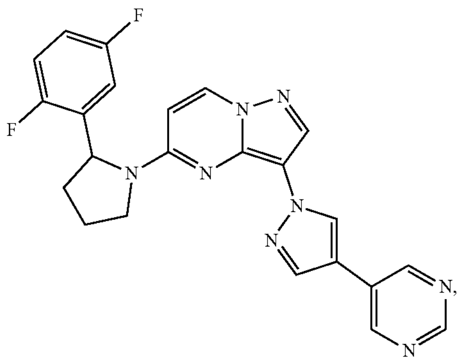
-continued
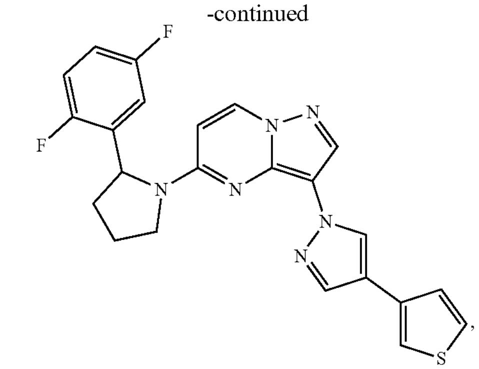
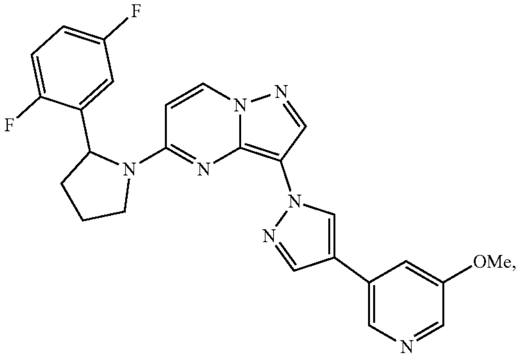
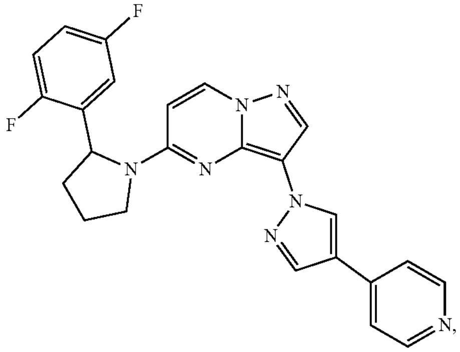
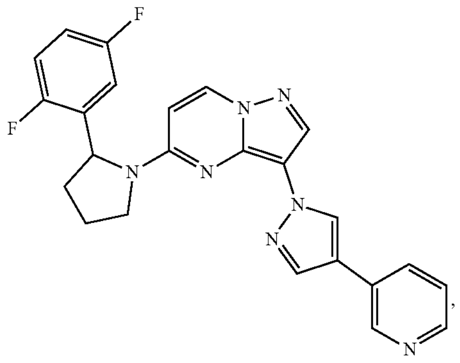

-continued
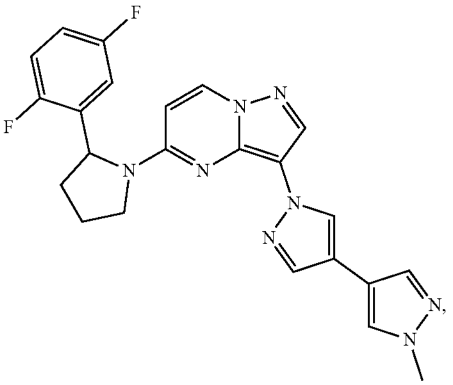
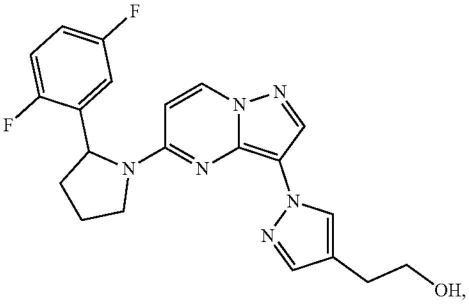
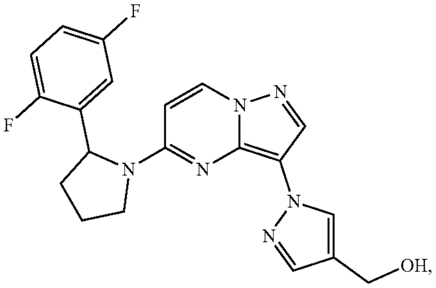
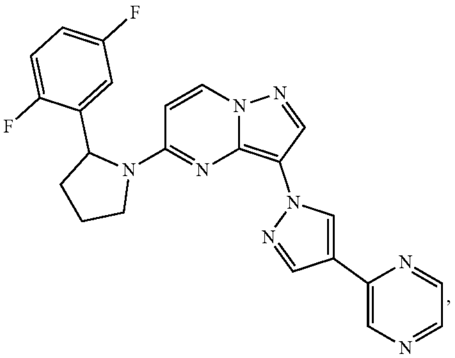
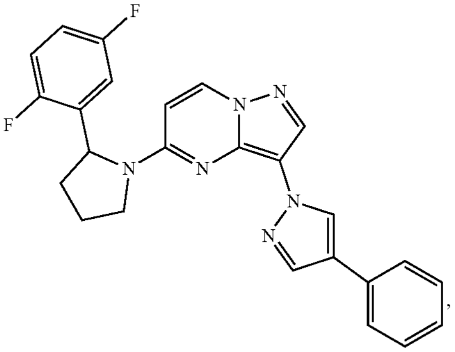
-continued
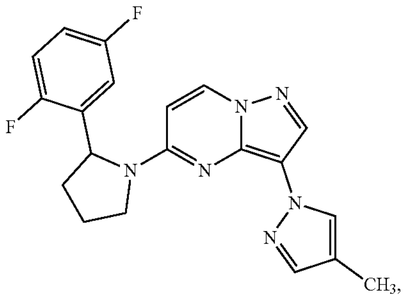
and
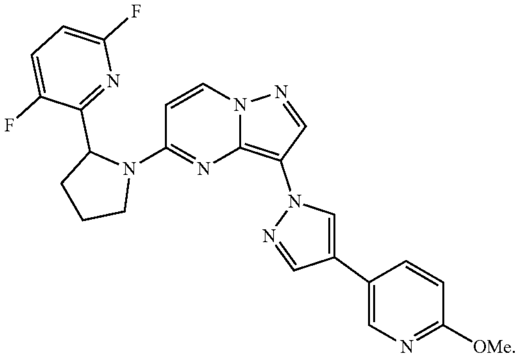
In some embodiments, the compound of formula (XV) is:
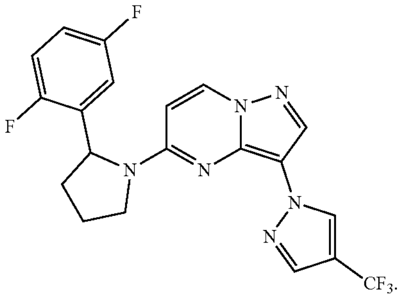
In some embodiments, the compound of formula (XV) is selected from:
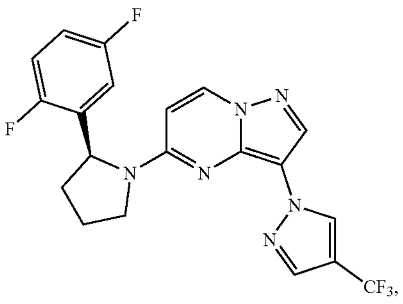

-continued
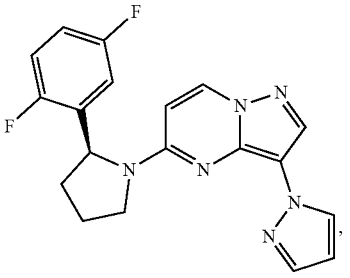
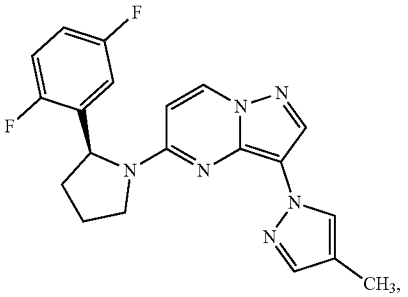
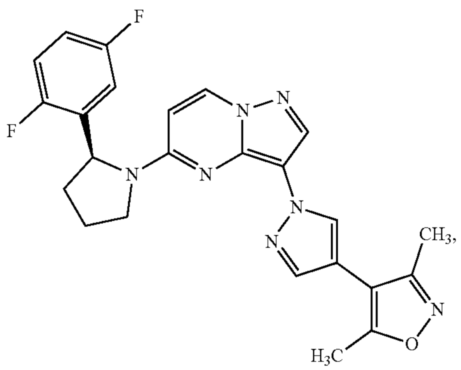
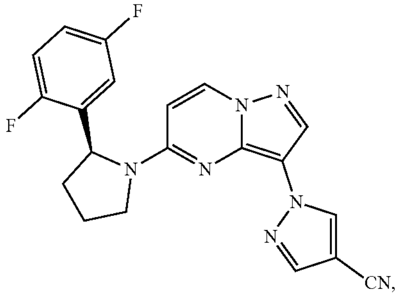 [SMILES: Fc1ccc(F)c([C@@H]2CCCN2c2ccn3ncc(-n4cc(C(F)(F)F)cn4)c3n2)c1]
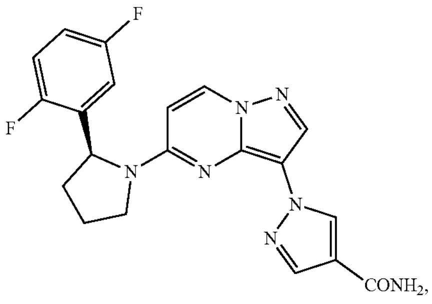
-continued
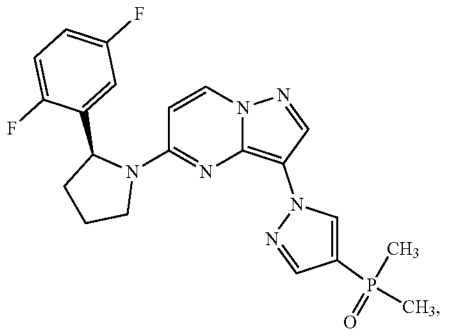
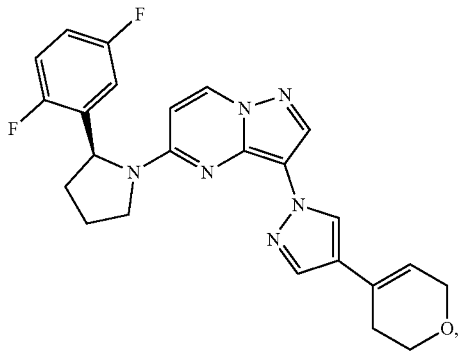
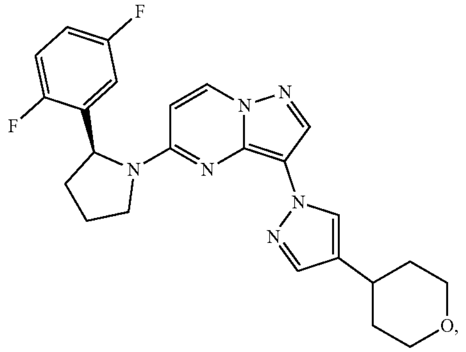
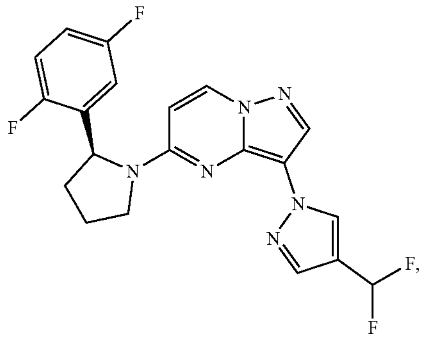

-continued
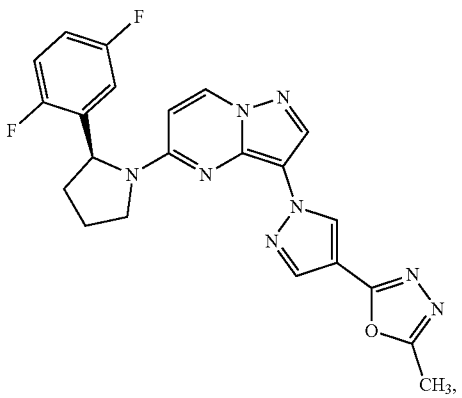
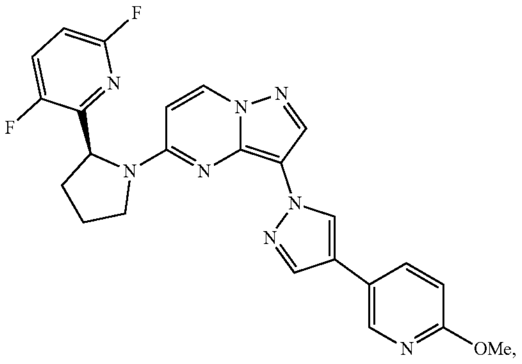
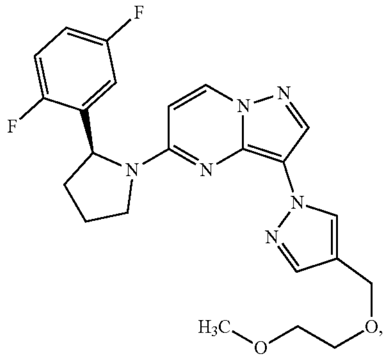
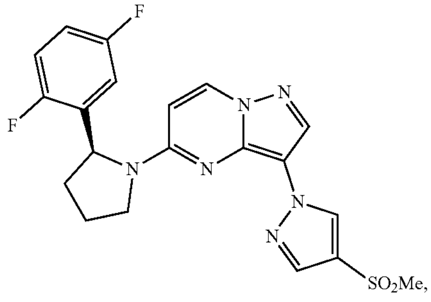
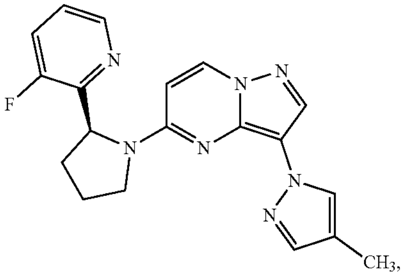
-continued
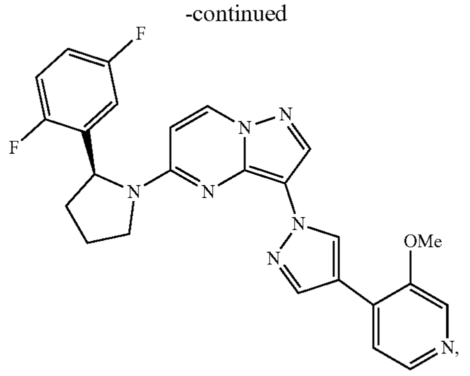
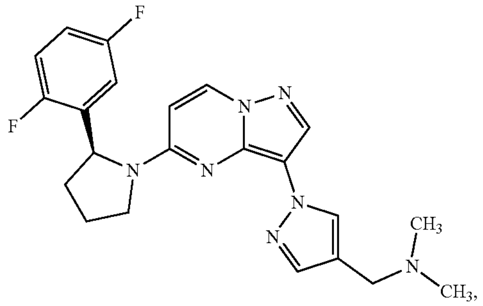
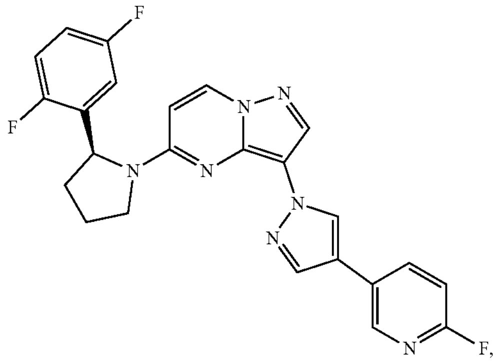
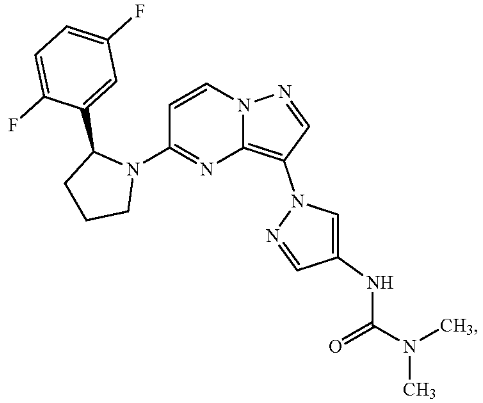

-continued
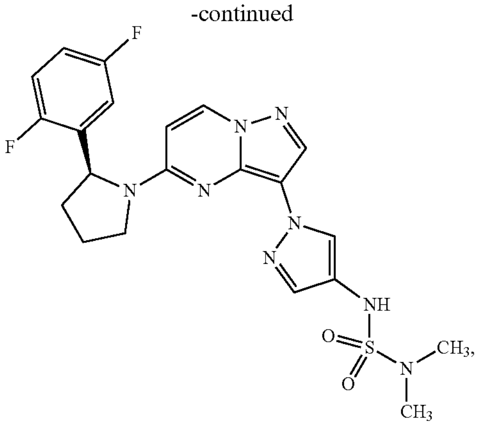
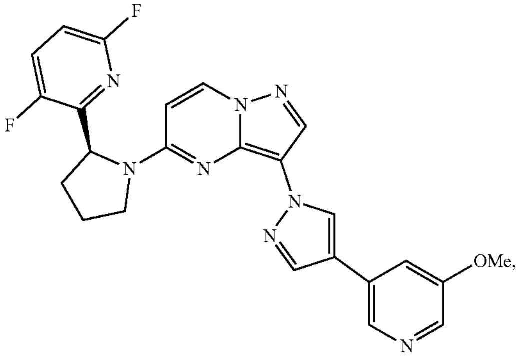
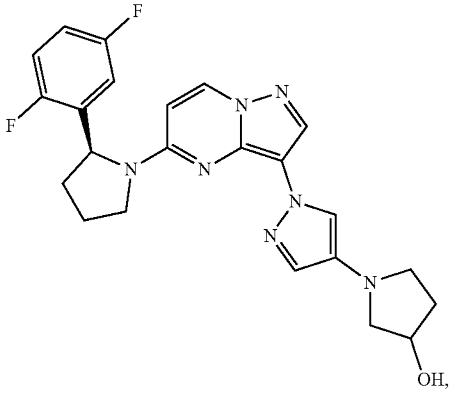
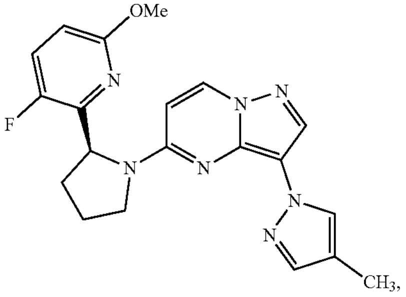
-continued
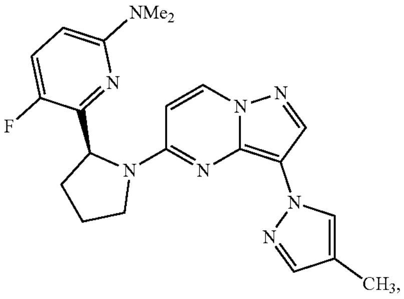
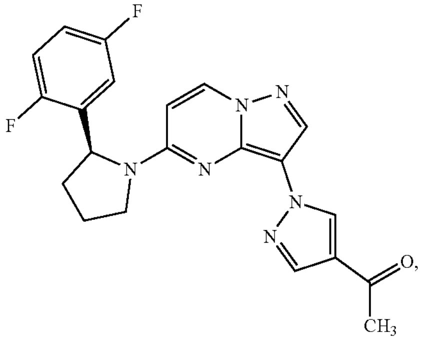
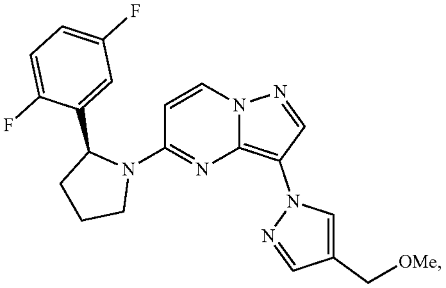
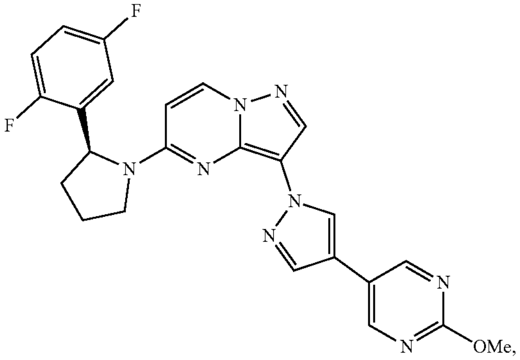
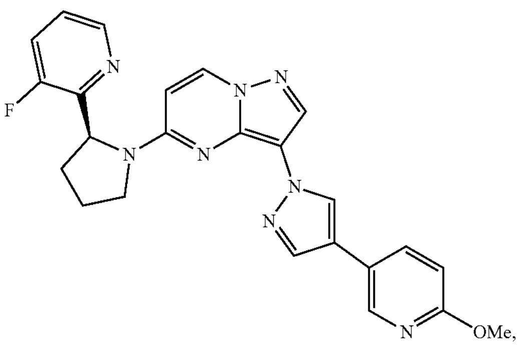

-continued
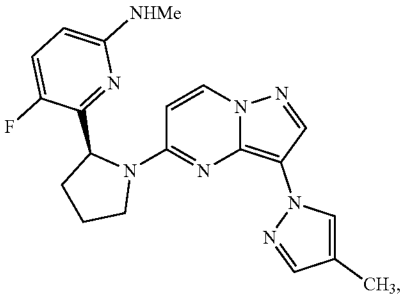
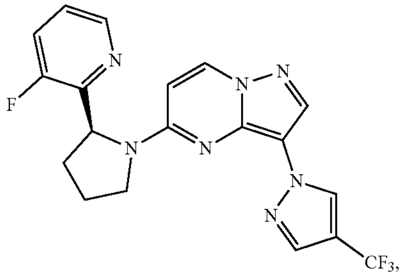
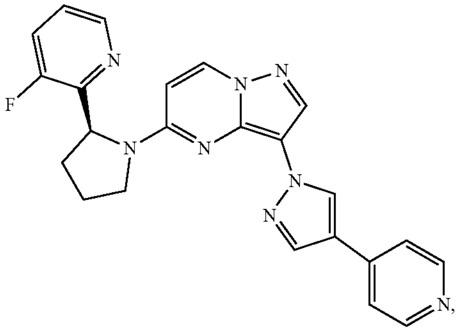
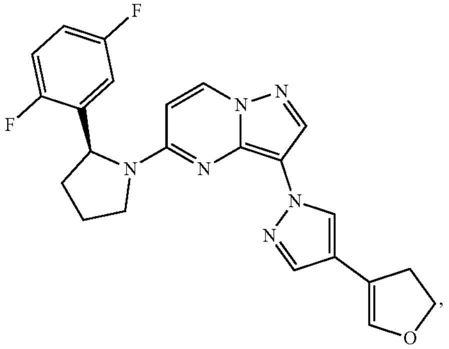
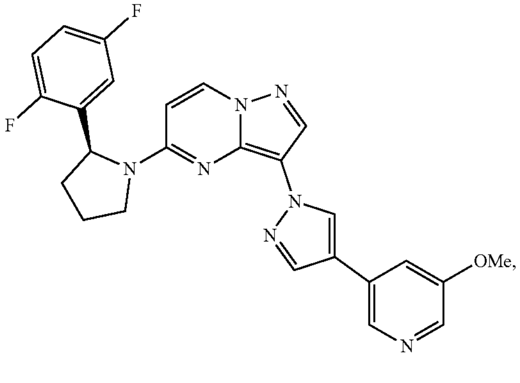
-continued
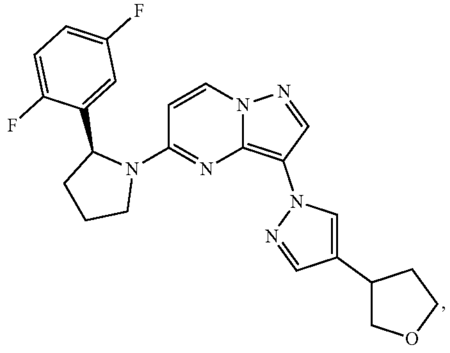
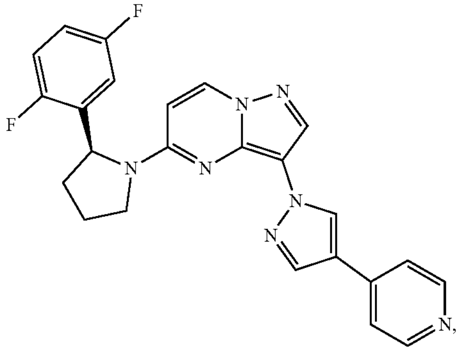
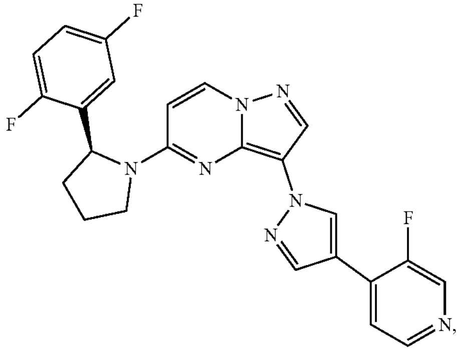
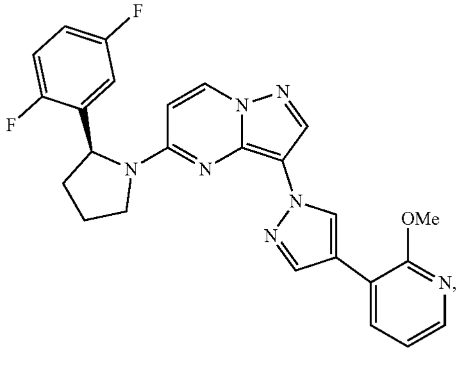

-continued
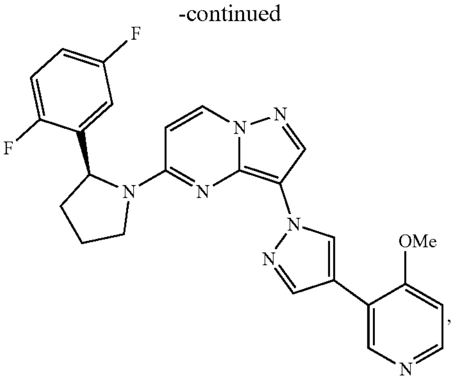
,
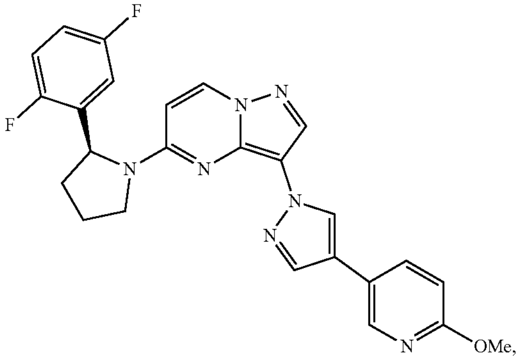
,
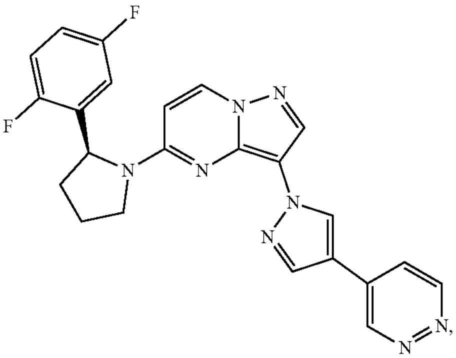
,
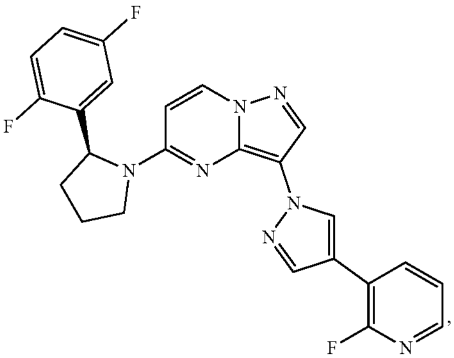
,
-continued
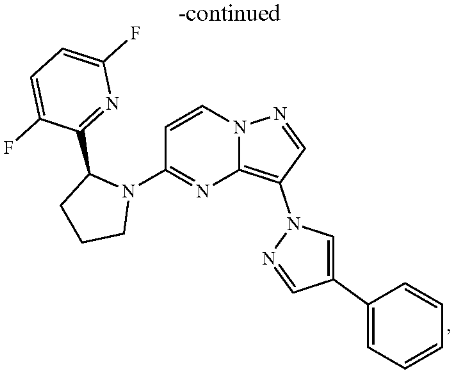
,
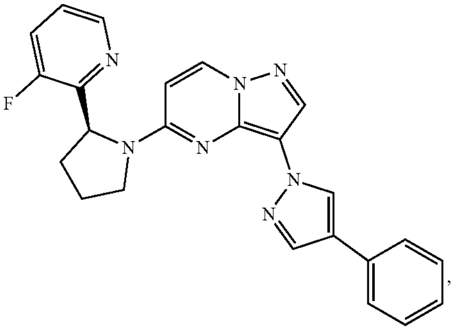
,
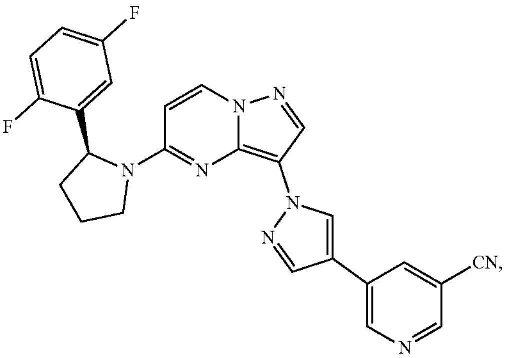
,
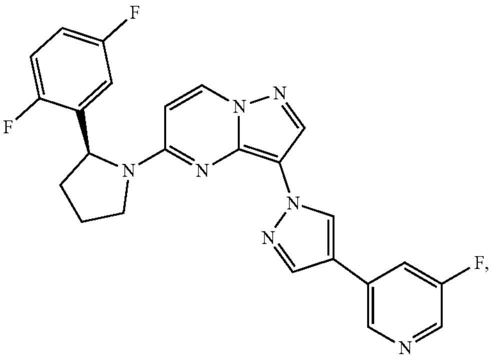
, -continued
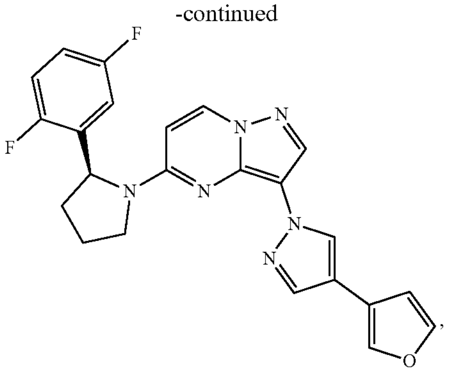
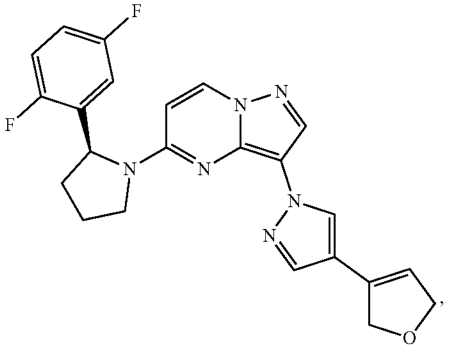
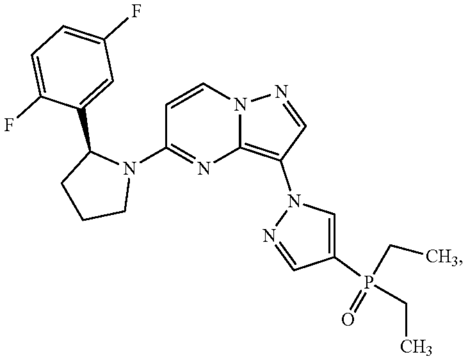
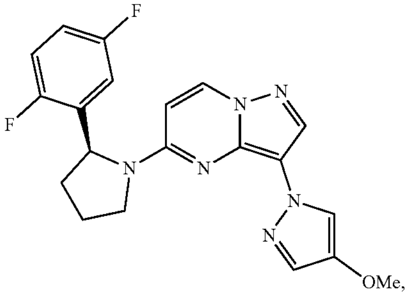
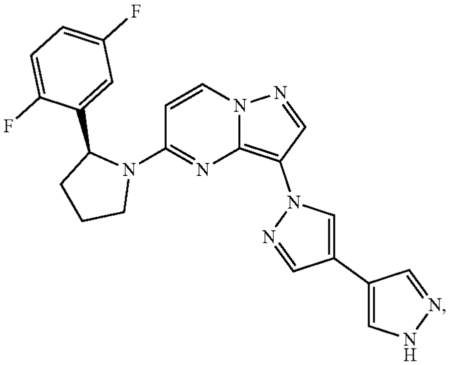
-continued
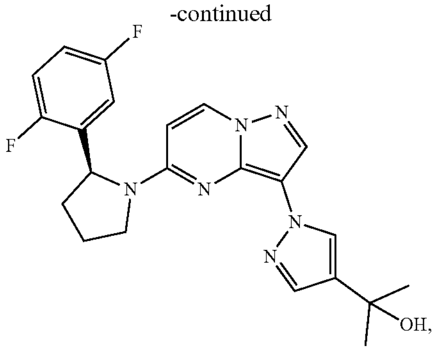
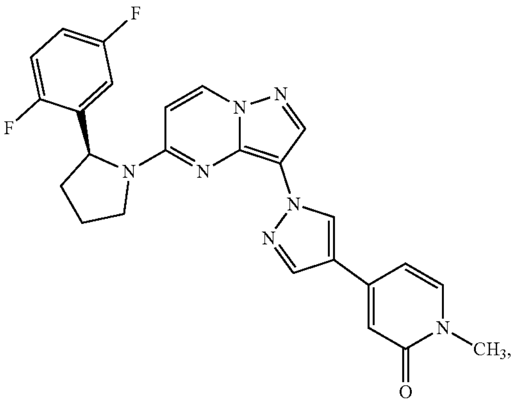
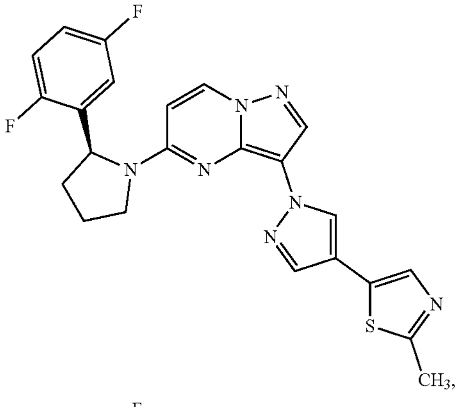
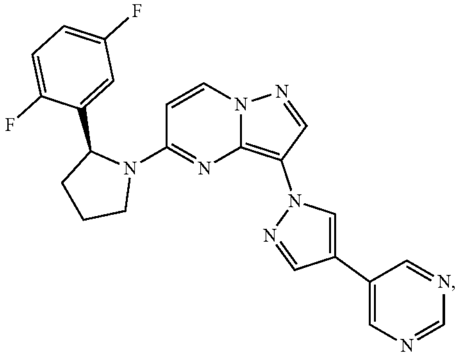

-continued
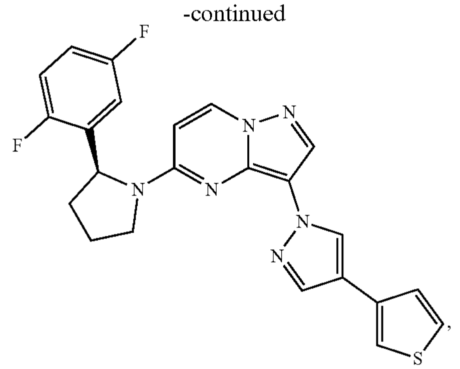
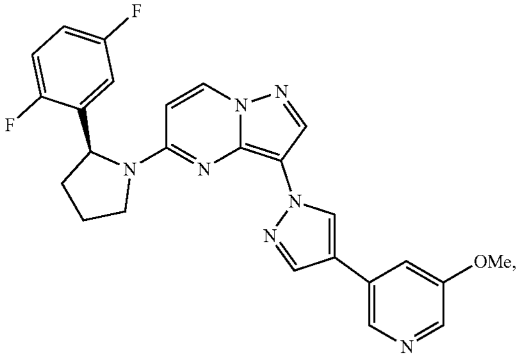
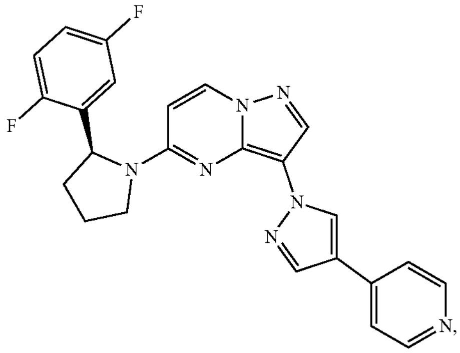
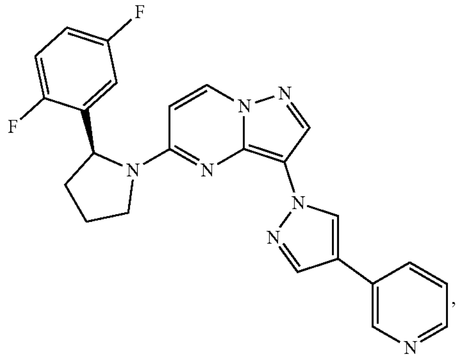
-continued
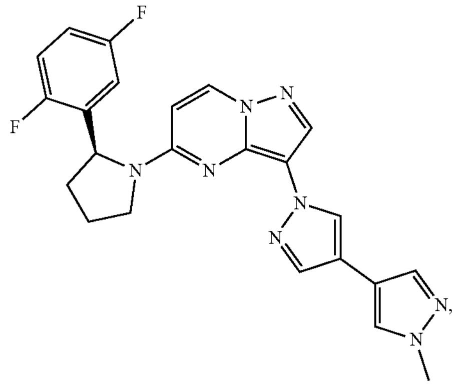
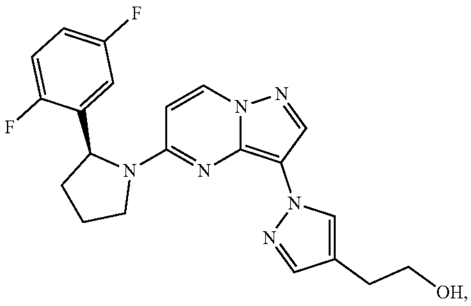
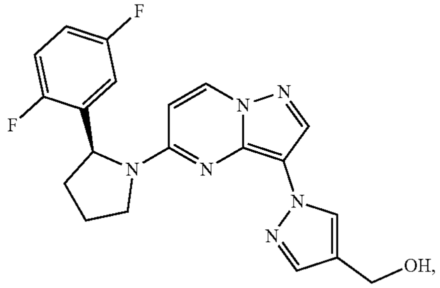
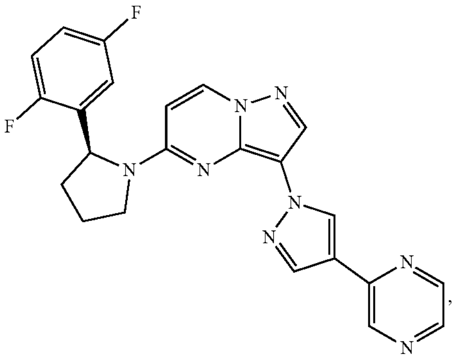
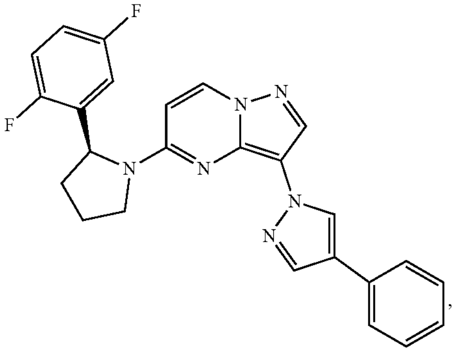

-continued
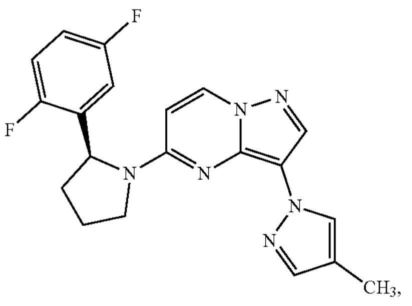
and
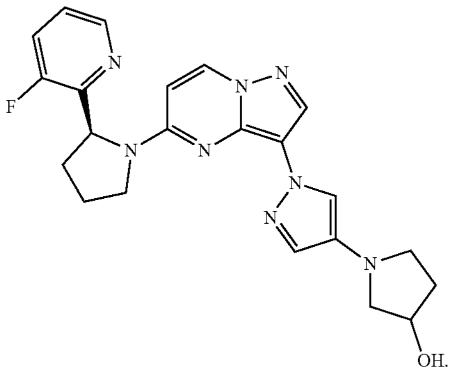
In some embodiments, the compound of formula (XV) is:
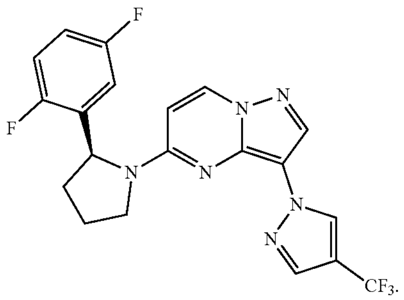
In some embodiments, the compound of formula (XV) is selected from:
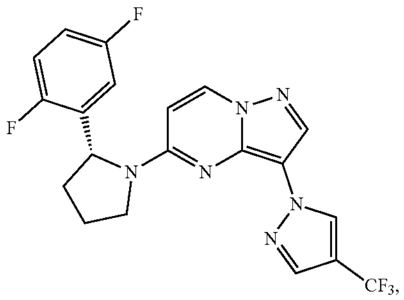
-continued
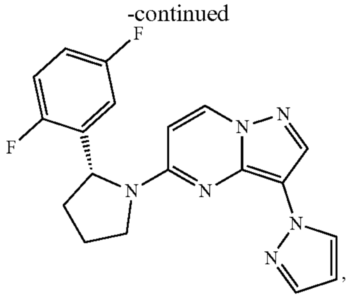
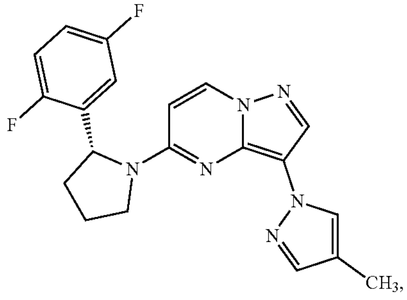
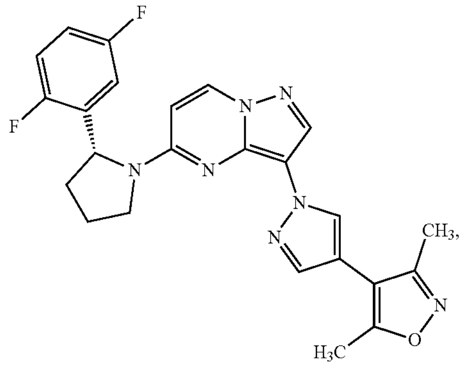
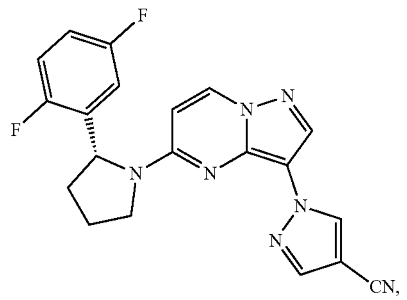
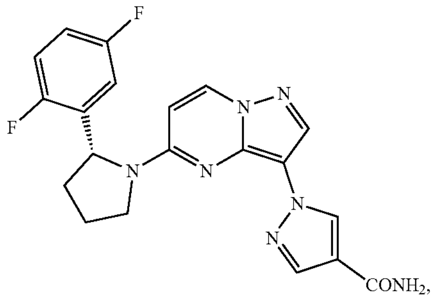

-continued
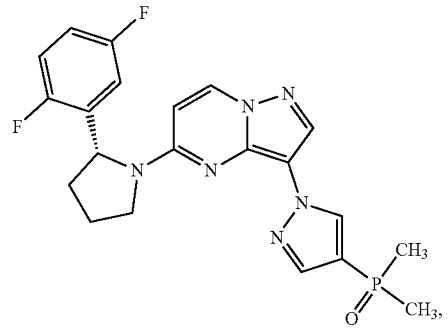
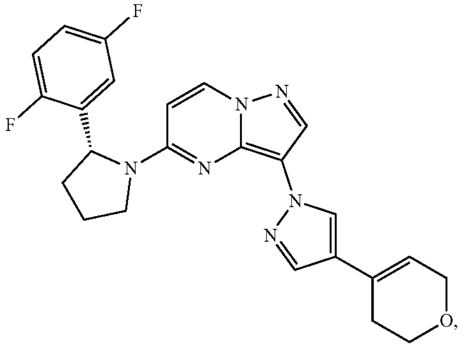
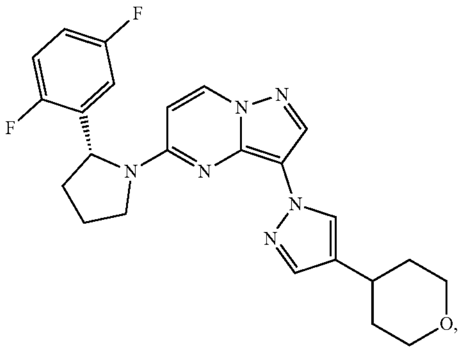
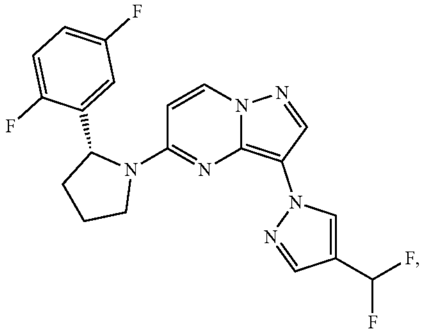
-continued
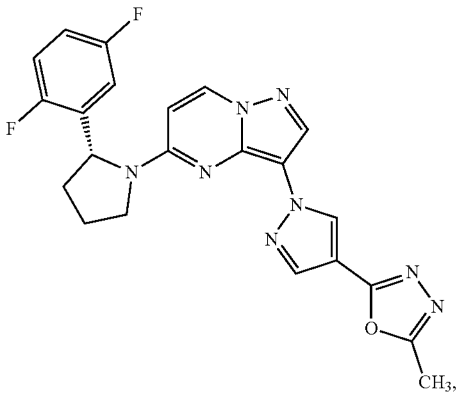
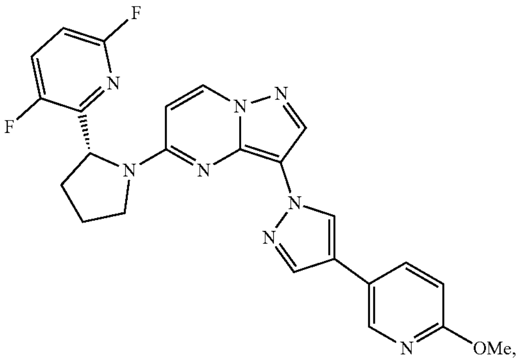
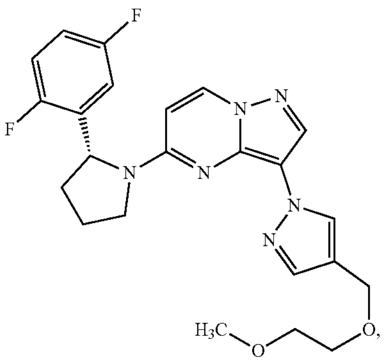
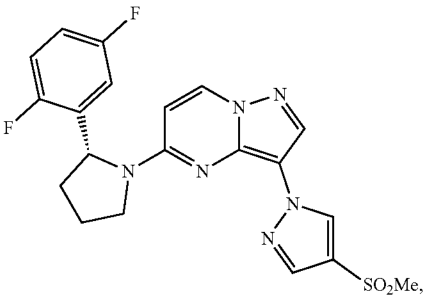
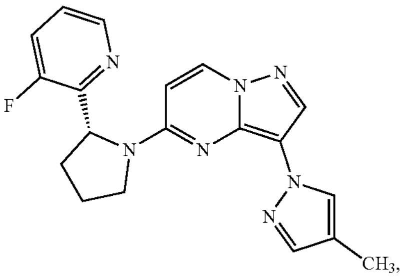

-continued
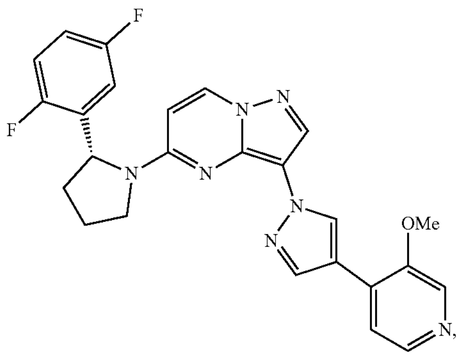
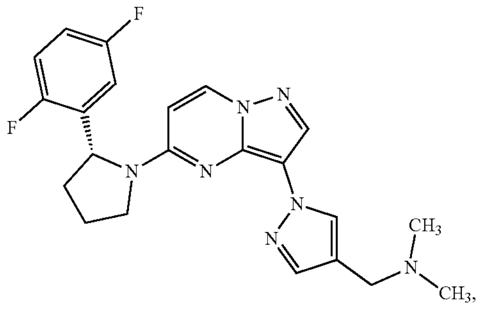
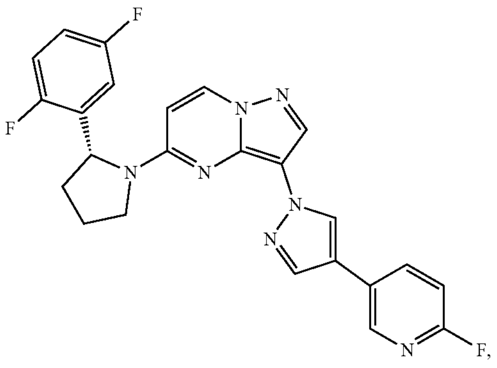
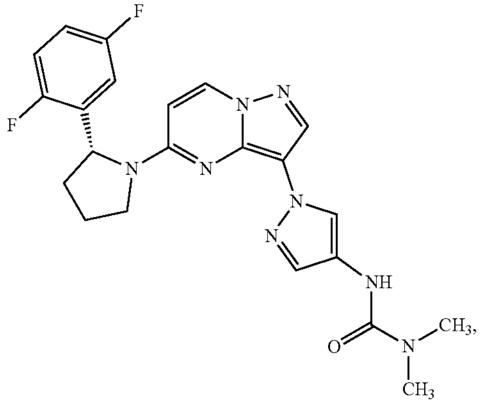
-continued
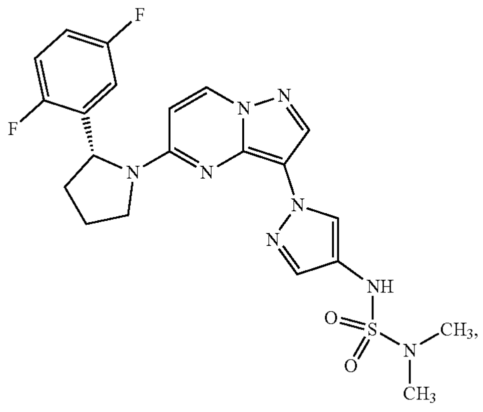
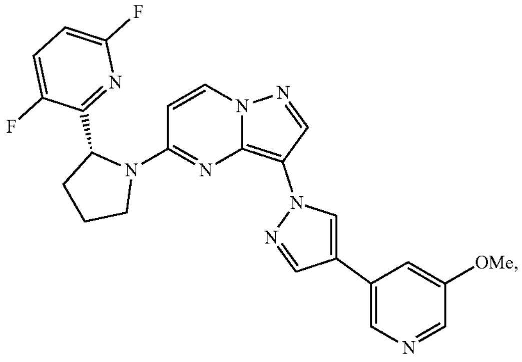
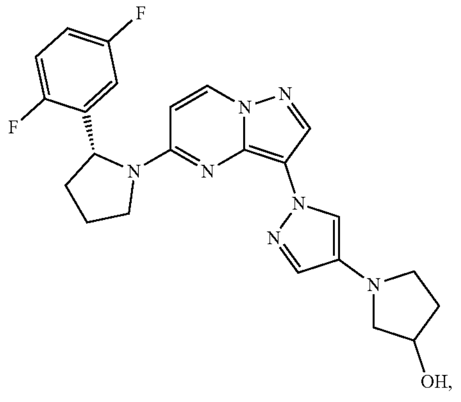
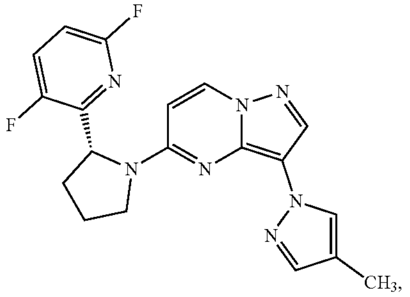

-continued
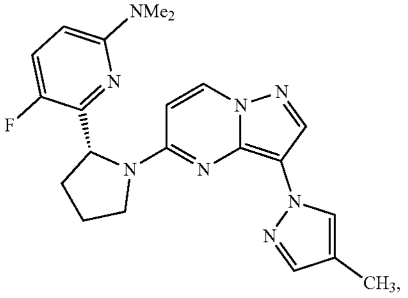
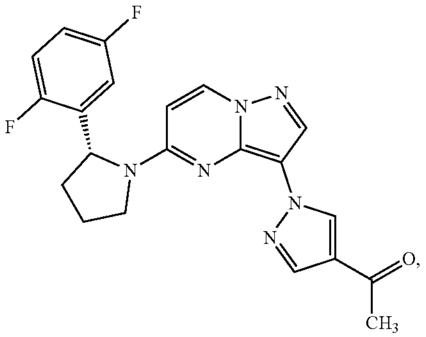 [SMILES: CC(=O)c1cnn(-c2cnn3ccc(N4CCC[C@@H]4c4cc(F)ccc4F)nc23)c1]
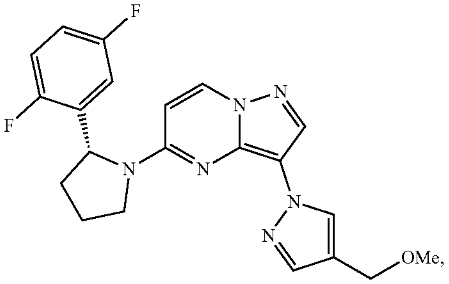
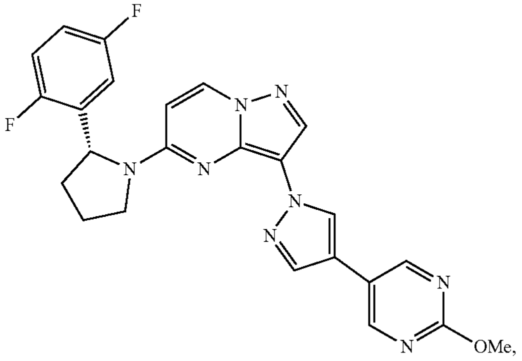
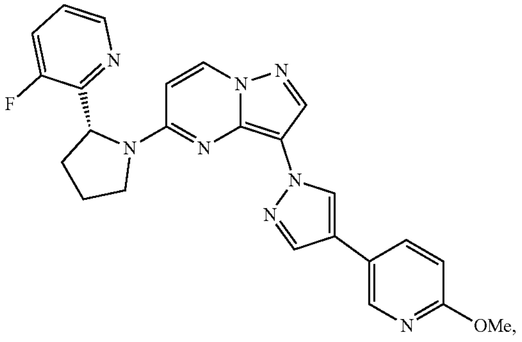
-continued
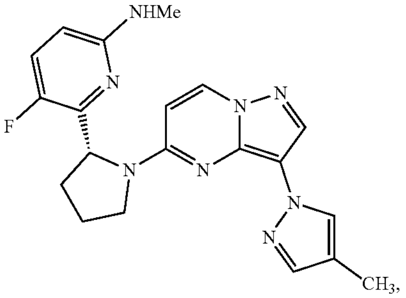
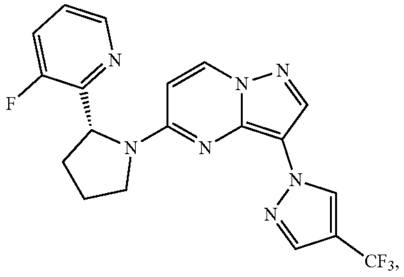
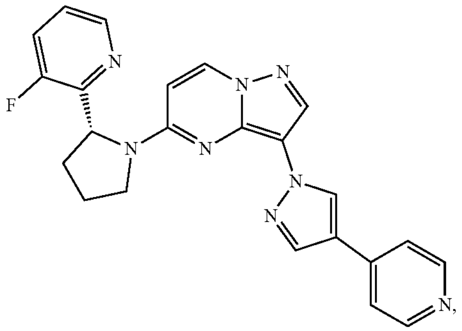
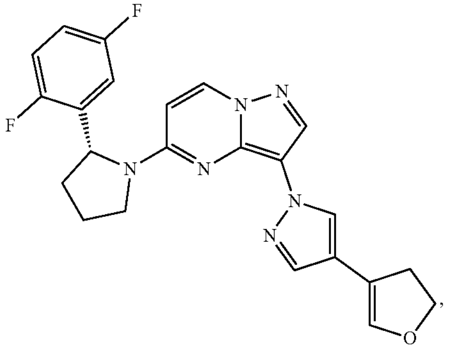
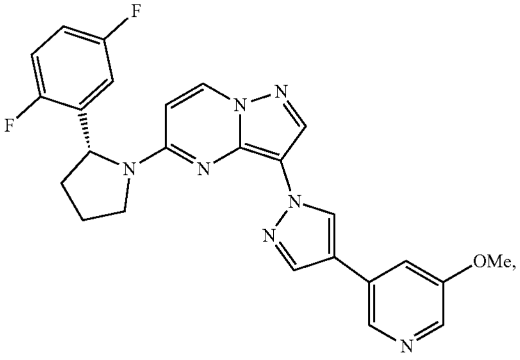

-continued
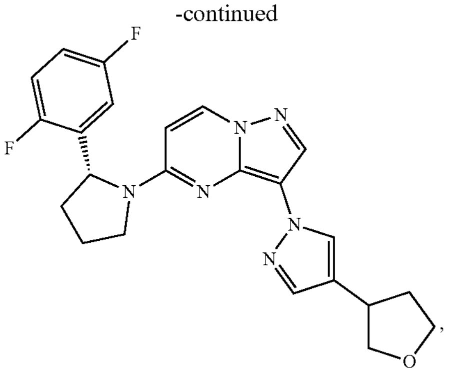
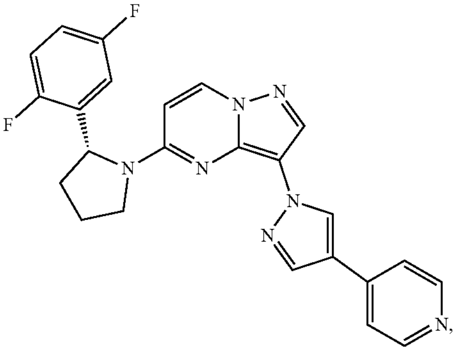
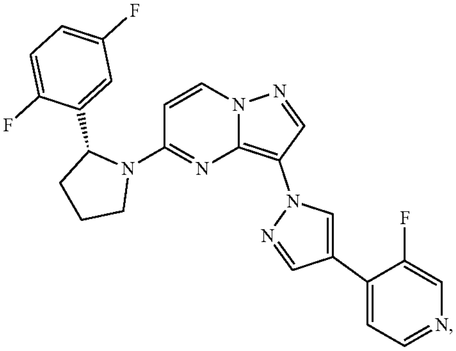
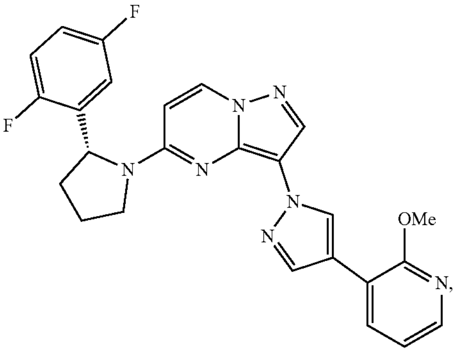
-continued
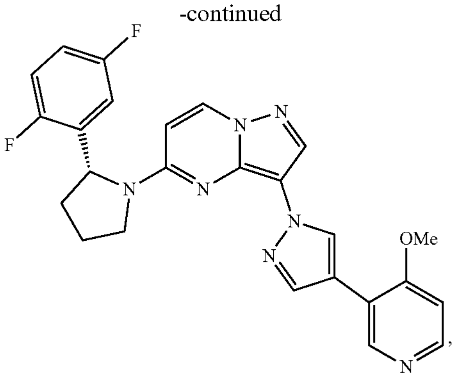
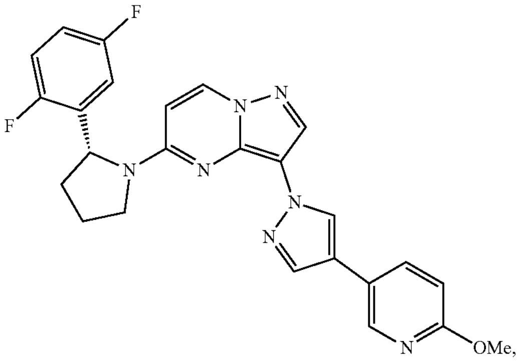
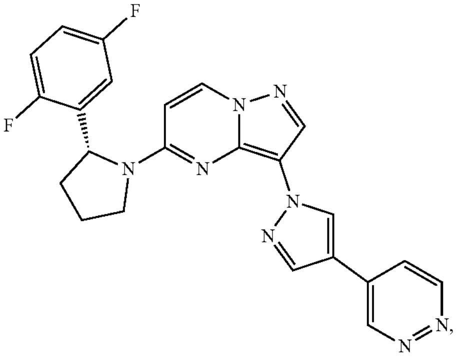
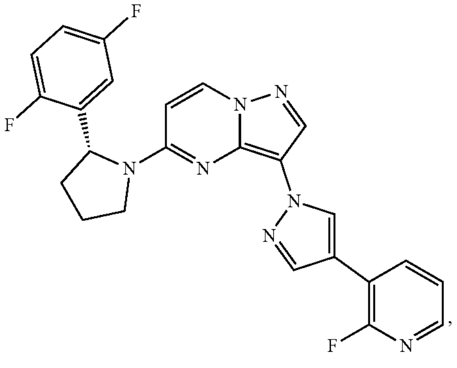

-continued
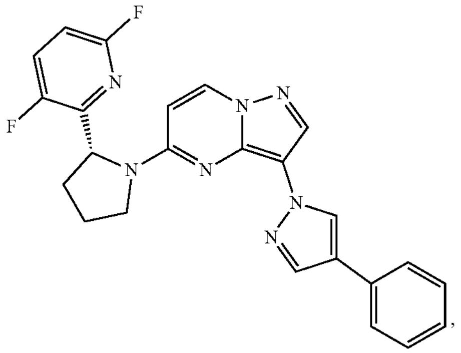
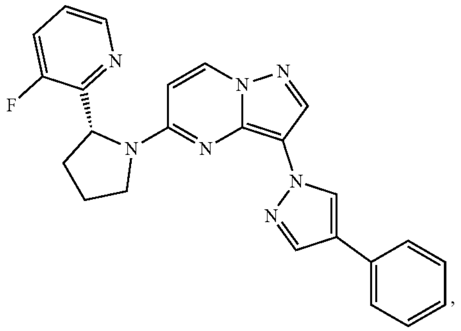
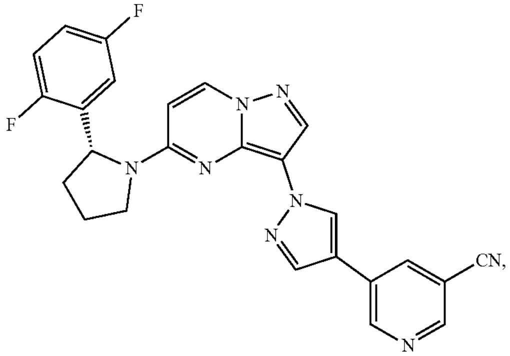
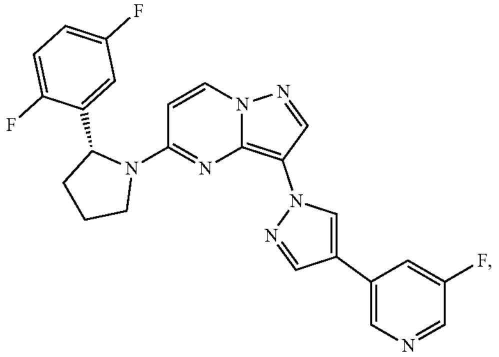
-continued
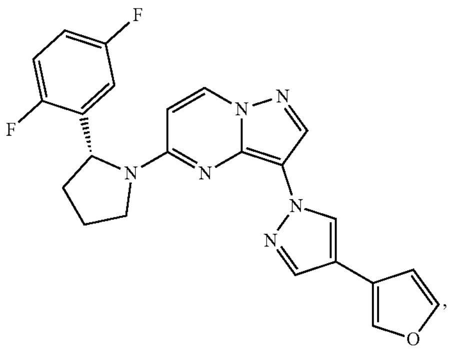
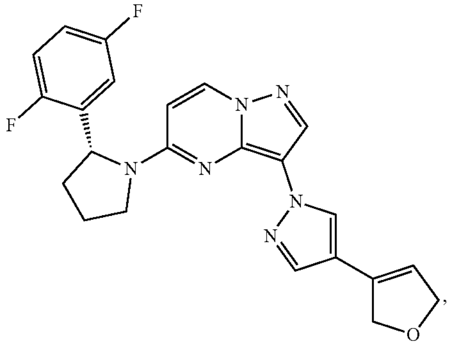
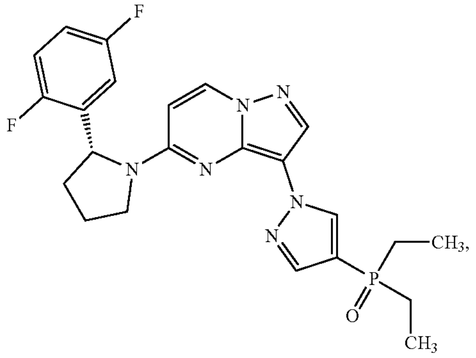
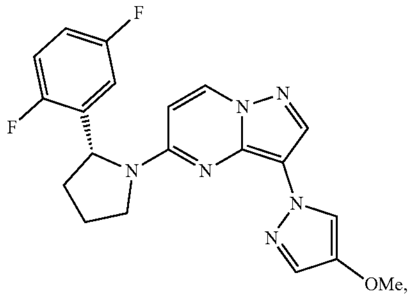
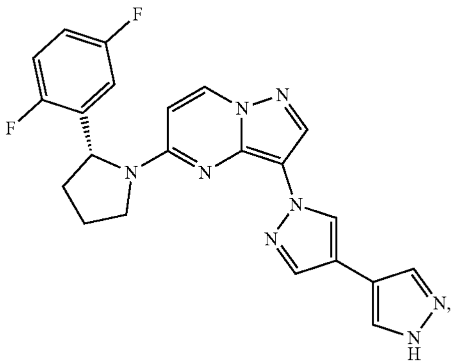

-continued
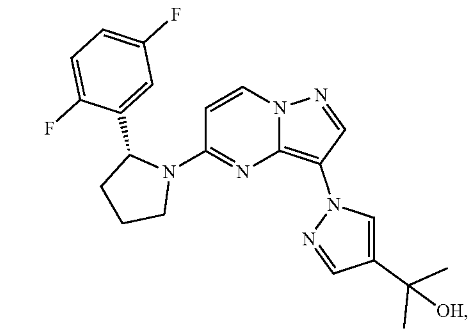
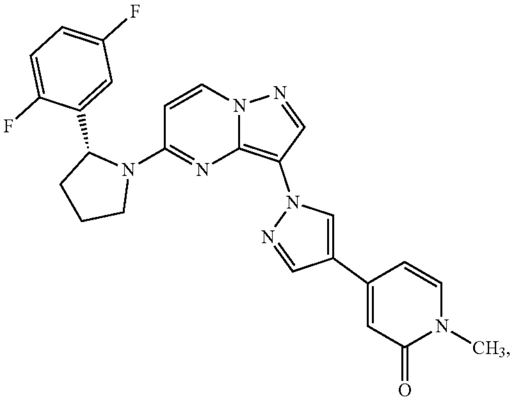
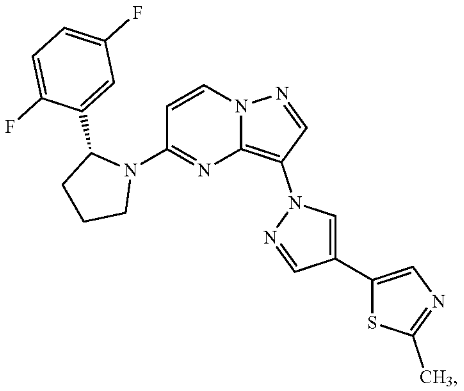
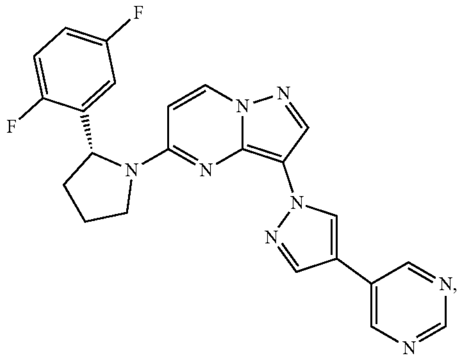
-continued
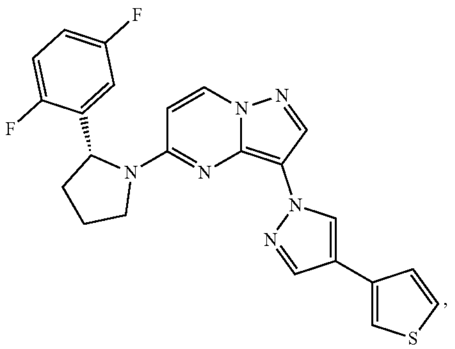
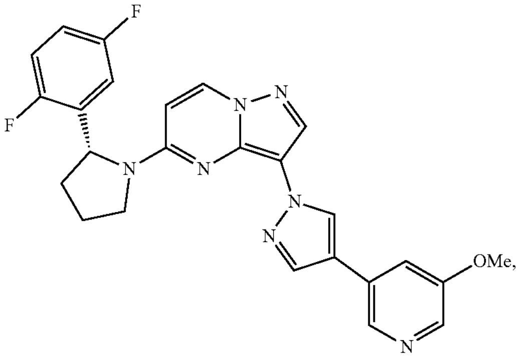
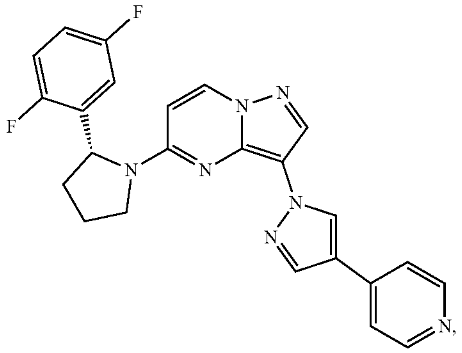
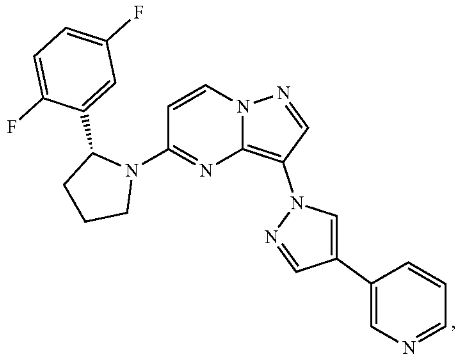

-continued

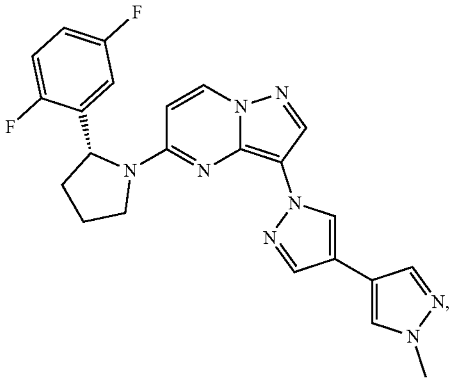

,

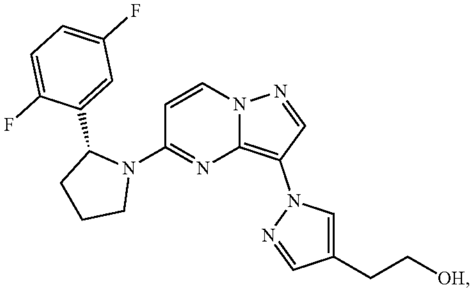

,

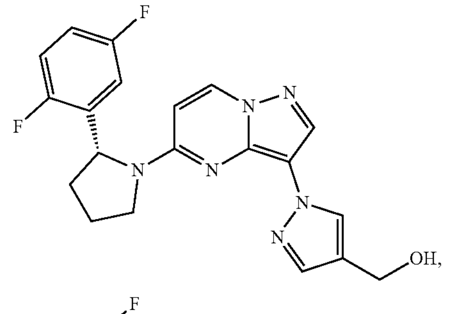

,

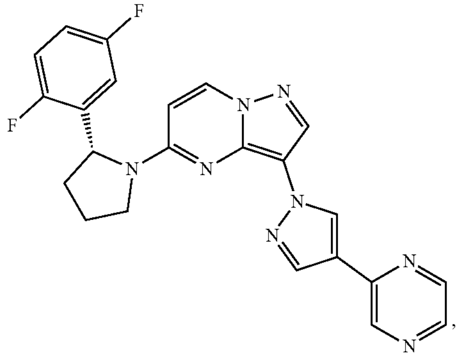

,

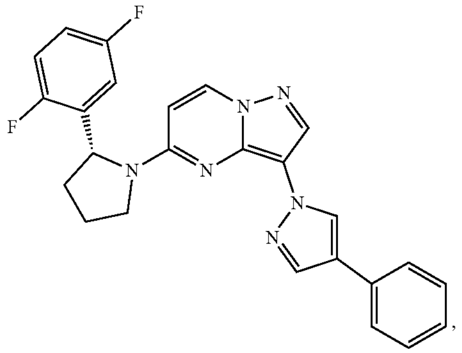

,

-continued

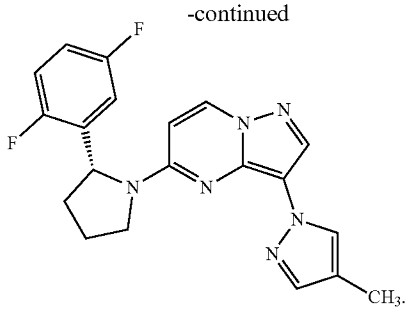

and

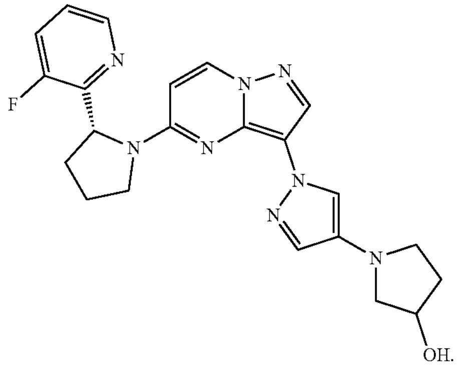 [SMILES: OC1CCN(c2cnn(-c3cnn4ccc(N5CCC[C@@H]5c5ncccc5F)nc34)c2)C1]

In some embodiments, the compound of formula (XV) is:

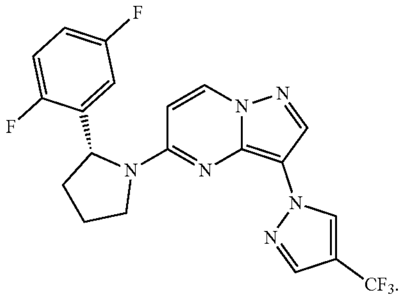 [SMILES: Fc1ccc(F)c([C@H]2CCCN2c2ccn3ncc(-n4cc(C(F)(F)F)cn4)c3n2)c1]

In some embodiments, the disclosed pyrazolo[1,5-a]pyrimidine compounds are enantiomerically pure. Thus, in various embodiments, disclosed the pyrazolo[1,5-a]pyrimidine compounds have an enantiomeric purity of at least about 80%, at least about 85%, at least about 90%, at least about 95%, at least about 99%, or greater than 99%.

In some embodiments, the disclosed pyrazolo[1,5-a]pyrimidine compounds can be provided in percent enantiomeric excess (e.e.). Thus, in various embodiments, the enantiomeric excess of the desired enantiomer of the disclosed pyrazolo[1,5-a]pyrimidine compounds is at least about 50%, at least about 60%, at least about 70%, at least about 75%, at least about 80%, at least about 85%, at least about 90%, at least about 95%, at least about 98%, or at least about 99%. In further embodiments, the "S" form of the disclosed pyrazolo[1,5-a]pyrimidine compounds is substantially free from the "R" form. In still further embodiments, the "R" form of the disclosed pyrazolo[1,5-a]pyrimidine compounds is substantially free from the "S" form.

In some embodiments, the "S" form of the disclosed pyrazolo[1,5-a]pyrimidine compounds is present in an amount of greater than about 50%, greater than about 60%, greater than about 70%, greater than about 75%, greater than about 80%, greater than about 85%, greater than about 90%, greater than about 95%, greater than about 98%, or greater than about 99% relative to the "R" form.

In some embodiments, the "R" form of the disclosed pyrazolo[1,5-a]pyrimidine compounds is present in an amount of greater than about 50%, greater than about 60%, greater than about 70%, greater than about 75%, greater than about 80%, greater than about 85%, greater than about 90%, greater than about 95%, greater than about 98%, or greater than about 99% relative to the "S" form.

a. $R^{10}$ Groups

In some embodiments, $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$. In some embodiments, $R^{10}$ is selected from hydrogen, —F, —Cl, —CN, C1-C4 alkyl, C1-C4 haloalkyl, C1-C4 cyanoalkyl, —$OR^{20}$, —$C(O)R^{20}$, —$S(O)R^{20}$, —$S(O)_2R^{20}$, —(C1-C4 alkyl)$OR^{20}$, —(C1-C4 alkyl)$SR^{20}$, —(C1-C4 alkyl)$C(O)R^{20}$, —(C1-C4 alkyl)$S(O)R^{20}$, —(C1-C4 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$. In some embodiments, $R^{10}$ is selected from hydrogen, —F, —Cl, —CN, methyl, ethyl, n-propyl, isopropyl, —$CH_2F$, —$CHF_2$, —$CF_3$, —$CH_2C_1$, —$CHCl_2$, —$CCl_3$, —$CH_2CH_2F$, —$CH_2CHF_2$, —$CH_2CF_3$, —$CH_2CH_2C_1$, —$CH_2CHCl_2$, —$CH_2CCl_3$, —$CH_2CH_2CH_2F$, —$CH_2CH_2CHF_2$, —$CH_2CH_2CF_3$, —$CH_2CH_2CH_2C_1$, —$CH_2CH_2CHCl_2$, —$CH_2CH_2CCl_3$, —$CH(CH_3)CH_2F$, —$CH(CH_3)CHF_2$, —$CH(CH_3)CF_3$, —$CH(CH_3)CH_2C_1$, —$CH(CH_3)CHCl_2$, —$CH(CH_3)CCl_3$, —$CH_2CN$, —$CH_2CH_2CN$, —$CH_2CH_2CH_2CN$, —$CH(CH_3)CH_2CN$, —$OR^{20}$, —$C(O)R^{20}$, —$S(O)R^{20}$, —$S(O)_2R^{20}$, —$CH_2OR^{20}$, —$CH_2CH_2OR^{20}$, —$CH_2CH_2CH_2OR^{20}$, —$CH(CH_3)CH_2OR^{20}$, —$CH_2SR^{20}$, —$CH_2CH_2SR^{20}$, —$CH_2CH_2CH_2SR^{20}$, —$CH(CH_3)CH_2SR^{20}$, —$CH_2C(O)R^{20}$, —$CH_2CH_2C(O)R^{20}$, —$CH_2CH_2CH_2C(O)R^{20}$, —$CH(CH_3)CH_2C(O)R^{20}$, —$CH_2C(S)R^{20}$, —$CH_2CH_2C(S)R^{20}$, —$CH_2CH_2CH_2C(S)R^{20}$, —$CH(CH_3)CH_2C(S)R^{20}$, —$CH_2SO_2R^{20}$, —$CH_2CH_2SO_2R^{20}$, —$CH_2CH_2CH_2SO_2R^{20}$, —$CH(CH_3)CH_2SO_2R^{20}$, —$NR^{21}C(O)R^{20}$, —$NR^{21}S(O)_2R^{20}$, —$NR^{22a}R^{22b}$, —$P(O)R^{22a}R^{22b}$, —$CH_2NR^{22a}R^{22b}$, —$CH_2CH_2NR^{22a}R^{22b}$, —$CH_2CH_2CH_2NR^{22a}R^{22b}$, —$CH(CH_3)CH_2NR^{22a}R^{22b}$, —$CH_2P(O)R^{22a}R^{22b}$, —$CH_2CH_2P(O)R^{22a}R^{22b}$, —$CH_2CH_2CH_2P(O)R^{22a}R^{22b}$, —$CH(CH_3)CH_2P(O)R^{22a}R^{22b}$, and $Cy^1$. In some embodiments, $R^{10}$ is selected from hydrogen, —F, —Cl, —CN, methyl, ethyl, —$CH_2F$, —$CHF_2$, —$CF_3$, —$CH_2C_1$, —$CHCl_2$, —$CCl_3$, —$CH_2CH_2F$, —$CH_2CHF_2$, —$CH_2CF_3$, —$CH_2CH_2C_1$, —$CH_2CHCl_2$, —$CH_2CCl_3$, —$CH_2CN$, —$CH_2CH_2CN$, —$OR^{20}$, —$C(O)R^{20}$, —$S(O)R^{20}$, —$S(O)_2R^{20}$, —$CH_2OR^{20}$, —$CH_2CH_2OR^{20}$, —$CH_2SR^{20}$, —$CH_2CH_2SR^{20}$, —$CH_2C(O)R^{20}$, —$CH_2CH_2C(O)R^{20}$, —$CH_2C(S)R^{20}$, —$CH_2CH_2C(S)R^{20}$, —$CH_2SO_2R^{20}$, —$CH_2CH_2SO_2R^{20}$, —$NR^{21}C(O)R^{20}$, —$NR^{21}S(O)_2R^{20}$, —$NR^{22a}R^{22b}$, —$P(O)R^{22a}R^{22b}$, —$CH_2NR^{22a}R^{22b}$, —$CH_2CH_2NR^{22a}R^{22b}$, —$CH_2P(O)R^{22a}R^{22b}$, —$CH_2CH_2P(O)R^{22a}R^{22b}$, and $Cy^1$. In some embodiments, $R^{10}$ is selected from hydrogen, —F, —$C_1$, —CN, methyl, —$CH_2F$, —$CHF_2$, —$CF_3$, —$CH_2C_1$, —$CHCl_2$, —$CCl_3$, —$CH_2CN$, —$OR^{20}$, —$C(O)R^{20}$, —$S(O)R^{20}$, —$S(O)_2R^{20}$, —$CH_2OR^{20}$, —$CH_2SR^{20}$, —$CH_2C(O)R^{20}$, —$CH_2C(S)R^{20}$, —$CH_2SO_2R^{20}$, —$NR^{21}C(O)R^{20}$, —$NR^{21}S(O)_2R^{20}$, —$NR^{22a}R^{22b}$, —$P(O)R^{22a}R^{22b}$, —$CH_2NR^{22a}R^{22b}$, —$CH_2P(O)R^{22a}R^{22b}$, and $Cy^1$.

In some embodiments, $R^{10}$ is selected from hydrogen, halogen, —CN, $C_1$-$C_6$ alkyl, $C_1$-$C_6$ haloalkyl, and $Cy^1$. In some embodiments, $R^{10}$ is selected from hydrogen, —F, —$C_1$, —CN, $C_1$-$C_4$ alkyl, $C_1$-$C_4$ haloalkyl, and $Cy^1$. In some embodiments, $R^{10}$ is selected from hydrogen, —F, —Cl, —CN, methyl, ethyl, n-propyl, isopropyl, —$CH_2F$, —$CHF_2$, —$CF_3$, —$CH_2C_1$, —$CHCl_2$, —$CCl_3$, —$CH_2CH_2F$, —$CH_2CHF_2$, —$CH_2CF_3$, —$CH_2CH_2C_1$, —$CH_2CHCl_2$, —$CH_2CCl_3$, —$CH_2CH_2CH_2F$, —$CH_2CH_2CHF_2$, —$CH_2CH_2CF_3$, —$CH_2CH_2CH_2C_1$, —$CH_2CH_2CHCl_2$, —$CH_2CH_2CCl_3$, —$CH(CH_3)CH_2F$, —$CH(CH_3)CHF_2$, —$CH(CH_3)CF_3$, —$CH(CH_3)CH_2C_1$, —$CH(CH_3)CHCl_2$, —$CH(CH_3)CCl_3$, and $Cy^1$. In some embodiments, $R^{10}$ is selected from hydrogen, —F, —Cl, —CN, methyl, ethyl, —$CH_2F$, —$CHF_2$, —$CF_3$, —$CH_2C_1$, —$CHCl_2$, —$CCl_3$, —$CH_2CH_2F$, —$CH_2CHF_2$, —$CH_2CF_3$, —$CH_2CH_2C_1$, —$CH_2CHCl_2$, —$CH_2CCl_3$, and $Cy^1$. In some embodiments, $R^{10}$ is selected from hydrogen, —F, —Cl, —CN, methyl, —$CH_2F$, —$CHF_2$, —$CF_3$, —$CH_2C_1$, —$CHCl_2$, —$CCl_3$, and $Cy^1$.

In some embodiments, $R^{10}$ is selected from hydrogen, halogen, —CN, $C_1$-$C_6$ alkyl, $C_1$-$C_6$ cyanoalkyl, and $Cy^1$. In some embodiments, $R^{10}$ is selected from hydrogen, —F, —Cl, —CN, $C_1$-$C_4$ alkyl, $C_1$-$C_4$ cyanoalkyl, and $Cy^1$. In some embodiments, $R^{10}$ is selected from hydrogen, —F, —Cl, —CN, methyl, ethyl, n-propyl, isopropyl, —$CH_2CN$, —$CH_2CH_2CN$, —$CH_2CH_2CH_2CN$, —$CH(CH_3)CH_2CN$, and $Cy^1$. In some embodiments, $R^{10}$ is selected from hydrogen, —F, —Cl, —CN, methyl, ethyl, —$CH_2CN$, —$CH_2CH_2CN$, and $Cy^1$. In some embodiments, $R^{10}$ is selected from hydrogen, —F, —Cl, —CN, methyl, —$CH_2CN$, and $Cy^1$.

In some embodiments, $R^{10}$ is selected from hydrogen, halogen, —CN, $C_1$-$C_6$ alkyl, —$OR^{20}$, —$C(O)R^{20}$, —($C_1$-$C_6$ alkyl)$OR^{20}$, —($C_1$-$C_6$ alkyl)$C(O)R^{20}$, —$NR^{21}C(O)R^{20}$, —$NR^{22a}R^{22b}$, and $Cy^1$. In some embodiments, $R^{10}$ is selected from hydrogen, —F, —Cl, —CN, $C_1$-$C_4$ alkyl, —$OR^{20}$, —$C(O)R^{20}$, —($C_1$-$C_4$ alkyl)$OR^{20}$, —($C_1$-$C_4$ alkyl)$C(O)R^{20}$, —$NR^{21}C(O)R^{20}$, and $Cy^1$. In some embodiments, $R^{10}$ is selected from hydrogen, —F, —Cl, —CN, methyl, ethyl, n-propyl, isopropyl, —$OR^{20}$, —$C(O)R^{20}$, —$CH_2OR^{20}$, —$CH_2CH_2OR^{20}$, —$CH_2CH_2CH_2OR^{20}$, —$CH(CH_3)CH_2OR^{20}$, —$CH_2C(O)R^{20}$, —$CH_2CH_2C(O)R^{20}$, —$CH_2CH_2CH_2C(O)R^{20}$, —$CH(CH_3)CH_2C(O)R^{20}$, —$NR^{21}C(O)R^{20}$, and $Cy^1$. In some embodiments, $R^{10}$ is selected from hydrogen, —F, —Cl, —CN, methyl, ethyl, —$OR^{20}$, —$C(O)R^{20}$, —$CH_2OR^{20}$, —$CH_2CH_2OR^{20}$, —$CH_2C(O)R^{20}$, —$CH_2CH_2C(O)R^{20}$, —$NR^{21}C(O)R^{20}$, and $Cy^1$. In some embodiments, $R^{10}$ is selected from hydrogen, —F, —Cl, —CN, methyl, —$OR^{20}$, —$C(O)R^{20}$, —$CH_2OR^{20}$, —$CH_2C(O)R^{20}$, —$NR^{21}C(O)R^{20}$, and $Cy^1$.

In some embodiments, $R^{10}$ is selected from hydrogen, halogen, —CN, $C_1$-$C_6$ alkyl, —$S(O)R^{20}$, —$S(O)_2R^{20}$, —($C_1$-$C_6$ alkyl)$SR^{20}$, —($C_1$-$C_6$ alkyl)$S(O)R^{20}$, —($C_1$-$C_6$ alkyl)$S(O)_2R^{20}$, —$NR^{21}S(O)_2R^{20}$, and $Cy^1$. In some embodiments, $R^{10}$ is selected from hydrogen, —F, —Cl, —CN, —$S(O)R^{20}$, —$S(O)_2R^{20}$, —($C_1$-$C_4$ alkyl)$SR^{20}$, —($C_1$-$C_4$ alkyl)$S(O)R^{20}$, —($C_1$-$C_4$ alkyl)$S(O)_2R^{20}$, —$NR^{21}S(O)_2R^{20}$, and $Cy^1$. In some embodiments, $R^{10}$ is selected from hydrogen, —F, —Cl, —CN, methyl, ethyl, n-propyl, isopropyl, —$S(O)R^{20}$, —$S(O)_2R^{20}$, —$CH_2SR^{20}$, —$CH_2CH_2SR^{20}$, —$CH_2CH_2CH_2SR^{20}$, —$CH(CH_3)CH_2SR^{20}$, —$CH_2C(S)R^{20}$, —$CH_2CH_2C(S)R^{20}$, —$CH_2CH_2CH_2C(S)R^{20}$, —$CH(CH_3)CH_2C(S)R^{20}$, $—CH_2SO_2R^{20}$, $—CH_2CH_2SO_2R^{20}$, $—CH_2CH_2CH_2SO_2R^{20}$, $—CH(CH_3)CH_2SO_2R^{20}$, $—NR^{21}S(O)_2R^{20}$, and $Cy^1$. In some embodiments, $R^{10}$ is selected from hydrogen, —F, —Cl, —CN, methyl, ethyl, $—S(O)R^{20}$, $—S(O)_2R^{20}$, $—CH_2SR^{20}$, $—CH_2CH_2SR^{20}$, $—CH_2C(S)R^{20}$, $—CH_2CH_2C(S)R^{20}$, $—CH_2SO_2R^{20}$, $—CH_2CH_2SO_2R^{20}$, $—NR^{21}S(O)_2R^{20}$, and $Cy^1$. In some embodiments, v selected from hydrogen, —F, —Cl, —CN, methyl, $—S(O)R^{20}$, $—S(O)_2R^{20}$, $—CH_2SR^{20}$, $—CH_2C(S)R^{20}$, $—CH_2SO_2R^{20}$, $—NR^{21}S(O)_2R^{20}$, and $Cy^1$.

In some embodiments, $R^{10}$ is selected from hydrogen, halogen, —CN, $—NR^{22a}R^{22b}$, $—(C_1-C_6\ alkyl)NR^{22a}R^{22b}$, and $Cy^1$. In some embodiments, $R^{10}$ is selected from hydrogen, —F, —Cl, —CN, $—NR^{22a}R^{22b}$, $—(C_1-C_6\ alkyl)NR^{22a}R^{22b}$, and $Cy^1$. In some embodiments, $R^{10}$ is selected from hydrogen, —F, —Cl, —CN, methyl, ethyl, n-propyl, isopropyl, $—NR^{22a}R^{22b}$, $—CH_2NR^{22a}R^{22b}$, $—CH_2CH_2NR^{22a}R^{22b}$, $—CH_2CH_2CH_2NR^{22a}R^{22b}$, $—CH(CH_3)CH_2NR^{22a}R^{22b}$, and $Cy^1$. In some embodiments, $R^{10}$ is selected from hydrogen, —F, —Cl, —CN, methyl, ethyl, $—NR^{22a}R^{22b}$, $—CH_2NR^{22a}R^{22b}$, $—CH_2CH_2NR^{22a}R^{22b}$, and $Cy^1$. In some embodiments, $R^{10}$ is selected from hydrogen, —F, —Cl, —CN, methyl, $—NR^{22a}R^{22b}$, $—CH_2NR^{22a}R^{22b}$, and $Cy^1$.

In some embodiments, $R^{10}$ is selected from hydrogen, halogen, —CN, $C_1-C_6$ alkyl, $—P(O)R^{22a}R^{22b}$, $—(C_1-C_6\ alkyl)P(O)R^{22a}R^{22b}$, and $Cy^1$. In some embodiments, $R^{10}$ is selected from hydrogen, —F, —Cl, —CN, $C_1-C_4$ alkyl, $—P(O)R^{22a}R^{22b}$, $—(C_1-C_6\ alkyl)P(O)R^{22a}R^{22b}$, and $Cy^1$. In some embodiments, $R^{10}$ is selected from hydrogen, —F, —Cl, —CN, methyl, ethyl, n-propyl, isopropyl, $—P(O)R^{22a}R^{22b}$, $—CH_2P(O)R^{22a}R^{22b}$, $—CH_2CH_2P(O)R^{22a}R^{22b}$, $—CH_2CH_2CH_2P(O)R^{22a}R^{22b}$, $—CH(CH_3)CH_2P(O)R^{22a}R^{22b}$, and $Cy^1$. In some embodiments, $R^{10}$ is selected from hydrogen, —F, —Cl, —CN, methyl, ethyl, $—P(O)R^{22a}R^{22b}$, $—CH_2P(O)R^{22a}R^{22b}$, $—CH_2CH_2P(O)R^{22a}R^{22b}$, and $Cy^1$. In some embodiments, $R^{10}$ is selected from hydrogen, —F, —Cl, —CN, methyl, $—P(O)R^{22a}R^{22b}$, $—CH_2P(O)R^{22a}R^{22b}$, and $Cy^1$.

In some embodiments, $R^{10}$ is selected from hydrogen, and C1-C6 alkyl. In some embodiments, $R^{10}$ is selected from hydrogen and C1-C4 alkyl. In some embodiments, $R^{10}$ is selected from hydrogen, methyl, ethyl, n-propyl, and isopropyl. In some embodiments, $R^{10}$ is selected from hydrogen, methyl, and ethyl. In some embodiments, $R^{10}$ is selected from hydrogen and ethyl. In some embodiments, $R^{10}$ is selected from hydrogen and methyl.

In some embodiments, $R^{10}$ is selected from hydrogen and halogen, In some embodiments, $R^{10}$ is selected from hydrogen, —F, —Cl, and —Br. In some embodiments, $R^{10}$ is selected from hydrogen, —F, and —Cl. In some embodiments, $R^{10}$ is selected from hydrogen and —Cl. In some embodiments, $R^{10}$ is selected from hydrogen and —F.

In some embodiments, $R^{10}$ is selected from hydrogen and $Cy^1$.

In some embodiments, $R^{10}$ is selected from hydrogen and C1-C6 haloalkyl. In further embodiments, $R^{10}$ is selected from hydrogen and C1-C4 haloalkyl. In further embodiments, $R^{10}$ is selected from hydrogen, $—CH_2F$, $—CHF_2$, $—CF_3$, $—CH_2C1$, $—CHCl_2$, $—CCl_3$, $—CH_2CH_2F$, $—CH_2CHF_2$, $—CH_2CF_3$, $—CH_2CH_2C1$, $—CH_2CHCl_2$, $—CH_2CCl_3$, $—CH_2CH_2CH_2F$, $—CH_2CH_2CHF_2$, $—CH_2CH_2CF_3$, $—CH_2CH_2CH_2C1$, $—CH_2CH_2CHCl_2$, $—CH_2CH_2CCl_3$, $—CH(CH_3)CH_2F$, $—CH(CH_3)CHF_2$, $—CH(CH_3)CF_3$, $—CH(CH_3)CH_2C1$, $—CH(CH_3)CHCl_2$, and $—CH(CH_3)CCl_3$. In further embodiments, $R^{10}$ is selected from hydrogen, $—CH_2F$, $—CHF_2$, $—CF_3$, $—CH_2C1$, $—CHCl_2$, $—CCl_3$, $—CH_2CH_2F$, $—CH_2CHF_2$, $—CH_2CF_3$, $—CH_2CH_2C1$, $—CH_2CHCl_2$, and $—CH_2CCl_3$. In further embodiments, $R^{10}$ is selected from hydrogen, $—CH_2F$, $—CHF_2$, $—CF_3$, $—CH_2C1$, $—CHCl_2$, and $—CCl_3$.

In some embodiments, $R^{10}$ is C1-C6 haloalkyl. In further embodiments, $R^{10}$ is C1-C4 haloalkyl. In further embodiments, $R^{10}$ is selected from $—CH_2F$, $—CHF_2$, $—CF_3$, $—CH_2C1$, $—CHCl_2$, $—CCl_3$, $—CH_2CH_2F$, $—CH_2CHF_2$, $—CH_2CF_3$, $—CH_2CH_2C1$, $—CH_2CHCl_2$, $—CH_2CCl_3$, $—CH_2CH_2CH_2F$, $—CH_2CH_2CHF_2$, $—CH_2CH_2CF_3$, $—CH_2CH_2CH_2C1$, $—CH_2CH_2CHCl_2$, $—CH_2CH_2CCl_3$, $—CH(CH_3)CH_2F$, $—CH(CH_3)CHF_2$, $—CH(CH_3)CF_3$, $—CH(CH_3)CH_2C1$, $—CH(CH_3)CHCl_2$, and $—CH(CH_3)CCl_3$. In further embodiments, $R^{10}$ is selected from $—CH_2F$, $—CHF_2$, $—CF_3$, $—CH_2C1$, $—CHCl_2$, $—CCl_3$, $—CH_2CH_2F$, $—CH_2CHF_2$, $—CH_2CF_3$, $—CH_2CH_2C1$, $—CH_2CHCl_2$, and $—CH_2CCl_3$. In further embodiments, $R^{10}$ is selected from $—CH_2F$, $—CHF_2$, $—CF_3$, $—CH_2C1$, $—CHCl_2$, and $—CCl_3$.

In further embodiments, $R^{10}$ is $—CF_3$.

b. $R^{20}$, $R^{21}$, $R^{22A}$, and $R^{22B}$ Groups

In some embodiments, each of $R^{20}$, $R^{21}$, $R^{22a}$, and $R^{22b}$, when present, is independently selected from hydrogen, $C_1-C_4$ alkyl, and $C_1-C_4$ haloalkyl. In some embodiments, each of $R^{20}$, $R^{21}$, $R^{22a}$, and $R^{22b}$, when present, is independently selected from hydrogen, methyl, ethyl, n-propyl, isopropyl, $—CH_2F$, $—CHF_2$, $—CF_3$, $—CH_2C_1$, $—CHCl_2$, $—CCl_3$, $—CH_2CH_2F$, $—CH_2CHF_2$, $—CH_2CF_3$, $—CH_2CH_2C_1$, $—CH_2CHCl_2$, $—CH_2CCl_3$, $—CH_2CH_2CH_2F$, $—CH_2CH_2CHF_2$, $—CH_2CH_2CF_3$, $—CH_2CH_2CH_2C_1$, $—CH_2CH_2CHCl_2$, $—CH_2CH_2CCl_3$, $—CH(CH_3)CH_2F$, $—CH(CH_3)CHF_2$, $—CH(CH_3)CF_3$, $—CH(CH_3)CH_2C_1$, $—CH(CH_3)CHCl_2$, and $—CH(CH_3)CCl_3$. In some embodiments, each of $R^{20}$, $R^{21}$, $R^{22a}$, and $R^{22b}$, when present, is independently selected from hydrogen, methyl, ethyl, $—CH_2F$, $—CHF_2$, $—CF_3$, $—CH_2C_1$, $—CHCl_2$, $—CCl_3$, $—CH_2CH_2F$, $—CH_2CHF_2$, $—CH_2CF_3$, $—CH_2CH_2C_1$, $—CH_2CHCl_2$, and $—CH_2CCl_3$. In some embodiments, each of $R^{20}$, $R^{21}$, $R^{22a}$, and $R^{22b}$, when present, is independently selected from hydrogen, methyl, $—CH_2F$, $—CHF_2$, $—CF_3$, $—CH_2C_1$, $—CHCl_2$, and $—CCl_3$.

In some embodiments, each of $R^{20}$, $R^{21}$, $R^{22a}$, and $R^{22b}$, when present, is independently selected from hydrogen and $C_1-C_4$ alkyl. In some embodiments, each of $R^{20}$, $R^{21}$, $R^{22a}$, and $R^{22b}$, when present, is independently selected from hydrogen, methyl, ethyl, n-propyl, and isopropyl. In some embodiments, each of $R^{20}$, $R^{21}$, $R^{22a}$, and $R^{22b}$, when present, is independently selected from hydrogen, methyl, and ethyl. In some embodiments, each of $R^{20}$, $R^{21}$, $R^{22a}$, and $R^{22b}$, when present, is independently selected from hydrogen and ethyl. In some embodiments, each of $R^{20}$, $R^{21}$, $R^{22a}$, and $R^{22b}$, when present, is independently selected from hydrogen and methyl.

In some embodiments, each of $R^{20}$, $R^{21}$, $R^{22a}$, and $R^{22b}$, when present, is independently selected from hydrogen and $C_1-C_4$ haloalkyl. In some embodiments, each of $R^{20}$, $R^{21}$, $R^{22a}$, and $R^{22b}$, when present, is independently selected from hydrogen, $—CH_2F$, $—CHF_2$, $—CF_3$, $—CH_2C_1$, $—CHCl_2$, $—CCl_3$, $—CH_2CH_2F$, $—CH_2CHF_2$, $—CH_2CF_3$, $—CH_2CH_2C_1$, $—CH_2CHCl_2$, $—CH_2CCl_3$, $—CH_2CH_2CH_2F$, $—CH_2CH_2CHF_2$, $—CH_2CH_2CF_3$, $—CH_2CH_2CH_2C_1$, $—CH_2CH_2CHCl_2$, $—CH_2CH_2CCl_3$, $—CH(CH_3)CH_2F$, $—CH(CH_3)CHF_2$, $—CH(CH_3)CF_3$, $—CH(CH_3)CH_2C_1$, $—CH(CH_3)CHCl_2$, and $—CH(CH_3)$ $CCl_3$. In some embodiments, each of $R^{20}$, $R^{21}$, $R^{22a}$, and $R^{22b}$, when present, is independently selected from hydrogen, —$CH_2F$, —$CHF_2$, —$CF_3$, —$CH_2C_1$, —$CHCl_2$, —$CCl_3$, —$CH_2CH_2F$, —$CH_2CHF_2$, —$CH_2CF_3$, —$CH_2CH_2C_1$, —$CH_2CHCl_2$, and —$CH_2CCl_3$. In some embodiments, each of $R^{20}$, $R^{21}$, $R^{22a}$, and $R^{22b}$, when present, is independently selected from hydrogen, —$CH_2F$, —$CHF_2$, —$CF_3$, —$CH_2C_1$, —$CHCl_2$, and —$CCl_3$.

In some embodiments, each of $R^{20}$, $R^{21}$, $R^{22a}$, and $R^{22b}$, when present, is hydrogen.

c. $R^{30A}$, $R^{30B}$, $R^{30C}$, $R^{30D}$, and $R^{30E}$ Groups

In some embodiments, each of $R^{30a}$, $R^{30b}$, $R^{30c}$, $R^{30d}$, and $R^{30e}$ is independently selected from hydrogen, halogen, C1-C6 alkyl, C1-C6 haloalkyl, C1-C6 alkoxy, and C1-C6 haloalkoxy, provided that at least two of $R^{30a}$, $R^{30b}$, $R^{30c}$, $R^{30d}$, and $R^{30e}$ are hydrogen. In some embodiments, each of $R^{30a}$, $R^{30b}$, $R^{30c}$, $R^{30d}$, and $R^{30e}$ is independently selected from hydrogen, halogen, C1-C4 alkyl, C1-C4 haloalkyl, C1-C4 alkoxy, and C1-C4 haloalkoxy. In some embodiments, each of $R^{30a}$, $R^{30b}$, $R^{30c}$, $R^{30d}$, and $R^{30e}$ is independently selected from hydrogen, —F, —Cl, methyl, ethyl, n-propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2CH_2F$, —$CH_2CH_2CHF_2$, —$CH_2CH_2CF_3$, —$CH_2CH_2CH_2Cl$, —$CH_2CH_2CHCl_2$, —$CH_2CH_2CCl_3$, —$CH(CH_3)CH_2F$, —$CH(CH_3)CHF_2$, —$CH(CH_3)CF_3$, —$CH(CH_3)CH_2Cl$, —$CH(CH_3)CHCl_2$, —$CH(CH_3)CCl_3$, —$OCH_3$, —$OCH_2CH_3$, —$OCH_2CH_2CH_3$, —$OCH(CH_3)CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2CH_2F$, —$OCH_2CH_2CHF_2$, —$OCH_2CH_2CF_3$, —$OCH_2CH_2CH_2Cl$, —$OCH_2CH_2CHCl_2$, —$OCH_2CH_2CCl_3$, —$OCH(CH_3)CH_2F$, —$OCH(CH_3)CHF_2$, —$OCH(CH_3)CF_3$, —$OCH(CH_3)CH_2Cl$, —$OCH(CH_3)CHCl_2$, and —$OCH(CH_3)CCl_3$. In some embodiments, each of $R^{30a}$, $R^{30b}$, $R^{30c}$, $R^{30d}$, and $R^{30e}$ is independently selected from hydrogen, —F, —Cl, methyl, ethyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$OCH_3$, —$OCH_2CH_3$, —$OCH_2F$, —$OCHF_2$, —$OCF_3$, —$OCH_2Cl$, —$OCHCl_2$, —$OCCl_3$, —$OCH_2CH_2F$, —$OCH_2CHF_2$, —$OCH_2CF_3$, —$OCH_2CH_2Cl$, —$OCH_2CHCl_2$, and —$OCH_2CCl_3$. In some embodiments, each of $R^{30a}$, $R^{30b}$, $R^{30c}$, $R^{30d}$, and $R^{30e}$ is independently selected from hydrogen, —F, —Cl, methyl, —$CH_2F$, —$CHF_2$, —$CF_3$, —$CH_2Cl$, —$CHCl_2$, —$CCl_3$, —$OCH_3$, —$OCH_2F$, —$OCHF_2$, —$OCF_3$, —$OCH_2Cl$, —$OCHCl_2$, and —$OCCl_3$.

In some embodiments, each of $R^{30a}$, $R^{30b}$, $R^{30c}$, $R^{30d}$, and $R^{30e}$ is independently selected from hydrogen, halogen, C1-C6 alkyl, and C1-C6 haloalkyl, provided that at least two of $R^{30a}$, $R^{30b}$, $R^{30c}$, $R^{30d}$, and $R^{30e}$ are hydrogen. In some embodiments, each of $R^{30a}$, $R^{30b}$, $R^{30c}$, $R^{30d}$, and $R^{30e}$ is independently selected from hydrogen, halogen, C1-C4 alkyl, and C1-C4 haloalkyl. In some embodiments, each of $R^{30a}$, $R^{30b}$, $R^{30c}$, $R^{30d}$, and $R^{30e}$ is independently selected from hydrogen, —F, —Cl, methyl, ethyl, n-propyl, isopropyl, —$CH_2F$, —$CHF_2$, —$CF_3$, —$CH_2Cl$, —$CHCl_2$, —$CCl_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2CH_2F$, —$CH_2CH_2CHF_2$, —$CH_2CH_2CF_3$, —$CH_2CH_2CH_2Cl$, —$CH_2CH_2CHCl_2$, —$CH_2CH_2CCl_3$, —$CH(CH_3)CH_2F$, —$CH(CH_3)CHF_2$, —$CH(CH_3)CF_3$, —$CH(CH_3)CH_2Cl$, —$CH(CH_3)CHCl_2$, and —$CH(CH_3)CCl_3$. In some embodiments, each of $R^{30a}$, $R^{30b}$, $R^{30c}$, $R^{30d}$, and $R^{30e}$ is independently selected from hydrogen, —F, —Cl, methyl, ethyl, —$CH_2F$, —$CHF_2$, —$CF_3$, —$CH_2C1$, —$CHCl_2$, —$CCl_3$, —$CH_2CH_2F$, —$CH_2CHF_2$, —$CH_2CF_3$, —$CH_2CH_2C1$, —$CH_2CHCl_2$, and —$CH_2CCl_3$. In some embodiments, each of $R^{30a}$, $R^{30b}$, $R^{30c}$, $R^{30d}$, and $R^{30e}$ is independently selected from hydrogen, —F, —Cl, methyl, —$CH_2F$, —$CHF_2$, —$CF_3$, —$CH_2C1$, —$CHCl_2$, and —$CCl_3$.

In some embodiments, each of $R^{30a}$, $R^{30b}$, $R^{30c}$, $R^{30d}$, and $R^{30e}$ is independently selected from hydrogen, C1-C6 alkoxy, and C1-C6 haloalkoxy, provided that at least two of $R^{30a}$, $R^{30b}$, $R^{30c}$, $R^{30d}$, and $R^{30e}$ are hydrogen. In some embodiments, each of $R^{30a}$, $R^{30b}$, $R^{30c}$, $R^{30d}$, and $R^{30e}$ is independently selected from hydrogen, C1-C4 alkoxy, and C1-C4 haloalkoxy. In some embodiments, each of $R^{30a}$, $R^{30b}$, $R^{30c}$, $R^{30d}$, and $R^{30e}$ is independently selected from hydrogen, —$OCH_3$, —$OCH_2CH_3$, —$OCH_2CH_2CH_3$, —$OCH(CH_3)CH_3$, —$OCH_2F$, —$OCHF_2$, —$OCF_3$, —$OCH_2C1$, —$OCHCl_2$, —$OCCl_3$, —$OCH_2CH_2F$, —$OCH_2CHF_2$, —$OCH_2CF_3$, —$OCH_2CH_2C1$, —$OCH_2CHCl_2$, —$OCH_2CCl_3$, —$OCH_2CH_2CH_2F$, —$OCH_2CH_2CHF_2$, —$OCH_2CH_2CF_3$, —$OCH_2CH_2CH_2C1$, —$OCH_2CH_2CHCl_2$, —$OCH_2CH_2CCl_3$, —$OCH(CH_3)CH_2F$, —$OCH(CH_3)CHF_2$, —$OCH(CH_3)CF_3$, —$OCH(CH_3)CH_2C1$, —$OCH(CH_3)CHCl_2$, and —$OCH(CH_3)CCl_3$. In some embodiments, each of $R^{30a}$, $R^{30b}$, $R^{30c}$, $R^{30d}$, and $R^{30e}$ is independently selected from hydrogen, —$OCH_3$, —$OCH_2CH_3$, —$OCH_2F$, —$OCHF_2$, —$OCF_3$, —$OCH_2C1$, —$OCHCl_2$, —$OCCl_3$, —$OCH_2CH_2F$, —$OCH_2CHF_2$, —$OCH_2CF_3$, —$OCH_2CH_2C1$, —$OCH_2CHCl_2$, and —$OCH_2CCl_3$. In some embodiments, each of $R^{30a}$, $R^{30b}$, $R^{30c}$, $R^{30d}$, and $R^{30e}$ is independently selected from hydrogen, —$OCH_3$, —$OCH_2F$, —$OCHF_2$, —$OCF_3$, —$OCH_2C1$, —$OCHCl_2$, and —$OCCl_3$.

In some embodiments, each of $R^{30a}$, $R^{30b}$, $R^{30c}$, $R^{30d}$, and $R^{30e}$ is independently selected from hydrogen and C1-C6 alkyl, provided that at least two of $R^{30a}$, $R^{30b}$, $R^{30c}$, $R^{30d}$, and $R^{30e}$ are hydrogen. In some embodiments, each of $R^{30a}$, $R^{30b}$, $R^{30c}$, $R^{30d}$, and $R^{30e}$ is independently selected from hydrogen and C1-C4 alkyl. In some embodiments, each of $R^{30a}$, $R^{30b}$, $R^{30c}$, $R^{30d}$, and $R^{30e}$ is independently selected from hydrogen, methyl, ethyl, n-propyl, and isopropyl. In some embodiments, each of $R^{30a}$, $R^{30b}$, $R^{30c}$, $R^{30d}$, and $R^{30e}$ is independently selected from hydrogen, methyl, and ethyl. In some embodiments, each of $R^{30a}$, $R^{30b}$, $R^{30c}$, $R^{30d}$, and $R^{30e}$ is independently selected from hydrogen and ethyl. In some embodiments, each of $R^{30a}$, $R^{30b}$, $R^{30c}$, $R^{30d}$, and $R^{30e}$ is independently selected from hydrogen and methyl.

In some embodiments, each of $R^{30a}$, $R^{30b}$, $R^{30c}$, $R^{30d}$, and $R^{30e}$ is independently selected from hydrogen, and C1-C6 haloalkyl, provided that at least two of $R^{30a}$, $R^{30b}$, $R^{30c}$, $R^{30d}$, and $R^{30e}$ are hydrogen. In some embodiments, each of $R^{30a}$, $R^{30b}$, $R^{30c}$, $R^{30d}$, and $R^{30e}$ is independently selected from hydrogen, and C1-C4 haloalkyl. In some embodiments, each of $R^{30a}$, $R^{30b}$, $R^{30c}$, $R^{30d}$, and $R^{30e}$ is independently selected from hydrogen, —$CH_2F$, —$CHF_2$, —$CF_3$, —$CH_2C1$, —$CHCl_2$, —$CCl_3$, —$CH_2CH_2F$, —$CH_2CHF_2$, —$CH_2CF_3$, —$CH_2CH_2C1$, —$CH_2CHCl_2$, —$CH_2CCl_3$, —$CH_2CH_2CH_2F$, —$CH_2CH_2CHF_2$, —$CH_2CH_2CF_3$, —$CH_2CH_2CH_2C1$, —$CH_2CH_2CHCl_2$, —$CH_2CH_2CCl_3$, —$CH(CH_3)CH_2F$, —$CH(CH_3)CHF_2$, —$CH(CH_3)CF_3$, —$CH(CH_3)CH_2C1$, —$CH(CH_3)CHCl_2$, and —$CH(CH_3)CCl_3$. In some embodiments, each of $R^{30a}$, $R^{30b}$, $R^{30c}$, $R^{30d}$, and $R^{30e}$ is independently selected from hydrogen, —$CH_2F$, —$CHF_2$, —$CF_3$, —$CH_2C1$, —$CHCl_2$, —$CCl_3$, —$CH_2CH_2F$, —$CH_2CHF_2$, —$CH_2CF_3$, —$CH_2CH_2C1$, —$CH_2CHCl_2$, and —$CH_2CCl_3$. In some embodiments, each of $R^{30a}$, $R^{30b}$, $R^{30c}$, $R^{30d}$, and $R^{30e}$ is independently selected from hydrogen, —$CH_2F$, —$CHF_2$, —$CF_3$, —$CH_2Cl$, —$CHCl_2$, and —$CCl_3$.

In some embodiments, each of $R^{30a}$, $R^{30b}$, $R^{30c}$, $R^{30d}$, and $R^{30e}$ is independently selected from hydrogen and halogen. In some embodiments, each of $R^{30a}$, $R^{30b}$, $R^{30c}$, $R^{30d}$, and $R^{30e}$ is independently selected from hydrogen, —F, —Cl, and —Br. In some embodiments, each of $R^{30a}$, $R^{30b}$, $R^{30c}$, $R^{30d}$, and $R^{30e}$ is independently selected from hydrogen, —F, and —Cl. each of $R^{30a}$, $R^{30b}$, $R^{30c}$, $R^{30d}$, and $R^{30e}$ is independently selected from hydrogen and —Cl. In some embodiments, each of $R^{30a}$, $R^{30b}$, $R^{30c}$, $R^{30d}$, and $R^{30e}$ is independently selected from hydrogen and —F.

In some embodiments, each of $R^{30a}$, $R^{30b}$, $R^{30c}$, $R^{30d}$, and $R^{30e}$ is hydrogen.

d. $Cy^1$ Groups

In some embodiments, $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C3-C8 cycloalkyl, a 3- to 8-membered heterocycloalkyl, a C6-C10 aryl, and a 5- to 10-membered heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C3-C8 cycloalkyl, a 3- to 8-membered heterocycloalkyl, a C6-C10 aryl, and a 5- to 10-membered heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C3-C8 cycloalkyl, a 3- to 8-membered heterocycloalkyl, a C6-C10 aryl, and a 5- to 10-membered heteroaryl, and is unsubstituted.

In some embodiments, $Cy^1$, when present, is selected from a C3-C8 cycloalkyl and a 3- to 8-membered heterocycloalkyl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C3-C8 cycloalkyl and a 3- to 8-membered heterocycloalkyl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C3-C8 cycloalkyl and a 3- to 8-membered heterocycloalkyl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C3-C8 cycloalkyl and a 3- to 8-membered heterocycloalkyl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C3-C8 cycloalkyl and a 3- to 8-membered heterocycloalkyl, and is unsubstituted.

In some embodiments, $Cy^1$, when present, is a C3-C8 cycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C3-C8 cycloalkyls include, but are not limited to, cyclobutyl, cyclopentyl, cyclohexyl, and spiro[2.4]heptane. In some embodiments, $Cy^1$, when present, is a C3-C8 cycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is a C3-C8 cycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is a C3-C8 cycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is an unsubstituted C3-C8 cycloalkyl.

In some embodiments, $Cy^1$, when present, is a 3- to 8-membered heterocycloalkyl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of 3- to 8-membered heterocycloalkyls include, but are not limited to, tetrahydrofuran, pyrrolidine, tetrahydrothiophene, piperidine, piperazine, tetrahydropyran, thiane, 1,3-dithiane, 1,4-dithiane, thiomorpholine, dioxane, morpholine, and hexahydro-1H-furo[3,4-c]pyrrole. In some embodiments, $Cy^1$, when present, is a 3- to 8-membered heterocycloalkyl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is a 3- to 8-membered heterocycloalkyl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is a 3- to 8-membered heterocycloalkyl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is an unsubstituted 3- to 8-membered heterocycloalkyl.

In some embodiments, $Cy^1$, when present, is selected from a C6-C10 aryl and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C6-C10 aryl and a 5- to 10-membered heteroaryl, and is substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C6-C10 aryl and a 5- to 10-membered heteroaryl, and is substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C6-C10 aryl and a 5- to 10-membered heteroaryl, and is monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is selected from a C6-C10 aryl and a 5- to 10-membered heteroaryl, and is unsubstituted.

In some embodiments, $Cy^1$, when present, is a C6-C10 aryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of C6-C10 aryls include, but are not limited to, phenyl and naphthyl.

In some embodiments, $Cy^1$, when present, is a C6-C10 aryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is a C6-C10 aryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is a C6-C10 aryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is unsubstituted C6-C10 aryl.

In some embodiments, $Cy^1$, when present, is a 5- to 10-membered heteroaryl substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. Examples of 5- to 10-membered heteroaryls include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl. In some embodiments, $Cy^1$, when present, is a 5- to 10-membered heteroaryl substituted with 0, 1, or 2 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is a 5- to 10-membered heteroaryl substituted with 0 or 1 group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is a 5- to 10-membered heteroaryl monosubstituted with a group selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In some embodiments, $Cy^1$, when present, is unsubstituted 5- to 10-membered heteroaryl.

e. $Ar^2$ Groups

In some embodiments, $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy. In some embodiments, $Ar^2$ is a C6-C10 aryl or a 5- to 6-membered heteroaryl, and is substituted with 0, 1, or 2 groups independently selected from halogen, C1-C6 alkyl, C1-C6 haloalkyl, C1-C6 alkoxy, and C1-C6 haloalkoxy. In some embodiments, $Ar^2$ is a C6-C10 aryl or a 5- to 6-membered heteroaryl, and is substituted with 0 or 1 group selected from halogen, C1-C6 alkyl, C1-C6 haloalkyl, C1-C6 alkoxy, and C1-C6 haloalkoxy. In some embodiments, $Ar^2$ is a C6-C10 aryl or a 5- to 6-membered heteroaryl, and is monosubstituted with a group selected from halogen, C1-C6 alkyl, C1-C6 haloalkyl, C1-C6 alkoxy, and C1-C6 haloalkoxy. In some embodiments, $Ar^2$ is a C6-C10 aryl or a 5- to 6-membered heteroaryl, and is unsubstituted.

In some embodiments, $Ar^2$ is a C6-C10 aryl substituted with 0, 1, 2, or 3 groups independently selected from halogen, C1-C6 alkyl, C1-C6 haloalkyl, C1-C6 alkoxy, and C1-C6 haloalkoxy. Examples of C6-C10 aryls include, but are not limited to, phenyl and naphthyl. In some embodiments, $Ar^2$ is a C6-C10 aryl substituted with 0, 1, or 2 groups independently selected from halogen, C1-C6 alkyl, C1-C6 haloalkyl, C1-C6 alkoxy, and C1-C6 haloalkoxy. In some embodiments, $Ar^2$ is a C6-C10 aryl substituted with 0 or 1 group selected from halogen, C1-C6 alkyl, C1-C6 haloalkyl, C1-C6 alkoxy, and C1-C6 haloalkoxy. In some embodiments, $Ar^2$ is a C6-C10 aryl monosubstituted with a group selected from halogen, C1-C6 alkyl, C1-C6 haloalkyl, C1-C6 alkoxy, and C1-C6 haloalkoxy. In some embodiments, $Ar^2$ is an unsubstituted C6-C10 aryl.

In some embodiments, $Ar^2$ is phenyl substituted with 0, 1, 2, or 3 groups independently selected from halogen, C1-C6 alkyl, C1-C6 haloalkyl, C1-C6 alkoxy, and C1-C6 haloalkoxy. In some embodiments, $Ar^2$ is phenyl substituted with 0, 1, or 2 groups independently selected from halogen, C1-C6 alkyl, C1-C6 haloalkyl, C1-C6 alkoxy, and C1-C6 haloalkoxy. In some embodiments, $Ar^2$ is phenyl substituted with 0 or 1 group selected from halogen, C1-C6 alkyl, C1-C6 haloalkyl, C1-C6 alkoxy, and C1-C6 haloalkoxy. In some embodiments, $Ar^2$ is phenyl monosubstituted with a group selected from halogen, C1-C6 alkyl, C1-C6 haloalkyl, C1-C6 alkoxy, and C1-C6 haloalkoxy. In some embodiments, $Ar^2$ is an unsubstituted phenyl.

In some embodiments, $Ar^2$ is a 5- to 6-membered heteroaryl substituted with 0, 1, 2, or 3 groups independently selected from halogen, C1-C6 alkyl, C1-C6 haloalkyl, C1-C6 alkoxy, and C1-C6 haloalkoxy. Examples of 5- to 6-membered heteroaryls include, but are not limited to, furyl, imidazolyl, pyrimidinyl, tetrazolyl, thienyl, pyridinyl, pyrrolyl, N-methylpyrrolyl, pyrazolyl, triazolyl, thiazolyl, oxazolyl, isoxazolyl, oxadiazolyl, thiadiazolyl, isothiazolyl, pyridazinyl, and pyrazinyl. In some embodiments, $Ar^2$ is a 5- to 6-membered heteroaryl substituted with 0, 1, or 2 groups independently selected from halogen, C1-C6 alkyl, C1-C6 haloalkyl, C1-C6 alkoxy, and C1-C6 haloalkoxy. In some embodiments, $Ar^2$ is a 5- to 6-membered heteroaryl substituted with 0 or 1 group selected from halogen, C1-C6 alkyl, C1-C6 haloalkyl, C1-C6 alkoxy, and C1-C6 haloalkoxy. In some embodiments, $Ar^2$ is a 5- to 6-membered heteroaryl monosubstituted with a group selected from halogen, C1-C6 alkyl, C1-C6 haloalkyl, C1-C6 alkoxy, and C1-C6 haloalkoxy. In some embodiments, $Ar^2$ is an unsubstituted 5- to 6-membered heteroaryl.

In some embodiments, $Ar^2$ is pyridinyl substituted with 0, 1, 2, or 3 groups independently selected from halogen, C1-C6 alkyl, C1-C6 haloalkyl, C1-C6 alkoxy, and C1-C6 haloalkoxy. In some embodiments, $Ar^2$ is pyridinyl substituted with 0, 1, or 2 groups independently selected from halogen, C1-C6 alkyl, C1-C6 haloalkyl, C1-C6 alkoxy, and C1-C6 haloalkoxy. In some embodiments, $Ar^2$ is pyridinyl substituted with 0 or 1 group selected from halogen, C1-C6 alkyl, C1-C6 haloalkyl, C1-C6 alkoxy, and C1-C6 haloalkoxy. In some embodiments, $Ar^2$ is pyridinyl monosubstituted with a group selected from halogen, C1-C6 alkyl, C1-C6 haloalkyl, C1-C6 alkoxy, and C1-C6 haloalkoxy. In some embodiments, $Ar^2$ is an unsubstituted pyridinyl.

2. Example Pyrazolo[1,5-A]pyrimidine Compounds

In some embodiments, a compound can be present as one or more of the following structures:

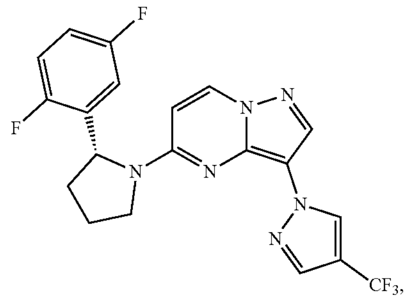

or a pharmaceutically acceptable salt thereof.

C. COMPOUNDS OF FORMULA (XVI)

In various embodiments, disclosed are compounds of formula (XVI) useful in the disclosed methods. It is understood that a disclosed compound can be provided by the disclosed methods.

In various embodiments, the disclosed compounds of formula (XVI) are useful as intermediates in the synthesis of pyrazolo[1,5-a]pyrimidine compounds useful as TRK inhibitors.

1. Structure

In some embodiments, the present disclosure provides compounds having the structure represented by formula (XVI):

(XVI)

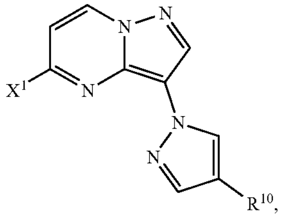

wherein $X^1$ is a leaving group; wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a salt thereof.

In some embodiments, the compound of formula (XVI) is selected from:
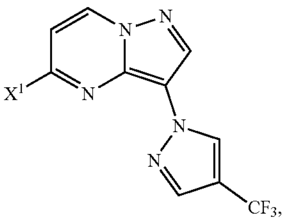
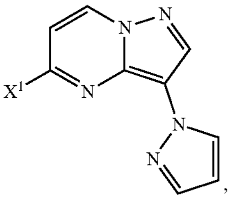
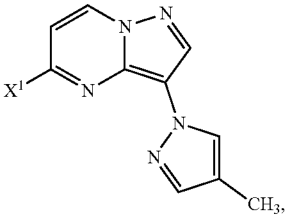
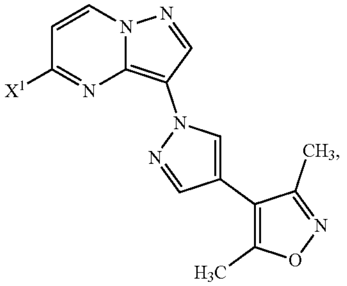
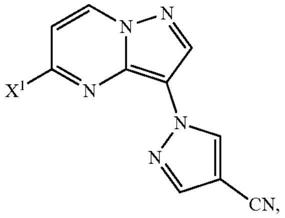
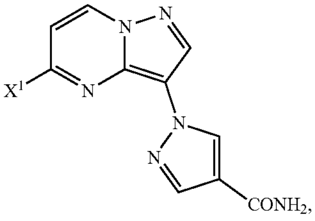
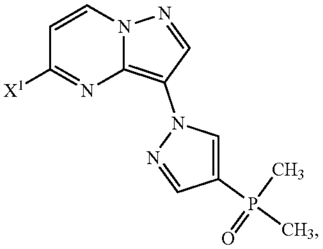
-continued
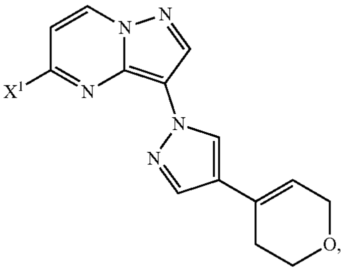
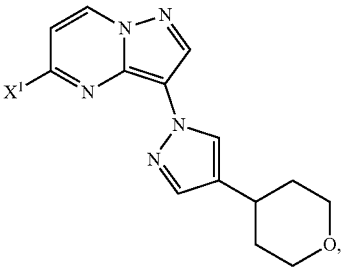
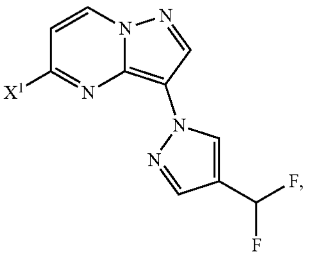
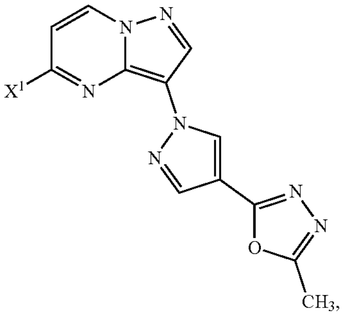
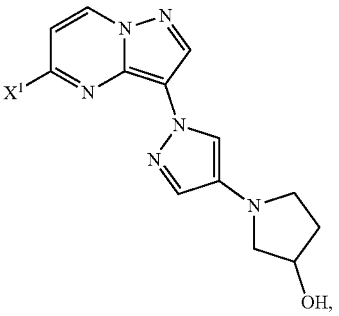
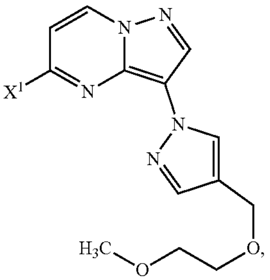

-continued
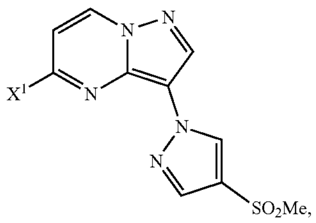
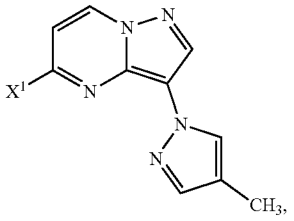
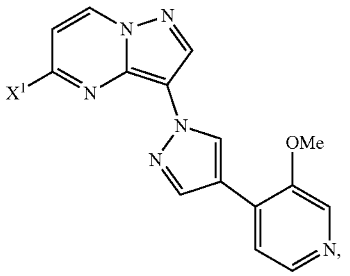
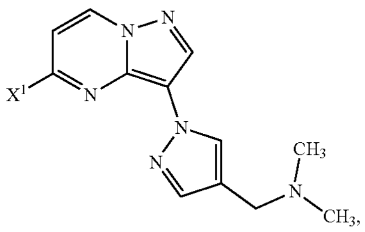
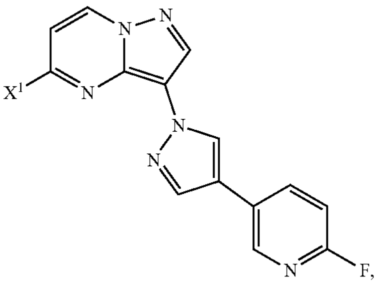
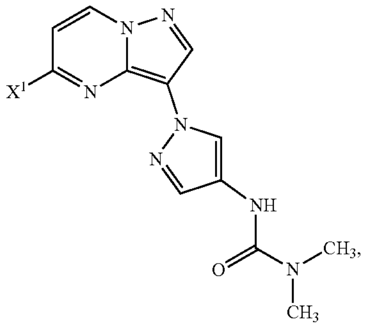
-continued
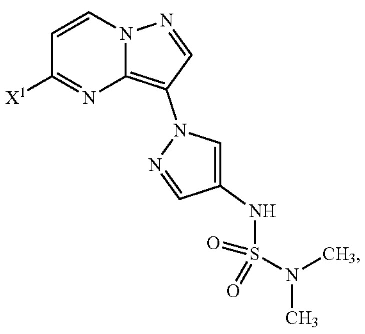
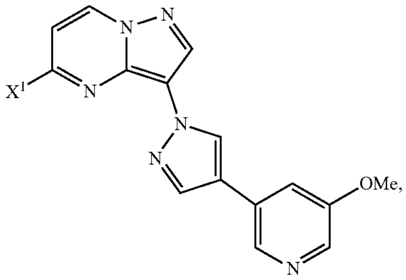
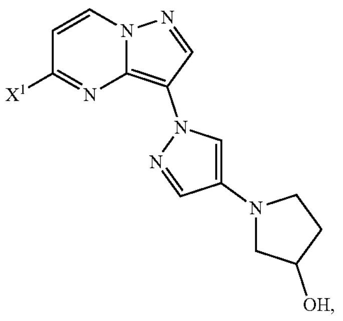
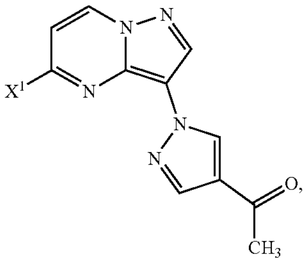
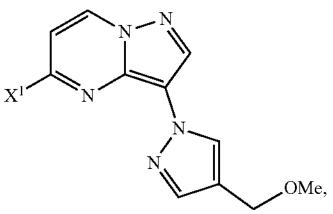
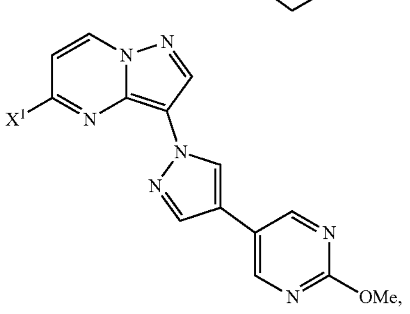

-continued
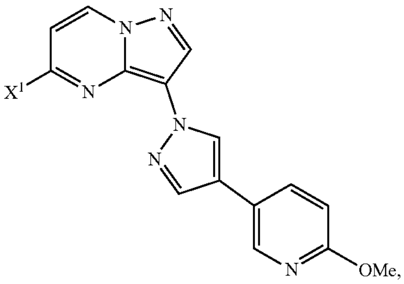
,
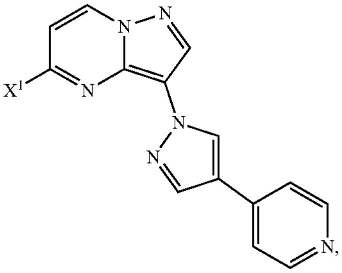
,
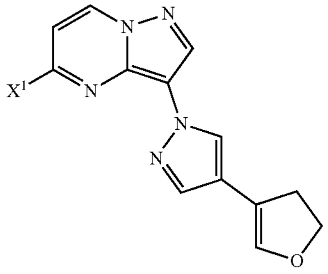
,
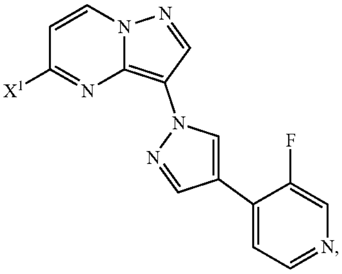
,
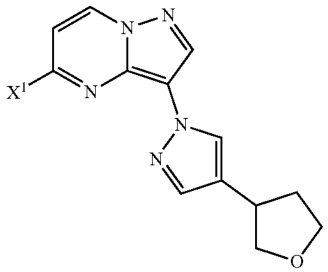
,
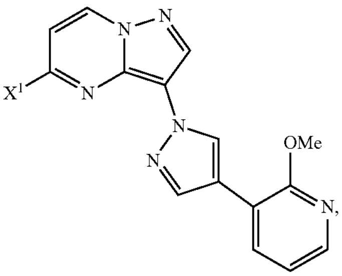
,
-continued
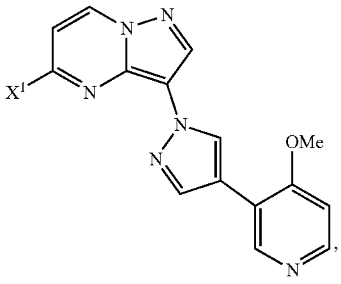
,
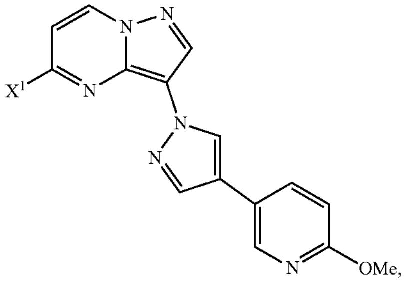
,
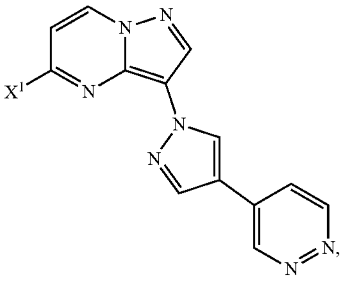
,
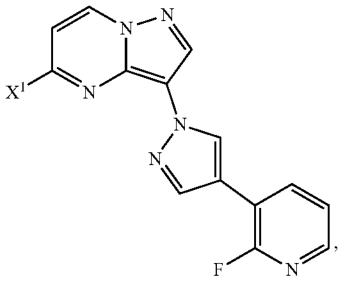
,
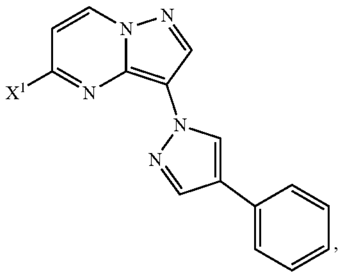
,
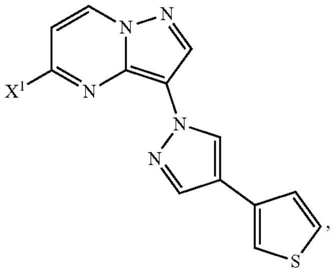
, -continued
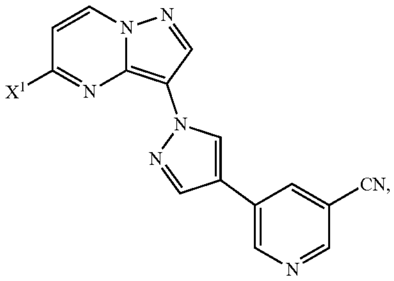
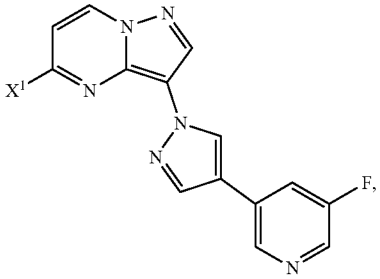
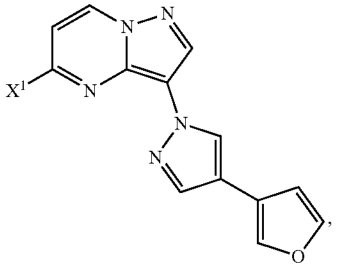
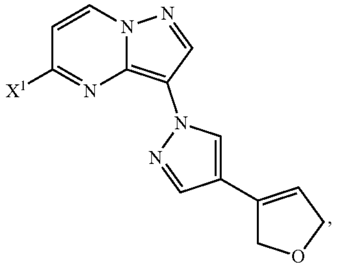
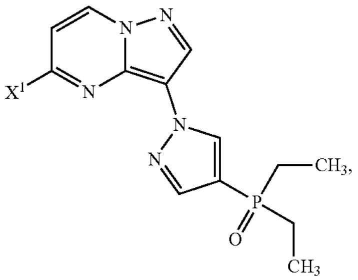
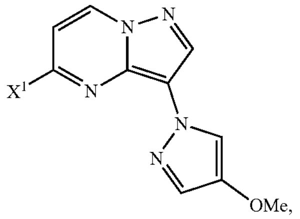
-continued
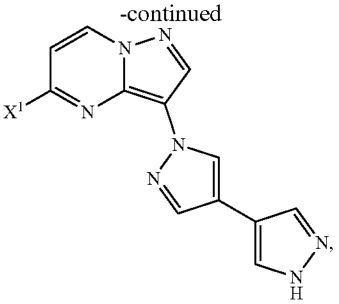
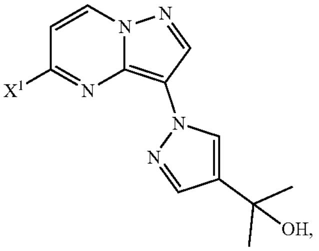
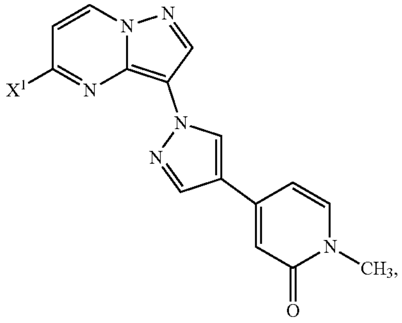
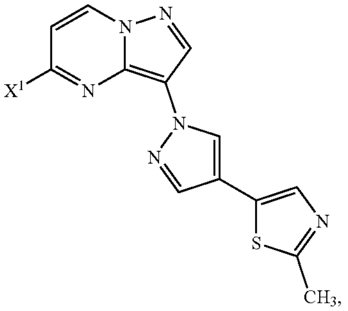
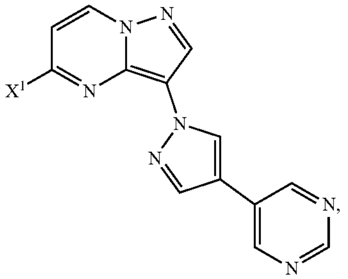
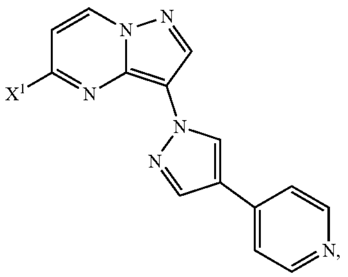

-continued

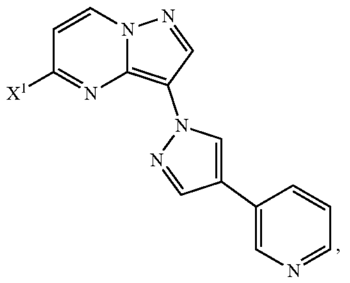

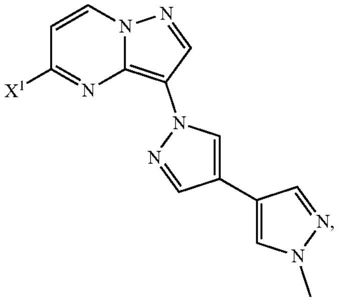

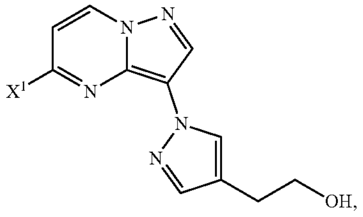

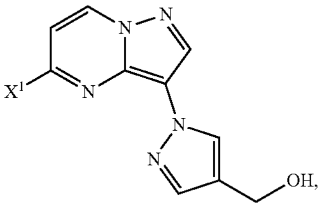

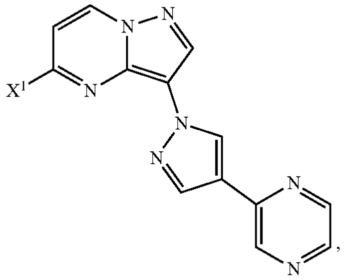

and

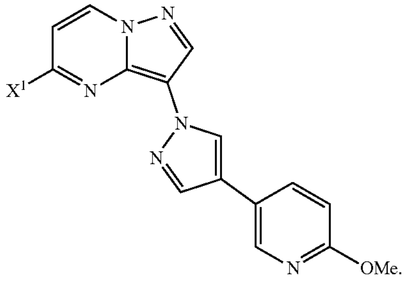

In some embodiments, the compound of formula (XVI) has the structure:

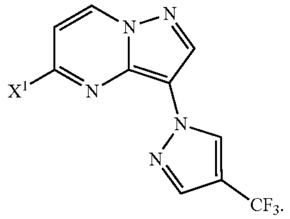

In some embodiments, $X^1$ is a leaving group. Examples of leaving groups include, but are not limited to, halides, alkyl halides (e.g., trifluoromethyl), and sulfonate esters, (e.g., triflate, mesylate, tosylate, brosylate). In further embodiments, $X^1$ is a halide. In still further embodiments, $X^1$ is fluoride, chloride, or bromide. In yet further embodiments, $X^1$ is fluoride or chloride. In even further embodiments, $X^1$ is chloride or bromide. In still further embodiments, $X^1$ is bromide or iodide. In even further embodiments, $X^1$ is chloride.

2. Example Compounds of Formula (XVI)

In some embodiments, the compound has the following structure:

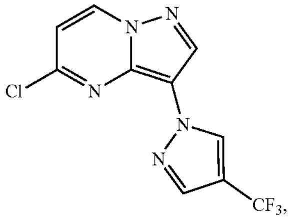 [SMILES: FC(F)(F)c1cnn(-c2cnn3ccc(Cl)nc23)c1]

or a pharmaceutically acceptable salt thereof.

D. AMIDES OF FORMULA (XVIII)

In various embodiments, disclosed are amides of formula (XVIII) useful in the disclosed methods. It is understood that a disclosed compound can be provided by the disclosed methods.

In various embodiments, the disclosed amides of formula (XVIII) are useful as intermediates in the synthesis of pyrazolo[1,5-a]pyrimidine compounds useful as TRK inhibitors.

1. Structure

In some embodiments, the present disclosure provides compounds having the structure represented by formula (XVIII):

(XVIII)

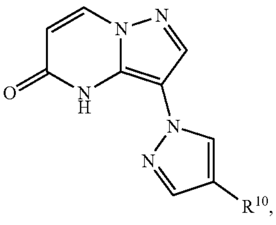

wherein $R^{10}$ is selected from hydrogen, halogen, —CN, C1-C6 alkyl, C1-C6 haloalkyl, C1-C6 cyanoalkyl, —$OR^{20}$, —C(O)$R^{20}$, —S(O)$R^{20}$, —$S(O)_2R^{20}$, —(C1-C6 alkyl)$OR^{20}$, —(C1-C6 alkyl)$SR^{20}$, —(C1-C6 alkyl)C(O)$R^{20}$, —(C1-C6 alkyl)S(O)$R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —P(O)$R^{22a}R^{22b}$, —(C1-C6 alkyl)$NR^{22a}R^{22b}$, —(C1-C6 alkyl)P(O)$R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a salt thereof.

In some embodiments, the compound of formula (XVIII) is selected from:

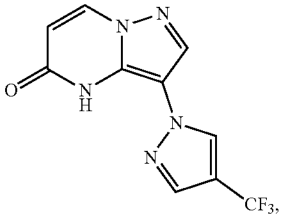

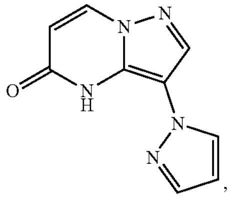

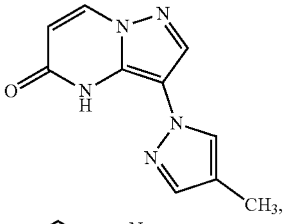

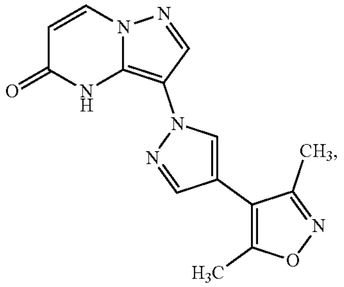

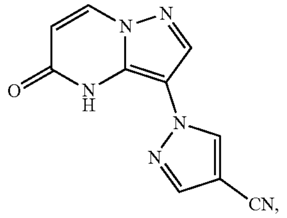

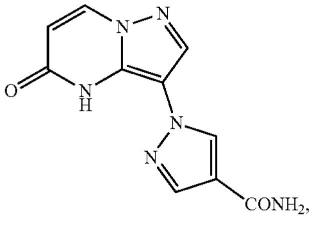

-continued

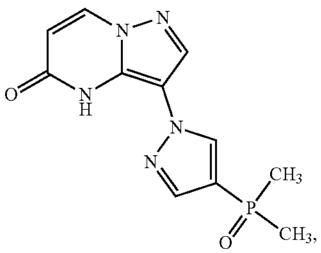

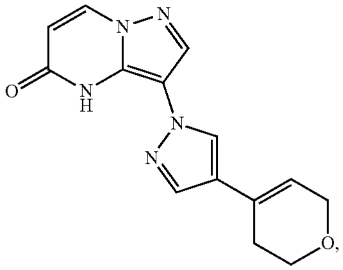

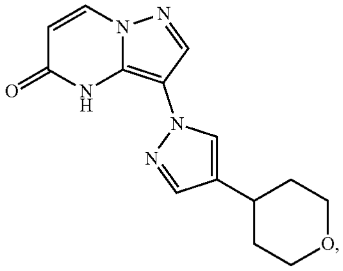

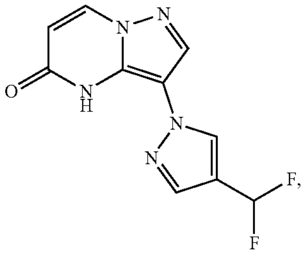

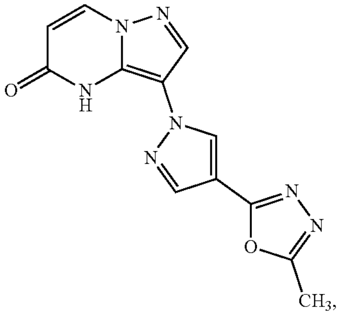

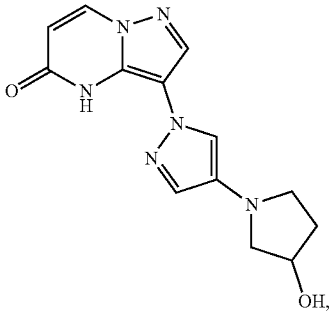

-continued
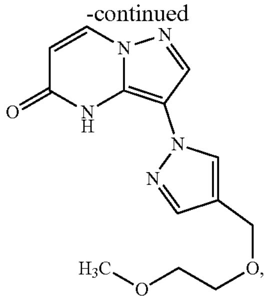
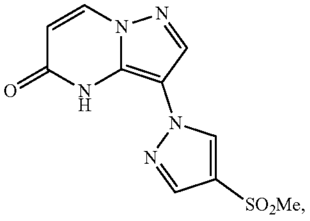
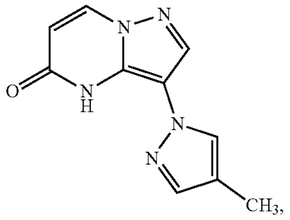
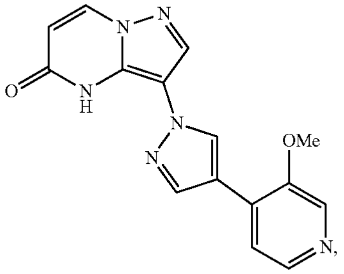
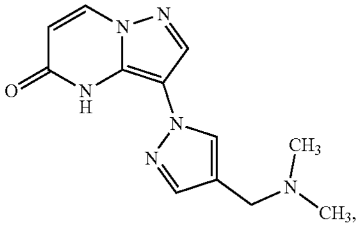
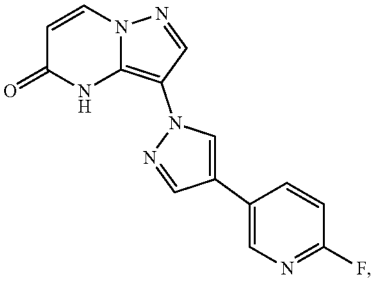
-continued
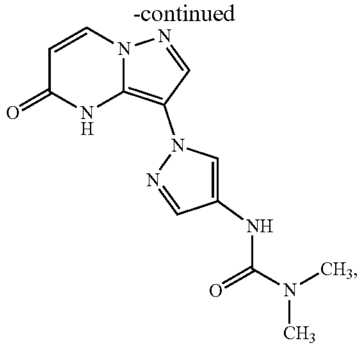
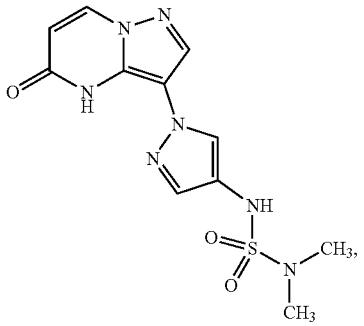
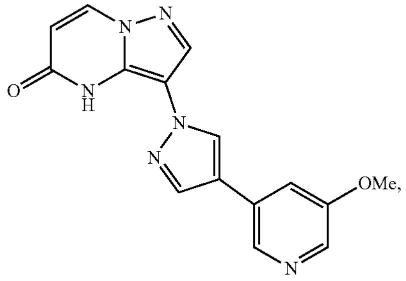
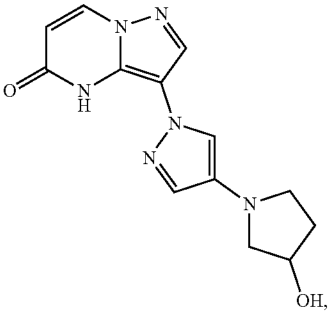
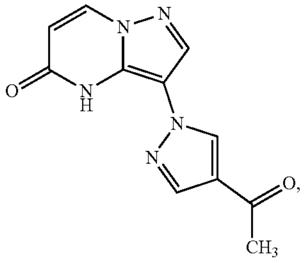
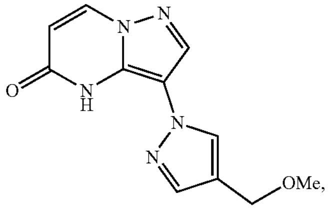

-continued
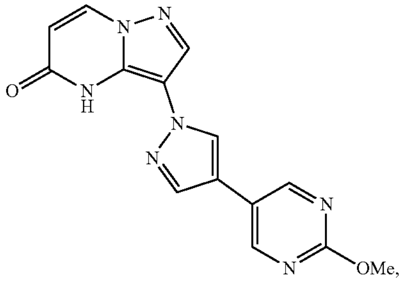
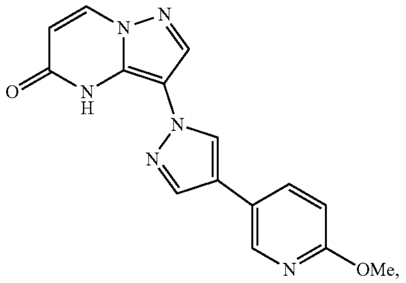
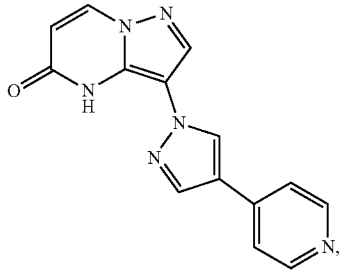
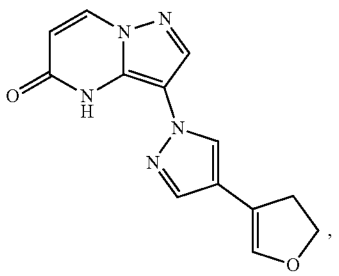
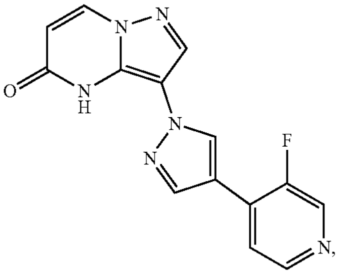
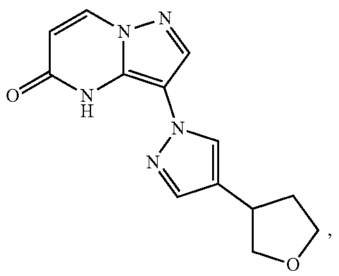
-continued
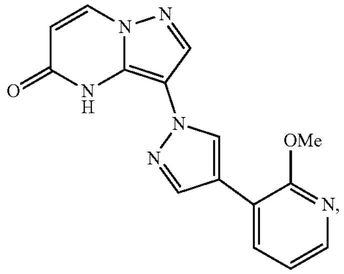
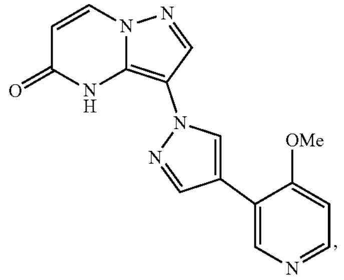
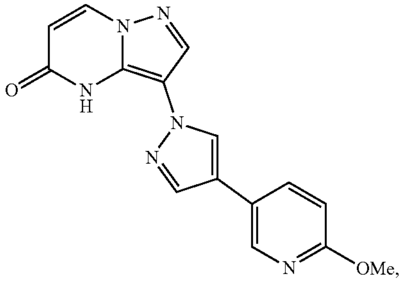
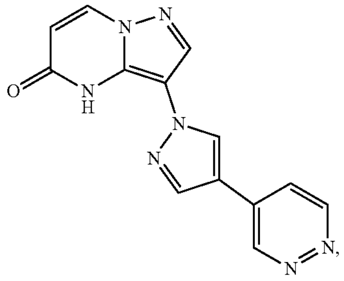
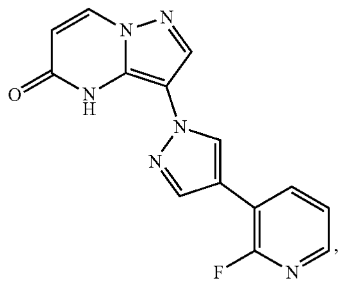
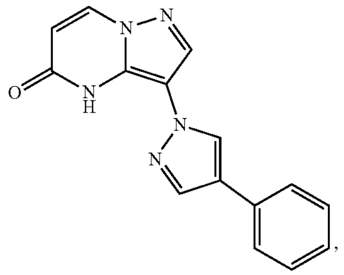

-continued
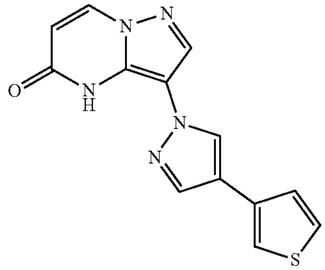
,
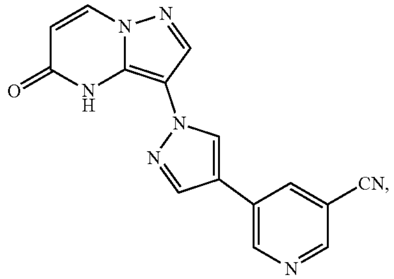
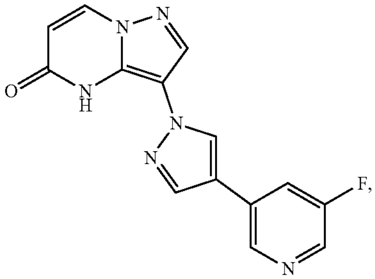
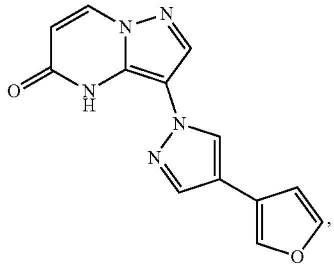
,
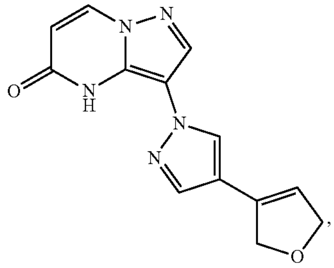
,
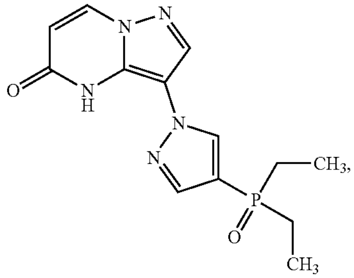
-continued
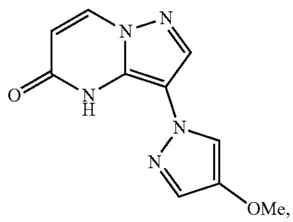
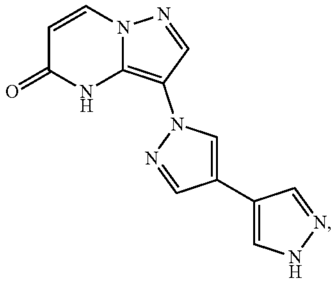
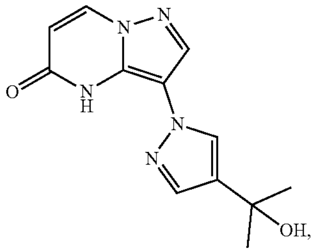
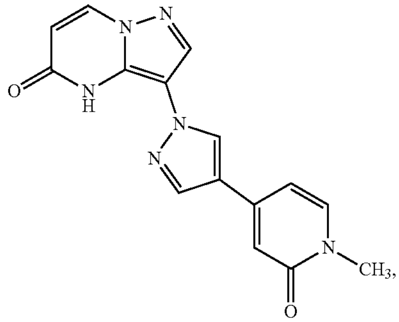
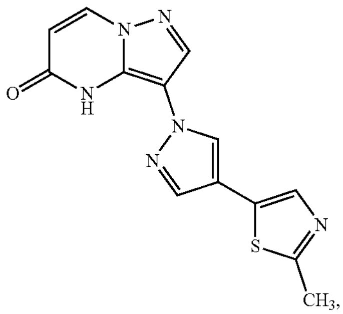
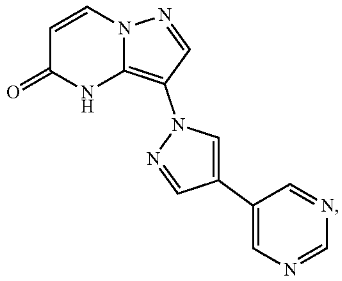

-continued

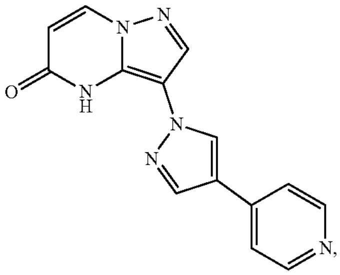

,

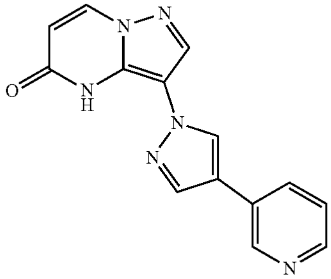

,

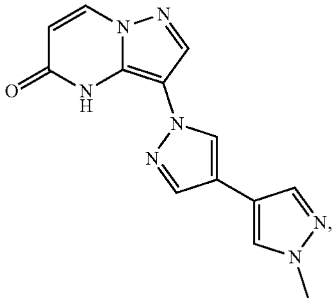

,

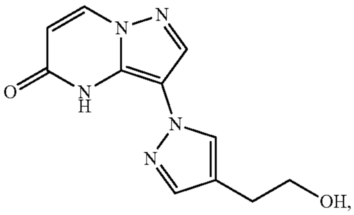

,

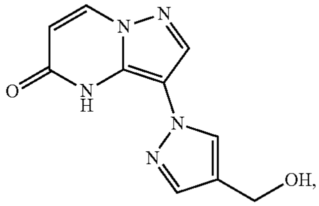

,

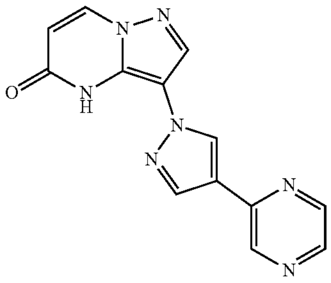

, and

-continued

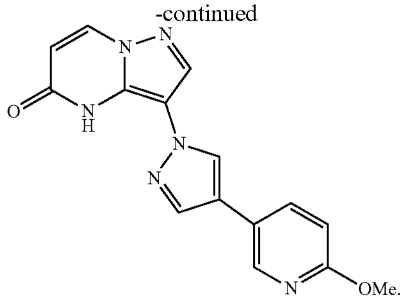

.

In some embodiments, the compound of formula (XVIII) has the structure:

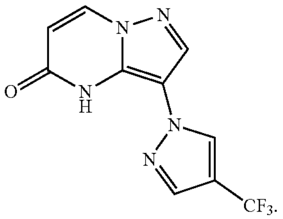 [SMILES: O=c1ccn2ncc(-n3cc(C(F)(F)F)cn3)c2[nH]1]

.

2. Example Amides of Formula (XVIII)

In some embodiments, a compound can be present as one or more of the following structures:

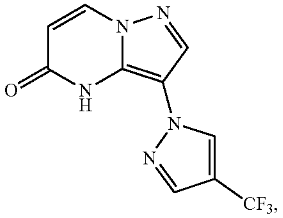 [SMILES: O=c1ccn2ncc(-n3cc(C(F)(F)F)cn3)c2[nH]1]

, or a pharmaceutically acceptable salt thereof.

E. ADDITIONAL COMPOUNDS

Various embodiments relate to compounds that are useful in the disclosed methods. It is understood that a disclosed compound can be provided by the disclosed methods.

In various embodiments, the disclosed compounds are useful as intermediates in the synthesis of pyrazolo[1,5-a] pyrimidine compounds useful as TRK inhibitors.

Thus, in some embodiments, the present disclosure provides compounds having the structure:

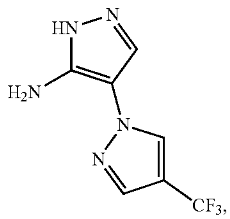 [SMILES: Nc1[nH]ncc1-n1cc(C(F)(F)F)cn1]

, or a salt thereof.

In some embodiments, the present disclosure provides compounds having the structure:

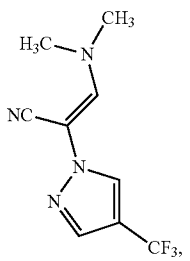

or a salt thereof.

In some embodiments, the present disclosure provides compounds having the structure represented by formula (XVII):

(XVII)

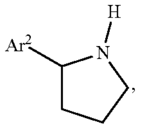

wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy, or a pharmaceutically acceptable salt thereof.

In further embodiments, the compound of formula (XVII) has the structure represented by formula selected from:

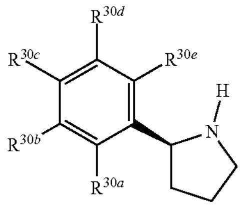

and

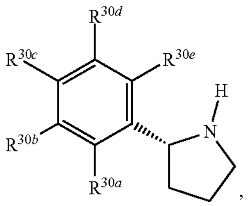

wherein each of $R^{30a}$, $R^{30b}$, $R^{30c}$, $R^{30d}$, and $R^{30e}$ is independently selected from hydrogen, halogen, C1-C6 alkyl, C1-C6 haloalkyl, C1-C6 alkoxy, and C1-C6 haloalkoxy, provided that at least two of $R^{30a}$, $R^{30b}$, $R^{30c}$, $R^{30d}$, and $R^{30e}$ are hydrogen.

In further embodiments, the compound of formula (XVII) has the structure represented by formula:

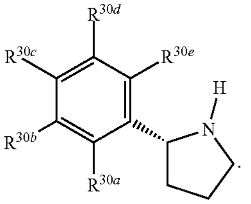

In further embodiments, the compound of formula (XVII) has the structure:

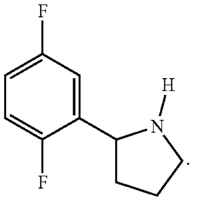 [SMILES: Fc1ccc(F)c(C2CCCN2)c1]

In further embodiments, the compound of formula (XVII) has the structure selected from:

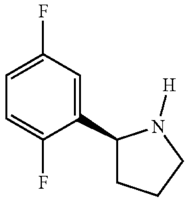

and

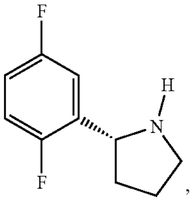

In further embodiments, the compound of formula (XVII) has the structure:

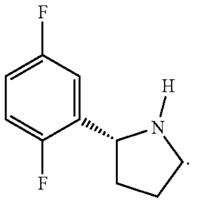 [SMILES: Fc1ccc(F)c([C@H]2CCCN2)c1]

In some embodiments, the present disclosure provides a compound having the structure represented by formula (XIX):

(XIX)

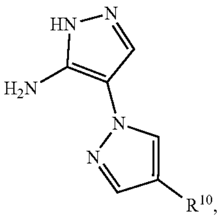

wherein $R^{10}$ is selected from hydrogen, halogen, —CN, C1-C6 alkyl, C1-C6 haloalkyl, C1-C6 cyanoalkyl, $—OR^{20}$, $—C(O)R^{20}$, $—S(O)R^{20}$, $—S(O)_2R^{20}$, $—(C1\text{-}C6\ alkyl)OR^{20}$, $—(C1\text{-}C6\ alkyl)SR^{20}$, $—(C1\text{-}C6\ alkyl)C(O)R^{20}$, $—(C1\text{-}C6\ alkyl)S(O)R^{20}$, $—(C1\text{-}C6\ alkyl)S(O)_2R^{20}$, $—NR^{21}C(O)R^{20}$, $—NR^{21}S(O)_2R^{20}$, $—NR^{22a}R^{22b}$, $—P(O)R^{22a}R^{22b}$, $—(C1\text{-}C6\ alkyl)NR^{22a}R^{22b}$, $—(C1\text{-}C6\ alkyl)P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In some embodiments, the compound of formula (XIX) has the structure:

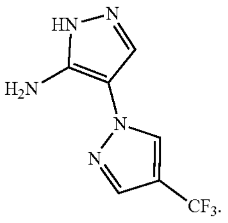 [SMILES: Nc1[nH]ncc1-n1cc(C(F)(F)F)cn1]

In some embodiments, the present disclosure provide compound having the structure represented by formula (XX):

(XX)

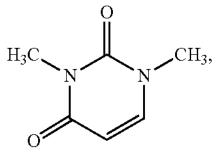

or a salt thereof.

In some embodiments, the present disclosure provides a compound having the structure represented by formula (XXI):

(XXI)

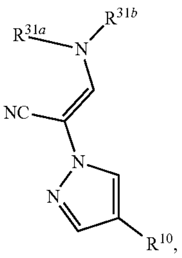

wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{31a}$ and $R^{31b}$ is independently C1-C4 alkyl, or a pharmaceutically acceptable salt thereof.

In some embodiments, the compound of formula (XXI) has the structure represented by formula:

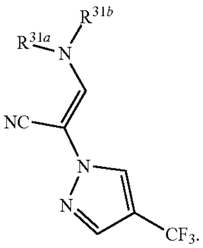

In some embodiments, the compound of formula (XXI) has the structure:

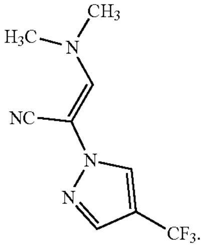

In some embodiments, each of $R^{31a}$ and $R^{31b}$ is independently C1-C4 alkyl. In some embodiments, each of $R^{31a}$ and $R^{31b}$ is independently selected from methyl, ethyl, n-propyl, and isopropyl. In some embodiments, each of $R^{31a}$ and $R^{31b}$ is independently selected from methyl and ethyl. In some embodiments, each of $R^{31a}$ and $R^{31b}$ is ethyl. In some embodiments, each of $R^{31a}$ and $R^{31b}$ is methyl.

In some embodiments, the present disclosure provide a compound having the structure represented by formula (XXII):

(XXII)

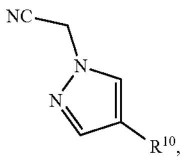

wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In some embodiments, the compound of formula (XXII) has the structure:

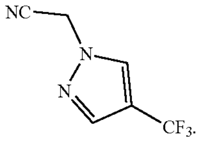

In some embodiments, the present disclosure provides compounds having the structure represented by formula (XXIII):

(XXIII)

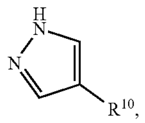

wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof.

In some embodiments, the compound of formula (XXIII) has the structure represented by formula:

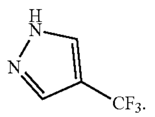

In some embodiments, the present disclosure provides compounds having the structure represented by formula (XXIV):

(XXIV)

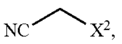

wherein $X^2$ is a halogen. Examples of halogens include, but are not limited to, —F, —Br, and —Cl. Thus, in some embodiments, $X^2$ is —F. In some embodiments, $X^2$ is —Br. In some embodiments, $X^2$ is —Cl.

In some embodiments, the compound of formula (XXIV) has the structure:

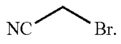

F. METHODS OF MAKING THE COMPOUNDS

In some embodiments, the present disclosure provides methods for making a compound having the structure represented by formula (XXV):

(XXV)

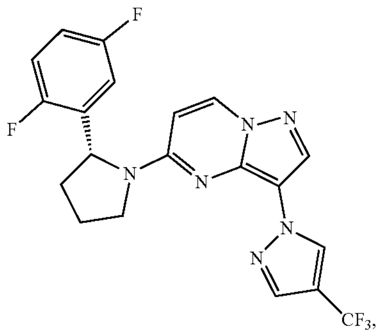

or a pharmaceutically acceptable salt thereof, the method comprising coupling a compound having the structure represented by formula (XXVI):

(XXVI)

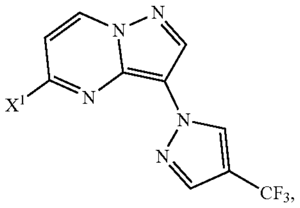

and a compound having the structure represented by formula:

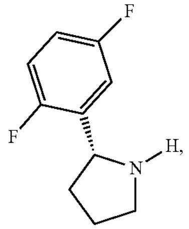

whereby

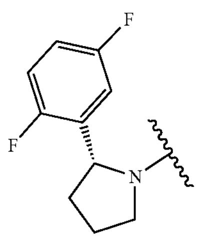 [SMILES: *N1CCC[C@@H]1c1cc(F)ccc1F]

replaces $X^1$, and wherein $X^1$ is a leaving group.

In some embodiments, the present disclosure provides methods for making a compound having the structure:

(XXV)

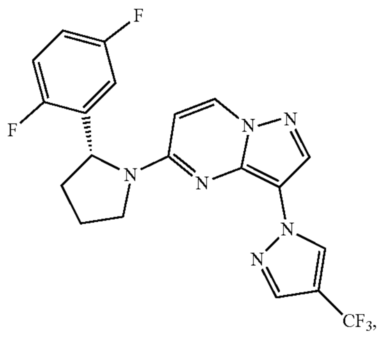

or a pharmaceutically acceptable salt thereof, the method comprising: (a) preparing a nitrile having the structure:

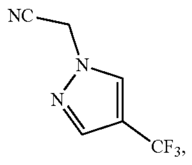

via reacting a heteroaryl having the structure

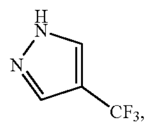

and a haloacetonitrile having the structure represented by formula (XXIV):

(XXIV)

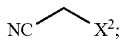

(b) preparing an acrylonitrile having the structure:

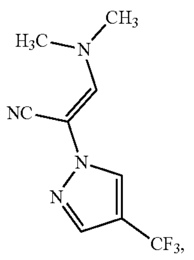 [SMILES: CN(C)/C=C(\C#N)n1cc(C(F)(F)F)cn1]

via reacting the nitrile and a formamidine acetal; (c) preparing an amine having the structure:

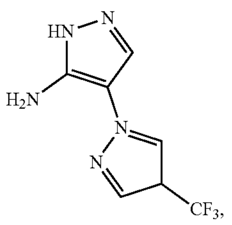

via cyclizing the acrylonitrile and a hydrazine; (d) preparing an amide having the structure:

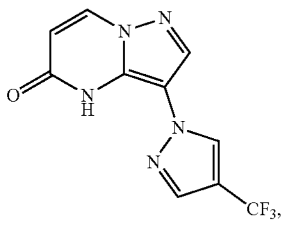 [SMILES: O=c1ccn2ncc(-n3cc(C(F)(F)F)cn3)c2[nH]1]

via reacting the amine and a uracil having the structure:

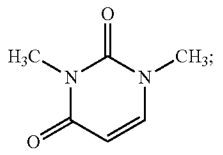

(e) preparing a compound having the structure represented by formula (XXVI):

(XXVI)

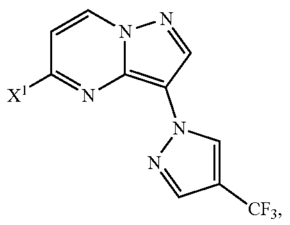

via reacting the amide and a halogenating agent; and (f) preparing the compound of formula (XXV) via coupling the compound of formula (XXVI) and a compound having the structure:

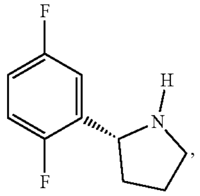

wherein $X^1$ is a leaving group; and wherein $X^2$ is a halogen.

In some embodiments, the present disclosure provides methods for making a compound having the structure represented by formula (XV):

(XV)

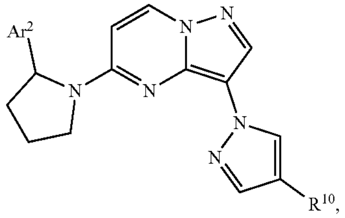

or a pharmaceutically acceptable salt thereof, the method comprising coupling a compound of formula (XVI):

(XVI)

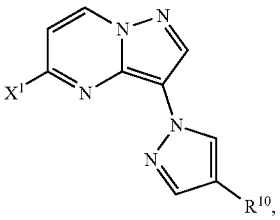

and a compound of formula (XVII):

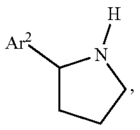

whereby $R^1$ replaces $X^1$; wherein $X^1$ is a leaving group; wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy.

In some embodiments, the present disclosure provides methods for making a compound having the structure represented by formula (XV):

(XV)

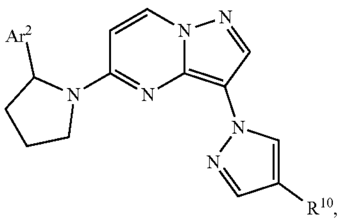

or a pharmaceutically acceptable salt thereof, the method comprising: (a) preparing a nitrile having the structure represented by formula (XXII):

(XXII)

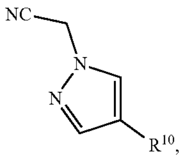

via reacting a heteroaryl having the structure represented by formula (XXIII):

(XXIII)

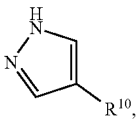

and a haloacetonitrile having the structure represented by formula (XXIV):

(XXIV)

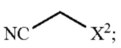

(b) preparing an acrylonitrile having the structure represented by formula (XXI):

(XXI)

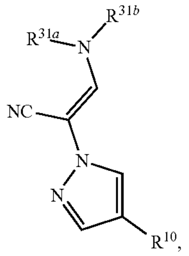

via reacting the nitrile of formula (XXII) and a formamidine acetal; (c) preparing an amine having the structure represented by formula (XIX):

(XIX)

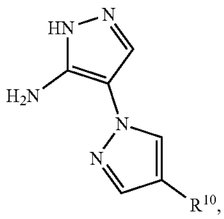

via cyclizing the acrylonitrile of formula (XXI); (d) preparing an amide having the structure represented by formula (XVIII):

(XVIII)

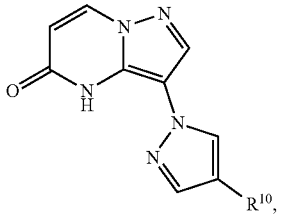

via reacting the amine of formula (XIX) and a uracil having the structure represented by formula (XX):

(XX)

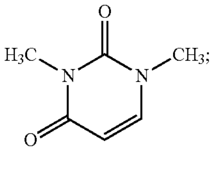

(e) preparing a compound having the structure represented by formula (XVI):

(XVI)

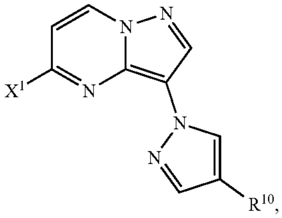

via reacting the amide of formula (XVIII) and an activating agent; and (f) preparing the compound of formula (XV) via coupling the compound of formula (XVI) and a compound having the structure represented by formula (XVII):

(XVII)

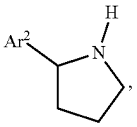

wherein $X^1$ is a leaving group; wherein $X^2$ is a halogen; wherein $R^{10}$ is selected from hydrogen, halogen, —CN, C1-C6 alkyl, C1-C6 haloalkyl, C1-C6 cyanoalkyl, $—OR^{20}$, $—C(O)R^{20}$, $—S(O)R^{20}$, $—S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, $—NR^{21}C(O)R^{20}$, $—NR^{21}S(O)_2R^{20}$, $—NR^{22a}R^{22b}$, $—P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy; and wherein each of $R^{31a}$ and $R^{31b}$ is independently C1-C4 alkyl.

In some embodiments, the present disclosure provides methods for making a compound having the structure represented by formula (XVI):

(XVI)

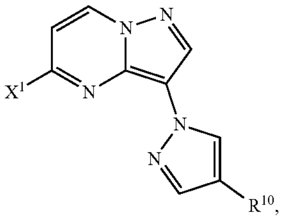

or a pharmaceutically acceptable salt thereof, the method comprising reacting an amide having the structure represented by formula (XVIII):

(XVIII)

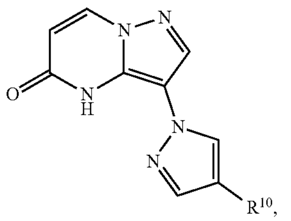

and an activating agent, wherein $X^1$ is a leaving group; wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In some embodiments, the present disclosure provides methods for making a compound having the structure represented by formula (XVIII):

(XVIII)

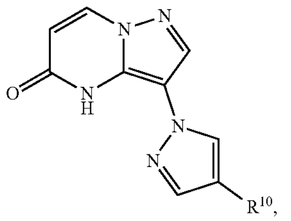

or a pharmaceutically acceptable salt thereof, the method comprising reacting an amine having the structure represented by formula (XIX):

(XIX)

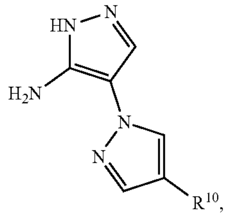

and a uracil having the structure represented by formula (XX):

(XX)

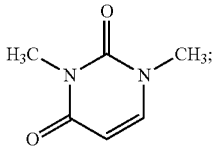

wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl.

In some embodiments, the present disclosure provides a compound prepared by a disclosed method.

In some embodiments, the coupling reaction is conducted in the presence of a base. Exemplary bases include, but are not limited to, 1,8-diazabicyclo[5.4.0]undec-7-ene (DBU), methylamine, ethylamine, N,N-diisopropylethylamine (Hunig's base), pyridine, and 2-tert-butyl-1,1,3,3-tetramethylguanidine (Barton's base). In further embodiments, the base is an amine base. In still further embodiments, the amine base is a trialkylamine or a pyridine (substituted or unsubstituted). In yet further embodiments, the amine base is a pyridine base. In further embodiments, the amine base is a trialkylamine base. In still further embodiments, the trialkylamine base is N,N-diisopropylethylamine.

In some embodiments, the coupling reaction is conducted at an elevated temperature. In further embodiments, the temperature is in the range of about 70° C. to about 110° C., about 70° C. to about 100° C., about 70° C. to about 90° C., about 70° C. to about 80° C., about 80° C. to about 110° C., about 90° C. to about 110° C., about 110° C. to about 110° C., about 80° C. to about 100° C., or about 85° C. to about 95° C.

In some embodiments, the compound of formula (XVI) has the structure:

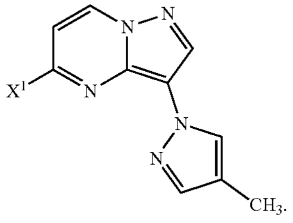

In some embodiments, the compound of formula (XVII) has the structure:

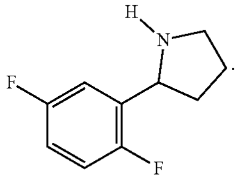 [SMILES: Fc1ccc(F)c(C2CCCN2)c1]

In some embodiments, the method further comprises the step of preparing the compound of formula (XVI) comprising reacting an amide having the structure represented by formula (XVIII):

(XVIII)

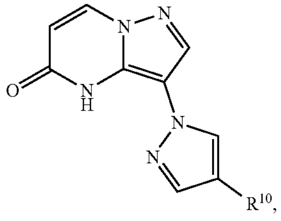

and an activating agent. Examples of activating agents include, but are not limited to halogenating agents (e.g., phosphorous oxychloride, thionyl chloride, phosphorous pentachloride, boron tribromide, phosphorous pentabromide) and agents for forming triflates (e.g., triflic acid, trifluoroacetic anhydride). Thus, in further embodiments, the activating agent is a halogenating agent. In still further embodiments, the halogenating agent is phosphorous oxychloride, thionyl chloride, or phosphorous pentachloride. In yet further embodiments, the halogenating agent is phosphorous oxychloride.

In some embodiments, the reaction is conducted at an elevated temperature. In further embodiments, the temperature is in the range of about 80° C. to about 120° C., about 80° C. to about 110° C., about 80° C. to about 100° C., about 80° C. to about 90° C., about 90° C. to about 120° C., about 100° C. to about 120° C., about 110° C. to about 120° C., about 90° C. to about 110° C., or about 95° C. to about 105° C.

In some embodiments, the method further comprises the step of preparing the amide of formula (XVIII) comprising reacting an amine having the structure represented by formula (XIX):

(XIX)

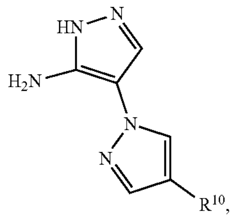

and a uracil having the structure represented by formula (XX):

(XX)

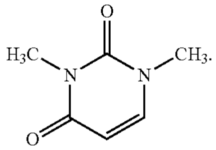

In some embodiments, the method further comprises the step of preparing the amine of formula (XIX) comprising cyclizing an acrylonitrile having the structure represented by formula (XXI):

(XXI)

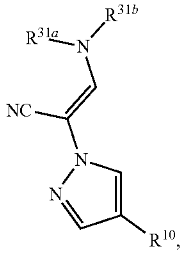

wherein each of $R^{31a}$ and $R^{31b}$ is independently C1-C4 alkyl.

In some embodiments, the cyclizing is via reaction with hydrazine.

In some embodiments, the method further comprises the step of preparing the acrylonitrile of formula (XXI) comprising reacting a nitrile having the structure represented by formula (XXII):

(XXII)

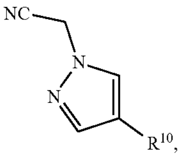

and a formamidine acetal. Examples of formamidine acetals include, but are not limited to, N,N-dimethylformamide diethyl acetal and N,N-dimethylformamide dimethyl acetal. Thus, in some embodiments, the formamidine acetal is N,N-dimethylformamide diethyl acetal.

In some embodiments, the method further comprises the step of preparing the nitrile of formula (XXII) comprising reacting a heteroaryl having the structure represented by formula (XXIII):

(XXIII)

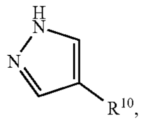

and a haloacetonitrile having the structure represented by formula (XXIV):

(XXIV)

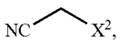

wherein $X^2$ is a halogen.

In some embodiments, the product of the disclosed methods is enantiomerically pure. Thus, in various embodiments, the product of the disclosed methods has an enantiomeric purity of at least about 80%, at least about 85%, at least about 90%, at least about 95%, at least about 99%, or greater than 99%.

In some embodiments, the product of the disclosed methods can be provided in percent enantiomeric excess (e.e.). Thus, in various embodiments, the enantomeric excess of the desired enantiomer of the product of the disclosed methods is greater than 50%, greater than 60%, greater than 70%, greater than 75%, greater than 80%, greater than 85%, greater than 90%, greater than 95%, greater than 98%, or greater than 99%. In further embodiments, the "S" form of the product of the disclosed methods is substantially free from the "R" form. In still further embodiments, the "R" form of the product of the disclosed methods is substantially free from the "S" form.

In some embodiments, the "S" form of the product of the disclosed methods is present in an amount of greater than 50%, greater than 60%, greater than 70%, greater than 75%, greater than 80%, greater than 85%, greater than 90%, greater than 95%, greater than 98%, or greater than 99% relative to the "R" form.

In some embodiments, the "R" form of the product of the disclosed methods is present in an amount of greater than 50%, greater than 60%, greater than 70%, greater than 75%, greater than 80%, greater than 85%, greater than 90%, greater than 95%, greater than 98%, or greater than 99% relative to the "S" form.

Preparation of Compounds of Formula (X) (e.g., Compound No. 10).

In some embodiments, the present disclosure provides a method of preparing a compound of Formula (X), comprising one or more of steps (i-1) to (i-3): (i-1) contacting a compound of Formula (VII) with an acetonitrile addition agent, thereby forming a compound of Formula (VIII); (i-2) contacting the compound of Formula (VIII) with N, N-dimethylformamide diethyl acetal or a synthetic equivalent thereof, thereby forming a compound of Formula (IX); or (i-3) contacting the compound of Formula (IX) with hydrazine, thereby forming a compound of Formula (X) or a salt thereof.

In some embodiments, the present disclosure provides use of compound of Formula (VII) in the manufacture of a compound of Formula (X) or a salt thereof, comprising one or more of steps (i-1) to (i-3).

In some embodiments, the method or use comprises two or more of steps (i-1) to (i-3).

In some embodiments, the method or use comprises steps (i-1) to (i-3).

Step (i-1).

In some embodiments, step (i-1) comprises contacting Compound No. 7 with the acetonitrile addition agent, thereby forming Compound No. 8.

In some embodiments, the acetonitrile addition agent is 2-chloroacetonitrile, 2-bromoacetonitrile, or 2-iodoacetonitrile. In some embodiments, the acetonitrile addition agent is 2-bromoacetonitrile.

In some embodiments, in step (i-1), the contacting is performed in the presence of a base. In some embodiments, the base is an inorganic base (e.g., potassium carbonate).

In some embodiments, in step (i-1), the contacting is performed in the presence of a solvent. In some embodiments, the solvent is an organic solvent. In some embodiments, the solvent is an aprotic solvent (e.g., N,N-dimethylformamide).

In some embodiments, step (i-1) comprises one or more of steps (i-1-1) to (i-1-3): (i-1-1) providing a first mixture of Compound No. 7 in the solvent (e.g., N,N-dimethylformamide); (i-1-2) adding the base (e.g., potassium carbonate) and the acetonitrile addition agent (e.g., 2-bromoacetonitrile) to the first mixture, thereby forming a second mixture; or (i-1-3) heating the second mixture.

In some embodiments, in step (i-1-2), the adding is performed at room temperature. In some embodiments, in step (i-1-2), the adding is performed at about 20±10° C., about 20±5° C., about 20±2° C., about 20±1° C. (e.g., about 20° C.).

In some embodiments, step (i-1-3) comprises heating the second mixture to about 70±20° C., about 70±15° C., about 70±10° C., about 70±5° C., about 70±2° C., about 70±1° C., (e.g., about 70° C.).

In some embodiments, step (i-1-3) comprises heating the second mixture for about 5±2 hours, about 5±1 hours, about 5±0.5 hours, about 5±0.2 hours, about 5±0.1 hours (e.g., about 5 hours).

In some embodiments, step (i-1) further comprises one or more of the following steps: i-1-4) cooling the second mixture (e.g., to room temperature); (i-1-5) adding the second mixture to water (e.g., ice water), thereby forming a third mixture; (i-1-6) extracting the third mixture one or more times with an organic solvent (e.g., ethyl acetate) and combining the one or more organic phases from the extraction, thereby forming a fourth mixture; and optionally washing the fourth mixture one or more times with brine solution; or (i-1-7) drying and filtering the fourth mixture; (i-1-8) removing at least a portion of the solvent from the fourth mixture, thereby isolating Compound No. 8.

Step (i-2).

In some embodiments, step (i-2) comprises contacting Compound No. 8 with N,N-dimethylformamide diethyl acetal or the synthetic equivalent thereof, thereby forming Compound No. 9.

In some embodiments, step (i-2) comprises one or both of steps (i-2-1) and (i-2-2): (i-2-1) providing a first mixture of Compound No. 8, and N,N-dimethylformamide diethyl acetal or the synthetic equivalent thereof; or (i-2-2) heating the first mixture.

In some embodiments, step (i-2-2) comprises heating the first mixture to about 115±20° C., about 115±15° C., about 115±10° C., about 115±5° C., about 115±2° C., about 115±1° C., (e.g., about 115° C.).

In some embodiments, step (i-2-2) comprises heating the first mixture for about 16±10 hours, about 16±5 hours, about 16±2 hours, about 16±1 hours, about 16±0.5 hours, about 16±0.2 hours, about 16±0.1 hours (e.g., about 16 hours).

In some embodiments, step (i-2) further comprises one or more of the following steps: (i-2-3) cooling the first mixture (e.g., to room temperature); (i-2-4) adding the first mixture to water (e.g., ice water), thereby forming a second mixture; (i-2-5) extracting the second mixture one or more times with an organic solvent (e.g., ethyl acetate) and combining the one or more organic phases from the extraction, thereby forming a third mixture; and optionally washing the third mixture one or more times with brine solution; or (i-2-6)

drying and filtering the third mixture; (i-2-7) removing at least a portion of the solvent from the third mixture, thereby isolating Compound No. 9.

Step (i-3).

In some embodiments, step (i-3) comprises contacting Compound No. 9, with hydrazine, thereby forming Compound No. 10 or the salt thereof.

In some embodiments, the hydrazine is in the form of a hydrazine hydrate. In some embodiments, the hydrazine is in the form of hydrazine monohydrate.

In some embodiments, in step (i-3), the contacting is performed in the presence of a solvent. In some embodiments, the solvent is an organic solvent. In some embodiments, the solvent is a protic solvent. In some embodiments, the solvent is an alcohol (e.g., ethanol).

In some embodiments, step (i-3) comprises one or more of steps (i-3-1) to (i-1-5): (i-3-1) providing a first mixture of Compound No. 9, in the solvent (e.g., ethanol); (i-3-2) adding hydrazine (e.g., hydrazine monohydrate) to the first mixture, thereby forming a second mixture; (i-3-3) cooling the second mixture; (i-3-4) adding an acid (e.g., hydrochloric acid) to the second mixture, thereby forming a third mixture; or (i-3-5) heating the third mixture In some embodiments, step (i-3-3) comprises cooling the second mixture to about −20±20° C., about −20±15° C., about −20±10° C., about −20±5° C., about −20±2° C., about −20±1° C., (e.g., about −20° C.).

In some embodiments, in step (i-3-4), the adding is performed at about −20±20° C., about −20±15° C., about −20±10° C., about −20±5° C., about −20±2° C., about −20±1° C., (e.g., about −20° C.).

In some embodiments, step (i-3-5) comprises heating the third mixture to about 90±20° C., about 90±15° C., about 90±10° C., about 90±5° C., about 90±2° C., about 90±1° C., (e.g., about 90° C.).

In some embodiments, step (i-3-5) comprises heating the second mixture for about 16±10 hours, about 16±5 hours, about 16±2 hours, about 16±1 hours, about 16±0.5 hours, about 16±0.2 hours, about 16±0.1 hours (e.g., about 16 hours).

In some embodiments, step (i-3) further comprises one or more of the following steps: (i-3-6) removing at least a portion of the solvent (e.g., ethanol) from the third mixture, thereby forming a concentrated third mixture; (i-3-7) adding water (e.g., ice water) and a base (e.g., potassium carbonate) to the concentrated third mixture, there by forming a fourth mixture; (i-3-8) filtering the fourth mixture, thereby isolating Compound No. 10 or the salt thereof.

Preparation of Compounds of Formula (XIV) (e.g., Compound No. 14).

In some embodiments, the present disclosure provides a method of preparing a compound of Formula (XIV) or a salt thereof, comprising one or more of the following steps (f-1) to (f-3): (f-1) contacting a compound of Formula (X) or a salt thereof, with Compound No. 11, or a synthetic equivalent thereof, thereby forming a compound of Formula (XII); (f-2) contacting the compound of Formula (XII) with a chlorination agent, thereby forming a compound of Formula (XIII); or (f-3) contacting the compound of Formula (XIII) with Compound No. 6 (e.g., Compound No. 6R or 6S (e.g., Compound No. 6R)) or a salt thereof, thereby forming a compound of Formula (XIV) or a salt thereof.

In some embodiments, the present disclosure provides use of compound of Formula (X) or a salt thereof, in the manufacture of a compound of Formula (XIV) or a salt thereof, comprising one or more of steps (f-1) to (f-3).

In some embodiments, the method or use comprises two or more of steps (f-1) to (f-3).

In some embodiments, the method or use comprises steps (f-1) to (f-3).

In some embodiments, the compound of Formula (X) or the salt thereof is prepared by a method disclosed herein.

In some embodiments, the method or use further comprises one or more of steps (i-1) to (i-3).

In some embodiments, the method or use further comprises two or more of steps (i-1) to (i-3).

In some embodiments, the method or use further comprises steps (i-1) to (i-3).

In some embodiments, Compound No. 6 (e.g., Compound No. 6R or 6S (e.g., Compound No. 6R)) is prepared by a method described in PCT Appl'n Pub. No. WO/2008/052734 (incorporated by reference in its entirety).

In some embodiments, Compound No. 6 (e.g., Compound No. 6R or 6S (e.g., Compound No. 6R)) is prepared by a method comprising one or more of steps (s-1) to (s-4): (s-1) contacting Compound No. 1 with Compound No. 2 (e.g., Compound No. 2R or 2S (e.g., Compound No. 2R)), thereby forming Compound No. 3 (e.g., Compound No. 3R or 3S (e.g., Compound No. 3R)); (s-2) contacting Compound No. 4, or a synthetic equivalent thereof, with magnesium or a synthetic equivalent thereof, thereby forming Compound No. 4a, or a synthetic equivalent thereof; (s-3) contacting Compound No. 3 (e.g., Compound No. 3R or 3S (e.g., Compound No. 3R)) with Compound No. 4a, or the synthetic equivalent thereof, thereby forming Compound No. 5 (e.g., Compound No. 5R or 5S (e.g., Compound No. 5R)); (s-4) contacting Compound No. 5 (e.g., Compound No. 5R or 5S (e.g., Compound No. 5R)) with an acid (e.g., HCl) and a reduction agent (e.g., $NaBH_4$), thereby forming Compound No. 6 (e.g., Compound No. 6R or 6S (e.g., Compound No. 6R)) or a salt thereof.

In some embodiments, the method or use further comprises one or more of steps (s-1) to (s-4).

In some embodiments, the method or use further comprises two or more of steps (s-1) to (s-4).

In some embodiments, the method or use further comprises three or more of steps (s-1) to (s-4).

In some embodiments, the method or use further comprises steps (s-1) to (s-4).

Step (f-1).

In some embodiments, step (f-1) comprises contacting Compound No. 10 or the salt thereof, with Compound No. 11, or the synthetic equivalent thereof, thereby forming Compound No. 12.

In some embodiments, step (f-1) comprises contacting Compound No. 10 or the salt thereof, with the synthetic equivalent of Compound No. 11, thereby forming Compound No. 12.

In some embodiments, in step (f-1), the contacting is performed in the presence of a base. In some embodiments, the base is an organic base (e.g., sodium methoxide (MeONa)).

In some embodiments, in step (f-1), the contacting is performed in the presence of a solvent. In some embodiments, the solvent is an organic solvent. In some embodiments, the solvent is a protic solvent. In some embodiments, the solvent is an alcohol (e.g., ethanol).

In some embodiments, step (f-1) comprises one or more of steps (f-1-1) to (f-1-4): (f-1-1) providing a first mixture of Compound No. 10 or the salt thereof, in the solvent (e.g, ethanol); (f-1-2) adding the base (e.g, MeONa) to first mixture, thereby forming a second mixture; (f-1-3) adding Compound No. 11, or the synthetic equivalent thereof, to the second mixture, thereby forming a third mixture; or (f-1-4) heating the third mixture.

In some embodiments, step (f-1-2) comprises adding a solution of the base (e.g., MeONa in methanol (e.g., 25% MeONa in methanol)) to the first mixture.

In some embodiments, in step (f-1-2), the adding is performed at room temperature. In some embodiments, in step (f-1-2), the adding is performed at about 20±10° C., about 20±5° C., about 20±2° C., about 20±1° C. (e.g., about 20° C.).

In some embodiments, in step (f-1-2), the adding is performed for about 15±10 minutes, about 15±5 minutes, about 15±2 minutes, about 15±1 minutes (e.g., about 15 minutes).

In some embodiments, in step (f-1-3), the adding is performed at room temperature. In some embodiments, in step (f-1-3), the adding is performed at about 20±10° C., about 20±5° C., about 20±2° C., about 20±1° C. (e.g., about 20° C.).

In some embodiments, step (f-1-4) comprises heating the third mixture to about 90±20° C., about 90±15° C., about 90±10° C., about 90±5° C., about 90±2° C., about 90±1° C., (e.g., about 90° C.).

In some embodiments, step (f-1-4) comprises heating the third mixture for about 16±10 hours, about 16±5 hours, about 16±2 hours, about 16±1 hours, about 16±0.5 hours, about 16±0.2 hours, about 16±0.1 hours (e.g., about 16 hours).

In some embodiments, step (f-1) further comprises one or more or the following steps: (f-1-5) removing at least a portion of the solvent from the third mixture, thereby forming a concentrated third mixture; (f-1-6) adding water (e.g., ice water) to the concentrated third mixture, thereby forming a diluted third mixture; (f-1-7) adding an acid (e.g, acetic acid) to the diluted third mixture, thereby forming a fourth mixture (e.g, having a pH value of about 5); or (f-1-8) filtering the fourth mixture, thereby isolating Compound No. 12.

Step (f-2).

In some embodiments, step (f-2) comprises contacting Compound No. 12 with the chlorination agent, thereby forming Compound No. 13.

In some embodiments, the chlorination agent is phosphoryl chloride ($POCl_3$, also known as phosphorus oxychloride), phosphorus pentachloride ($PCl_5$), or thionyl chloride ($SOCl_2$).

In some embodiments, the chlorination agent is phosphoryl chloride.

In some embodiments, in step (f-2), the contacting is performed in the presence of a catalyst. In some embodiments, the catalyst is N,N-dimethylformamide.

In some embodiments, in step (f-2), the contacting is performed in the presence of a solvent. In some embodiments, the solvent is an organic solvent. In some embodiments, the solvent is an aprotic solvent (e.g., 1,2-dichloroethane, toluene, acetonitrile, or any combination thereof). In some embodiments, the solvent is 1,2-dichloroethane.

In some embodiments, step (f-2) comprises one or more of steps (f-2-1) to (f-2-3): (f-2-1) providing a first mixture of Compound No. 12 in the solvent (e.g., 1,2-dichloroethane, toluene, acetonitrile, or any combination thereof); (f-2-2) adding the chlorination agent (e.g., phosphoryl chloride) and the catalyst (e.g., N,N-dimethylformamide) to the first mixture, thereby forming a second mixture; or (f-2-3) heating the second mixture.

In some embodiments, in step (f-2-2), the adding is performed at room temperature. In some embodiments, in step (f-2-2), the adding is performed at about 20±10° C., about 20±5° C., about 20±2° C., about 20±1° C. (e.g., about 20° C.).

In some embodiments, step (f-2-3) comprises heating the second mixture to about 100±20° C., about 100±15° C., about 100±10° C., about 100±5° C., about 100±2° C., about 100±1° C., (e.g., about 100° C.).

In some embodiments, step (f-2-3) comprises heating the second mixture for about 16±10 hours, about 16±5 hours, about 16±2 hours, about 16±1 hours, about 16±0.5 hours, about 16±0.2 hours, about 16±0.1 hours (e.g., about 16 hours).

In some embodiments, step (f-2) further comprises one or more of the following steps: (f-2-4) removing at least a portion of the solvent from the second mixture, thereby forming a concentrated second mixture; (f-2-5) adding a solvent (e.g., methyl tert-butyl ether) to the concentrated mixture, thereby forming a diluted second mixture; (f-2-6) adding the diluted second mixture to an aqueous solution (e.g., a saturated sodium bicarbonate solution), there by forming a third mixture having an organic phase and an aqueous phase; (f-2-7) isolating the organic phase from the third mixture, and optionally washing the organic phase one or more times with brine solution; (f-2-8) drying and filtering the organic phase; or (f-2-9) removing at least a portion of the solvent from the organic phase, thereby isolating Compound No. 13.

Step (f-3).

In some embodiments, step (f-3) comprises contacting Compound No. 13 with Compound No. 6 (e.g., Compound No. 6R or 6S (e.g., Compound No. 6R)) or the salt thereof, thereby forming Compound No. 14 (e.g., Compound No. 14R or 14S (e.g., Compound No. 14R)) or the salt thereof.

In some embodiments, in step (f-3), the contacting is performed in the presence of a base. In some embodiments, the base is an organic base (e.g., N,N-diisopropylethylamine).

In some embodiments, in step (f-3), the contacting is performed in the presence of a solvent. In some embodiments, the solvent is an organic solvent. In some embodiments, the solvent is an aprotic solvent (e.g., N,N-dimethylformamide).

In some embodiments, step (f-3) comprises one or more of steps (f-3-1) to (f-3-3): (f-3-1) providing a first mixture of Compound No. 13 in the solvent (e.g., N,N-dimethylformamide); (f-3-2) adding Compound No. 6 (e.g., Compound No. 6R or 6S (e.g., Compound No. 6R)) or the salt thereof, and the base (e.g., N,N-diisopropylethylamine) to the first mixture, thereby forming a second mixture; or (f-3-3) heating the second mixture.

In some embodiments, in step (f-3-2), the adding is performed at room temperature. In some embodiments, in step (f-3-2), the adding is performed at about 20±10° C., about 20±5° C., about 20±2° C., about 20±1° C. (e.g., about 20° C.).

In some embodiments, step (f-3-3) comprises heating the second mixture to about 90±20° C., about 90±15° C., about 90±10° C., about 90±5° C., about 90±2° C., about 90±1° C., (e.g., about 90° C.).

In some embodiments, step (f-3-3) comprises heating the second mixture for about 4±2 hours, about 4±1 hours, about 4±0.5 hours, about 4±0.2 hours, about 4±0.1 hours (e.g., about 4 hours).

In some embodiments, step (f-3) further comprises one or more of following steps: (f-3-4) adding the second mixture to water (e.g., ice water), thereby forming a third mixture; (f-3-5) extracting the third mixture one or more times with an organic solvent (e.g., ethyl acetate) and combining the one or more organic phases from the extraction, thereby forming a fourth mixture; and optionally washing the c one or more times with brine solution; (f-3-6) drying and filtering the fourth mixture; (f-3-7) removing at least a portion of the solvent from the fourth mixture, thereby forming a concentrated fourth mixture; (f-3-8) adding ethanol to the fourth mixture, thereby forming a fifth mixture; (f-3-9) filtering the fifth mixture, thereby isolating Compound No. 14 (e.g., Compound No. 14R or 14S (e.g., Compound No. 14R)) or the salt thereof.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Routes I-VI, as described and exemplified below. The following examples are provided so that the invention might be more fully understood, are illustrative only, and should not be construed as limiting.

1. Route I

In one aspect, a disclosed compound can be prepared as shown below.

SCHEME 1A.

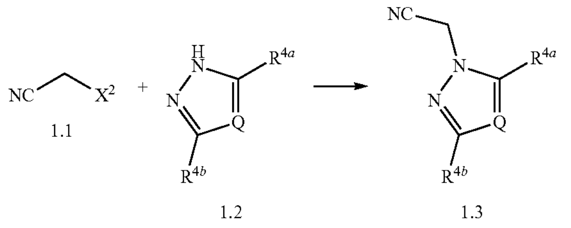

1.1 1.2 1.3

Compounds are represented in generic form, wherein each of $R^{4a}$ and $R^{4b}$ is hydrogen, wherein Q is —$CR^{10}$, and with other substituents as noted in compound descriptions elsewhere herein. A more specific example is set forth below.

SCHEME 1B.

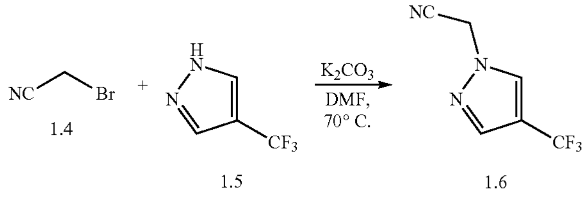

1.4 1.5 1.6

In one aspect, compounds of type 1.3, and similar compounds, can be prepared according to reaction Scheme 1B above. Thus, compounds of type 1.3 can be prepared by an alkylation reaction between an appropriate pyrazole, e.g., 1.2 as shown above, and an appropriate halide, e.g., 1.1 as shown above. Appropriate pyrazoles and appropriate halides are commercially available or prepared by methods known to one skilled in the art. The alkylation is carried out in the presence of an appropriate base, e.g., potassium carbonate, in an appropriate solvent, e.g., dimethylformamide (DMF), at an appropriate temperature, e.g., 70° C. As can be appreciated by one skilled in the art, the above reaction provides an example of a generalized approach wherein compounds similar in structure to the specific reactants above (compounds similar to compounds of type 1.4 and 1.5), can be substituted in the reaction to provide compounds similar to Formula 1.6.

2. Route II

In one aspect, a disclosed compound can be prepared as shown below.

SCHEME 2A.

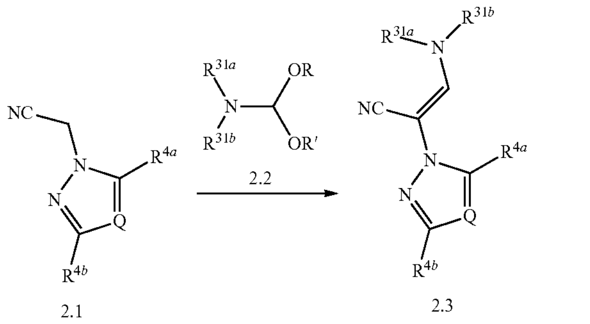

2.1 2.3

Compounds are represented in generic form, wherein each of R and R' are independently C1-C8 alkyl, wherein each of $R^{4a}$ and $R^{4b}$ is hydrogen, wherein Q is —$CR^{10}$, and with other substituents as noted in compound descriptions elsewhere herein. A more specific example is set forth below.

SCHEME 2B.

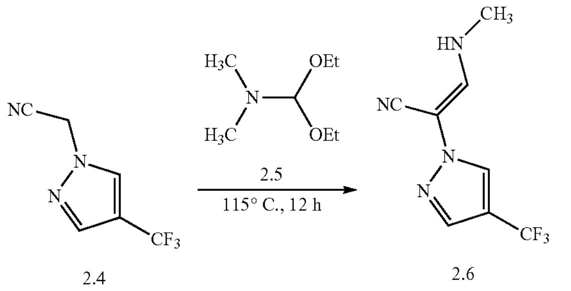

2.4 2.6

In one aspect, compounds of type 2.3, and similar compounds, can be prepared according to reaction Scheme 2B above. Thus, compounds of type 2.3 can be prepared by activating an appropriate cyano compound, e.g., 2.1 as shown above. The activation is carried out in the presence of an appropriate formamidine acetal, e.g., 2.5 as shown above, at an appropriate temperature, e.g., 115° C., for an appropriate period of time, e.g., 12 hours. Appropriate formamidine acetals are commercially available or prepared by methods known to one skilled in the art. As can be appreciated by one skilled in the art, the above reaction provides an example of a generalized approach wherein compounds similar in structure to the specific reactants above (compounds similar to compounds of type 2.4 and 2.5), can be substituted in the reaction to provide compounds similar to Formula 2.6.

3. Route III

In one aspect, a disclosed compound can be prepared as shown below.

SCHEME 3A.

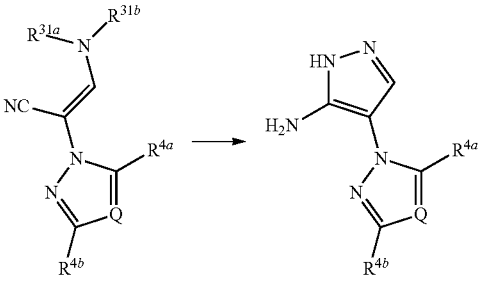

3.1 3.2

Compounds are represented in generic form, wherein each of $R^{4a}$ and $R^{4b}$ is hydrogen, wherein Q is —$CR^{10}$, and with other substituents as noted in compound descriptions elsewhere herein. A more specific example is set forth below.

SCHEME 3B.

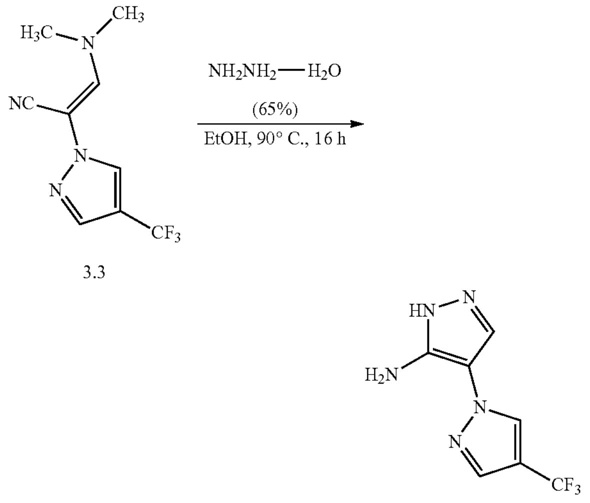

3.3

3.4

In one aspect, compounds of type 3.2, and similar compounds, can be prepared according to reaction Scheme 3B above. Thus, compounds of type 3.2 can be prepared by cyclizing an appropriate cyano amine, e.g., 3.1 as shown above. The cyclization is carried out in the presence of an appropriate cyclizing agent, e.g., hydrazine monohydrate, in an appropriate solvent, e.g., ethanol (EtOH), at an appropriate temperature, e.g., 90° C., for an appropriate period of time, e.g., 16 hours. As can be appreciated by one skilled in the art, the above reaction provides an example of a generalized approach wherein compounds similar in structure to the specific reactants above (compounds similar to compounds of type 3.3), can be substituted in the reaction to provide compounds similar to Formula 3.4.

4. Route IV

In one aspect, a disclosed compound can be prepared as shown below.

SCHEME 4A.

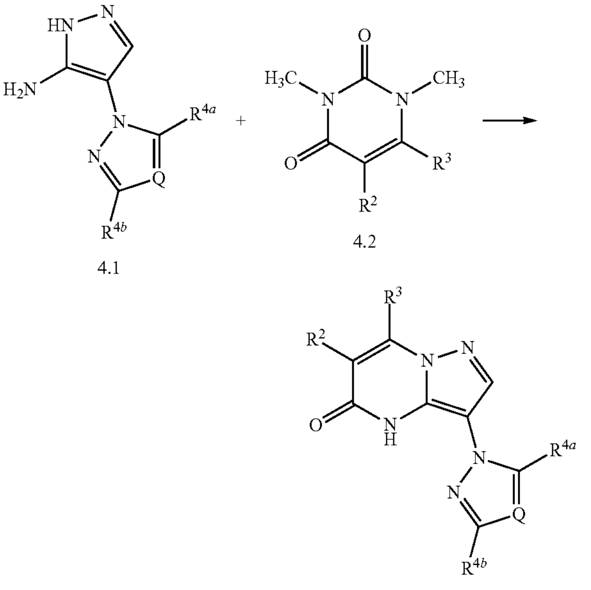

4.1 4.2

4.3

Compounds are represented in generic form, wherein each of $R^2$, $R^3$, $R^{4a}$, and $R^{4b}$ is hydrogen, wherein Q is —$CR^{10}$, and with other substituents as noted in compound descriptions elsewhere herein. A more specific example is set forth below.

SCHEME 4B.

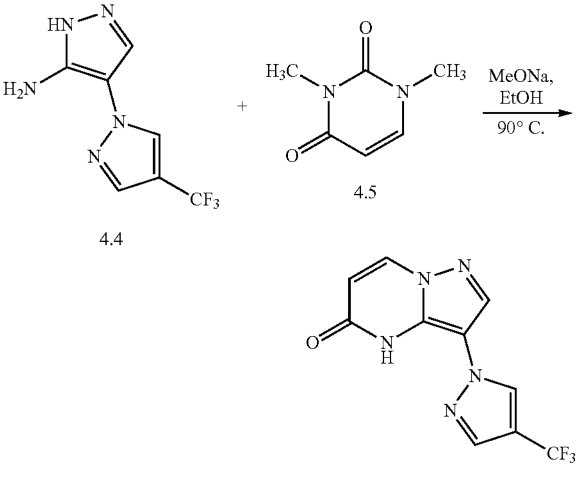

4.4 4.5

4.6

In one aspect, compounds of type 4.3, and similar compounds, can be prepared according to reaction Scheme 4B above. Thus, compounds of type 4.3 can be prepared by reacting an appropriate amino pyrazole, e.g., 4.1 as shown above, and an appropriate uracil derivative, e.g., 4.2 as shown above. As would be readily appreciated by one of skill in the art, alternative 1,3-dicarbonyl agents including, but not limited to, dialkyl malonates, alkyl oxopropanoates, alkyl propiolates, 2-cyanoacetohydrazides, and substituted alkyloxy methacrylates could also be used in place of the uracil derivative. The reaction is carried out in the presence of an appropriate base, e.g., sodium methoxide, in an appropriate solvent, e.g., ethanol (EtOH), at an appropriate temperature, e.g., 90° C. As can be appreciated by one skilled in the art, the above reaction provides an example of a generalized approach wherein compounds similar in structure to the specific reactants above (compounds similar to compounds of type 4.4 and 4.5), can be substituted in the reaction to provide compounds similar to Formula 4.6.

5. Route V

In one aspect, a disclosed compound can be prepared as shown below.

SCHEME 5A.

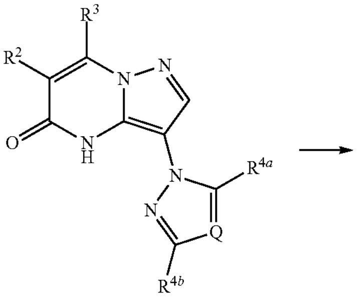

5.1

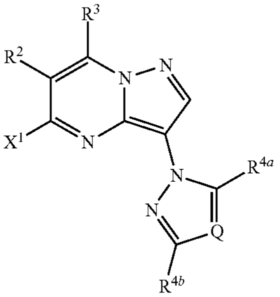

5.2

Compounds are represented in generic form, wherein each of $R^2$, $R^3$, $R^{4a}$, and $R^{4b}$ is hydrogen, wherein Q is —$CR^{10}$, and with other substituents as noted in compound descriptions elsewhere herein. A more specific example is set forth below.

SCHEME 5B.

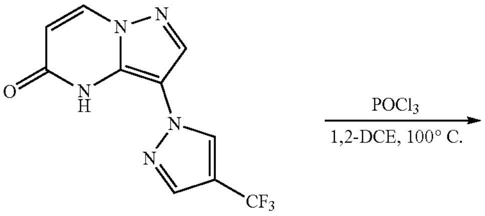

5.3

-continued

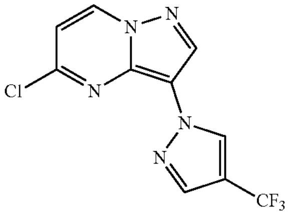

5.4

In one aspect, compounds of type 5.2, and similar compounds, can be prepared according to reaction Scheme 5B above. Thus, compounds of type 5.2 can be prepared by activating an appropriate amide, e.g., 5.3 as shown above. The reaction is carried out in the presence of an appropriate activating agent, e.g., phosphoryl chloride, in an appropriate solvent, e.g., 1,2-dichloroethane (1,2-DCE), at an appropriate temperature, e.g., 100° C. As can be appreciated by one skilled in the art, the above reaction provides an example of a generalized approach wherein compounds similar in structure to the specific reactants above (compounds similar to compounds of type 5.3), can be substituted in the reaction to provide compounds similar to Formula 5.4.

6. Route VI

In one aspect, a disclosed compound can be prepared as shown below.

SCHEME 6A.

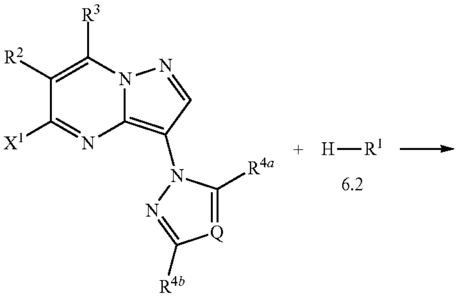

6.1

6.2

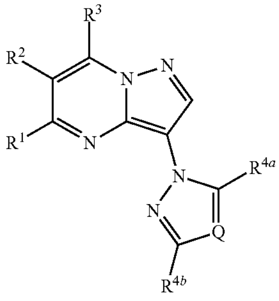

6.3

Compounds are represented in generic form, wherein $R^1$ is

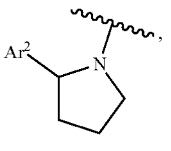

wherein each of $R^2$, $R^3$, $R^{4a}$, and $R^{4b}$ is hydrogen, wherein Q is —$CR^{10}$, and with other substituents as noted in compound descriptions elsewhere herein. A more specific example is set forth below.

SCHEME 6B.

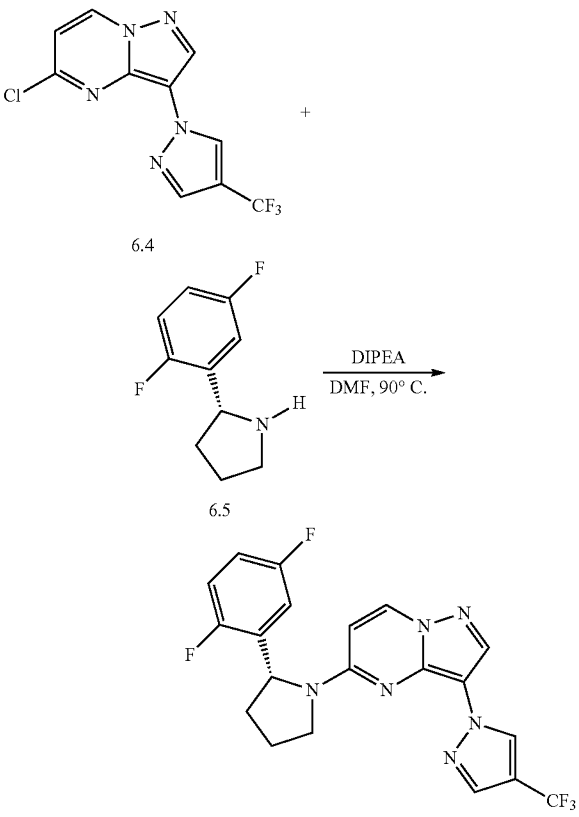

6.4 + 6.5 → 6.6

In one aspect, compounds of type 6.3, and similar compounds, can be prepared according to reaction Scheme 6B above. Thus, compounds of type 6.3 can be prepared by a coupling reaction between an appropriate activated pyrazolo[1,5-a]pyrimidine, e.g., 6.4 as shown above, and an appropriate alcohol or an appropriate amine, e.g., 6.5. Appropriate alcohols and appropriate amines are commercially available or prepared by methods known to one skilled in the art. The coupling reaction is carried out in the presence of an appropriate base, e.g., N,N-diisopropylethylamine (DIPEA), in an appropriate solvent, e.g., dimethylformamide (DMF), at an appropriate temperature, e.g., 90° C. As can be appreciated by one skilled in the art, the above reaction provides an example of a generalized approach wherein compounds similar in structure to the specific reactants above (compounds similar to compounds of type 6.1 and 6.2), can be substituted in the reaction to provide substituted pyrazolo[1,5-a]pyrimidine compounds similar to Formula 6.3.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed methods of using.

G. COMBINATIONS

In some embodiments, the present disclosure provides a combination comprising a compound of Formula (VII) and an acetonitrile addition agent (e.g., 2-bromoacetonitrile).

In some embodiments, the present disclosure provides a combination comprising a compound of Formula (VII) and an acetonitrile addition agent (e.g., 2-bromoacetonitrile) for preparing a compound of Formula (X) or a salt thereof.

In some embodiments, the combination comprises Compound No. 7 and the acetonitrile addition agent (e.g., 2-bromoacetonitrile).

In some embodiments, the present disclosure provides a combination comprising Compound No. 7 and an acetonitrile addition agent (e.g., 2-bromoacetonitrile) for preparing Compound No. 10 or a salt thereof.

In some embodiments, the present disclosure provides a combination comprising a compound of Formula (VIII) and N,N-dimethylformamide diethyl acetal or a synthetic equivalent thereof.

In some embodiments, the present disclosure provides a combination comprising a compound of Formula (VIII) and N,N-dimethylformamide diethyl acetal or a synthetic equivalent thereof, for preparing a compound of Formula (X) or a salt thereof.

In some embodiments, the combination comprises Compound No. 8 and N,N-dimethylformamide diethyl acetal or a synthetic equivalent thereof.

In some embodiments, the present disclosure provides a combination comprising Compound No. 8 and N,N-dimethylformamide diethyl acetal or a synthetic equivalent thereof, for preparing Compound No. 10 or a salt thereof.

In some embodiments, the present disclosure provides a combination comprising a compound of Formula (IX) and hydrazine (e.g., hydrazine monohydrate).

In some embodiments, the present disclosure provides a combination comprising a compound of Formula (IX) and hydrazine (e.g., hydrazine monohydrate) for preparing a compound of Formula (X) or a salt thereof.

In some embodiments, the combination comprises Compound No. 9 and hydrazine (e.g., hydrazine monohydrate).

In some embodiments, the present disclosure provides a combination comprising Compound No. 9 and hydrazine (e.g., hydrazine monohydrate) for preparing Compound No. 10 or a salt thereof.

In some embodiments, the present disclosure provides a combination comprising a compound of Formula (X) or a salt thereof, and Compound No. 11, or a synthetic equivalent thereof.

In some embodiments, the present disclosure provides a combination comprising a compound of Formula (X) or a salt thereof, and Compound No. 11, or a synthetic equivalent thereof, for preparing a compound of Formula (XIV) or a salt thereof.

In some embodiments, the combination comprises Compound No. 10 or a salt thereof, and Compound No. 11.

In some embodiments, the present disclosure provides a combination comprising Compound No. 10 or a salt thereof, and Compound No. 11, for preparing Compound No. 14 (e.g., Compound No. 14R or 14S (e.g., Compound No. 14R)) or a salt thereof.

In some embodiments, the present disclosure provides a combination comprising a compound of Formula (XII) and a chlorination agent (e.g., phosphoryl chloride).

In some embodiments, the present disclosure provides a combination comprising a compound of Formula (XII) and a chlorination agent (e.g., phosphoryl chloride) for preparing a compound of Formula (XIV) or a salt thereof.

In some embodiments, the combination comprises Compound No. 12 and the chlorination agent (e.g., phosphoryl chloride).

In some embodiments, the present disclosure provides a combination comprising Compound No. 12 and a chlorination agent (e.g., phosphoryl chloride) for preparing Compound No. 14 (e.g., Compound No. 14R or 14S (e.g., Compound No. 14R)) or a salt thereof.

In some embodiments, the present disclosure provides a combination comprising a compound of Formula (XIII) and Compound No. 6 (e.g., Compound No. 6R or 6S (e.g., Compound No. 6R)) or a salt thereof.

In some embodiments, the present disclosure provides a combination comprising a compound of Formula (XIII) and Compound No. 6 (e.g., Compound No. 6R or 6S (e.g., Compound No. 6R)) or a salt thereof, for preparing a compound of Formula (XIV) or a salt thereof.

In some embodiments, the combination comprises Compound No. 13 and Compound No. 6 (e.g., Compound No. 6R or 6S (e.g., Compound No. 6R)) or a salt thereof.

In some embodiments, the present disclosure provides a combination comprising Compound No. 13 and Compound No. 6 (e.g., Compound No. 6R or 6S (e.g., Compound No. 6R)) or a salt thereof, for preparing Compound No. 14 (e.g., Compound No. 14R or 14S (e.g., Compound No. 14R)) or a salt thereof.

In some embodiments, the present disclosure provides a composition comprising an effective amount of a compound having the structure represented by formula (XVI):

(XVI)

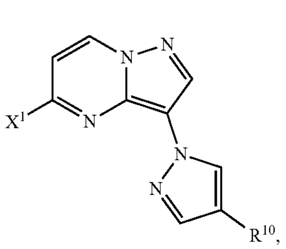

and an effective amount of a compound of formula (XVII):

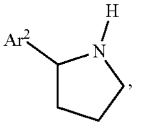

wherein $X^1$ is a leaving group; wherein $R^{10}$ is selected from hydrogen, halogen, —CN, C1-C6 alkyl, C1-C6 haloalkyl, C1-C6 cyanoalkyl, $—OR^{20}$, $—C(O)R^{20}$, $—S(O)R^{20}$, $—S(O)_2R^{20}$, $—(C1\text{-}C6\ alkyl)OR^{20}$, $—(C1\text{-}C6\ alkyl)SR^{20}$, $—(C1\text{-}C6\ alkyl)C(O)R^{20}$, $—(C1\text{-}C6\ alkyl)S(O)R^{20}$, $—(C1\text{-}C6\ alkyl)S(O)_2R^{20}$, $—NR^{21}C(O)R^{20}$, $—NR^{21}S(O)_2R^{20}$, $—NR^{22a}R^{22b}$, $—P(O)R^{22a}R^{22b}$, $—(C1\text{-}C6\ alkyl)NR^{22a}R^{22b}$, $—(C1\text{-}C6\ alkyl)P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy.

In some embodiments, the present disclosure provides a composition comprising an effective amount of a compound having the structure represented by formula (XVIII):

(XVIII)

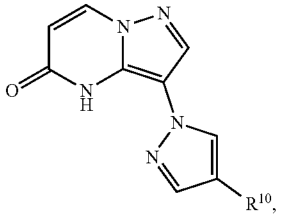

and an activating agent, wherein $R^{10}$ is selected from hydrogen, halogen, —CN, C1-C6 alkyl, C1-C6 haloalkyl, C1-C6 cyanoalkyl, $—OR^{20}$, $—C(O)R^{20}$, $—S(O)R^{20}$, $—S(O)_2R^{20}$, $—(C1\text{-}C6\ alkyl)OR^{20}$, $—(C1\text{-}C6\ alkyl)SR^{20}$, $—(C1\text{-}C6\ alkyl)C(O)R^{20}$, $—(C1\text{-}C6\ alkyl)S(O)R^{20}$, $—(C1\text{-}C6\ alkyl)S(O)_2R^{20}$, $—NR^{21}C(O)R^{20}$, $—NR^{21}S(O)_2R^{20}$, $—NR^{22a}R^{22b}$, $—P(O)R^{22a}R^{22b}$, $—(C1\text{-}C6\ alkyl)NR^{22a}R^{22b}$, $—(C1\text{-}C6\ alkyl)P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; and wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a salt thereof.

H. PHARMACEUTICAL COMPOSITIONS

In some embodiments, the present disclosure provides a pharmaceutical composition comprising a compound described herein and one or more pharmaceutically acceptable carriers or excipients.

In some embodiments, the present disclosure provides a pharmaceutical composition comprising a compound being prepared by a method described herein (e.g., Compound No. 14 (e.g., Compound No. 14R or 14S (e.g., Compound No. 14R))) and one or more pharmaceutically acceptable carriers or excipients.

In some embodiments, the present disclosure provides a pharmaceutical composition comprising an effective amount of a compound of formula (XXV):

(XXV)

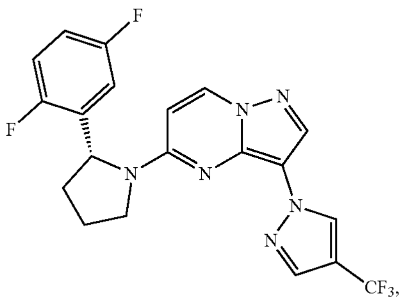

or a pharmaceutically acceptable salt thereof, and a pharmaceutically acceptable carrier, wherein the compound has an enantiomeric purity of at least about 80%, at least about 85%, at least about 90%, at least about 95%, at least about 99%, or greater than 99%. In some embodiments, the compound of formula (XXV) can be provided in percent enantiomeric excess (e.e.). Thus, in various embodiments, the enantiomeric excess of the desired enantiomer of the disclosed pyrazolo[1,5-a]pyrimidine compounds is at least about 50%, at least about 60%, at least about 70%, at least about 75%, at least about 80%, at least about 85%, at least about 90%, at least about 95%, at least about 98%, or at least about 99%. In further embodiments, the "S" form of the disclosed pyrazolo[1,5-a]pyrimidine compounds is substantially free from the "R" form. In still further embodiments, the "R" form of the disclosed pyrazolo[1,5-a]pyrimidine compounds is substantially free from the "S" form.

In some embodiments, the "S" form of the compound of formula (XXV) is present in the composition in an amount of greater than about 50%, greater than about 60%, greater than about 70%, greater than about 75%, greater than about 80%, greater than about 85%, greater than about 90%, greater than about 95%, greater than about 98%, or greater than about 99% relative to the "R" form.

In some embodiments, the "R" form of the compound of formula (XXV) is present in the composition in an amount of greater than about 50%, greater than about 60%, greater than about 70%, greater than about 75%, greater than about 80%, greater than about 85%, greater than about 90%, greater than about 95%, greater than about 98%, or greater than about 99% relative to the "S" form.

In some embodiments, the present disclosure provides a pharmaceutical composition comprising an effective amount of a compound of formula (XV):

(XV)

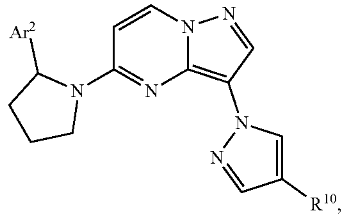

or a pharmaceutically acceptable salt thereof, wherein $R^{10}$ is selected from hydrogen, halogen, —CN, C1-C6 alkyl, C1-C6 haloalkyl, C1-C6 cyanoalkyl, —$OR^{20}$, —$C(O)R^{20}$, —$S(O)R^{20}$, —$S(O)_2R^{20}$, —(C1-C6 alkyl)$OR^{20}$, —(C1-C6 alkyl)$SR^{20}$, —(C1-C6 alkyl)$C(O)R^{20}$, —(C1-C6 alkyl)$S(O)R^{20}$, —(C1-C6 alkyl)$S(O)_2R^{20}$, —$NR^{21}C(O)R^{20}$, —$NR^{21}S(O)_2R^{20}$, —$NR^{22a}R^{22b}$, —$P(O)R^{22a}R^{22b}$, —(C1-C6 alkyl)$NR^{22a}R^{22b}$, —(C1-C6 alkyl)$P(O)R^{22a}R^{22b}$, and $Cy^1$; wherein each of $R^{20}$, $R^{21}$, $R^{22a}$, and $R^{22b}$, when present, is independently selected from hydrogen, C1-C4 alkyl, and C1-C4 haloalkyl; wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy, and a pharmaceutically acceptable carrier, wherein the compound has an enantiomeric purity of at least about 80%, at least about 85%, at least about 90%, at least about 95%, at least about 99%, or greater than 99%. In some embodiments, the compound of formula (XV) can be provided in percent enantiomeric excess (e.e.). Thus, in various embodiments, the enantiomeric excess of the desired enantiomer of the disclosed pyrazolo[1,5-a]pyrimidine compounds is at least about 50%, at least about 60%, at least about 70%, at least about 75%, at least about 80%, at least about 85%, at least about 90%, at least about 95%, at least about 98%, or at least about 99%. In further embodiments, the "S" form of the disclosed pyrazolo[1,5-a]pyrimidine compounds is substantially free from the "R" form. In still further embodiments, the "R" form of the disclosed pyrazolo[1,5-a]pyrimidine compounds is substantially free from the "S" form.

In some embodiments, the "S" form of the compound of formula (XV) is present in the composition in an amount of greater than about 50%, greater than about 60%, greater than about 70%, greater than about 75%, greater than about 80%, greater than about 85%, greater than about 90%, greater than about 95%, greater than about 98%, or greater than about 99% relative to the "R" form.

In some embodiments, the "R" form of the compound of formula (XV) is present in the composition in an amount of greater than about 50%, greater than about 60%, greater than about 70%, greater than about 75%, greater than about 80%, greater than about 85%, greater than about 90%, greater than about 95%, greater than about 98%, or greater than about 99% relative to the "S" form.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle.

The aqueous vehicle component may comprise water and at least one pharmaceutically acceptable excipient. Suitable acceptable excipients include those selected from the group consisting of a solubility-enhancing agent, chelating agent, preservative, tonicity agent, viscosity/suspending agent, buffer, and pH modifying agent, and a mixture thereof.

Any suitable solubility-enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974, and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof, including disodium tetraborate), a citrate buffer (such as citric acid, or salts thereof, including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavoring.

According to a further embodiment of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more colouring, sweetening, flavoring and/or preservative agents.

The size of the dose for therapeutic or prophylactic purposes of a compound of Formulae (VII)-(X) and (XII)-(XIV) or Compound Nos. 1-14 will naturally vary according to the nature and severity of the conditions, the age and sex of the animal or patient and the route of administration, according to well-known principles of medicine.

I. METHODS OF USE

In some embodiments, the present disclosure provides a method of inhibiting a tyrosine receptor kinase (TRK) in a subject, comprising administering to the subject a pharmaceutically effective amount of a compound being prepared by a method disclosed herein (e.g., Compound No. 14 (e.g., Compound No. 14R or 14S (e.g., Compound No. 14R))).

In some embodiments, the present disclosure provides a compound being prepared by a method disclosed herein (e.g., Compound No. 14 (e.g., Compound No. 14R or 14S (e.g., Compound No. 14R))) for inhibiting a tyrosine receptor kinase (TRK) in a subject.

In some embodiments, the present disclosure provides use of a compound being prepared by a method disclosed herein (e.g., Compound No. 14 (e.g., Compound No. 14R or 14S (e.g., Compound No. 14R))) in the manufacture of a medicament for inhibiting a tyrosine receptor kinase (TRK) in a subject.

In some embodiments, the present disclosure provides a method of preventing or treating a disease or disorder in a subject, comprising administering to the subject a pharmaceutically effective amount of a compound being prepared by a method disclosed herein (e.g., Compound No. 14 (e.g., Compound No. 14R or 14S (e.g., Compound No. 14R))).

In some embodiments, the present disclosure provides a compound being prepared by a method disclosed herein (e.g., Compound No. 14 (e.g., Compound No. 14R or 14S (e.g., Compound No. 14R))) for preventing or treating a disease or disorder in a subject.

In some embodiments, the present disclosure provides use of a compound being prepared by a method disclosed herein (e.g., Compound No. 14 (e.g., Compound No. 14R or 14S (e.g., Compound No. 14R))) in the manufacture of a medicament for preventing or treating a disease or disorder in a subject.

In some embodiments, the subject is a mammal.

In some embodiments, the subject in need thereof, is a human.

In some embodiments, the disease is associated with elevated expression or activity of a tyrosine receptor kinase (TRK).

In some embodiments, the administration of the formulation results in an inhibition of the tyrosine receptor kinase (TRK).

In some embodiments, the administration of the formulation results in a reduced activity of the tyrosine receptor kinase (TRK).

In some embodiments, the TRK is TRKA, TRKB, or TRKC.

In some embodiments, the TRK is TRKA.

In some embodiments, the TRK is TRKB.

In some embodiments, the TRK is TRKC.

In some embodiments, the disease or disorder is selected from inflammatory diseases, infections, autoimmune disorders, stroke, ischemia, cardiac disorder, neurological disorders, dermatological disorders, fibrogenic disorders, proliferative disorders, hyperproliferative disorders, non-cancer hyper-proliferative disorders, tumors, leukemias, neoplasms, cancers, carcinomas, metabolic diseases, malignant disease, vascular restenosis, psoriasis, atopic dermatitis, pruritis, eczema, Gorlin Syndrome, Netherton Syndrome, basal cell carcinoma, dermatomyocytis, cylindromas, atherosclerosis, rheumatoid arthritis, osteoarthritis, heart failure, chronic pain, and neuropathic pain.

In some embodiments, the disease or disorder is selected from inflammatory diseases, autoimmune diseases, and cancers.

In some embodiments, the disease or disorder is cancer.

In some embodiments, the disease or disorder is selected from adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, liver cancer, non-small cell lung cancer, small cell lung cancer, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g., renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodennal and pineal tumors, cutaneous t-cell lymphoma, testicular cancer, malignant thymoma, thyroid cancer, mammary analogue secretory carcinoma (MASC), lung adenocarcinoma, intrahepatic cholangicarcinoma, papillary thyroid cancer, pediatric glioma, sarcoma, glioblastoma, spitzoid neoplasms, astrocytoma, head and neck squamous cell carcinoma, low grade glioma, high grade glioma, congenital mesoblastic nephroma, adenoid cystic carcinoma, cylindromas, gestational trophoblastic tumor, urethral cancer, uterine sarcoma, vaginal cancer, vulvar cancer, and Wilms' tumor.

In some embodiments, the cancer is selected from glioma, thyroid carcinoma, breast carcinoma, small-cell lung carcinoma, non-small-cell carcinoma, gastric carcinoma, colon carcinoma, gastrointestinal stromal carcinoma, pancreatic carcinoma, bile duct carcinoma, CNS carcinoma, ovarian carcinoma, endometrial carcinoma, prostate carcinoma, renal carcinoma, anaplastic large-cell lymphoma, leukemia, multiple myeloma, mesothelioma, and melanoma.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent documents cited herein are incorporated herein by reference in its entirety, as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

J. EXAMPLES

Representative examples of the disclosed compounds and the disclosed methods are illustrated in the following non-limiting schemes and examples.

1. CHEMISTRY METHODS a. General Experimental Method

General starting materials used were obtained from commercial sources or prepared in other examples, unless otherwise noted.

UPLC-MS Analysis Conditions.

Figure 1B:
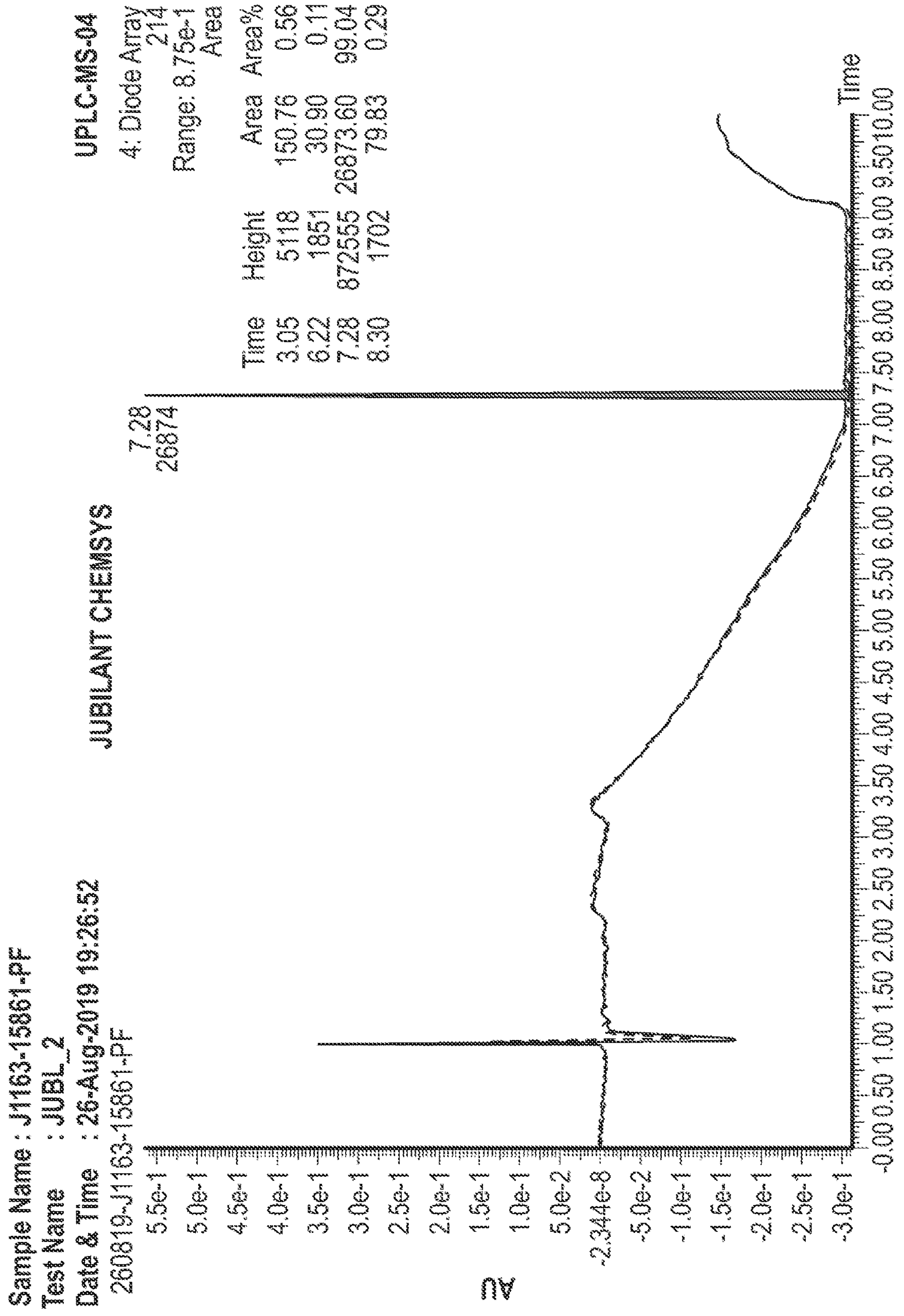
Figure 1C:
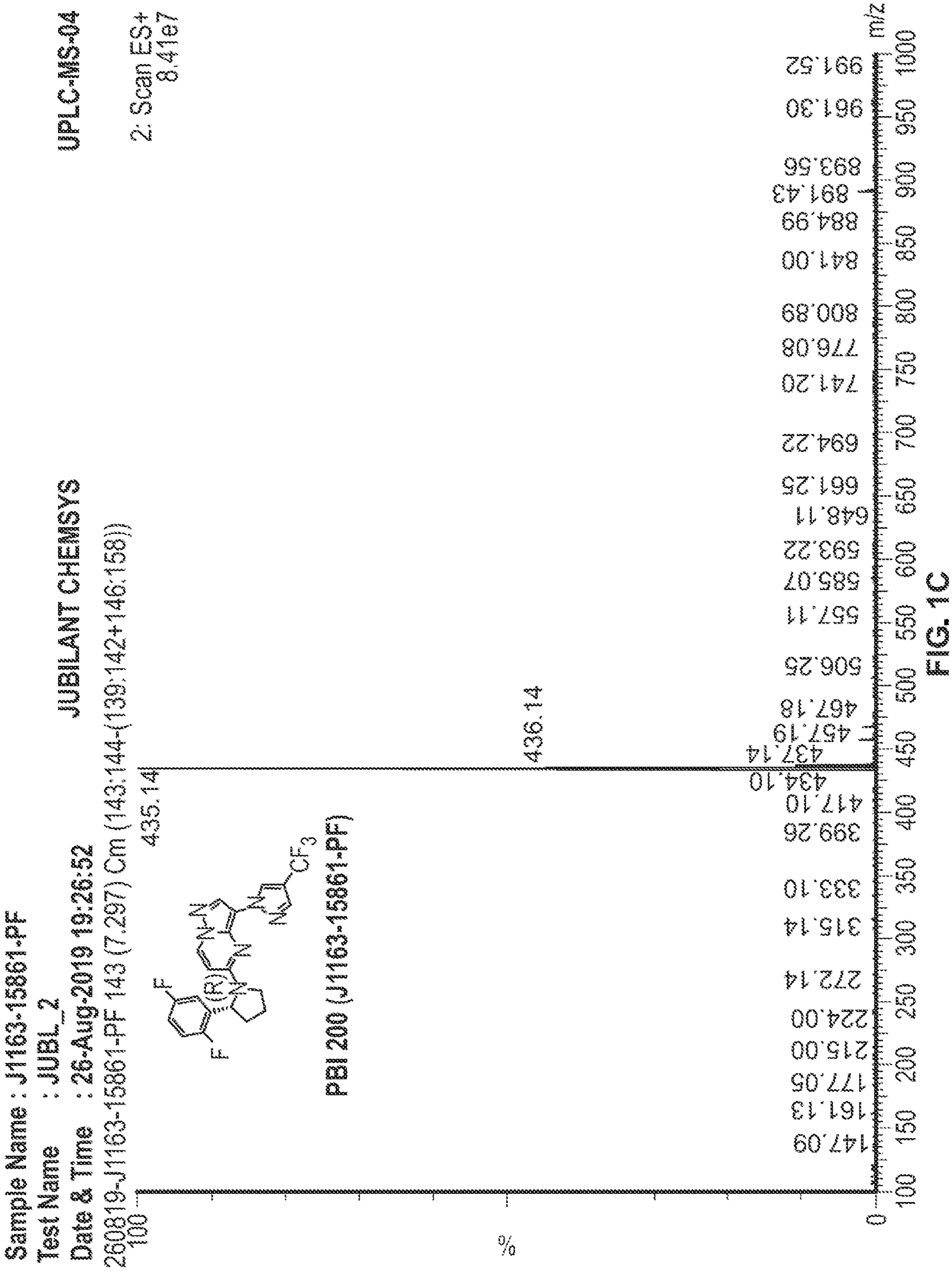
Figure 1D:
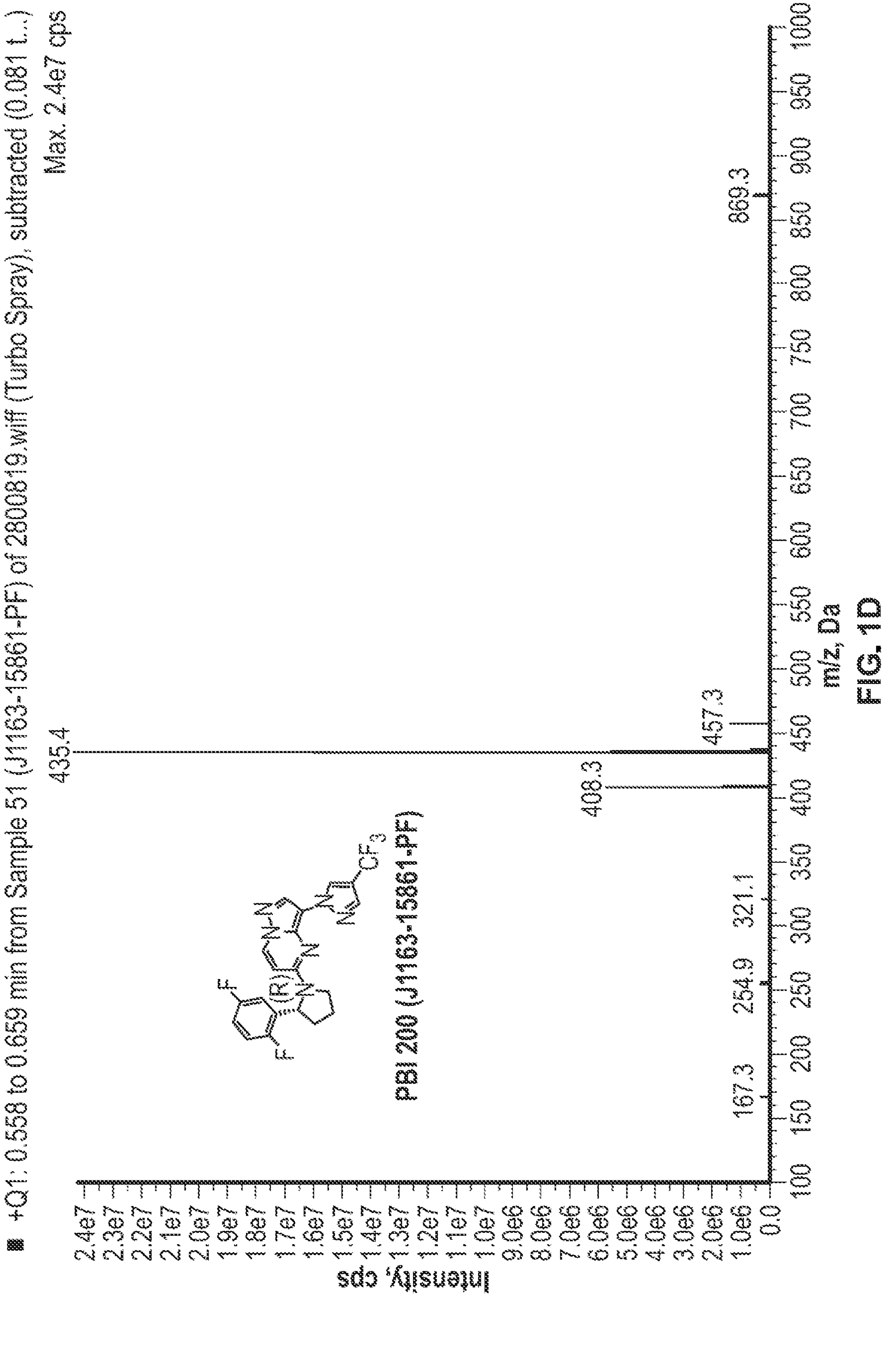
Figure 2A:
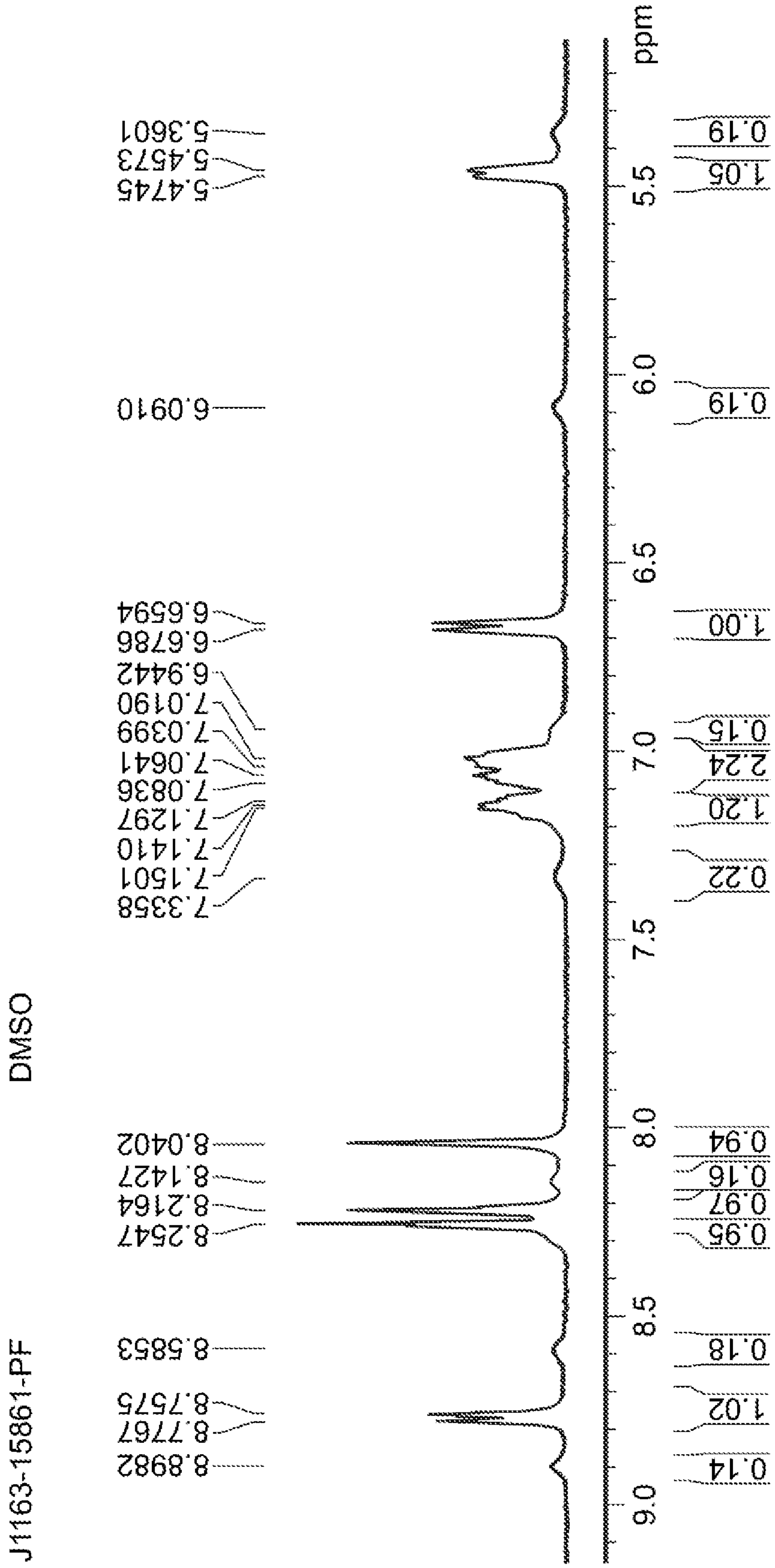
FIG. 2A-D show representative $^{1}$H NMR spectral data of compound no. 14R.
Figure 2A:
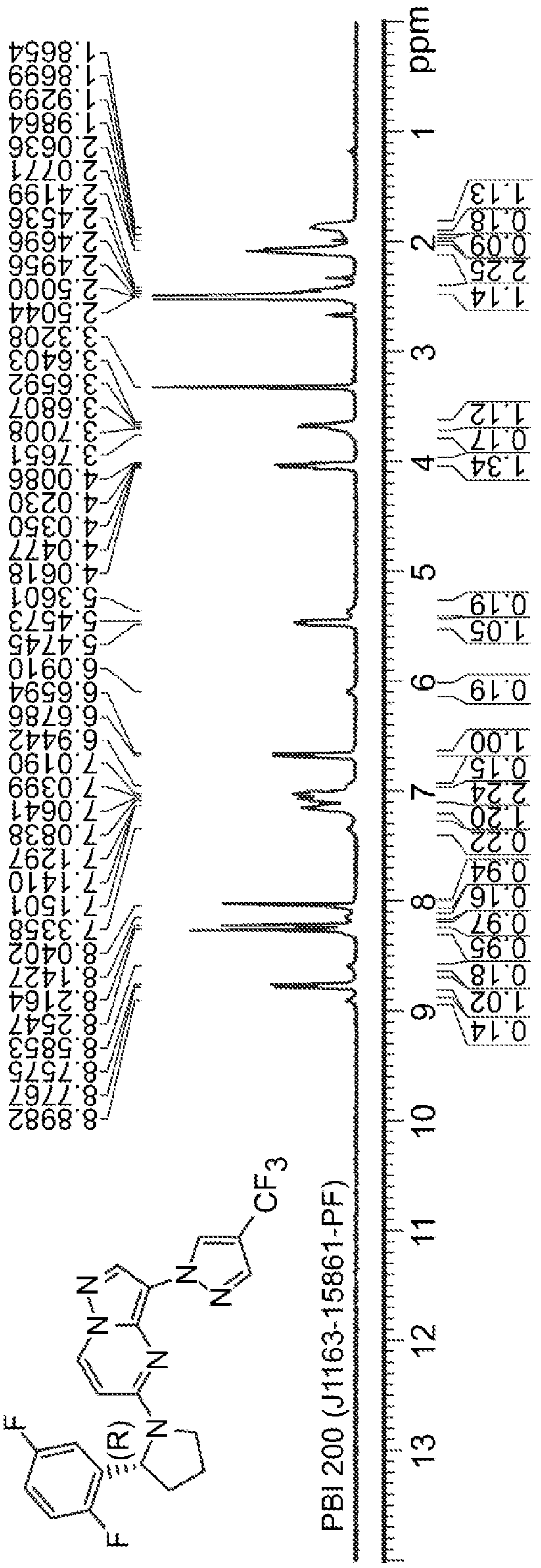
Figure 2B:
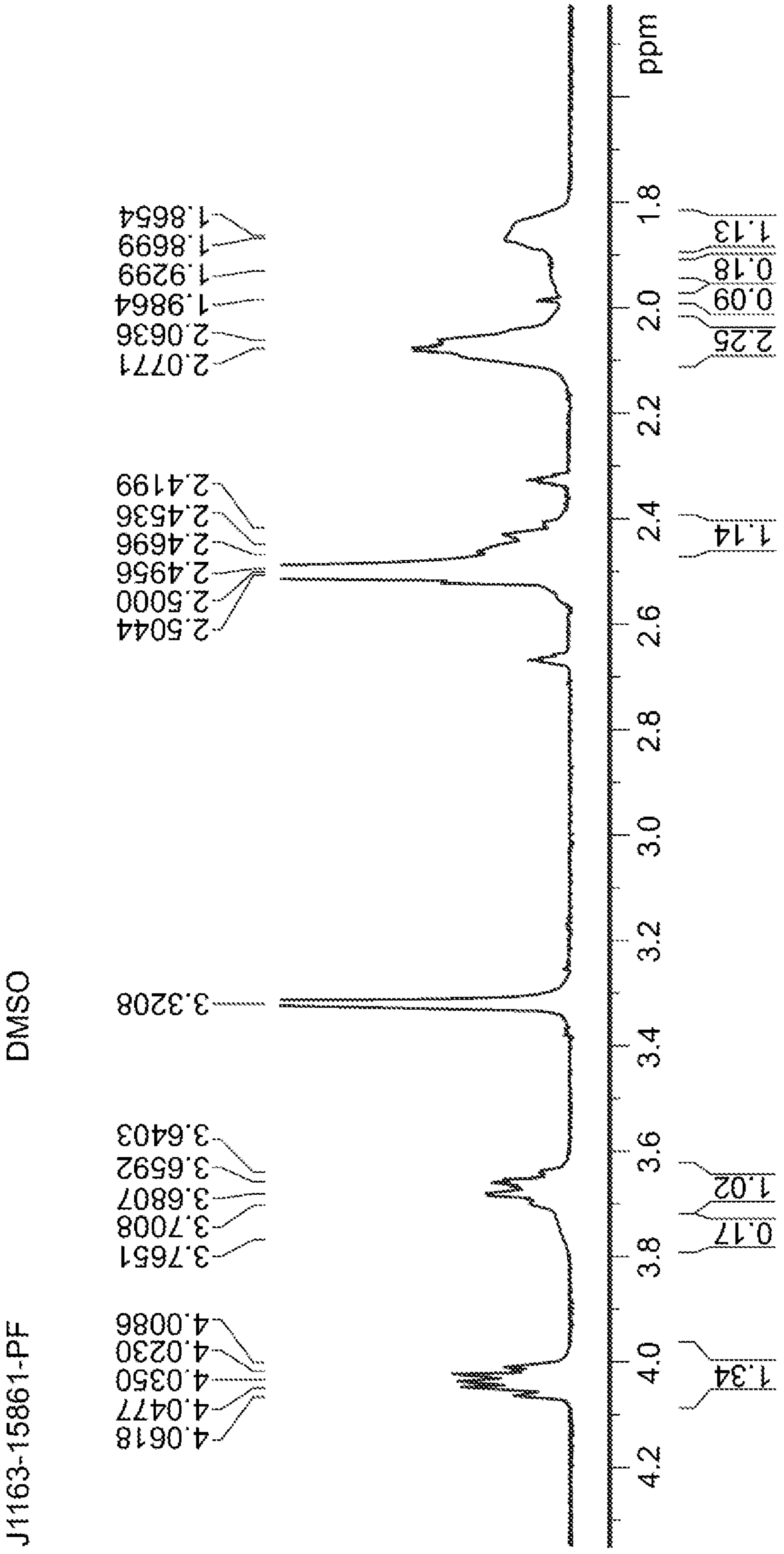
Figure 2B:
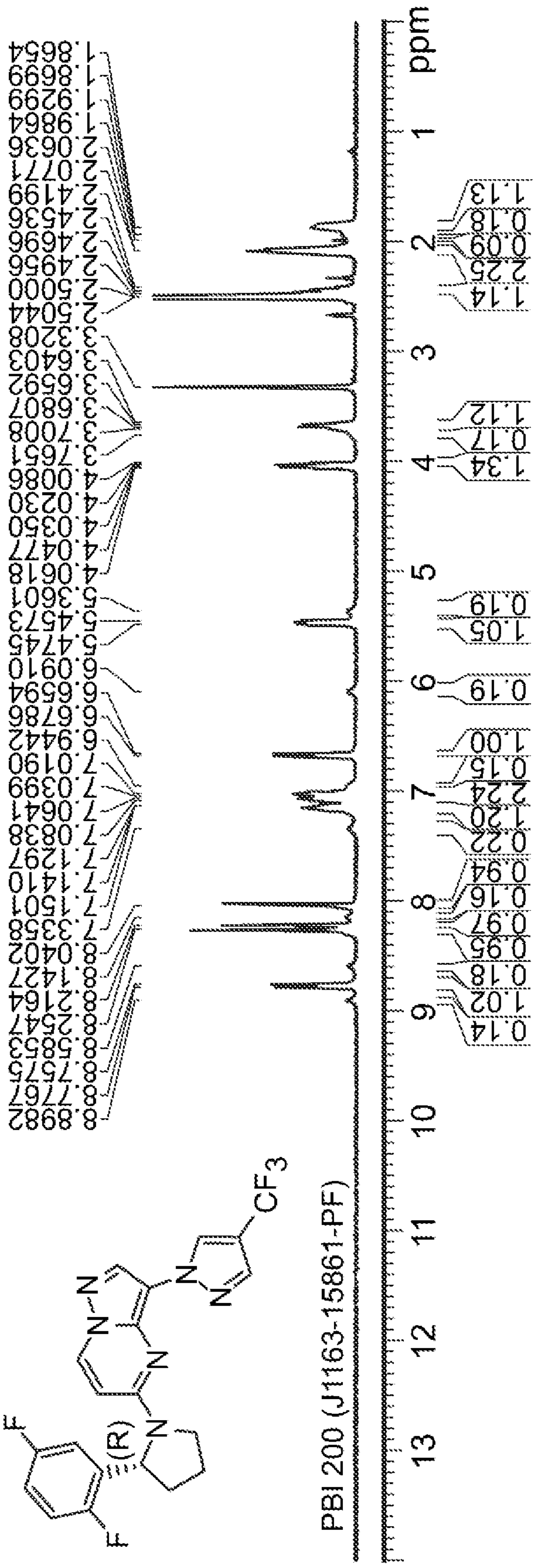
Figure 2C:
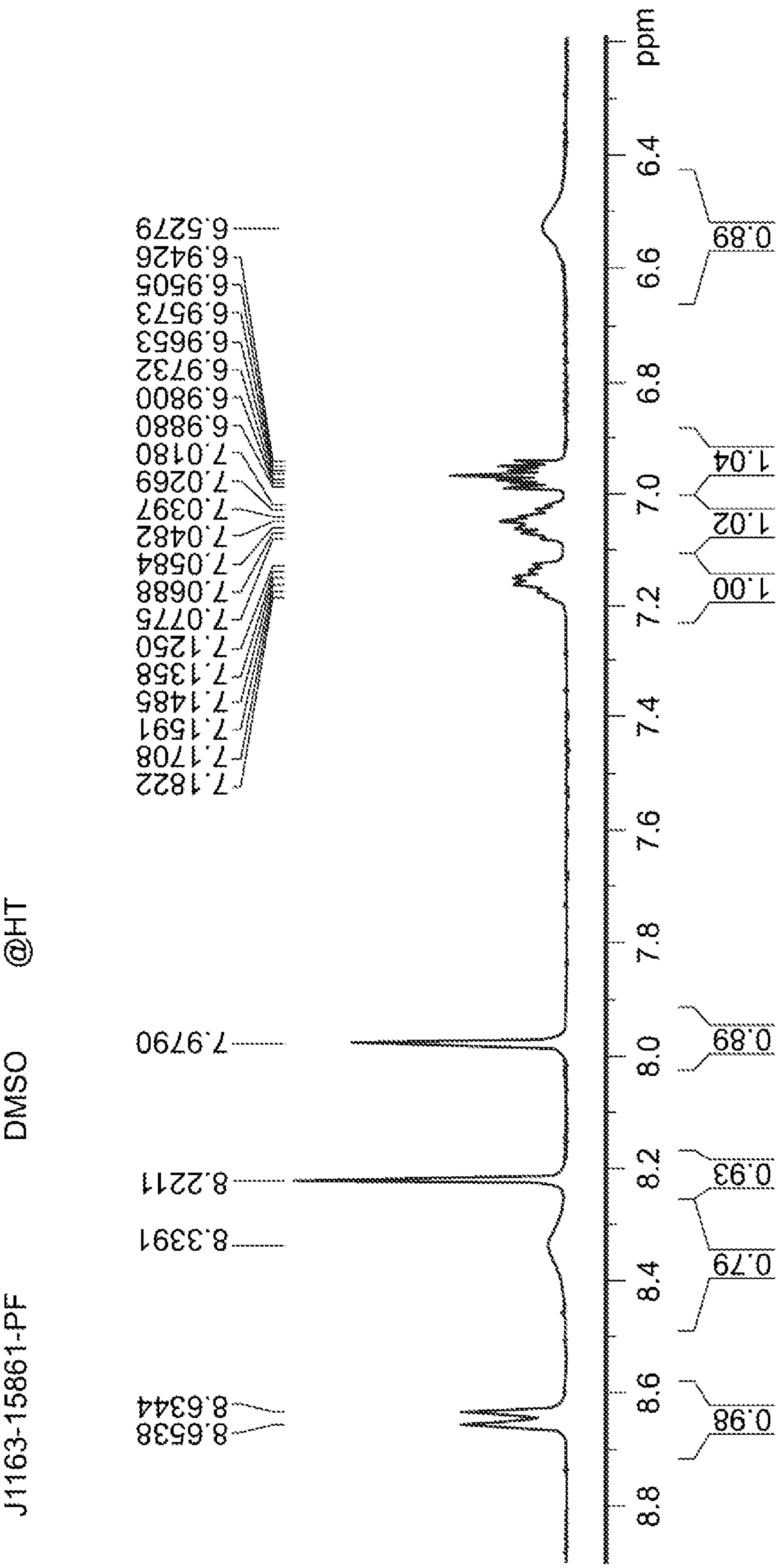
Figure 2C:
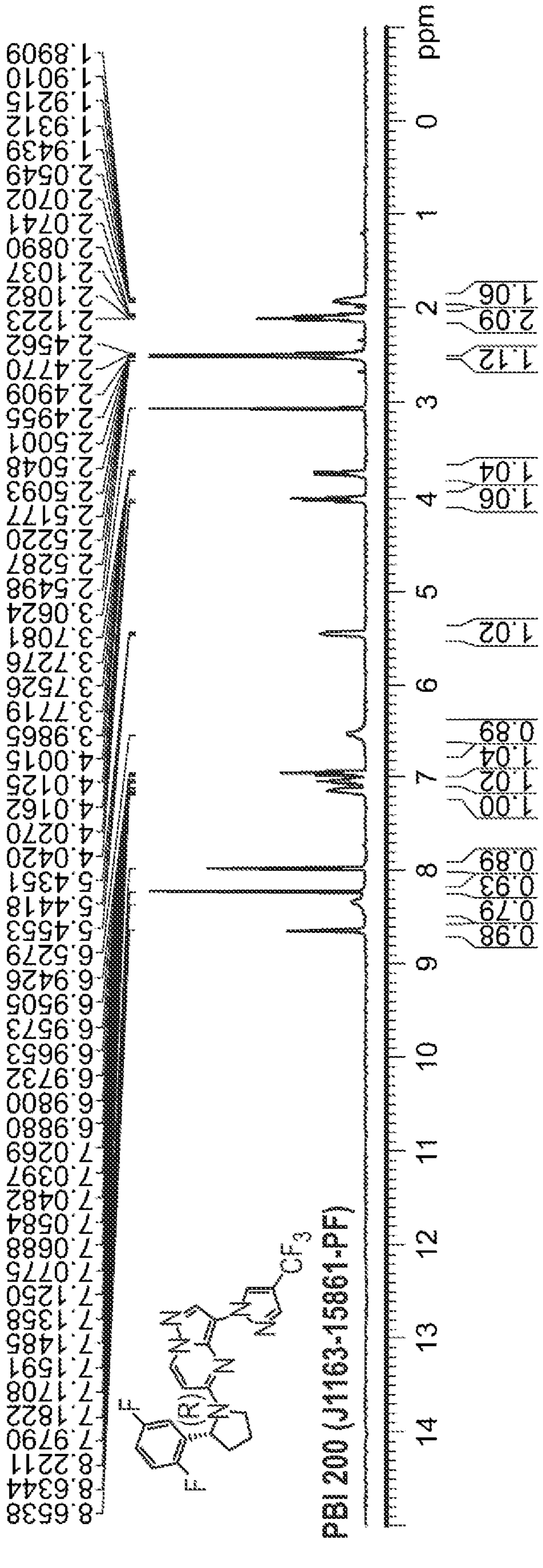
Figure 2D:
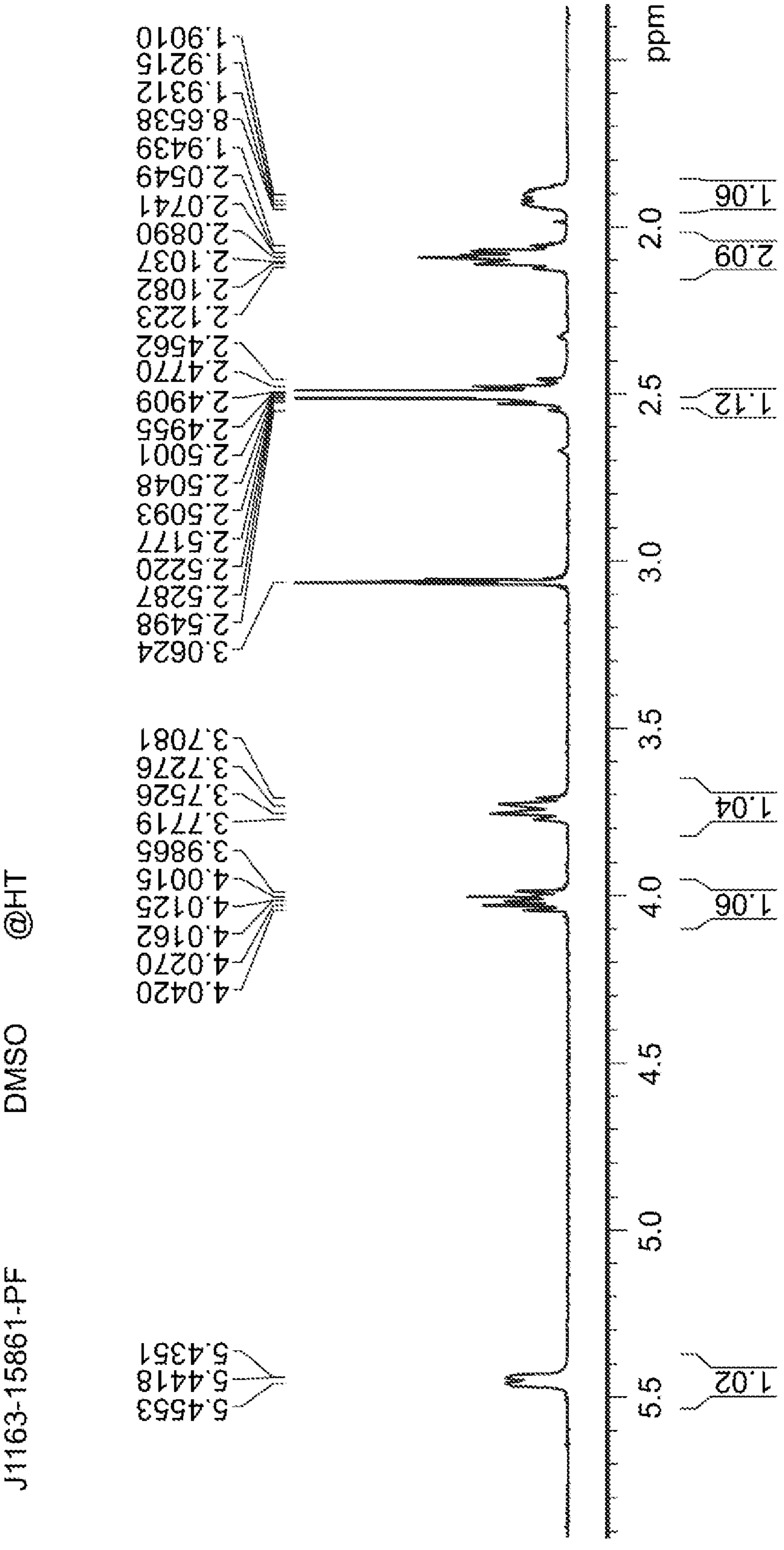
Figure 2D:
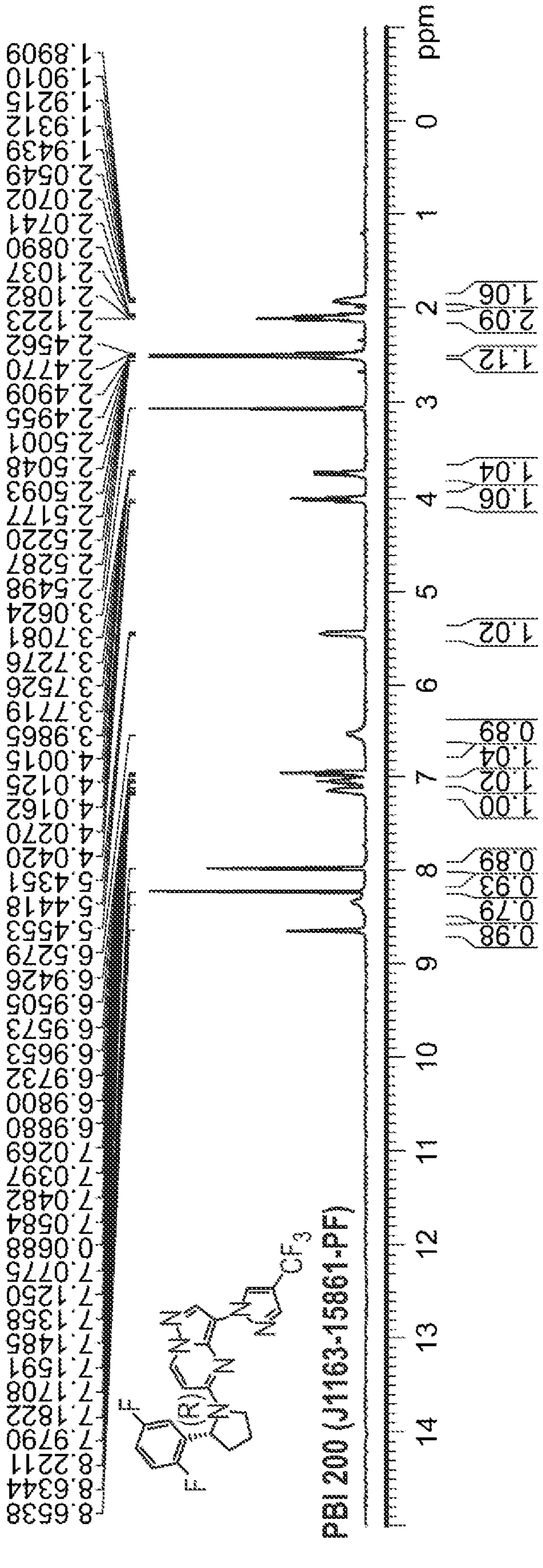
Figure 3A:
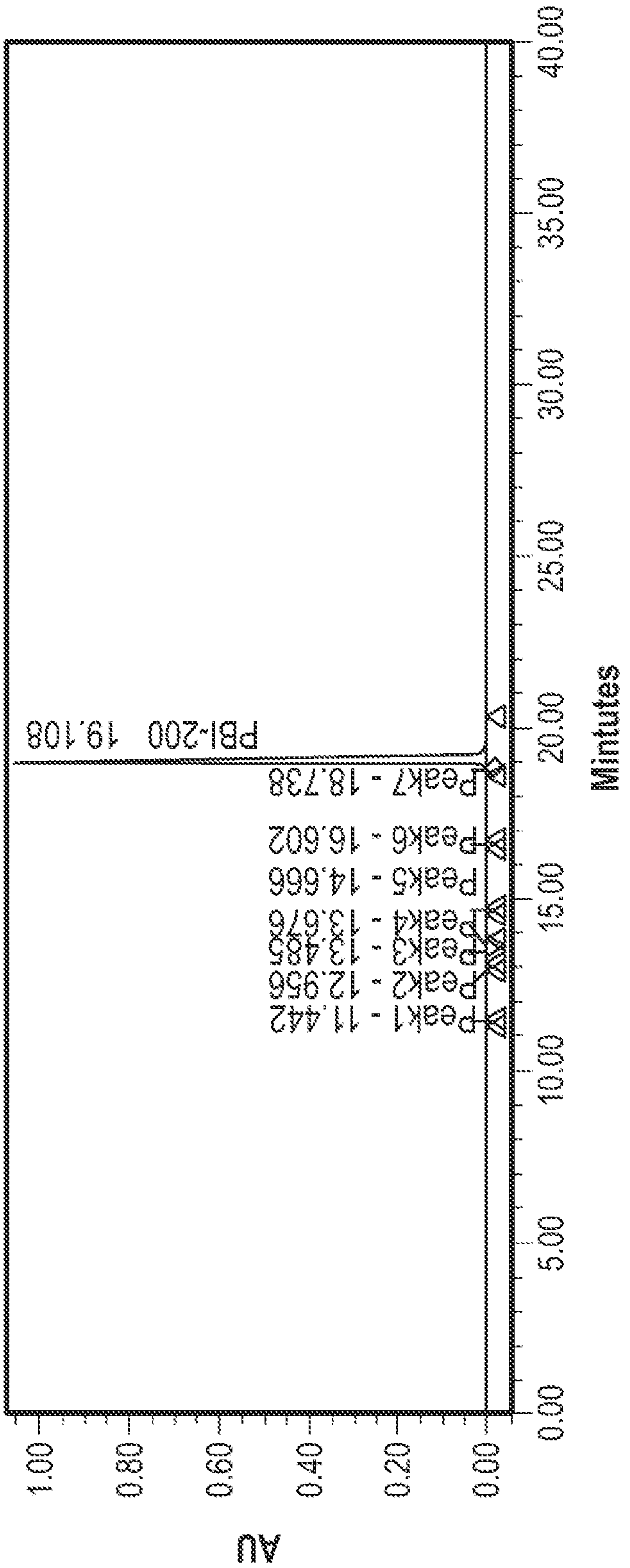
FIG. 3A and FIG. 3B show representative high performance liquid chromatography (HPLC) data of compound no. 14R.
Figure 3B:
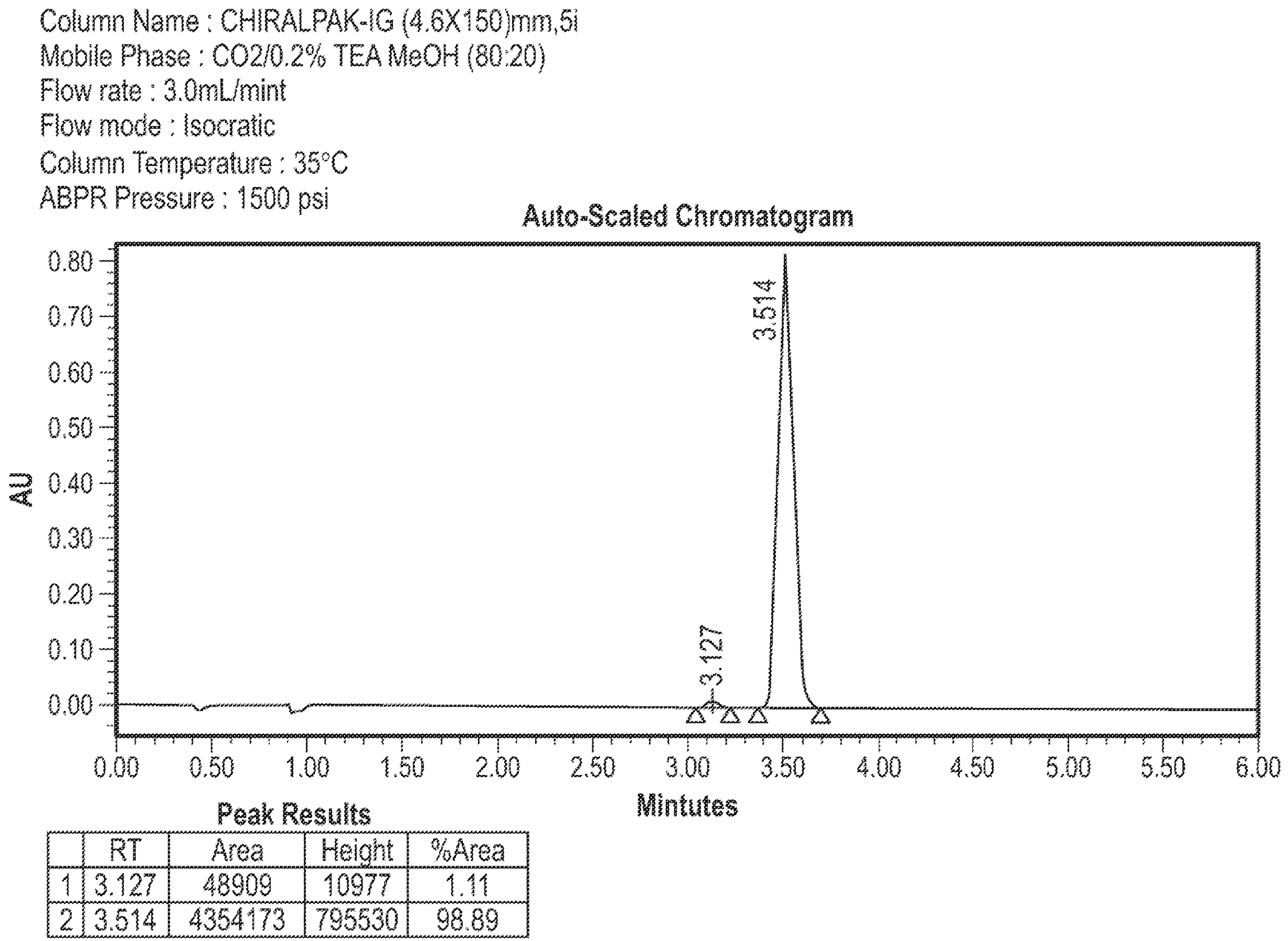

The UPLC-MS analysis conditions used to analyze compound no. 14R are shown in Table 2 below. See also FIG. 1A-D.

TABLE 2

| Column | Acquity HSS-T3 (2.1 × 100 mm, 1.8 μM) | | |
|---|---|---|---|
| Mobile Phase | A - 0.1% TFA in water; B - acetonitrile | | |
| | Gradient | | |
| Flow Mode | Time | A | B |
| | 0.0 | 90.0 | 10.0 |
| | 1.0 | 90.0 | 10.0 |
| | 2.0 | 85.0 | 15.0 |
| | 4.5 | 45.0 | 55.0 |
| | 6.0 | 10.0 | 90.0 |
| | 8.0 | 10.0 | 90.0 |
| | 9.0 | 90.0 | 10.0 |
| | 10.0 | 90.0 | 10.0 |

TABLE 2-continued

| | | |
|---|---|---|
| Flow | 0.3 | ml/min |
| UV Max | 214.0 | nm |
| Column Temp. | 30.0 | deg |

The following abbreviations have the indicated meanings:

aq aqueous $CDCl_3$ chloroform-d d doublet

DCE dichloroethane

DCM dichloromethane

DEA diethylamine

DIPEA N,N-diisopropylethylamine

DMF N,N-dimethylformamide

DMF-DEA N,N-dimethylformamide diethyl acetal

DMSO dimethylsulfoxide

DMSO-$d_6$ hexadeuterodimethylsulfoxide

ESI electrospray ionization

EtOAc ethyl acetate

EtOH ethanol g gram(s)

h hour(s)

$^1H$ NMR proton nuclear magnetic resonance spectroscopy

HPLC high performance liquid chromatography

Hz Hertz i-PrOH isopropanol

LC-MS liquid chromatography-mass spectrometry m multiplet

MeOH methanol

MeONa sodium methoxide mg milligram

MHz megahertz min minute(s)

mL milliliter(s)

mmol millimole(s)

MS mass spectrometry

N normal

Nm nanometer(s)

NMR nuclear magnetic resonance ppm parts per million psi pounds per square inch q quartet RT room temperature s singlet t triplet TEA triethylamine TFA trifluoroacetic acid THF tetrahydrofuran UPLC ultra performance liquid chromatography vol volume(s)

b. Synthesis of (R)-2-(2,5-difluorophenyl)pyrrolidine (Compound No. 6R)

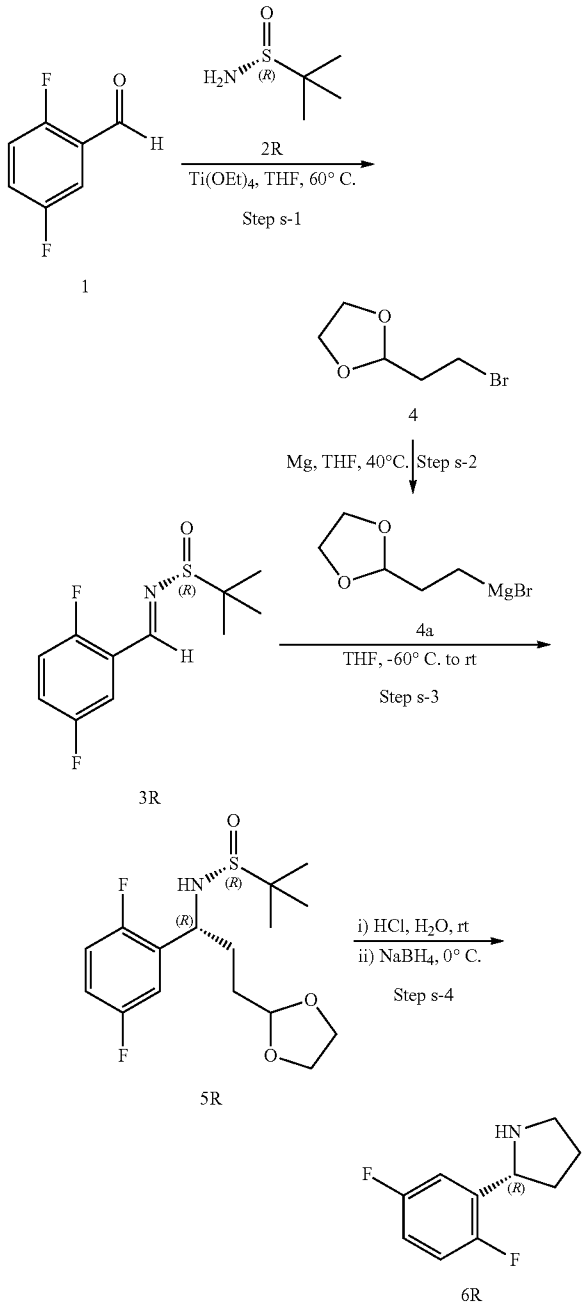

Synthesis of Compound No. 3R.

To a solution of 2,5-difluorobenzaldehyde (Compound No. 1, 50.0 g, 352 mmol) in tetrahydrofuran (500 mL) was added (R)-2-methylpropane-2-sulfinamide (Compound No. 2R, 51.0 g, 422 mmol). To this solution was added titanium ethoxide (160 mL, 704 mmol) dropwise at room temperature and heated to 60° C., stirred for 1 h. After completion, the reaction mixture was cooled to room temperature, poured into brine solution, diluted with ethyl acetate, filtered through Celite bed. The celite bed was washed with ethyl acetate and organic layer was separated from the filtrate. The organic layer was washed with water, brine solution, dried with anhydrous sodium sulfate, filtered and concentrated under reduced pressure to get the crude. The crude mass was purified by column chromatography using silica gel (60-120 mesh) using 50% ethyl acetate in hexanes as eluent. The desired fractions were concentrated under reduced pressure to afford (R,E)-N-(2,5-difluorobenzylidene)-2-methylpropane-2-sulfinamide (Compound No. 3R) as a light green liquid. Yield: 80 g, 93%; MS (ESI) m/z 246.07 $[M+1]^+$; $^1H$ NMR (400 MHz, DMSO-d6) δ 8.64 (s, 1H), 7.76-7.73 (t, J=8.08 Hz, 1H), 7.54-7.47 (m, 2H), 1.19 (s, 9H); chiral HPLC (column: CHIRALPAK IC (4.6×250 mm), 5 μm; mobile phase: $CO_2$/i-PrOH (90:10, isocratic); flow rate: 2.0 mL/min; column temperature: 35° C.; automated back pressure regulator: 1500 psi): retention time: 5.14 min, peak area: 0.3%; retention time: 6.24, peak area: 99.7%.

Synthesis of Compound No. 4a.

To a 2 L flask containing magnesium turnings (29.3 g, 204 mmol) was added dry tetrahydrofuran (234 mL, 8.0 vol). A solution of 2-(2-bromoethyl)-1,3-dioxolane (Compound No. 4, 110.8 g, 612 mmol) dissolved in THF (664 mL, 6.0 vol) was prepared in a separate flask and 50 mL of the solution was added to above magnesium turnings containing flask. Iodine (1.3 g) was added to the magnesium turnings containing flask and stirred at 45° C. (internal temperature should have maintained at <45° C.) until the iodine color disappeared. The remaining solution of 2-(2-bromoethyl)-1,3-dioxolane (Compound No. 4) in tetrahydrofuran (614 mL) was added dropwise to the mixture at room temperature at a rate that did not allow the internal temperature of the reaction to rise above 30° C. After completion, the reaction was allowed to stir an additional 45 min at room temperature to afford (2-(1,3-dioxolan-2-yl)ethyl)magnesium bromide (Compound No. 4a). The solution was used as such for further step.

Synthesis of Compound No. 5R.

The above (2-(1,3-dioxolan-2-yl)ethyl)magnesium bromide (Compound No. 4a) solution was added to the solution of (R,E)-N-(2,5-difluorobenzylidene)-2-methylpropane-2-sulfinamide (Compound No. 3R, 50.0 g, 204 mmol) in tetrahydrofuran (250 mL, 5.0 vol) at −60° C. The reaction mixture was allowed to stir at 0° C. for 2 h. After completion, the mixture was poured into ice cooled ammonium chloride solution and extracted with ethyl acetate. The organic layer was washed with brine solution, dried with anhydrous sodium sulfate, filtered and concentrated under reduced pressure to get the crude. The resulting crude was triturated with n-pentane, stirred for 30 min, filtered the solid, dried under high vacuum to afford (R)—N-((R)-1-(2,5-difluorophenyl)-3-(1,3-dioxolan-2-yl)propyl)-2-methylpropane-2-sulfinamide (Compound No. 5R) as a white solid. Yield: 60.0 g, 85%; MS (ESI) m/z 348.14 $[M+1]^+$; $^1H$ NMR (400 MHz, DMSO-d6) δ 7.36 (s, 1H), 7.23-7.17 (m, 1H), 7.15-7.10 (m, 1H), 5.78 (d, J=9.56 Hz, 1H), 4.78-4.76 (t, J=3.96 Hz, 1H), 4.46 (d, J=4.96 Hz, 1H), 3.84-3.82 (t, J=4.44 Hz, 2H), 3.74-3.71 (t, J=6.12 Hz, 2H), 1.87-1.78 (m, 1H), 1.72-1.65 (m, 2H), 1.52-1.47 (m, 1H), 1.10 (s, 9H); HPLC (column: CHIRALPAK IC (4.6×250 mm), 5 μm; mobile phase: $CO_2$/i-PrOH (80:20, isocratic); flow rate: 3.0 mL/min; column temperature: 35° C.; automated back pressure regulator: 1500 psi): retention time: 3.16 min, peak area: 99.8%; retention time: 3.69, peak area: 0.2%.

Synthesis of Compound No. 6R.

A solution of (R)—N-((R)-1-(2,5-difluorophenyl)-3-(1,3-dioxolan-2-yl)propyl)-2-methylpropane-2-sulfinamide (Compound No. 5R, 50.0 g, 144 mmol) in 5N aqueous hydrochloric acid (800 mL, 16 vol) was stirred for 1 h at room temperature. The reaction mixture was cooled to 0° C. and a solution of sodium borohydride (27.2 g, 720 mmol) in water (272 mL) was added drop wise at 0° C. and stirred for 1 h. After completion, the reaction mixture was poured into ice water, basified with solid potassium carbonate (up to pH=8) and extracted with ethyl acetate. The organic layer was washed with brine solution, dried over anhydrous sodium sulfate, filtered and concentrated to afford (R)-2-(2,5-difluorophenyl)pyrrolidine (Compound No. 6R) as brown liquid. Yield: 26.0 g, 82%; MS (ESI) m/z 183.97 $[M+1]^+$; $^1H$ NMR (400 MHz, DMSO-d6) δ 7.35-7.30 (m, 1H), 7.18-7.10 (m, 1H), 7.08-7.02 (m, 1H), 4.29-4.26 (m, 1H), 2.99-2.85 (m, 3H), 2.19-2.14 (m, 1H), 1.75-1.68 (m, 2H), 1.45-1.37 (m, 1H); HPLC (column: CHIRALPAK IG (4.6×250 mm), 5 μm; mobile phase: $CO_2$/0.2% TEA in MeOH (80:20, isocratic); flow rate: 2.0 mL/min; column temperature: 35° C.; automated back pressure regulator: 1500 psi): retention time: 1.72 min, peak area: 99.5%; retention time: 2.04, peak area: 0.5%.

c. Synthesis of 4-(trifluoromethyl)-1'H-[1,4'-bipyrazol]-5'-amine (Compound No. 10)

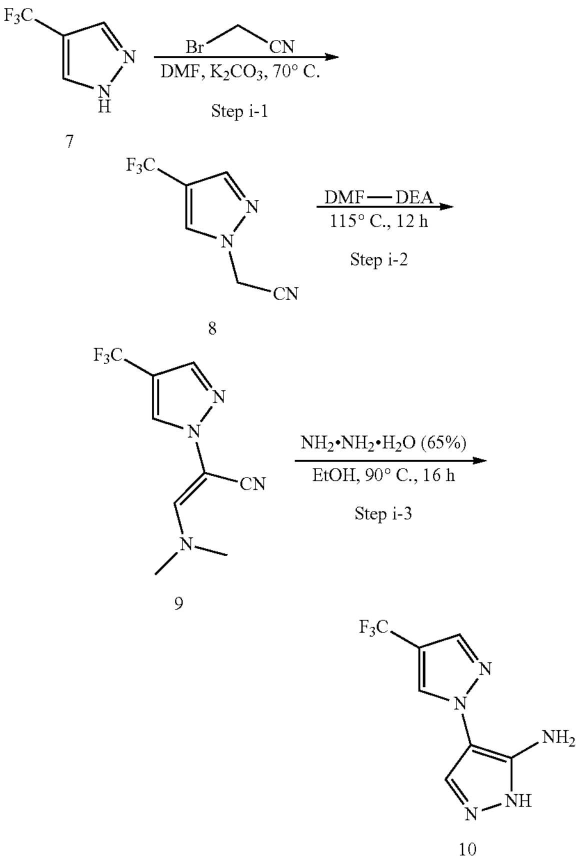

Synthesis of Compound No. 8.

To a solution of 4-(trifluoromethyl)-1H-pyrazole (Compound No. 7, 10.0 g, 73.5 mmol) in N,N-dimethylformamide (70 mL) was added potassium carbonate (30.4 g, 220 mmol) and bromoacetonitrile (7.1 mL, 102 mmol) at room temperature. The reaction mixture was heated to 70° C. and stirred for 5 h. After completion, the reaction mass was allowed to cooled to room temperature, poured into ice water and extracted methyl tert-butyl ether. The organic layer was washed with brine solution, dried over anhydrous sodium sulfate, filtered and concentrated to afford 2-(4-(trifluoromethyl)-1H-pyrazol-1-yl)acetonitrile (Compound No. 8) as a light brown liquid. Yield: 12.5 g, 96%; MS (ESI) m/z 174.12 $[M-1]^+$; $^1H$ NMR (400 MHz, DMSO-d6) δ 8.50 (s, 1H), 8.06 (s, 1H), 5.56 (s, 2H).

Synthesis of Compound No. 9.

A solution of 2-(4-(trifluoromethyl)-1H-pyrazol-1-yl)acetonitrile (Compound No. 8, 12.5 g, 71.42 mmol) in N,N-Dimethylformamide diethyl acetal (21.1 mL, 142.8 mmol) was heated to 115° C. and stirred for 16 h. After completion, the reaction mass was allowed to cool at room temperature, poured into ice water and extracted methyl tert-butyl ether. The organic part was washed with brine solution, dried over anhydrous sodium sulfate, filtered and concentrated to afford (E/Z-mixture) of 3-(dimethylamino)-2-(4-(trifluoromethyl)-1H-pyrazol-1-yl)acrylonitrile (Compound No. 9) as alight brown liquid. Yield: 14.0 g, 85%; MS (ESI) m/z 231.10 $[M+1]^+$.

Synthesis of Compound No. 10.

To a solution of (E/Z-mixture) of 3-(dimethylamino)-2-(4-(trifluoromethyl)-1H-pyrazol-1-yl)acrylonitrile (Compound No. 9, 12.0 g, 52.1 mmol) in ethanol (120 mL, 10 Vol) was added hydrazine monohydrate (65%, 12.6 mL, 26.0 mmol) and cooled to −20° C. To this solution was added concentrated hydrochloric acid (27 mL, up to pH=1) drop-wise at −20° C. The reaction mixture was heated to 90° C. for 16 h. After completion, the reaction mass was concentrated to remove ethanol. The resulting crude was diluted with ice water and basified with potassium carbonate, filtered the solid compound, washed with diethyl ether and dried under high vacuum to afford 4-(trifluoromethyl)-1'H-[1,4'-bipyrazol]-5'-amine (Compound No. 10) as an off white solid. Yield: 8.7 g, 76%; MS (ESI) m/z 218.20 $[M+1]^+$; $^1H$ NMR (400 MHz, DMSO-d6) δ 11.90 (br s, 1H), 8.63 (s, 1H), 8.05 (s, 1H), 7.81 (s, 1H), 5.04 (s, 2H).

d. Synthesis of (R)-5-(2-(2,5-difluorophenyl)pyrrolidin-1-yl)-3-(4-(trifluoro-methyl)-1H-pyrazol-1-yl)pyrazolo[1,5-a]pyrimidine (Compound No. 14R)

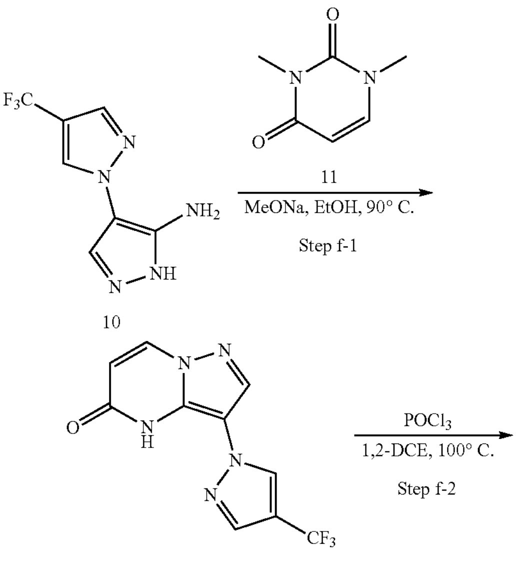

12

-continued

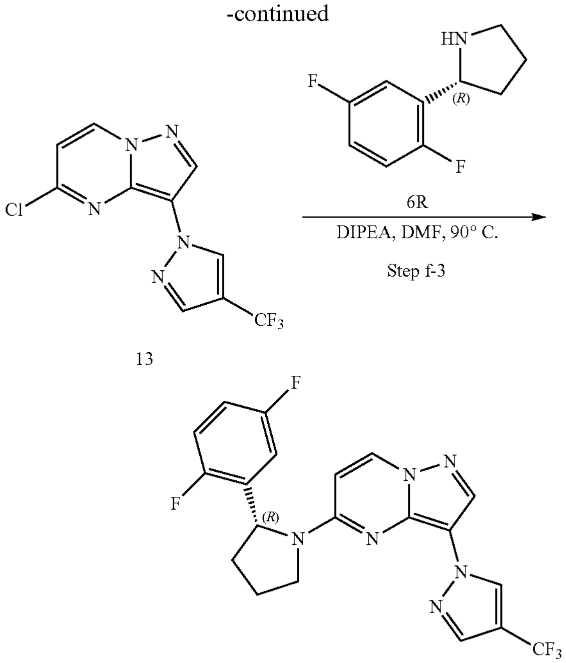

13

14R

Synthesis of Compound No. 12.

To a solution of 4-(trifluoromethyl)-1'H-[1,4'-bipyrazol]-5'-amine (Compound No. 10, 9.4 g, 43.3 mmol) in ethanol (94 mL) was added sodium methoxide solution (25% in methanol, 46.7 mL, 216 mmol) at room temperature and stirred for 15 min, followed by 1,3-dimethylpyrimidine-2,4 (1H,3H)-dione (Compound No. 11, 9.0 g, 64.9 mmol) was added at room temperature. The reaction mixture was heated to 90° C. for 16 h. After completion, the reaction mass was concentrated. The resulting crude was diluted with ice water, acidified with acetic acid (up to pH=5), filtered the solid compound, washed with n-pentane and dried under high vacuum to afford 3-(4-(trifluoromethyl)-1H-pyrazol-1-yl) pyrazolo[1,5-a]pyrimidin-5(4H)-one (Compound No. 12) as a yellow solid. Yield: 9.0 g, 77%; MS (ESI) m/z 270.09 $[M+1]^+$; $^1$H NMR (400 MHz, DMSO-d6) δ 12.37 (s, 1H), 8.72 (s, 1H), 8.61 (s, 1H), 8.19 (s, 1H), 8.14 (s, 1H), 6.15 (s, 1H).

Synthesis of Compound No. 13.

To a solution of 3-(4-(trifluoromethyl)-1H-pyrazol-1-yl) pyrazolo[1,5-a]pyrimidin-5(4H)-one (Compound No. 12, 8.5 g, 31.5 mmol) in 1,2-dichloroethene (130 mL, 15 Vol) were added Phosphorus oxychloride (14.7 mL, 157.9 mmol) and catalytic amount of N,N-Dimethylformamide (0.25 ml, 3 mmol) at room temperature. The reaction mixture was heated to 100° C. for 16 h. After completion, the reaction mass was concentrated. The resulting crude was dissolved in methyl tert-butyl ether and poured into saturated sodium bicarbonate (pH=8). The organic part was washed with brine solution, dried over anhydrous sodium sulfate, filtered and concentrated to afford 5-chloro-3-(4-(trifluoromethyl)-1H-pyrazol-1-yl)pyrazolo[1,5-a]pyrimidine (Compound No. 13) as a yellow solid. Yield: 7.8 g, 86%; MS (ESI) m/z 288.15 $[M+1]^+$; $^1$H NMR (400 MHz, DMSO-d6) δ 9.30 (d, J=7.28 Hz, 1H), 8.84 (s, 1H), 8.73 (s, 1H), 8.25 (s, 1H), 7.32 (d, J=7.28 Hz, 1H).

Synthesis of Compound No. 14R.

To a solution of 5-chloro-3-(4-(trifluoromethyl)-1H-pyrazol-1-yl)pyrazolo[1,5-a]pyrimidine (Compound No. 13, 7.8 g, 27 mmol) in NN-dimethylformamide (54 mL, 7.0 vol) were added (R)-2-(2,5-difluorophenyl)pyrrolidine (Compound No. 6R, 5.47 g, 29.8 mmol) and N,N-diisopropylethylamine (25 mL, 135 mmol) at room temperature. The reaction mixture was heated to 90° C. for 4 h. After completion, the reaction mixture was poured into ice water, extracted with ethyl acetate. The organic layer was washed with brine solution, dried over anhydrous sodium sulfate, filtered and concentrated under reduced pressure to get the crude. The resulting crude was triturated with ethanol and filtered the solid to afford (R)-5-(2-(2,5-difluorophenyl) pyrrolidin-1-yl)-3-(4-(trifluoromethyl)-1H-pyrazol-1-yl) pyrazolo[1,5-a]pyrimidine (Compound No. 14R) as off-white solid. Yield: 7.5 g, 63%; MS (ESI) m/z 435.03 [M+1]+; $^1$H NMR (400 MHz, DMSO-d6) δ 8.76 (d, J=7.68 Hz, 1H), 8.25-8.04 (m, 3H), 7.33-6.95 (m, 3H), 6.66 (d, J=7.72 Hz, 1H), 5.46-5.35 (m, 1H), 4.06-4.00 (m, 1H), 3.77-3.63 (m, 1H), 2.45-2.40 (m, 1H), 2.07-2.03 (m, 2H), 1.86-1.82 (m, 1H). $^1$H NMR (400 MHz, DMSO-d6 @ HT) δ 8.64 (d, J=7.76 Hz, 1H), 8.34 (s, 1H), 8.22 (s, 1H), 7.97 (s, 1H), 7.18-7.12 (m, 1H), 7.06-7.01 (m, 1H), 6.98-6.94 (m, 1H), 6.52 (s, 1H), 5.45 (d, J=5.40 Hz, 1H), 4.04-3.98 (m, 1H), 3.77-3.71 (m, 1H), 2.55-2.45 (m, 1H), 2.12-2.05 (m, 2H), 1.94-1.89 (m, 1H); HPLC (column: CHIRALPAK IG (4.6×250 mm), 5 μm; mobile phase: $CO_2$/0.2% TEA in MeOH (80:20, isocratic); flow rate: 2.0 m/min; column temperature: 35° C.; automated back pressure regulator: 1500 psi): retention time: 3.15 min, peak area: 0.6%; retention time: 3.56, peak area: 99.4%; HPLC (column: X BRIDGESHIELD RP18 (4.6×50 mm), 5 μm; mobile phase: [A: 5 mM ammonium acetate in water: B: acetonitrile], A % 0-10%, 10 min; flow rate: 1.0 mL/min; column temperature: ambient): retention time: 3.15 min, peak area: 0.6%; retention time: 3.56, peak area: 99.4%; UPLC-MS (column: Acquity HSS-T3 (2.1×100 mm), 1.8 μm; mobile phase: [A: 0.1% TFA in water, B: acetonitrile], B % 10-90%, 8 min; flow rate: 0.3 m/min; column temperature: 30° C.; UV max 214.0 nm): retention time: 7.16 min, peak area: 99.5%, MS (ESI) m/z 435.37; melting point: 182-184° C.

2. Biological Methods

TrkA kinase domain was supplied by SignalChem. Ulight PolyGT peptide substrate and Europium labeled W1024 antiphosphotyrosine antibody were supplied by Perkin Elmer. Assay buffer contained 50 mM HEPES, 10 mM $MgCl_2$, 1 mM EGTA, 2 mM DTT, 0.1 mg/mL BSA, and 0.005% w/v tween 20, pH 7.5. Enzyme dilution buffer was made by supplementing assay buffer with 25% w/v glycerol. Antibody dilution buffer contained 20 mM Tris, 137 mM NaCl, and 0.05% w/v tween 20, pH 8.0. Buffers were prepared at room temperature. Enzyme solutions were made on ice, while other solutions were made at room temperature and all subsequent assay steps were performed at room temperature. The TrkA stock solution (0.1 mg/mL) was diluted 156× in enzyme dilution buffer and then 100× in assay buffer. Five μL/well of enzyme solution was added to the assay plate (Greiner black 384-well nonbinding plate), with buffer containing no enzyme added to negative control wells. Test compounds were serially diluted in DMSO at 300× final assay concentration. One μL of each test compound dilution was mixed with 99 μL assay buffer plus ATP (30 μM) and five μL of each test compound-ATP solution was added to wells containing enzyme. Positive control wells contained enzyme and substrates but no test compounds. After a 15 minute enzyme-test compound pre-incubation, five μL of substrate diluted in assay buffer was added to all wells. Final assay concentrations were 33 pM TrkA, 100 nM peptide substrate, and 10 μM ATP. After a five minute reaction, five μL of 80 mM EDTA was added, followed five minutes later by five μL two nM antibody solution. The ratio of fluorescence at 665 nm vs. 615 nM in each well was determined using a Tecan Infinite Pro F200 plate reader. For each test compound well, percent inhibition was calculated (% inhib.=100−100*(test value-neg. control)/(pos. control-neg. control)). Percent inhibition values were fit to a four parameter logistic to determine $IC_{50}$ values for each test compound.

A list of pyrazolo[1,5-a]pyrimidine compounds evaluated for their ability to inhibit TRK is shown in Table 3 below. As would be readily appreciated by one of skill in the art, these compounds can be prepared by the disclosed methods or by alternative methods known in the art. All of the examples inhibit TrK kinase with an $IC_{50}$ below 5 nM.

TABLE 3

| No. | Structure |
|---|---|
| 1 | 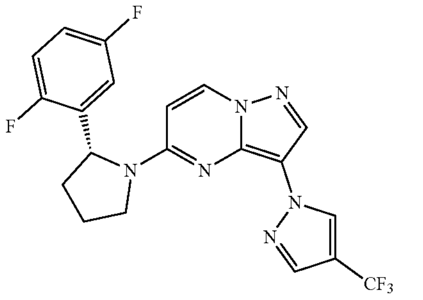 |
| 2 | 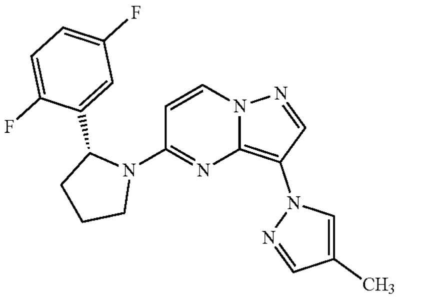 |
| 3 | 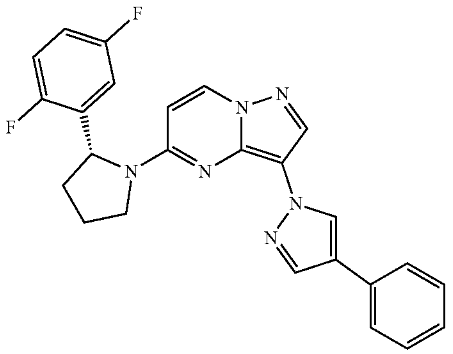 [SMILES: Fc1ccc(F)c([C@H]2CCCN2c2ccn3ncc(-n4cc(-c5ccccc5)cn4)c3n2)c1] |

TABLE 3-continued

| No. | Structure |
|---|---|
| 4 | 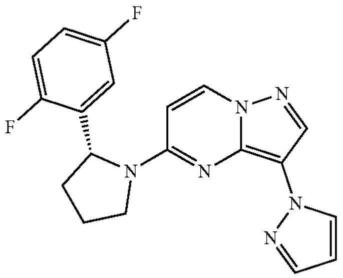 [SMILES: Fc1ccc(F)c([C@H]2CCCN2c2ccn3ncc(-n4cccn4)c3n2)c1] |
| 5 | 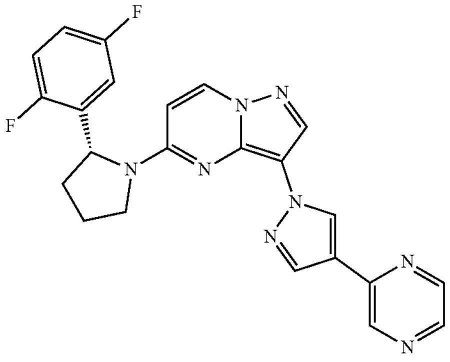 [SMILES: Fc1ccc(F)c([C@H]2CCCN2c2ccn3ncc(-n4cc(-c5cnccn5)cn4)c3n2)c1] |
| 6 | 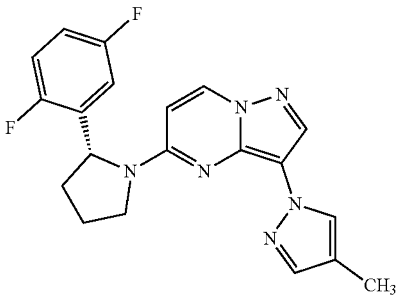 |
| 7 | 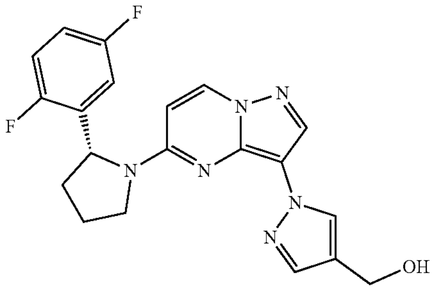 [SMILES: OCc1cnn(-c2cnn3ccc(N4CCC[C@@H]4c4cc(F)ccc4F)nc23)c1] |
| 8 | 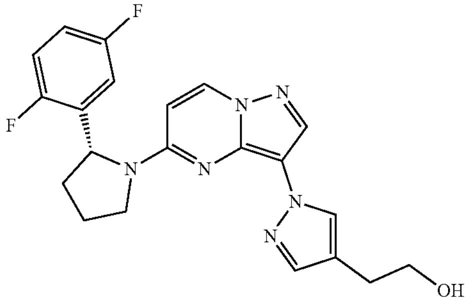 [SMILES: OCCc1cnn(-c2cnn3ccc(N4CCC[C@@H]4c4cc(F)ccc4F)nc23)c1] |

TABLE 3-continued
| No. | Structure |
| --- | --- |
| 9 | 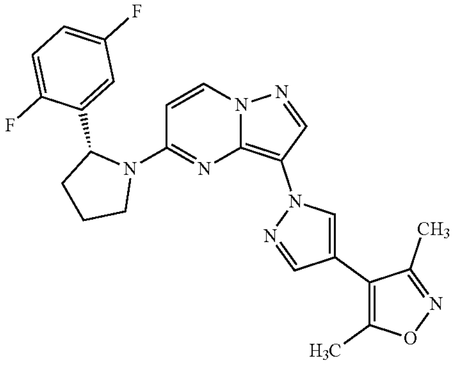 [SMILES: Cc1noc(C)c1-c1cnn(-c2cnn3ccc(N4CCC[C@@H]4c4cc(F)ccc4F)nc23)c1] |
| 10 | 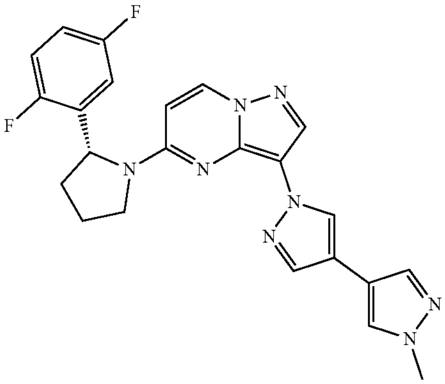 [SMILES: Cn1cc(-c2cnn(-c3cnn4ccc(N5CCC[C@@H]5c5cc(F)ccc5F)nc34)c2)cn1] |
| 11 | 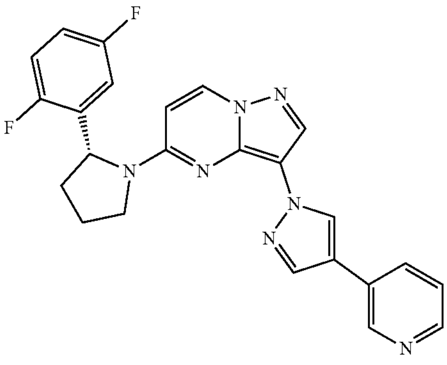 [SMILES: Fc1ccc(F)c([C@H]2CCCN2c2ccn3ncc(-n4cc(-c5cccnc5)cn4)c3n2)c1] |
| 12 | 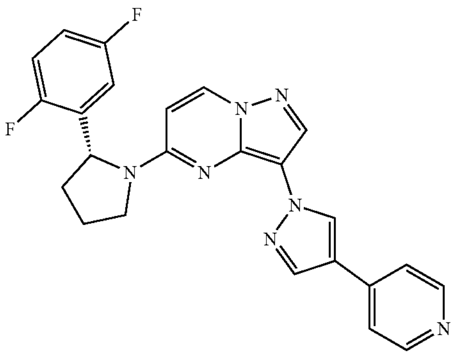 [SMILES: Fc1ccc(F)c([C@H]2CCCN2c2ccn3ncc(-n4cc(-c5ccncc5)cn4)c3n2)c1] |
TABLE 3-continued
| No. | Structure |
| --- | --- |
| 13 | 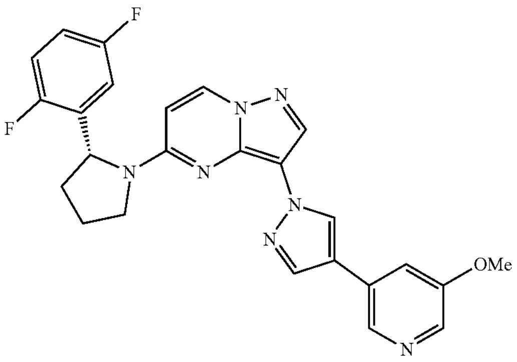 [SMILES: COc1cncc(-c2cnn(-c3cnn4ccc(N5CCC[C@@H]5c5cc(F)ccc5F)nc34)c2)c1] |
| 14 | 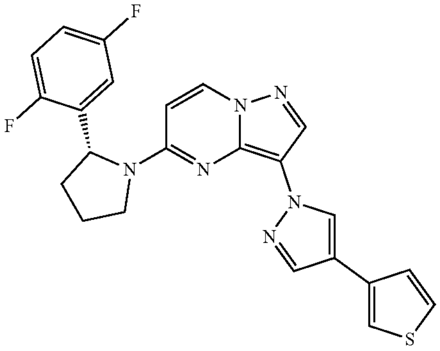 [SMILES: Fc1ccc(F)c([C@H]2CCCN2c2ccn3ncc(-n4cc(-c5ccsc5)cn4)c3n2)c1] |
| 15 | 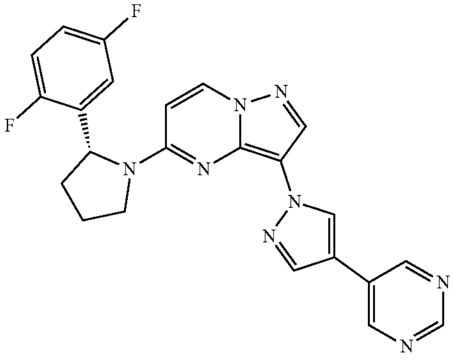 [SMILES: Fc1ccc(F)c([C@H]2CCCN2c2ccn3ncc(-n4cc(-c5cncnc5)cn4)c3n2)c1] |
| 16 | 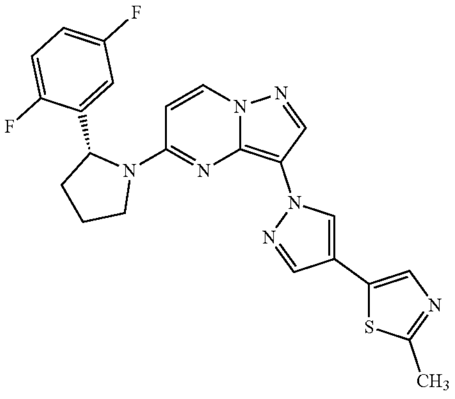 [SMILES: Cc1ncc(-c2cnn(-c3cnn4ccc(N5CCC[C@@H]5c5cc(F)ccc5F)nc34)c2)s1] |

TABLE 3-continued
| No. | Structure |
|---|---|
| 17 | 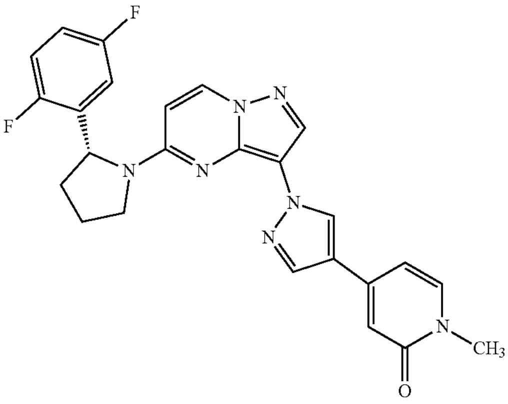 [SMILES: Cn1ccc(-c2cnn(-c3cnn4ccc(N5CCC[C@@H]5c5cc(F)ccc5F)nc34)c2)cc1=O] |
| 18 | 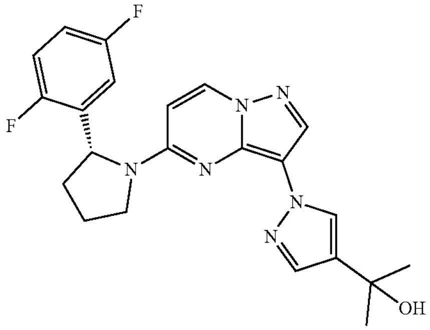 [SMILES: CC(C)(O)c1cnn(-c2cnn3ccc(N4CCC[C@@H]4c4cc(F)ccc4F)nc23)c1] |
| 19 | 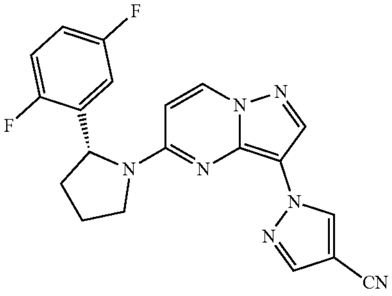 [SMILES: N#Cc1cnn(-c2cnn3ccc(N4CCC[C@@H]4c4cc(F)ccc4F)nc23)c1] |
| 20 | 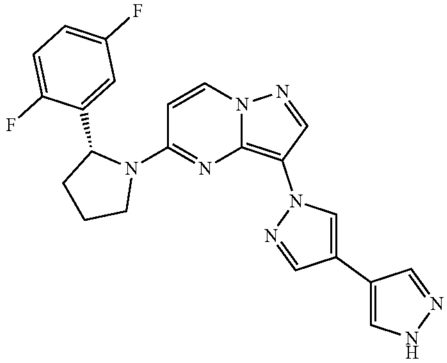 [SMILES: Fc1ccc(F)c([C@H]2CCCN2c2ccn3ncc(-n4cc(-c5cn[nH]c5)cn4)c3n2)c1] |
| 21 | 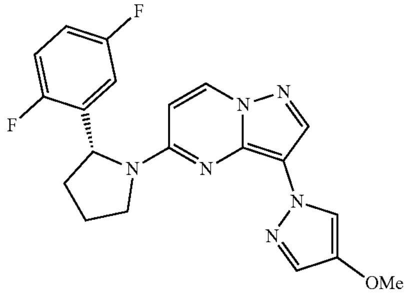 [SMILES: COc1cnn(-c2cnn3ccc(N4CCC[C@@H]4c4cc(F)ccc4F)nc23)c1] |
| 22 | 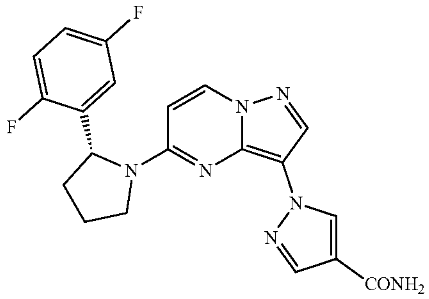 [SMILES: NC(=O)c1cnn(-c2cnn3ccc(N4CCC[C@@H]4c4cc(F)ccc4F)nc23)c1] |
| 23 | 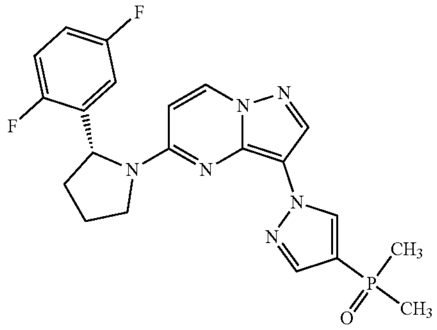 [SMILES: CP(C)(=O)c1cnn(-c2cnn3ccc(N4CCC[C@@H]4c4cc(F)ccc4F)nc23)c1] |
| 24 | 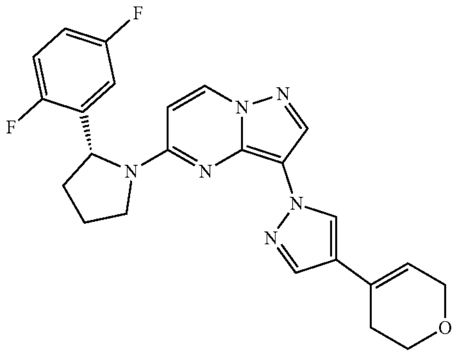 [SMILES: Fc1ccc(F)c([C@H]2CCCN2c2ccn3ncc(-n4cc(C5=CCOCC5)cn4)c3n2)c1] |

TABLE 3-continued
| No. | Structure |
|---|---|
| 25 | 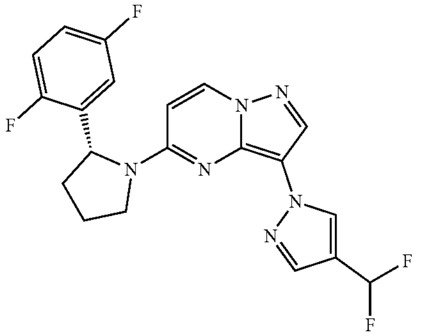 [SMILES: Fc1ccc(F)c([C@H]2CCCN2c2ccn3ncc(-n4cc(C(F)F)cn4)c3n2)c1] |
| 26 | 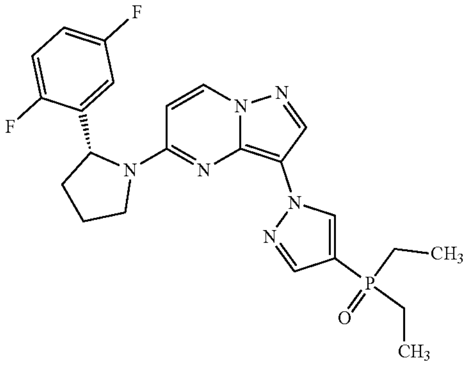 [SMILES: CCP(=O)(CC)c1cnn(-c2cnn3ccc(N4CCC[C@@H]4c4cc(F)ccc4F)nc23)c1] |
| 27 | 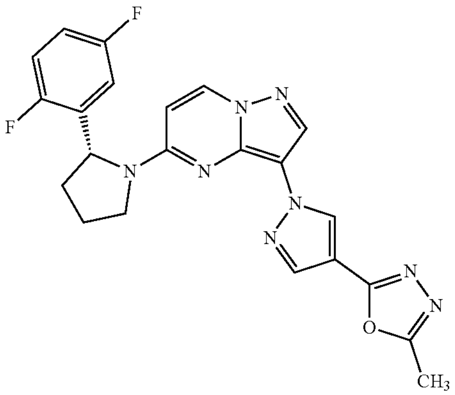 [SMILES: Cc1nnc(-c2cnn(-c3cnn4ccc(N5CCC[C@@H]5c5cc(F)ccc5F)nc34)c2)o1] |
| 28 | 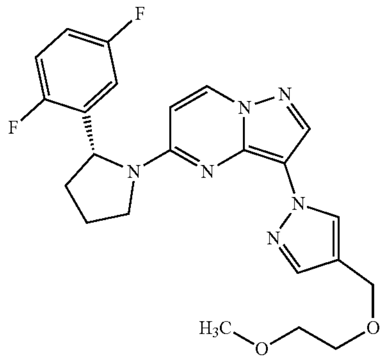 [SMILES: COCCOCc1cnn(-c2cnn3ccc(N4CCC[C@@H]4c4cc(F)ccc4F)nc23)c1] |
TABLE 3-continued
| No. | Structure |
|---|---|
| 29 | 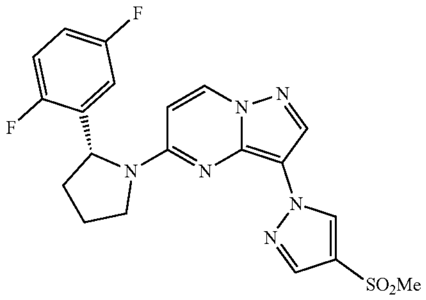 [SMILES: CS(=O)(=O)c1cnn(-c2cnn3ccc(N4CCC[C@@H]4c4cc(F)ccc4F)nc23)c1] |
| 30 | 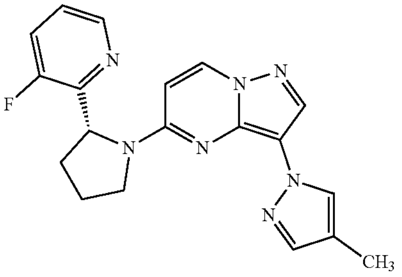 [SMILES: Cc1cnn(-c2cnn3ccc(N4CCC[C@@H]4c4ncccc4F)nc23)c1] |
| 31 | 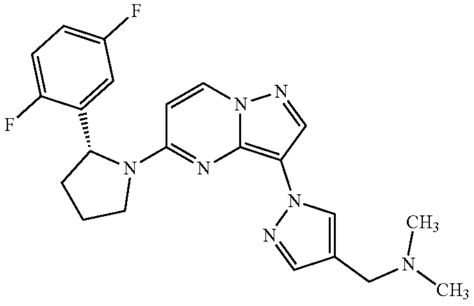 [SMILES: CN(C)Cc1cnn(-c2cnn3ccc(N4CCC[C@@H]4c4cc(F)ccc4F)nc23)c1] |
| 32 | 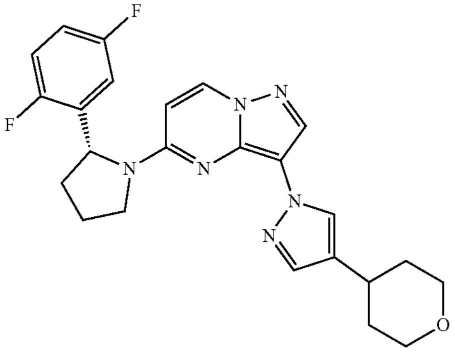 |
| 33 | 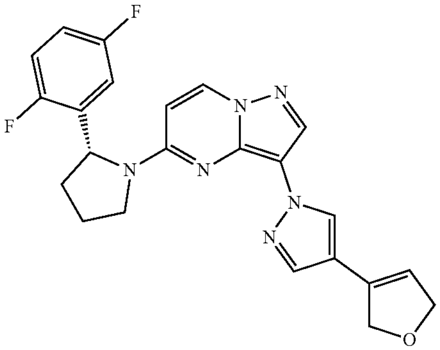 [SMILES: Fc1ccc(F)c([C@H]2CCCN2c2ccn3ncc(-n4cc(C5=CCOC5)cn4)c3n2)c1] |

TABLE 3-continued
| No. | Structure |
| --- | --- |
| 34 | 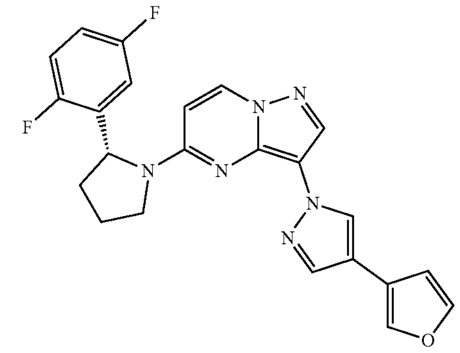 [SMILES: Fc1ccc(F)c([C@H]2CCCN2c2ccn3ncc(-n4cc(-c5ccoc5)cn4)c3n2)c1] |
| 35 | 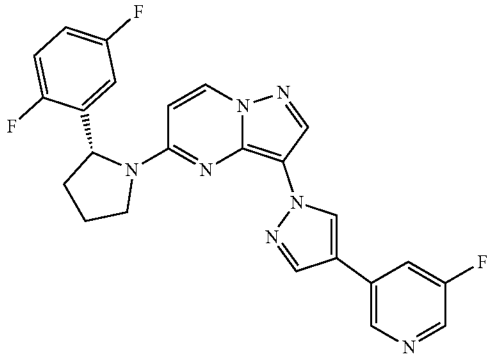 [SMILES: Fc1cncc(-c2cnn(-c3cnn4ccc(N5CCC[C@@H]5c5cc(F)ccc5F)nc34)c2)c1] |
| 36 | 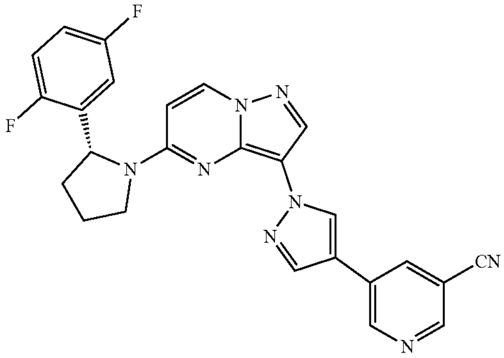 [SMILES: N#Cc1cncc(-c2cnn(-c3cnn4ccc(N5CCC[C@@H]5c5cc(F)ccc5F)nc34)c2)c1] |
| 37 | 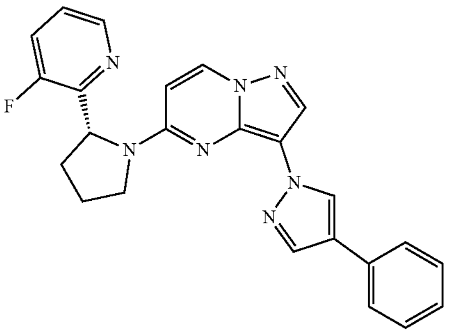 [SMILES: Fc1cccnc1[C@H]1CCCN1c1ccn2ncc(-n3cc(-c4ccccc4)cn3)c2n1] |
TABLE 3-continued
| No. | Structure |
| --- | --- |
| 38 | 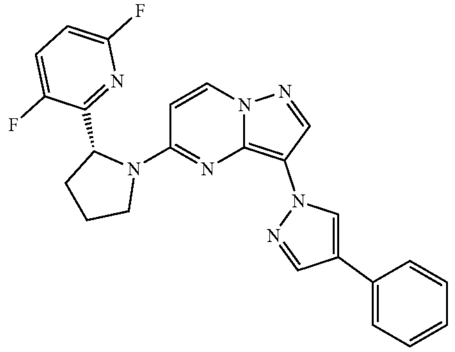 [SMILES: Fc1ccc(F)c([C@H]2CCCN2c2ccn3ncc(-n4cc(-c5ccccc5)cn4)c3n2)n1] |
| 39 | 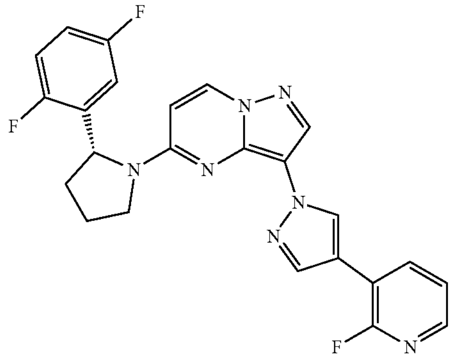 [SMILES: Fc1ccc(F)c([C@H]2CCCN2c2ccn3ncc(-n4cc(-c5cccnc5F)cn4)c3n2)c1] |
| 40 | 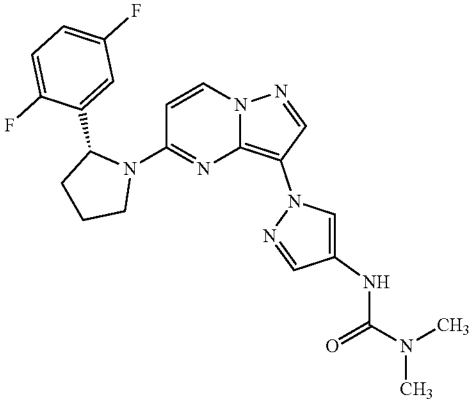 [SMILES: CN(C)C(=O)Nc1cnn(-c2cnn3ccc(N4CCC[C@@H]4c4cc(F)ccc4F)nc23)c1] |
| 41 | 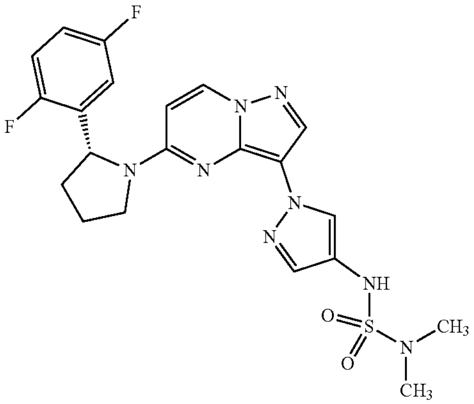 [SMILES: CN(C)S(=O)(=O)Nc1cnn(-c2cnn3ccc(N4CCC[C@@H]4c4cc(F)ccc4F)nc23)c1] |

TABLE 3-continued
| No. | Structure |
| --- | --- |
| 42 | 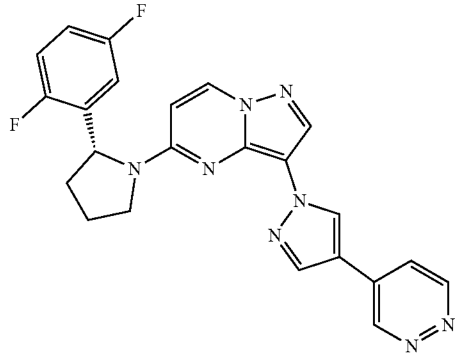 [SMILES: Fc1ccc(F)c([C@H]2CCCN2c2ccn3ncc(-n4cc(-c5ccnnc5)cn4)c3n2)c1] |
| 43 | 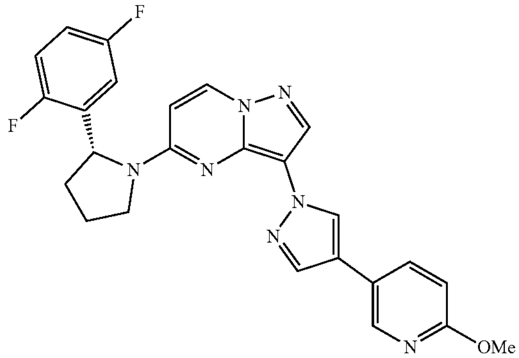 [SMILES: COc1ccc(-c2cnn(-c3cnn4ccc(N5CCC[C@@H]5c5cc(F)ccc5F)nc34)c2)cn1] |
| 44 | 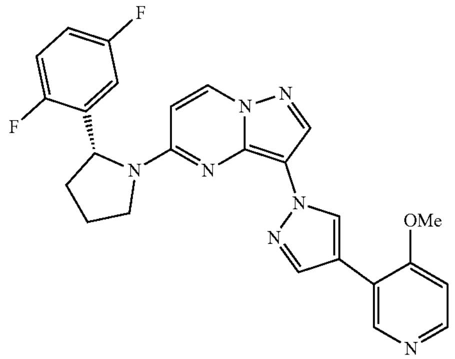 [SMILES: COc1ccncc1-c1cnn(-c2cnn3ccc(N4CCC[C@@H]4c4cc(F)ccc4F)nc23)c1] |
| 45 | 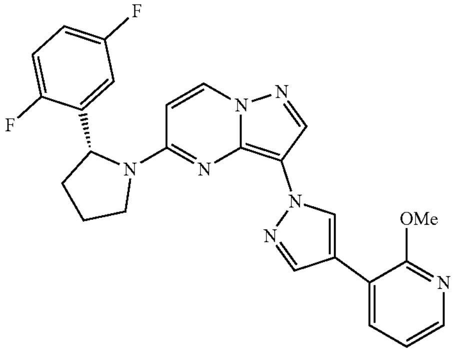 [SMILES: COc1ncccc1-c1cnn(-c2cnn3ccc(N4CCC[C@@H]4c4cc(F)ccc4F)nc23)c1] |
TABLE 3-continued
| No. | Structure |
| --- | --- |
| 46 | 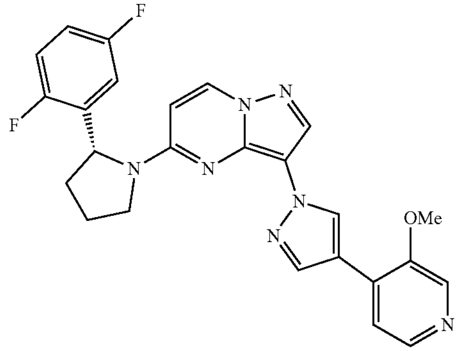 [SMILES: COc1cnccc1-c1cnn(-c2cnn3ccc(N4CCC[C@@H]4c4cc(F)ccc4F)nc23)c1] |
| 47 | 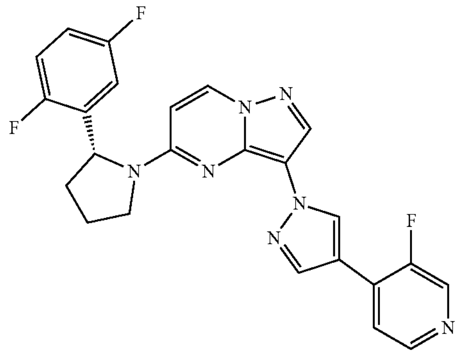 [SMILES: Fc1ccc(F)c([C@H]2CCCN2c2ccn3ncc(-n4cc(-c5ccncc5F)cn4)c3n2)c1] |
| 48 | 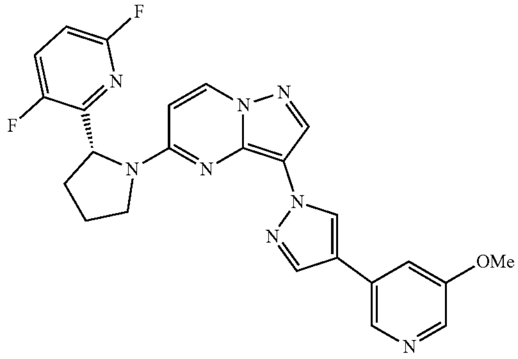 [SMILES: COc1cncc(-c2cnn(-c3cnn4ccc(N5CCC[C@@H]5c5nc(F)ccc5F)nc34)c2)c1] |
| 49 | 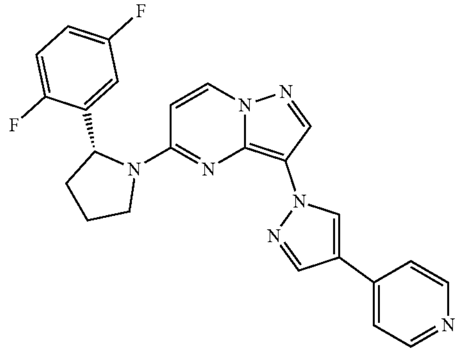 [SMILES: Fc1ccc(F)c([C@H]2CCCN2c2ccn3ncc(-n4cc(-c5ccncc5)cn4)c3n2)c1] |

TABLE 3-continued
| No. | Structure |
| --- | --- |
| 50 | 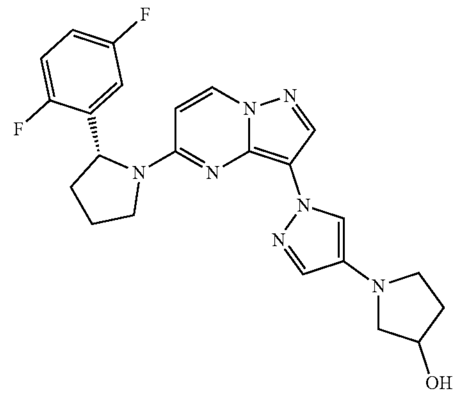 [SMILES: OC1CCN(c2cnn(-c3cnn4ccc(N5CCC[C@@H]5c5cc(F)ccc5F)nc34)c2)C1] |
| 51 | 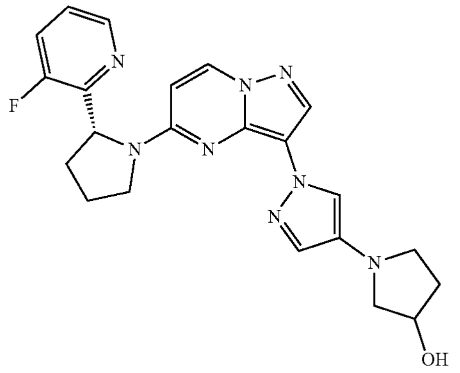 [SMILES: OC1CCN(c2cnn(-c3cnn4ccc(N5CCC[C@@H]5c5ncccc5F)nc34)c2)C1] |
| 52 | 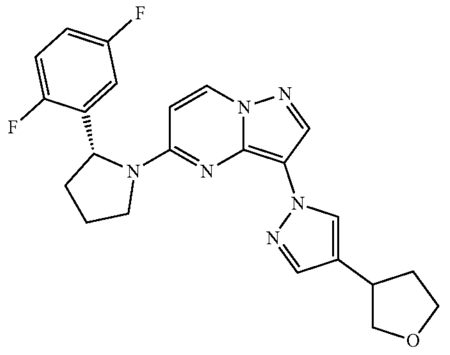 [SMILES: Fc1ccc(F)c([C@H]2CCCN2c2ccn3ncc(-n4cc(C5CCOC5)cn4)c3n2)c1] |
| 53 | 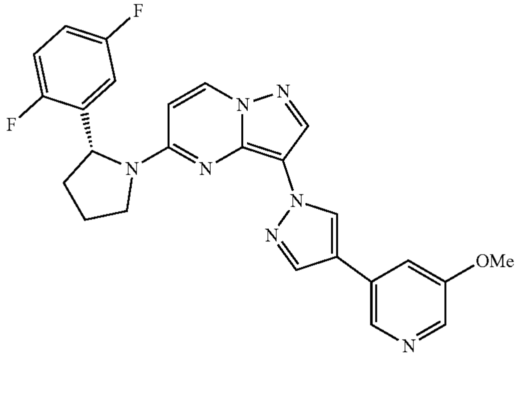 [SMILES: COc1cncc(-c2cnn(-c3cnn4ccc(N5CCC[C@@H]5c5cc(F)ccc5F)nc34)c2)c1] |
TABLE 3-continued
| No. | Structure |
| --- | --- |
| 54 | 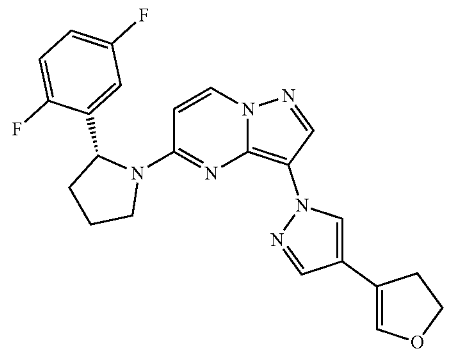 [SMILES: Fc1ccc(F)c([C@H]2CCCN2c2ccn3ncc(-n4cc(C5=COCC5)cn4)c3n2)c1] |
| 55 | 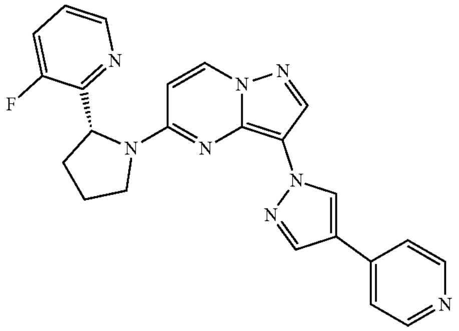 [SMILES: Fc1cccnc1[C@H]1CCCN1c1ccn2ncc(-n3cc(-c4ccncc4)cn3)c2n1] |
| 56 | 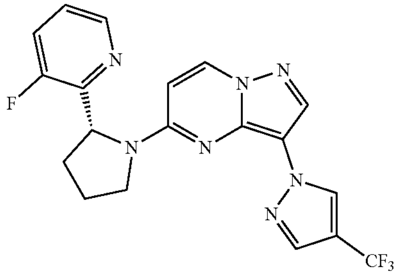 |
| 57 | 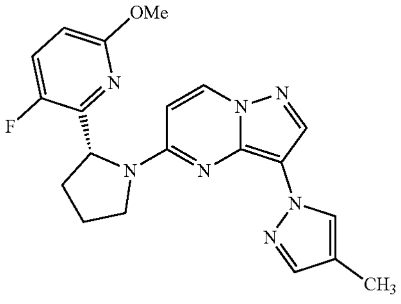 [SMILES: COc1ccc(F)c([C@H]2CCCN2c2ccn3ncc(-n4cc(C)cn4)c3n2)n1] |
| 58 | 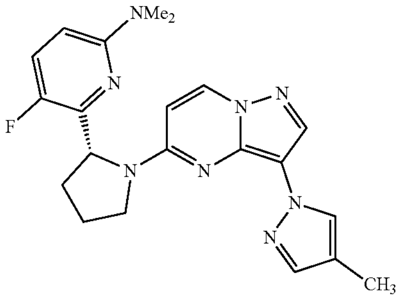 [SMILES: Cc1cnn(-c2cnn3ccc(N4CCC[C@@H]4c4nc(N(C)C)ccc4F)nc23)c1] |

TABLE 3-continued
| No. | Structure |
|---|---|
| 59 | 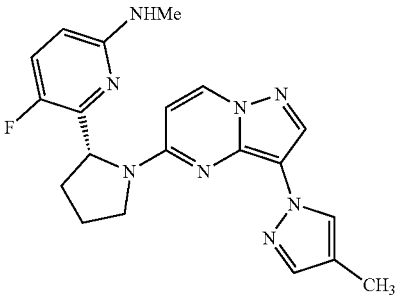 [SMILES: CNc1ccc(F)c([C@H]2CCCN2c2ccn3ncc(-n4cc(C)cn4)c3n2)n1] |
| 60 | 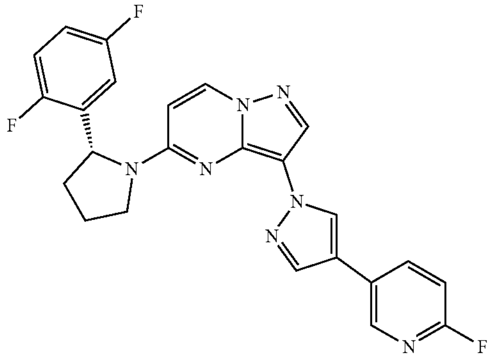 [SMILES: Fc1ccc(F)c([C@H]2CCCN2c2ccn3ncc(-n4cc(-c5ccc(F)nc5)cn4)c3n2)c1] |
| 61 | 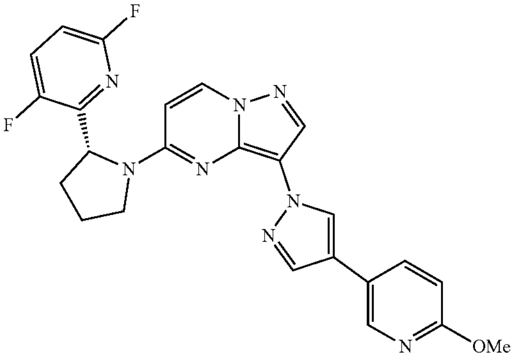 [SMILES: COc1ccc(-c2cnn(-c3cnn4ccc(N5CCC[C@@H]5c5nc(F)ccc5F)nc34)c2)cn1] |
| 62 | 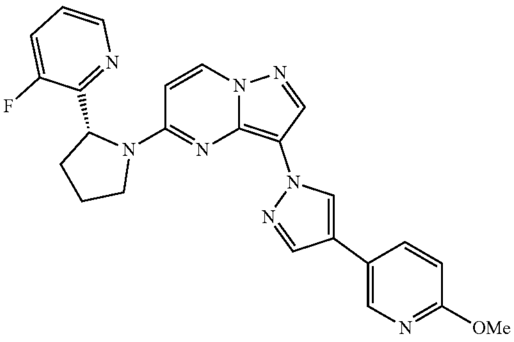 [SMILES: COc1ccc(-c2cnn(-c3cnn4ccc(N5CCC[C@@H]5c5ncccc5F)nc34)c2)cn1] |
| 63 | 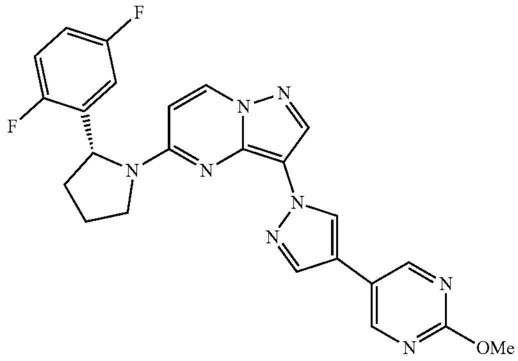 [SMILES: COc1ncc(-c2cnn(-c3cnn4ccc(N5CCC[C@@H]5c5cc(F)ccc5F)nc34)c2)cn1] |
| 64 | 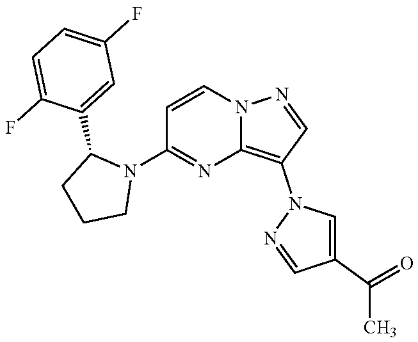 [SMILES: CC(=O)c1cnn(-c2cnn3ccc(N4CCC[C@@H]4c4cc(F)ccc4F)nc23)c1] |
| 65 | 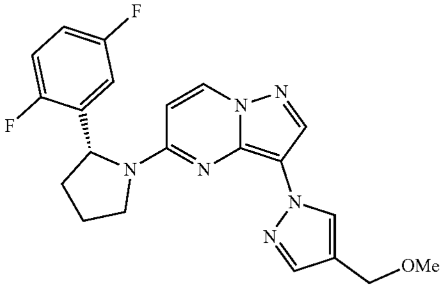 [SMILES: COCc1cnn(-c2cnn3ccc(N4CCC[C@@H]4c4cc(F)ccc4F)nc23)c1] |
TABLE 3A
| No. | $R^{10}$ Group |
|---|---|
| 1a | $—CF_3$ |
| 2a | $—CH_3$ |
| 3a | —Ph |
| 4a | —H |
| 5a | 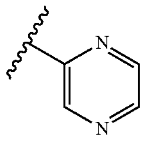 [SMILES: *c1cnccn1] |
| 6a | $—CH_3$ |
| 7a | $—CH_2OH$ |
| 8a | $—CH_2CH_2OH$ |

TABLE 3A-continued
| No. | $R^{10}$ Group |
|---|---|
| 9a | 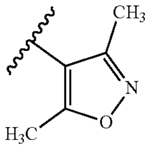 |
| 10a | 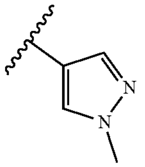 [SMILES: *c1cnn(C)c1] |
| 11a | 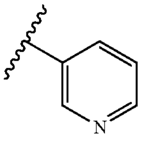 [SMILES: *c1cccnc1] |
| 12a | 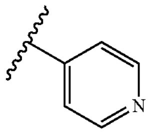 [SMILES: *c1ccncc1] |
| 13a | 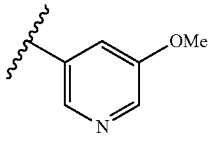 [SMILES: *c1cncc(OC)c1] |
| 14a | 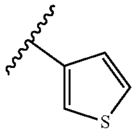 [SMILES: *c1ccsc1] |
| 15a | 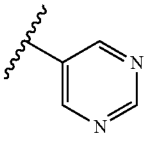 [SMILES: *c1cncnc1] |
| 16a | 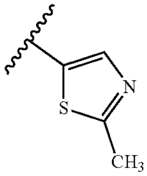 [SMILES: *c1cnc(C)s1] |
| 17a | 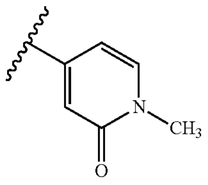 [SMILES: *c1ccn(C)c(=O)c1] |
TABLE 3A-continued
| No. | $R^{10}$ Group |
|---|---|
| 18a | 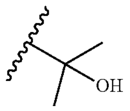 [SMILES: *C(C)(C)O] |
| 19a | $—CN$ |
| 20a | 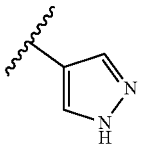 [SMILES: *c1cn[nH]c1] |
| 21a | $—OCH_3$ |
| 22a | $—C(O)NH_2$ |
| 23a | $—P(O)(CH_3)_2$ |
| 24a | 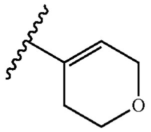 [SMILES: *C1=CCOCC1] |
| 25a | $—CHF_2$ |
| 26a | $—P(O)(CH_2CH_3)_2$ |
| 27a | 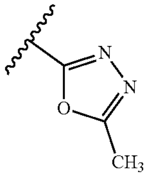 [SMILES: *c1nnc(C)o1] |
| 28a | $—CH_2OCH_2CH_2OCH_3$ |
| 29a | $—SO_2CH_3$ |
| 30a | $—CH_3$ |
| 31a | $—CH_2N(CH_3)_2$ |
| 32a | 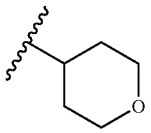 [SMILES: *C1CCOCC1] |
| 33a | 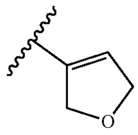 [SMILES: *C1=CCOC1] |
| 34a | 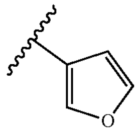 [SMILES: *c1ccoc1] |
| 35a | 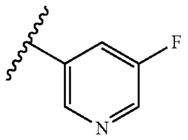 [SMILES: *c1cncc(F)c1] |

TABLE 3A-continued
| No. | $R^{10}$ Group |
|---|---|
| 36a | 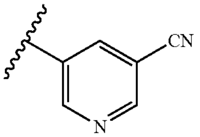 [SMILES: *c1cncc(C#N)c1] |
| 37a | —Ph |
| 38a | —Ph |
| 39a | 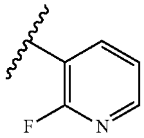 [SMILES: *c1cccnc1F] |
| 40a | $—NHC(O)N(CH_3)_2$ |
| 41a | $—NHSO_2N(CH_3)_2$ |
| 42a | 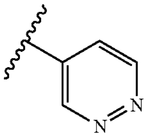 [SMILES: *c1ccnnc1] |
| 43a | 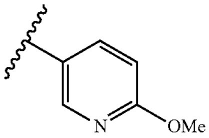 [SMILES: *c1ccc(OC)nc1] |
| 44a | 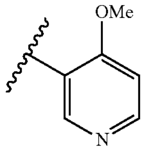 [SMILES: *c1cnccc1OC] |
| 45a | 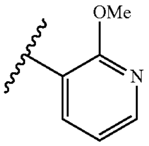 [SMILES: *c1cccnc1OC] |
| 46a | 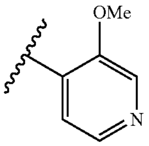 [SMILES: *c1ccncc1OC] |
| 47a | 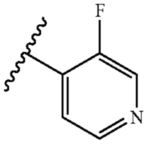 [SMILES: *c1ccncc1F] |
| 48a | 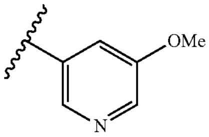 [SMILES: *c1cncc(OC)c1] |
TABLE 3A-continued
| No. | $R^{10}$ Group |
|---|---|
| 49a | 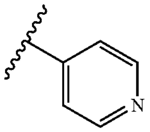 [SMILES: *c1ccncc1] |
| 50a | 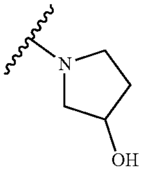 [SMILES: *N1CCC(O)C1] |
| 51a | 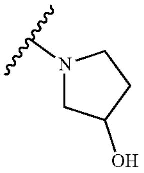 [SMILES: *N1CCC(O)C1] |
| 52a | 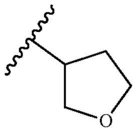 [SMILES: *C1CCOC1] |
| 53a | 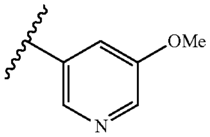 [SMILES: *c1cncc(OC)c1] |
| 54a | 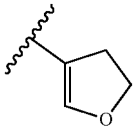 [SMILES: *C1=COCC1] |
| 55a | 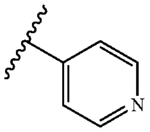 [SMILES: *c1ccncc1] |
| 56a | $—CF_3$ |
| 57a | $—CH_3$ |
| 58a | $—CH_3$ |
| 59a | $—CH_3$ |
| 60a | 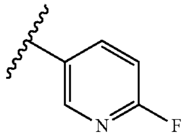 [SMILES: *c1ccc(F)nc1] |
| 61a | 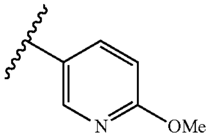 [SMILES: *c1ccc(OC)nc1] |

TABLE 3A-continued

| No. | $R^{10}$ Group |
|---|---|
| 62a | 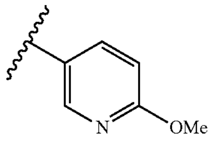 [SMILES: *c1ccc(OC)nc1] |
| 63a | 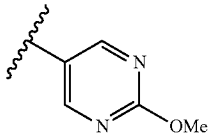 [SMILES: *c1cnc(OC)nc1] |
| 64a | $—C(O)CH_3$ |
| 65a | $—CH_2OCH_3$ |

K. EQUIVALENTS

It is to be understood that the invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for making a compound having the structure represented by formula (XV):

(XV)

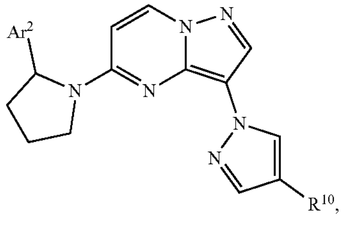

or a pharmaceutically acceptable salt thereof, the method comprising coupling a compound of formula (XVI):

(XVI)

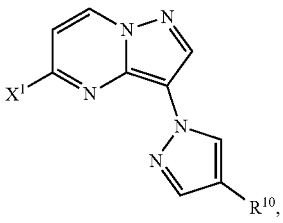

and a compound of formula (XVII):

(XVII)

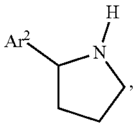

whereby

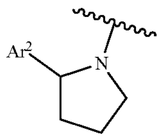

replaces $X^1$;

wherein $X^1$ is a leaving group;

wherein $R^{10}$ is selected from hydrogen, halogen, —CN, C1-C6 alkyl, C1-C6 haloalkyl, C1-C6 cyanoalkyl, $—OR^{20}$, $—C(O)R^{20}$, $—S(O)R^{20}$, $—S(O)_2R^{20}$, $—(C1\text{-}C6\ alkyl)OR^{20}$, $—(C1\text{-}C6\ alkyl)SR^{20}$, $—(C1\text{-}C6\ alkyl)C(O)R^{20}$, $—(C1\text{-}C6\ alkyl)S(O)R^{20}$, $—(C1\text{-}C6\ alkyl)S(O)_2R^{20}$, $—NR^{21}C(O)R^{20}$, $—NR^{21}S(O)_2R^{20}$, $—NR^{22a}R^{22b}$, $—P(O)R^{22a}R^{22b}$, $—(C1\text{-}C6\ alkyl)NR^{22a}R^{22b}$, $—(C1\text{-}C6\ alkyl)P(O)R^{22a}R^{22b}$, and $Cy^1$;

wherein each of $R^{20}$, $R^{21}$, $R^{22a}$, and $R^{22b}$, when present, is independently selected from hydrogen, C1-C4 alkyl, and C1-C4 haloalkyl;

wherein $Cy^1$, when present, is selected from a C3-C8 cycloalkyl, a 3- to 8-membered heterocycloalkyl, a C6-C10 aryl, and a 5- to 10-membered heteroaryl, and is substituted with 0, 1, 2, or 3 groups independently selected from halogen, —CN, $—NH_2$, —OH, $—NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4) (C1-C4) dialkylamino, and C1-C4 aminoalkyl; and wherein $Ar^2$ is a C6-C10 aryl or a 5- to 6-membered heteroaryl, and is substituted with 0, 1, 2, or 3 groups independently selected from halogen, C1-C6 alkyl, C1-C6 haloalkyl, C1-C6 alkoxy, and C1-C6 haloalkoxy.

2. The method of claim 1, wherein $R^{10}$ is $—CF_3$.

3. The method of claim 1, wherein $Ar^2$ is a phenyl with 2 halogen groups.

4. The method of claim 1, wherein the compound of formula (XV) has the structure represented by formula:

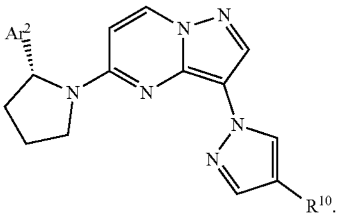

5. The method of claim 1, wherein the compound of formula (XV) is:

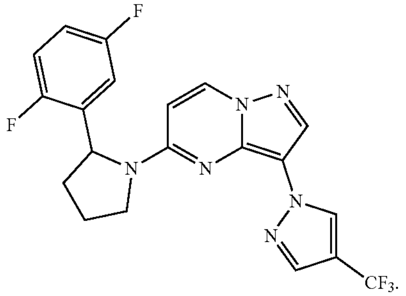

6. The method of claim 1, wherein the method is for making a compound having the structure represented by formula (XXV):

(XXV)

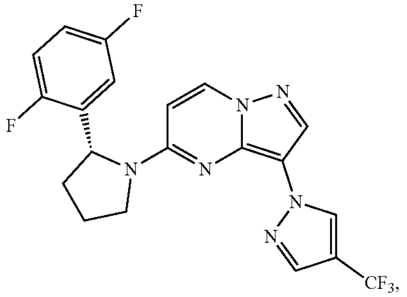

or a pharmaceutically acceptable salt thereof, the method comprising coupling a compound having the structure represented by formula (XXVI):

(XXVI)

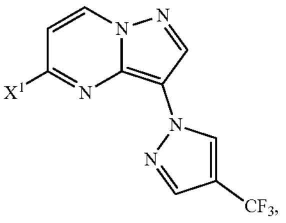

and a compound having the structure represented by formula:

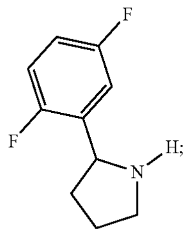

and whereby

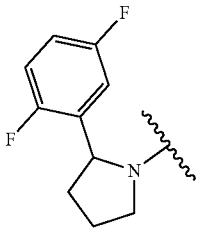 [SMILES: *N1CCCC1c1cc(F)ccc1F]

replaces $X^1$, wherein $X^1$ is a leaving group.

7. The method of claim 6, wherein $X^1$ is a halogen.

8. The method of claim 6, wherein the coupling reaction is conducted in the presence of a base.

9. The method of claim 8, wherein the base is an amine base.

10. The method of claim 9, wherein the amine base is a trialkylamine or pyridine.

11. The method of claim 1, wherein the coupling reaction is conducted at an elevated temperature, wherein the temperature is in the range of about 70° C. to about 110° C.

* * * * *